(12) United States Patent
Liu et al.

(10) Patent No.: US 9,174,994 B2
(45) Date of Patent: Nov. 3, 2015

(54) ENHANCED TREATMENT REGIMENS USING MTOR INHIBITORS

(71) Applicant: INTELLIKINE LLC, La Jolla, CA (US)

(72) Inventors: Yi Liu, San Diego, CA (US); Lynne Bui, Saratoga, CA (US); Michael Martin, Carlsbad, CA (US); Troy Edward Wilson, San Marino, CA (US); Christian Rommel, La Jolla, CA (US)

(73) Assignee: Intellikine, LLC, La Jolla, CA (US)

( * ) Notice: Subject to any disclaimer, the term of this patent is extended or adjusted under 35 U.S.C. 154(b) by 0 days.

(21) Appl. No.: 14/360,267

(22) PCT Filed: Nov. 21, 2012

(86) PCT No.: PCT/US2012/066431
§ 371 (c)(1),
(2) Date: May 22, 2014

(87) PCT Pub. No.: WO2013/078440
PCT Pub. Date: May 30, 2013

(65) Prior Publication Data
US 2014/0287031 A1 Sep. 25, 2014

Related U.S. Application Data

(60) Provisional application No. 61/563,516, filed on Nov. 23, 2011.

(51) Int. Cl.
| *A61K 31/535* | (2006.01) |
| *A61K 31/4965* | (2006.01) |
| *C07D 487/04* | (2006.01) |
| *C07D 519/00* | (2006.01) |
| *A61K 31/519* | (2006.01) |
| *A61K 31/5377* | (2006.01) |

(52) U.S. Cl.
CPC .......... *C07D 487/04* (2013.01); *A61K 31/4965* (2013.01); *A61K 31/519* (2013.01); *A61K 31/535* (2013.01); *A61K 31/5377* (2013.01); *C07D 519/00* (2013.01)

(58) Field of Classification Search
CPC .. C07D 487/04; C07D 519/00; A61K 31/535; A61K 31/4965
USPC ........... 514/234.2, 252.16; 424/450; 544/118, 544/262
See application file for complete search history.

(56) References Cited

U.S. PATENT DOCUMENTS

| 3,657,744 | A | 4/1972 | Ersek |
| 3,714,357 | A | 1/1973 | Gueremy et al. |
| 4,739,762 | A | 4/1988 | Palmaz |
| 5,040,458 | A | 8/1991 | Jiruse et al. |
| 5,061,273 | A | 10/1991 | Yock |
| 5,171,744 | A | 12/1992 | Cross et al. |
| 5,195,984 | A | 3/1993 | Schatz |
| 5,292,331 | A | 3/1994 | Boneau |
| 5,451,233 | A | 9/1995 | Yock |
| 5,496,346 | A | 3/1996 | Horzewski et al. |
| 5,674,278 | A | 10/1997 | Boneau |
| 5,759,787 | A | 6/1998 | Strulovici |
| 5,879,382 | A | 3/1999 | Boneau |
| 6,166,037 | A | 12/2000 | Budhu et al. |
| 6,344,053 | B1 | 2/2002 | Boneau |
| 6,423,546 | B1 * | 7/2002 | Lusk et al. .................. 435/7.92 |
| 7,612,189 | B2 | 11/2009 | Hancock et al. |
| 7,651,687 | B2 | 1/2010 | Buck et al. |
| 7,700,594 | B2 | 4/2010 | Chen et al. |
| 8,067,536 | B2 | 11/2011 | Klink et al. |
| 2003/0165902 | A1 * | 9/2003 | Bieglecki et al. ................. 435/6 |
| 2003/0198969 | A1 * | 10/2003 | Bieglecki et al. ................. 435/6 |
| 2004/0072161 | A1 * | 4/2004 | Bieglecki et al. ................. 435/6 |
| 2005/0119288 | A1 | 6/2005 | Bhattacharya et al. |
| 2007/0254883 | A1 | 11/2007 | Crew et al. |
| 2009/0149511 | A1 | 6/2009 | Burk et al. |
| 2009/0274698 | A1 | 11/2009 | Bhagwat et al. |
| 2010/0015140 | A1 | 1/2010 | Danter |

FOREIGN PATENT DOCUMENTS

| EP | 0409595 A2 | 1/1991 |
| EP | 0424021 A1 | 4/1991 |
| EP | 1241176 A1 | 9/2002 |
| EP | 1052264 B1 | 3/2005 |
| JP | 2004107299 A | 4/2004 |
| WO | WO 92/19594 A1 | 11/1992 |
| WO | WO 93/19749 A1 | 10/1993 |
| WO | WO 93/19750 A1 | 10/1993 |
| WO | WO 93/19751 A1 | 10/1993 |

(Continued)

OTHER PUBLICATIONS

Chan-Hui, et al. Applications of eTag trade mark assay platform to systems biology approaches in molecular oncology and toxicology studies. Clin Immunol. May 2004;111(2):162-74.
Donahue, et al. Measuring phosphorylated Akt and other phosphoinositide 3-kinase-regulated phosphoproteins in primary lymphocytes. Methods Enzymol. 2007;434:131-54.
Fan, et al. A dual PI3 kinase/mTOR inhibitor reveals emergent efficacy in glioma. Cancer Cell. May 2006;9(5):341-9.
Gaestel, et al. Protein kinases as small molecule inhibitor targets in inflammation. Curr Med Chem. 2007;14(21):2214-34.
Graupera, et al. Angiogenesis selectively requires the p110alpha isoform of PI3K to control endothelial cell migration. Nature. May 29, 2008;453(7195):662-6. doi: 10.1038/nature06892. Epub Apr. 30, 2008.
International search report and written opinion dated Jan. 22, 2013 for PCT Application No. PCT/US2012/064719.
Jacinto, et al. Mammalian TOR complex 2 controls the actin cytoskeleton and is rapamycin insensitive. Nat Cell Biol. Nov. 2004;6(11):1122-8. Epub Oct. 3, 2004.

(Continued)

*Primary Examiner* — Raymond Henley, III
(74) *Attorney, Agent, or Firm* — Honigman Miller Schwartz and Cohn LLP; Lucy X. Yang; Jonathan P. O'Brien

(57) ABSTRACT

The present invention provides for methods and pharmaceutical compositions comprising inhibitors of mTorC1 and/or mTorC2. In some aspects, the invention provides for treatment regimens resulting in enhanced treatment efficacy and better tolerability.

21 Claims, 8 Drawing Sheets

(56) References Cited

FOREIGN PATENT DOCUMENTS

| | | |
|---|---|---|
| WO | WO 94/17090 A1 | 8/1994 |
| WO | WO 96/02543 A1 | 2/1996 |
| WO | WO 96/02553 A2 | 2/1996 |
| WO | WO 98/18796 A1 | 5/1998 |
| WO | WO 98/28319 A1 | 7/1998 |
| WO | WO 99/16766 A1 | 4/1999 |
| WO | WO 99/24449 A2 | 5/1999 |
| WO | WO 99/24450 A2 | 5/1999 |
| WO | WO 99/24451 A2 | 5/1999 |
| WO | WO 99/38877 A2 | 8/1999 |
| WO | WO 99/41267 A1 | 8/1999 |
| WO | WO 99/67263 A1 | 12/1999 |
| WO | WO 99/67264 A1 | 12/1999 |
| WO | WO 99/67265 A1 | 12/1999 |
| WO | WO 99/67266 A1 | 12/1999 |
| WO | WO 00/00531 A1 | 1/2000 |
| WO | WO 00/23457 A1 | 4/2000 |
| WO | WO 00/66558 A1 | 11/2000 |
| WO | WO 00/66559 A1 | 11/2000 |
| WO | WO 00/75114 A1 | 12/2000 |
| WO | WO 00/77018 A2 | 12/2000 |
| WO | WO 00/78774 A2 | 12/2000 |
| WO | WO 01/04118 A2 | 1/2001 |
| WO | WO 01/13953 A2 | 3/2001 |
| WO | WO 01/23399 A1 | 4/2001 |
| WO | WO 01/24684 A2 | 4/2001 |
| WO | WO 01/27130 A1 | 4/2001 |
| WO | WO 01/27131 A1 | 4/2001 |
| WO | WO 01/60835 A1 | 8/2001 |
| WO | WO 01/94368 A1 | 12/2001 |
| WO | WO 02/00652 A1 | 1/2002 |
| WO | WO 02/00676 A1 | 1/2002 |
| WO | WO 02/00679 A2 | 1/2002 |
| WO | WO 02/10143 A1 | 2/2002 |
| WO | WO 02/12266 A1 | 2/2002 |
| WO | WO 02/22630 A1 | 3/2002 |
| WO | WO 02/42298 A1 | 5/2002 |
| WO | WO 02/051841 A1 | 7/2002 |
| WO | WO 02/053564 A2 | 7/2002 |
| WO | WO 02/088167 A1 | 11/2002 |
| WO | WO 02/096462 A1 | 12/2002 |
| WO | WO 02/100879 A1 | 12/2002 |
| WO | WO 03/000840 A2 | 1/2003 |
| WO | WO 03/033495 A1 | 4/2003 |
| WO | WO 03/035668 A2 | 5/2003 |
| WO | WO 03/039544 A1 | 5/2003 |
| WO | WO 03/048181 A1 | 6/2003 |
| WO | WO 03/053966 A1 | 7/2003 |
| WO | WO 03/062259 A1 | 7/2003 |
| WO | WO 03/064445 A1 | 8/2003 |
| WO | WO 03/072592 A1 | 9/2003 |
| WO | WO 03/082280 A1 | 10/2003 |
| WO | WO 03/082787 A1 | 10/2003 |
| WO | WO 03/086408 A1 | 10/2003 |
| WO | WO 03/087094 A2 | 10/2003 |
| WO | WO 03/099807 A1 | 12/2003 |
| WO | WO 03/104195 A1 | 12/2003 |
| WO | WO 03/104204 A1 | 12/2003 |
| WO | WO 03/104205 A1 | 12/2003 |
| WO | WO 2004/000814 A1 | 12/2003 |
| WO | WO 2004/000839 A1 | 12/2003 |
| WO | WO 2004/005229 A1 | 1/2004 |
| WO | WO 2004/005258 A1 | 1/2004 |
| WO | WO 2004/005285 A1 | 1/2004 |
| WO | WO 2004/016601 A1 | 2/2004 |
| WO | WO 2004/018422 A1 | 3/2004 |
| WO | WO 2004/018425 A1 | 3/2004 |
| WO | WO 2004/018450 A1 | 3/2004 |
| WO | WO 2004/018451 A1 | 3/2004 |
| WO | WO 2004/018457 A1 | 3/2004 |
| WO | WO 2004/019944 A1 | 3/2004 |
| WO | WO 2004/019945 A1 | 3/2004 |
| WO | WO 2004/026841 A1 | 4/2004 |
| WO | WO 2004/026873 A1 | 4/2004 |
| WO | WO 2004/033412 A1 | 4/2004 |
| WO | WO 2004/037805 A1 | 5/2004 |
| WO | WO 2004/039762 At | 5/2004 |
| WO | WO 2004/039766 A2 | 5/2004 |
| WO | WO 2004/045607 A1 | 6/2004 |
| WO | WO 2004/045618 A2 | 6/2004 |
| WO | WO 2004/046083 At | 6/2004 |
| WO | WO2010/049481 | 5/2010 |
| WO | WO 2011/053938 A1 | 5/2011 |

OTHER PUBLICATIONS

Knight, et al. A pharmacological map of the PI3-K family defines a role for p110alpha in insulin signaling. Cell. May 19, 2006;125(4):733-47. Epub Apr. 27, 2006.

Boulay et al. "Antitumor of Intermittent Treatment Schedules with the Rapamycin Derivative RAD001 Correlates with Prolonged Inacticvation of Ribosomal Protein S6 Kinase 1 in Peripheral Blood Mononuclear Cells." Cancer Res 2004; 64:252-261.

Han et al. "Aberrant Hyperactivition of Akt and Mammalian Target of Rapamycin Complex 1 Signaling in Sporadic Chordomas." Clin Cancer Res 2009; 15(6): 1940-1946.

STN CAS Registry FIle (1224844-38-5, entered May 21, 2010).

Mita et al. "The Role of mTOR Inhibitors for Treament of Sarcomas." Current Oncology Reports, 2007; 9(4):316-322.

* cited by examiner

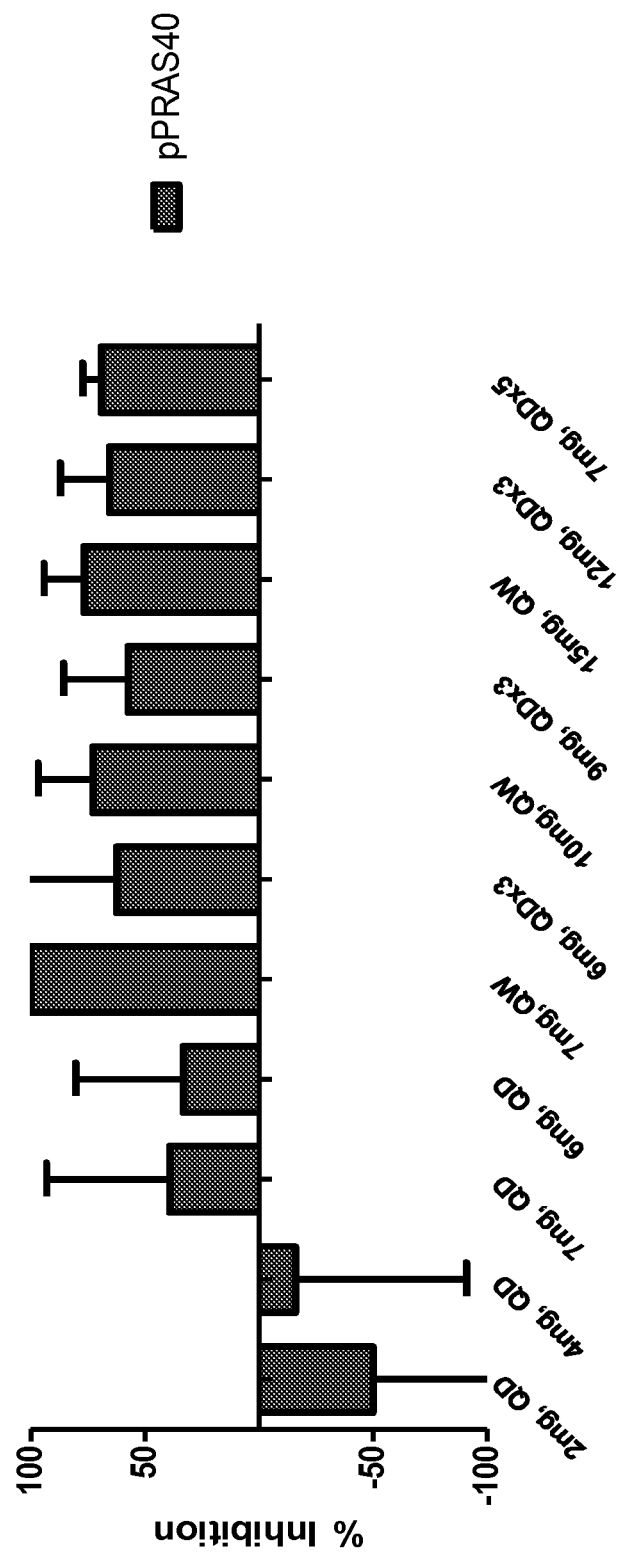

ENHANCED TREATMENT REGIMENS USING MTOR INHIBITORS

CROSS-REFERENCE TO RELATED APPLICATIONS

This application claims the benefit of priority of Provisional Application Nos. 61/563,516 entitled "ENHANCED TREATMENT REGIMENS USING MTOR INHIBITORS" and filed Nov. 23, 2011; which is fully incorporated by reference herein for all purposes.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, AT, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules, play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation (Katso et al., 2001). The class I PI3Ks (p110a, p110b, p110d, and p110 g) are typically activated by tyrosine kinases or G-protein coupled receptors to generate phosphatidylinositol-3,4,5-trisphosphate ($PIP_3$), which engages downstream effectors such as those in the Akt/PDK1 pathway, mTOR, the Tec family kinases, and the Rho family GTPases. The class II and III PI3-Ks play a key role in intracellular trafficking through the synthesis of PI(3)P and PI(3,4)P2. The PIKKs are protein kinases that control cell growth (mTORC1) or monitor genomic integrity (ATM, AT, DNA-PK, and hSmg-1).

The production of $PIP_3$ initiates potent growth and survival signals. In some epithelial cancers the PI3K pathway is activated by direct genetic mutation. As PI3K signaling pathway plays a pivotal role in cell proliferation and differentiation, inhibition of this pathway is believed to be beneficial in hyperproliferative diseases.

Downstream mediators of the PI3K signal transduction pathway include Akt and mammalian target of rapamycin (mTOR). Akt possesses a plckstrin homology (PH) domain that bind PIP3, leading to Akt kinase activation. Akt phosphorylates many substrates and is a central downstream effector of PI3K for diverse cellular responses. Full activation of Akt typically requires phosphorylation of T308 in the activation loop and S473 in a hydrophobic motif. One important function of Akt is to augment the activity of mTOR, through phosphorylation of TSC2 and other mechanisms.

mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

mTOR exists in two complexes, mTORC1 and mTORC2. mTORC1 contains the raptor subunit and mTORC2 contains rictor. These complexes are differentially regulated, and have distinct substrate specificities and rapamycin sensitivity. For example, mTORC1 phosphorylates S6 kinase (S6K) and 4EBP1, promoting increased translation and ribosome biogenesis to facilitate cell growth and cell cycle progression. S6K also acts in a feedback pathway to attenuate PI3K/Akt activation. mTORC2 is generally insensitive to rapamycin. mTORC2 is though to modulate growth factor signaling by phosphorylating the C-terminal hydrophobic motif of some AGC kinases such as Akt. In many cellular contexts, mTORC2 is required for phosphorylation of the S473 site of Akt.

Over the past decade, mTOR has drawn considerable attention due to its role in cell growth control and its involvement in human diseases. mTor has been implicated in a wide range of disorders including but not limited to cancer, diabetes, obesity, cardiovascular diseases and neurological disorders. It has been shown that mTOR modulates many fundamental biological processes including transcription, translation, autophagy, actin organization and ribosome biogenesis by integrating intracellular and extracellular signals, such as signals mediated by growth factors, nutrients, energy levels and cellular stress.

As such, kinases particularly protein kinases such as mTor and Akt, as well as lipid kinases such as PI3Ks are prime targets for drug development.

At the same time, tolerability and prevalence of side effects are important considerations in structuring courses of treatment for many diseases. For example, treatments which require the use of therapeutic agents which result in severe adverse events may become ineffective due to insufficient patient compliance or because an effective therapeutic dose cannot be administered to the patient. Similarly, treatments which result in a higher effective concentration of the drug being present in the blood stream for a longer period of time may provide better therapeutic efficacy. The present invention addresses this need in the art by providing methods and compositions for mTor inhibition and treatment regimens utilizing such methods and compositions.

SUMMARY OF THE INVENTION

The invention provides a method of treating a disorder in a subject in need thereof, comprising administering an mTorC1/mTorC2 inhibitor to said subject according to an intermittent regimen effective to achieve an mTorC1/mTorC2 inhibitor plasma concentration at or above about 100 nM for a duration of time that is longer than that achieved by administering an equivalent dose of the mTorC1/mTorC2 inhibitor once daily. In some embodiments, the intermittent regimen is effective to achieve an mTorC1/mTorC2 inhibitor plasma concentration of greater than about 100 nM for a duration longer than about 20 hours during a 7-day period of administration. In other embodiments, the intermittent regimen is effective to achieve an mTorC1/mTorC2 inhibitor plasma concentration of greater than about 100 nM for a duration of at least about 30 hours during a 7-day period of administration.

The invention further provides a method of treating a disorder in a subject in need thereof, comprising administering an mTorC1/mTorC2 inhibitor to said subject according to an intermittent regimen, such that the achieved Cmax is greater than that achieved by administering an equivalent dose of the mTorC1/mTorC2 inhibitor once daily. For example, the intermittent regimen is effective to achieve a Cmax which is greater by about 10%, 20%, 30%, 40%, 50%, 100%, 200%, or 300% than the Cmax achieved by administering an equivalent dose of the mTorC1/mTorC2 inhibitor once daily. In some embodiments, the intermittent regimen is effective to achieve a Cmax of greater than about 200, 250, 300, 350, 400, 450, 500, 550 or 600 nM. For example, the intermittent regimen is effective to achieve a Cmax of greater than about 300 nM.

The intermittent regimens of the invention may achieve similar or better pathway inhibition than administering an equivalent dose of the mTorC1/mTorC2 once daily. In some embodiments, the pathway inhibition is measured as percentage of decrease in phosphorylation of a protein chosen from p4EBP1, pS6, and pRAS40.

The intermittent regimens of the invention may also achieve similar or better therapeutic efficacy than administering an equivalent dose of the mTorC1/mTorC2 once daily. Further, the intermittent regimens of the invention may achieve at least the same level of tolerability as compared to administering an equivalent dose of the mTorC1/mTorC2 inhibitor once daily. In some embodiments, the level of tolerability is measured as the occurrence or lack of occurrence in the subject of a grade 3 or higher adverse event. For example, the adverse event is rash.

In some embodiments, an intermittent regimen of the invention comprises at least one cycle in which the mTorC1/mTorC2 inhibitor is administered for at least 1 day, followed by an intermission in which the mTorC1/mTorC2 inhibitor is not administered for at least 1 day. For instance, the mTorC1/mTorC2 inhibitor is administered for 2, 3, 4, 5, 6 or 7 consecutive days followed by an intermission in which the mTorC1/mTorC2 inhibitor is not administered for at least 1 day. Alternatively, the regimen comprises at least one cycle in which the mTorC1/mTorC2 inhibitor is administered for 1 day followed by an intermission in which the mTorC1/mTorC2 inhibitor is not administered for 6 consecutive days. Alternatively, the regimen comprises at least one cycle in which the mTorC1/mTorC2 inhibitor is administered for 2, 3, 4, 5, 6 or 7 consecutive days followed by an intermission in which the mTorC1/mTorC2 inhibitor is not administered for at least 3, 4, or 5 consecutive days. In some embodiments, the regimen comprises at least one 7-day cycle in which the mTorC1/mTorC2 inhibitor is administered for 3 consecutive days followed by an intermission of 4 consecutive days. In other embodiments, the regimen comprises at least one 7-day cycle in which the mTorC1/mTorC2 inhibitor is administered for 5 consecutive days followed by an intermission of 2 consecutive days. In still other embodiments, the regimen comprises at least one 7-day cycle in which the mTorC1/mTorC2 inhibitor is administered at least 3 times on alternate days within the 7 days.

Also provided herein is a dosage form for administration to a subject comprising an mTorC1/mTorC2 inhibitor, wherein the dosage form is formulated to provide a Cmax of greater than about 200 nM when administered to the subject. In some embodiments, the dosage form is capable of providing a plasma concentration of said mTorC1/mTorC2 inhibitor of greater than about 100 nM for a duration of time longer than about 20 hours during a 7-day period of administration. For example, the dosage form is capable of providing a plasma concentration of greater than 100 nM for a duration of time that is at least about 30 hours during a 7-day period of administration. In some embodiments, the dosage form comprises about 45, 50, 55, 60, 70, 75 mg or less of the mTorC1/mTorC2 inhibitor.

The invention also provides a method of treating a disorder in a subject in need thereof, comprising administering a dosage form of the invention.

Further provided herein is a kit comprising a dosage form as described and additionally comprising instructions for administration to a subject in need thereof. For example, the instructions provide for at least one 7-day cycle of administration to the subject for 2, 3, 4, or 5 consecutive days followed by an intermission of 5, 4, 3, or 2 days, respectively. In some embodiments, the instructions provide for administration of the mTorC1/mTorC2 inhibitor to the subject for 3 consecutive days followed by an intermission of 4 consecutive days.

The invention further provides a pharmaceutical regimen for the treatment of a disorder, the regimen comprising an mTorC1/mTorC2 inhibitor, wherein the regimen provides an area under the curve that is similar to that obtained by administering the mTorC1/mTorC2 inhibitor once daily, and wherein the regimen results in higher therapeutic efficacy as compared to administering said inhibitor once daily.

For any method of treatment provided by the invention, the disorders to be treated include, but are not limited to, a neoplastic condition, autoimmune disease, inflammatory disease, fibrotic disease or kidney disease. For example, the disorder is a neoplastic condition such as cancer.

Also provided is a method of treating a disorder in a subject in need thereof, comprising administering an mTorC1/mTorC2 inhibitor to said subject according to an intermittent regimen effective to achieve (a) higher therapeutic efficacy, (b) similar or better tolerability of the mTorC1/mTorC2 inhibitor, and (c) similar or smaller area under the curve, as compared to administering an equivalent dose of the mTorC1/mTorC2 inhibitor once daily.

In any method, dosage form, or pharmaceutical regimen of the invention, the mTorC1/mTorC2 inhibitor may be administered parenterally, orally, intraperitoneally, intravenously, intraarterially, transdermally, intramuscularly, liposomally, via local delivery by catheter or stent, subcutaneously, intraadiposally, or intrathecally. In some embodiments, the mTorC1/mTorC2 inhibitor is administered orally.

In some embodiments of the invention, the mTorC1/mTorC2 inhibitor inhibits both mTORC1 and mTORC2 with an IC50 value of about 100 nM or less as ascertained in an in vitro kinase assay. For example, the mTorC1/mTorC2 inhibitor inhibits both mTORC1 and mTORC2 with an IC50 value of about 10 nM or less as ascertained in an in vitro kinase assay. In some embodiments, the mTorC1/mTorC2 inhibitor inhibits both mTORC1 and mTORC2 with an IC50 value of about 10 nM or less as ascertained in an in vitro kinase assay, and that the mTorC1/mTorC2 inhibitor is substantially inactive against one or more types I PI3-kinases selected from the group consisting of PI3-kinase α, PI3-kinase β, PI3-kinase γ, and PI3-kinase δ. In other embodiments, the mTorC1/mTorC2 inhibitor inhibits both mTORC1 and mTORC2 with an IC50 value of about 100 nM or less as ascertained in an in vitro kinase assay, and said IC50 value is at least 5 times less than its IC50 value against all other type I PI3-kinases selected from the group consisting of PI3-kinase α, PI3-kinase β, PI3-kinase γ, and PI3-kinase δ.

In some embodiments of the invention, the mTorC1/mTorC2 inhibitor is a compound of Formula I:

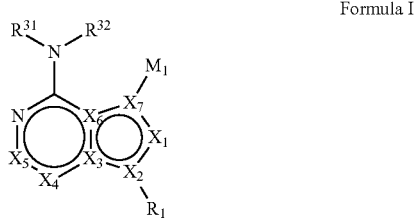

Formula I or a pharmaceutically acceptable salt thereof, wherein:
$X_1$ is N or C-$E^1$, $X_2$ is N or C, $X_3$ is N or C, $X_4$ is C—$R^9$ or N, $X_5$ is N or C-$E^1$, $X_6$ is C or $N_1$ and $X_7$ is C or N; and wherein no more than two nitrogen ring atoms are adjacent;
$R_1$ is H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;
L is absent, —(C═O)—, —C(═O)O—, —C(═O)N($R^{31}$)—, —S—, —S(O)—, —S(O)$_2$—, —S(O)$_2$N($R^{31}$)—, or —N($R^{31}$)—;
$E^1$ and $E^2$ are independently —($W^1$)$_j$—$R^4$;
$M_1$ is a 5, 6, 7, 8, 9, or -10 membered ring system, wherein the ring system is monocyclic or bicyclic, substituted with $R_5$ and additionally optionally substituted with one or more —($W^2$)$_k$—$R^2$;
each k is 0 or 1;
j in $E^1$ or j in $E^2$, is independently 0 or 1;
$W^1$ is —O—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;
$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S (O)—, —N($R^7$)S(O)$_2$—, —C(O)O—, —CH($R^7$)N(C(O) O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N ($R^8$)C(O)—, —CH($R^7$)N($R^8$)S(O)—, or —CH($R^7$)N($R^8$)S (O)$_2$—;
$R^2$ is hydrogen, halogen, —OH, —$R^{31}$, —CF$_3$, —OCF$_3$, —O$R^{31}$, —N$R^{31}R^{32}$, —N$R^{34}R^{35}$, (O)$R^{31}$, —CO$_2R^{31}$, —C(═O)N$R^{31}R^{32}$, —C(═O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C (═O)$R^{32}$, —N$R^{31}$C(═O)O$R^{32}$, —N$R^{31}$C(═O)N$R^{32}R^{33}$, —N$R^{31}$S(O)$_{0-2}R^{32}$, —C(═S)O$R^{31}$, —C(═O)S$R^{31}$, —N$R^{31}$C(═N$R^{32}$)N$R^{33}R^{32}$, —N$R^{31}$C(═N$R^{32}$)O$R^{33}$, —N$R^{31}$C(═N$R^{32}$)S$R^{33}$, —OC(═O)O$R^{33}$, —OC(═O) N$R^{31}R^{32}$, —OC(═O)S$R^{31}$, —SC(═O)O$R^{31}$, —P(O) O$R^{31}$O$R^{32}$, —SC(═O)N$R^{31}R^{32}$, aryl (e.g. bicyclic aryl, unsubstituted aryl, or substituted monocyclic aryl), hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyicyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —N$R^{34}R^{35}$, (O)$R^{31}$, —CO$_2R^{31}$, —C(═O) N$R^{31}R^{32}$, —C(═O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(═O)$R^{32}$, —N$R^{31}$C(═O)O$R^{32}$, —N$R^{31}$C(═O)N$R^{32}R^{33}$, —N$R^{31}$S (O)$_{0-2}R^{32}$, —C(═S)O$R^{31}$, —C(═O)S$R^{31}$, —N$R^{31}$C (═N$R^{32}$)N$R^{33}R^{32}$, —N$R^{31}$C(═N$R^{32}$)O$R^{33}$, —N$R^{31}$C (═N$R^{32}$)S$R^{33}$, —OC(═O)O$R^{33}$, —OC(═O)N$R^{31}R^{32}$, —OC(═O)S$R^{31}$, —SC(═O)O$R^{31}$, —P(O)O$R^{31}$O$R^{32}$, or —SC(═O)N$R^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(═O)N$R^{34}R^{35}$, or —C(═O)N$R^{31}R^{32}$;
$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(═O)N$R^{31}R^{32}$, —C(═O) N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(═O)$R^{32}$, —N$R^{31}$C(═O)O$R^{32}$, —N$R^{31}$C(═O)N$R^{32}R^{33}$, —N$R^{31}$S(O)$_{0-2}R^{32}$, —C(═S) O$R^{31}$, —OC(═O)S$R^{31}$, —N$R^{31}$C(═N$R^{32}$)N$R^{33}R^{32}$, —N$R^{31}$C(═N$R^{32}$)O$R^{33}$, —N$R^{31}$C(═N$R^{32}$)S$R^{33}$, —OC (═O)O$R^{33}$, —OC(═O)N$R^{31}R^{32}$, —OC(═O)S$R^{31}$, —SC (O=O)OR$^{31}$, P(O)OR$^{31}$OR$^{32}$, —SC(=O)NR$^{31}$R$^{32}$, aryl, hetaryl, C$_{1-4}$alkyl, C$_{1-10}$alkyl, C$_{3-8}$Cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl, C$_{1-10}$alkylhetaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylhetaryl, C$_{2-10}$alkenylheteroalkyl, C$_{2-10}$alkenylheterocycicyl, C$_{2-10}$alkenyl-C$_{3-8}$cycloalkyl, C$_{2-10}$alkynyl-C$_{3-8}$cycloalkyl, C$_{2-10}$alkynylaryl, C$_{2-10}$alkynylhetaryl, C$_{2-10}$alkynylheteroalkyl, C$_{2-10}$alkynylheterocyclyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heterocyclyl-C$_{1-10}$alkyl, heterocyclyl-C$_{2-10}$alkenyl, heterocyclyl-C$_{2-10}$alkynyl, aryl-C$_{1-10}$alkyl, aryl-C$_{2-10}$alkenyl, aryl-C$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^5$ is hydrogen, halogen, —OH, —R$^{31}$, —CF$_3$, —OCF$_3$, —OR$^{31}$, —NR$^{31}$R$^{32}$, —NR$^{34}$R$^{35}$, (O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O) OR$^{31}$OR$^{32}$, or —SC(=O)NR$^{31}$R$^{32}$;

each of R$^{31}$, R$^{32}$, and R$^{33}$ is independently H or C$_{1-10}$alkyl, wherein the C$_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_1$-10alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$ C$_{1-10}$alkylaryl, —S(O)$_{0-2}$ aryl, —SO$_2$N(aryl), —SO$_2$ N(C$_{1-10}$alkyl)(C$_{1-10}$alkyl), —SO$_2$NH(C$_{1-10}$alkyl) or —SO$_2$NR$^{34}$R$^{35}$;

R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen atom;

each of R$^7$ and R$^8$ is independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$;

R$^6$ is halo, —OR$^{31}$, —SH, —NH$_2$, —NR$^{34}$R$^{35}$, —NR$^{31}$R$^{32}$, —CO$_2$R$^{31}$, —CO$_2$aryl, —C(=O)NR$^{31}$R$^{32}$, C(=O)NR$^{34}$R$^{35}$, —NO$_2$, —CN, —S(O)$_{0-2}$ C$_{1-10}$alkyl, —S(O)$_{0-2}$ aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl; aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, hetaryl-C$_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, halo C$_{2-10}$alkenyl, halo C$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$; and R$^9$ is H, halo, —OR$^{31}$, —SH, —NH$_2$, —NR$^{34}$R$^{35}$, —NR$^{31}$R$^{32}$, —CO$_2$R$^{31}$, —CO$_2$aryl, —C(=O)NR$^{31}$R$^{32}$, C(=O)NR$^{34}$R$^{35}$, —NO$_2$, —CN, —S(O)$_{0-2}$ C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl; aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, hetaryl-C$_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, halo C$_{2-10}$alkenyl, halo C$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$.

In some embodiments, the mTorC1/mTorC2 inhibitor has the Formula:

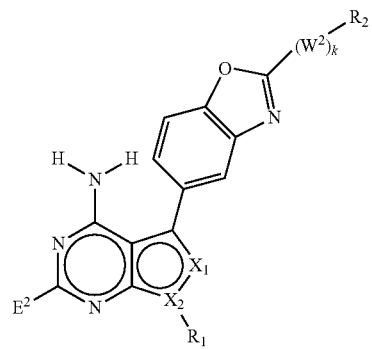

or a pharmaceutically acceptable salt thereof, wherein: E$^2$ is —H; X$_1$ is N; X$_2$ is N; W$^2$ is —NH; and k is 1.

In some embodiments, R$_2$ is H. In other embodiments, R$_1$ is isopropyl. In other embodiments, R$_1$ is

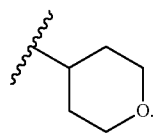 [SMILES: *C1CCOCC1]

In yet other embodiments, $R_1$ is

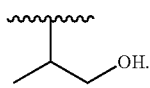

In still other embodiments, $R_1$ is

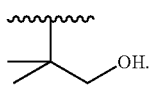 [SMILES: *C(C)(C)CO]

In some embodiments of the compound of Formula I, $E^2$ is —H; $X_1$ is CH; $X_2$ is N; $W^2$ is —NH; $R_2$ is H; k is 1; and $R_1$ is isopropyl or

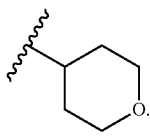 [SMILES: *C1CCOCC1]

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 shows mTor C pathway inhibition (pPRAS40) in skin biopsies by an intermittent dosing regimen using compound A.

DETAILED DESCRIPTION OF THE INVENTION

Figure 1:
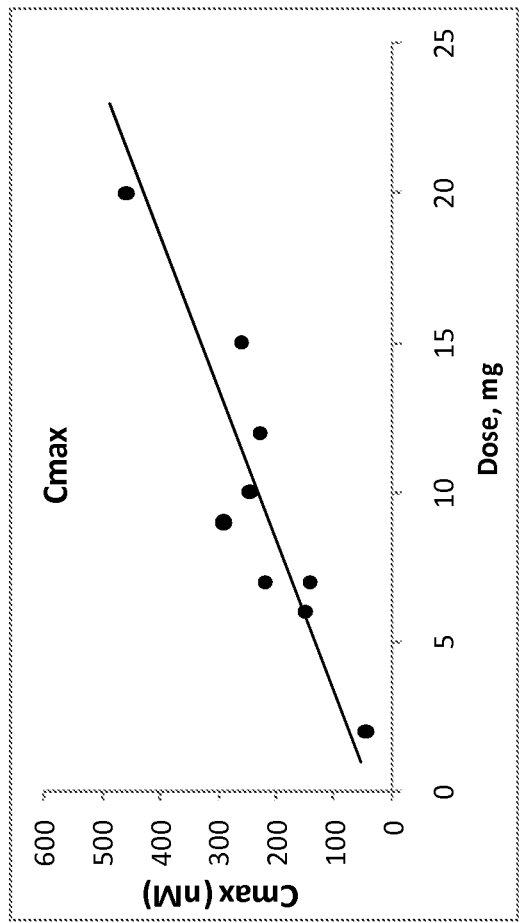
FIG. 1 shows the Cmax observed upon administration of compound A at various dose levels.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. Unless stated otherwise, the present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Treatment", "treating", "palliating" and "ameliorating", as used herein, are used interchangeably. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

As used herein, the term "neoplastic condition" refers to the presence of cells possessing abnormal growth characteristics, such as uncontrolled proliferation, immortality, metastatic potential, rapid growth and proliferation rate, perturbed oncogenic signaling, and certain characteristic morphological features. This includes but is not limited to the growth of: (1) benign or malignant cells (e.g., tumor cells) that correlates with overexpression of a tyrosine or serine/threonine kinase; (2) benign or malignant cells (e.g., tumor cells) that correlates with abnormally high level of tyrosine or serine/threonine kinase activity. Exemplary tyrosine kinases implicated in a neoplastic condition include but are not limited to receptor tyrosine kinases such as epidermal growth factor receptors (EGF receptor), platelet derived growth factor (PDGF) receptors, and cyotsolic tyrosine kinases such as src and abl kinase.

Non-limiting serine/threonine kinases implicated in neoplastic condition include but are not limited to raf and mek.

The term "effective amount" or "therapeutically effective amount" refers to that amount of an inhibitor described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

A "synergistically effective" therapeutic amount or "synergistically effective" amount of an agent or therapy is an amount which, when combined with an effective or sub-therapeutic amount of another agent or therapy, produces a greater effect than when either of the two agents are used alone. In some embodiments, a syngergistically effective therapeutic amount of an agent or therapy produces a greater effect when used in combination than the additive effects of each of the two agents or therapies when used alone. The term "greater effect" encompasses not only a reduction in symptoms of the disorder to be treated, but also an improved side effect profile, improved tolerability, improved patient compliance, improved efficacy, or any other improved clinical outcome.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

The phrases "mTorC1/C2 inhibitor", "mTorC1/mTorC2 inhibitor", or "mTOR inhibitor that binds to and directly inhibits both mTORC1 and mTORC2 kinases" are used interchangeably and refer to an mTOR inhibitor that interacts with and reduces the kinase activity of both mTORC1 and mTORC2 complexes.

An "anti-neoplastic", "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

As used herein, the term "antiangiogenic" refers to the ability to inhibit or impair the formation of blood vessels, including but not limited to inhibiting endothelial cell proliferation, endothelial cell migration, and capillary tube formation.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, encompass administration of two or more agents to an animal so that both agents and/or their metabolites are present in the animal at the same time. Co-administration includes simultaneous administration in separate compositions, administration at different times in separate compositions, or administration in a composition in which both agents are present. Co-administered agents may be in the same formulation. Co-administered agents may also be in different formulations.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Signal transduction" is a process during which stimulatory or inhibitory signals are transmitted into and within a cell to elicit an intracellular response. A modulator of a signal transduction pathway refers to a compound that modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target.

"Subject" refers to an animal, such as a mammal, for example a human. The methods described herein can be useful in both human therapeutics, pre-clinical, and veterinary applications. In some embodiments, the subject is a mammal, and in some embodiments, the subject is human.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, the connections of compound name moieties are at the rightmost recited moiety. That is, the substituent name starts with a terminal moiety, continues with any linking moieties, and ends with the linking moiety. For example, heteroarylthio $C_{1-4}$ alkyl has a heteroaryl group connected through a thio sulfur to a $C_{1-4}$ alkyl radical that connects to the chemical species bearing the substituent. This condition does not apply where a formula such as, for example "-L-$C_{1-10}$ alkyl-$C_{3-8}$cycloalkyl" is represented. In such case, the terminal group is a $C_{3-8}$cycloalkyl group attached to a linking $C_{1-10}$ alkyl moiety which is attached to an element L, which is itself connected to the chemical species bearing the substituent.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl(iso-propyl), n-butyl, n-pentyl, 1,1-dimethylethyl(t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S($O$)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "halo" or "halogen" refers to fluoro, chloro, bromo, or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, and the like.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., $C_2$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a)_2$, —C(O)N($R^a)_2$, —N($R^a$)C(O)O$R^a$, —N($R^a$)C(O)$R^a$, —N($R^a$)C(O)N($R^a)_2$, N($R^a$)C(N$R^a$)N($R^a)_2$, —N($R^a$)S(O)$_t$$R^a$ (where t is 1 or 2), —S(O)$_t$O$R^a$ (where t is 1 or 2), —S(O)$_t$N($R^a)_2$ (where t is 1 or 2), or PO$_3$($R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "$C_{1-10}$alkyl-$C_{3-8}$cycloalkyl" is used to describe an alkyl group, branched or straight chain and containing 1 to 10 carbon atoms, attached to a linking cycloalkyl group which contains 3 to 8 carbons, such as for example, 2-methyl cyclopropyl, and the like. Either portion of the moiety is unsubstituted or substituted.

The term "bicycloalkyl" refers to a structure consisting of two cycloalkyl moieties, unsubstituted or substituted, that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[3.2.1]heptyl ("norbornyl"), bicyclo[2.2.2]octyl, and the like.

As used herein, the term "heteroatom" or "ring heteroatom" is meant to include oxygen (O), nitrogen (N), sulfur (S), phosphorus (P), and silicon (Si).

"Heteroalkyl", "heteroalkenyl" and "heteralkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g., $C_1$-$C_4$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the rest of the molecule may be through either a heteroatom or a carbon in the heteroalkyl chain. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —N($R^a$)C(O)$R^a$, —N($R^a$)S(O)$_t$$R^a$ (where t is 1 or 2), —S(O)$_t$O$R^a$ (where t is 1 or 2), —S(O)$_t$N($R^a)_2$ (where t is 1 or 2), or PO$_3$($R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "heteroalkylaryl" refers to a heteroalkyl group as defined above which is attached to an aryl group, and may be attached at a terminal point or through a branched portion of the heteroalkyl, for example, an benzyloxymethyl moiety. Either portion of the moiety is unsubstituted or substituted.

The term "heteroalkylheteroaryl" refers likewise to a heteroalkyl group which is attached to a heteroaryl moiety, for example, an ethoxymethylpyridyl group. Either portion of the moiety is unsubstituted or substituted.

The term "heteroalkyl-heterocyclyl" refers to a heteroalkyl group as defined above, which is attached to a heterocyclic group, for example, 4(3-aminopropyl)-N-piperazinyl. Either portion of the moiety is unsubstituted or substituted.

The term "heteroalkyl-$C_{3-8}$cycloalkyl" refers to a heteroalkyl group as defined above, which is attached to a cyclic alkyl containing 3 to 8 carbons, for example, 1-aminobutyl-4-cyclohexyl. Either portion of the moiety is unsubstituted or substituted.

The term "heterobicycloalkyl" refers to a bicycloalkyl structure, which is unsubstituted or substituted, in which at least one carbon atom is replaced with a heteroatom independently selected from oxygen, nitrogen, and sulfur.

The term "heterospiroalkyl" refers to a spiroalkyl structure, which is unsubstituted or substituted, in which at least one carbon atom is replaced with a heteroatom independently selected from oxygen, nitrogen, and sulfur.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a)_2$, —C(O)N($R^a)_2$, —N($R^a$)C(O)O$R^a$, —N($R^a$)C(O)$R^a$, —N($R^a$)C(O)N($R^a)_2$, N($R^a$)C(N$R^a$)N($R^a)_2$, —N($R^a$)S(O)$_t$$R^a$ (where t is 1 or 2), —S(O)$_t$O$R^a$ (where t is 1 or 2), —S(O)$_t$N($R^a)_2$ (where t is 1 or 2), or PO$_3$($R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "$C_{2-10}$ alkenyl-heteroalkyl" refers to a group having an alkenyl moiety, containing 2 to 10 carbon atoms and is branched or straight chain, which is attached to a linking heteroalkyl group, such as, for example, allyloxy, and the like. Either portion of the moiety is unsubstituted or substituted.

The term "$C_{2-10}$ alkynyl-heteroalkyl" refers to a group having an alkynyl moiety, which is unsubstituted or substituted, containing 2 to 10 carbon atoms and is branched or straight chain, which is attached to a linking heteroalkyl group, such as, for example, 4-but-1-ynoxy, and the like. Either portion of the moiety is unsubstituted or substituted.

The term "haloalkenyl" refers to an alkenyl group substituted with one or more halo groups.

Unless otherwise specified, the term "cycloalkenyl" refers to a cyclic aliphatic 3 to 8 membered ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

"Alkynyl" refers to a straight or branched hydrocarbon chain radical group consisting solely of carbon and hydrogen atoms, containing at least one triple bond, having from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term $C_{2-10}$ alkynyl-$C_{3-8}$ cycloalkyl refers to a group containing an alkynyl group, containing 2 to 10 carbons and branched or straight chain, which is attached to a linking cycloalkyl group containing 3 to 8 carbons, such as, for example 3-prop-3-ynyl-cyclopent-lyl, and the like. Either portion of the moiety is unsubstituted or substituted.

The term "haloalkynyl" refers to an alkynyl group substituted with one or more independent halo groups.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ other than hydrogen they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties may be optionally substituted as defined herein.

"Amide" or "amido" refers to a chemical moiety with formula —C(O)N(R)$_2$ or NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a $C_1$-$C_4$ amido or amide radical, which includes the amide carbonyl in the total number of carbons in the radical. The R$^{2'}$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroaryl" or, alternatively, "heteroaromatic" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms"

means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteraryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The terms "aryl-alkyl", "arylalkyl" and "aralkyl" are used to describe a group wherein the alkyl chain can be branched or straight chain forming a linking portion with the terminal aryl, as defined above, of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxphenyl)butyl, and 10-phenyldecyl. Either portion of the moiety is unsubstituted or substituted.

The term "C$_{1-10}$alkylaryl" as used herein refers to an alkyl group, as defined above, containing 1 to 10 carbon atoms, branched or unbranched, wherein the aryl group replaces one hydrogen on the alkyl group, for example, 3-phenylpropyl. Either portion of the moiety is unsubstituted or substituted.

The term C$_{2-10}$ alkyl monocycloaryl" refers to a group containing a terminal alkyl group, branched or straight chain and containing 2 to 10 atoms attached to a linking aryl group which has only one ring, such as for example, 2-phenyl ethyl. Either portion of the moiety is unsubstituted or substituted.

The term "C$_{1-10}$ alkyl bicycloaryl" refers to a group containing a terminal alkyl group, branched or straight chain and containing 2 to 10 atoms attached to a linking aryl group which is bicyclic, such as for example, 2-(1-naphthyl)-ethyl. Either portion of the moiety is unsubstituted or substituted.

The terms "aryl-cycloalkyl" and "arylcycloalkyl" are used to describe a group wherein the terminal aryl group is attached to a cycloalkyl group, for example phenylcyclopentyl and the like. Either portion of the moiety is unsubstituted or substituted.

The terms "heteroaryl-C$_{3-8}$cycloalkyl" and "heteroaryl-C$_{3-8}$cycloalkyl" are used to describe a group wherein the terminal heteroaryl group is attached to a cycloalkyl group, which contains 3 to 8 carbons, for example pyrid-2-yl-cyclopentyl and the like. Either portion of the moiety is unsubstituted or substituted.

The term "heteroaryl-heteroalkyl" refers to a group wherein the terminal heteroaryl group is attached to a linking heteroalkyl group, such as for example, pyrid-2-yl methylenoxy, and the like. Either portion of the moiety is unsubstituted or substituted.

The terms "aryl-alkenyl", "arylalkenyl" and "aralkenyl" are used to describe a group wherein the alkenyl chain can be branched or straight chain forming a linking portion of the aralkenyl moiety with the terminal aryl portion, as defined above, for example styryl(2-phenylvinyl), phenpropenyl, and the like. Either portion of the moiety is unsubstituted or substituted.

The term "aryl-C$_{2-10}$alkenyl" means an arylalkenyl as described above wherein the alkenyl moiety contains 2 to 10 carbon atoms such as for example, styryl(2-phenylvinyl), and the like. Either portion of the moiety is unsubstituted or substituted.

The term "C$_{2-10}$alkenyl-aryl" is used to describe a group wherein the terminal alkenyl group, which contains 2 to 10 carbon atoms and can be branched or straight chain, is attached to the aryl moiety which forms the linking portion of the alkenyl-aryl moiety, such as for example, 3-propenyl-naphth-1-yl, and the like. Either portion of the moiety is unsubstituted or substituted.

The terms "aryl-alkynyl", "arylalkynyl" and "aralkynyl" are used to describe a group wherein the alkynyl chain can be branched or straight chain forming a linking portion of the aryl-alkynyl moiety with the terminal aryl portion, as defined above, for example 3-phenyl-1-propynyl, and the like. Either portion of the moiety is unsubstituted or substituted.

The term "aryl-$C_{2-10}$alkynyl" means an arylalkynyl as described above wherein the alkynyl moiety contains two to ten carbons, such as, for example 3-phenyl-1-propenyl, and the like. Either portion of the moiety is unsubstituted or substituted.

The term "$C_{2-10}$alkynyl-aryl" means a group containing an alkynyl moiety attached to an aryl linking group, both as defined above, wherein the alkynyl moiety contains two to ten carbons, such as, for example 3-propynyl-naphth-1-yl. Either portion of the moiety is unsubstituted or substituted.

The terms "aryl-oxy", "aryloxy" and "aroxy" are used to describe a terminal aryl group attached to a linking oxygen atom. Typical aryl-oxy groups include phenoxy, 3,4-dichlorophenoxy, and the like. Either portion of the moiety is unsubstituted or substituted.

The terms "aryl-oxyalkyl", "aryloxyalkyl" and "aroxyalkyl" are used to describe a group wherein an alkyl group is substituted with a terminal aryl-oxy group, for example pentafluorophenoxymethyl and the like. Either portion of the moiety is unsubstituted or substituted.

The term "$C_{1-10}$alkoxy-$C_{1-10}$alkyl" refers to a group wherein an alkoxy group, containing 1 to 10 carbon atoms and an oxygen atom within the branching or straight chain, is attached to a linking alkyl group, branched or straight chain which contains 1 to 10 carbon atoms, such as, for example methoxypropyl, and the like. Either portion of the moiety is unsubstituted or substituted.

The term "$C_{1-10}$alkoxy-$C_{2-10}$alkenyl" refers to a group wherein an alkoxy group, containing 1 to 10 carbon atoms and an oxygen atom within the branching or straight chain, is attached to a linking alkenyl group, branched or straight chain which contains 1 to 10 carbon atoms, such as, for example 3-methoxybut-2-en-1-yl, and the like. Either portion of the moiety is unsubstituted or substituted.

The term "$C_{1-10}$alkoxy-$C_{2-10}$alkynyl" refers to a group wherein an alkoxy group, containing 1 to 10 carbon atoms and an oxygen atom within the branching or straight chain, is attached to a linking alkynyl group, branched or straight chain which contains 1 to 10 carbon atoms, such as, for example 3-methoxybut-2-in-1-yl, and the like. Either portion of the moiety is unsubstituted or substituted.

The term "heterocycloalkenyl" refers to a cycloalkenyl structure, which is unsubstituted or substituted in which at least one carbon atom is replaced with a heteroatom selected from oxygen, nitrogen, and sulfur.

The terms "heteroaryl-oxy", "heteroaryl-oxy", "heteroaryloxy", "heteroaryloxy", "hetaroxy" and "heteroaroxy" are used to describe a terminal heteroaryl group, which is unsubstituted or substituted, attached to a linking oxygen atom. Typical heteroaryl-oxy groups include 4,6-dimethoxypyrimidin-2-yloxy and the like.

The terms "heteroarylalkyl", "heteroarylalkyl", "heteroaryl-alkyl", "heteroaryl-alkyl", "hetaralkyl" and "heteroaralkyl" are used to describe a group wherein the alkyl chain can be branched or straight chain forming a linking portion of the heteroaralkyl moiety with the terminal heteroaryl portion, as defined above, for example 3-furylmethyl, thenyl, furfuryl, and the like. Either portion of the moiety is unsubstituted or substituted.

The term "heteroaryl-$C_{1-10}$alkyl" is used to describe a heteroaryl alkyl group as described above where the alkyl group contains 1 to 10 carbon atoms. Either portion of the moiety is unsubstituted or substituted.

The term "$C_{1-10}$alkyl-heteroaryl" is used to describe a alkyl attached to a hetary group as described above where the alkyl group contains 1 to 10 carbon atoms. Either portion of the moiety is unsubstituted or substituted.

The terms "heteroarylalkenyl", "heteroarylalkenyl", "heteroaryl-alkenyl", "heteroaryl-alkenyl", "hetaralkenyl" and "heteroaralkenyl" are used to describe a heteroarylalkenyl group wherein the alkenyl chain can be branched or straight chain forming a linking portion of the heteroaralkenyl moiety with the terminal heteroaryl portion, as defined above, for example 3-(4-pyridyl)-1-propenyl. Either portion of the moiety is unsubstituted or substituted.

The term "heteroaryl-$C_{2-10}$alkenyl" group is used to describe a group as described above wherein the alkenyl group contains 2 to 10 carbon atoms. Either portion of the moiety is unsubstituted or substituted.

The term "$C_{2-10}$alkenyl-heteroaryl" is used to describe a group containing an alkenyl group, which is branched or straight chain and contains 2 to 10 carbon atoms, and is attached to a linking heteroaryl group, such as, for example 2-styryl-4-pyridyl, and the like. Either portion of the moiety is unsubstituted or substituted.

The terms "heteroarylalkynyl", "heteroarylalkynyl", "heteroaryl-alkynyl", "heteroaryl-alkynyl", "hetaralkynyl" and "heteroaralkynyl" are used to describe a group wherein the alkynyl chain can be branched or straight chain forming a linking portion of the heteroaralkynyl moiety with the heteroaryl portion, as defined above, for example 4-(2-thienyl)-1-butynyl, and the like. Either portion of the moiety is unsubstituted or substituted.

The term "heteroaryl-$C_{2-10}$alkynyl" is used to describe a heteroarylalkynyl group as described above wherein the alkynyl group contains 2 to 10 carbon atoms. Either portion of the moiety is unsubstituted or substituted.

The term "$C_{2-10}$alkynyl-heteroaryl" is used to describe a group containing an alkynyl group which contains 2 to 10 carbon atoms and is branched or straight chain, which is attached to a linking heteroaryl group such as, for example, 4(but-1-ynyl) thien-2-yl, and the like. Either portion of the moiety is unsubstituted or substituted.

The term "heterocyclyl" refers to a four-, five-, six-, or seven-membered ring containing one, two, three or four heteroaroms independently selected from nitrogen, oxygen and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to se-membered aromatic or nonaromatic carbocyclic ring. The heterocyclyl group can be attached to the parent molecular moiety through any carbon atom or nitrogen atom in the group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated.

The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocloalkyl, aryl, arylalkyl, heteroaryl, heteroarylalkyl, hydroxy, halo, cyano, nitro, oxo, thioxo, trimethylsilanyl, —$OR^a$, $SR^a$, —$OC(O)$—$R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_t R^a$ (where t is 1 or 2), —$S(O)_t OR^a$ (where t is 1 or 2), —$S(O)_t N(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

The terms "heterocyclylalkyl", "heterocyclyl-alkyl", "hetcyclylalkyl", and "hetcyclyl-alkyl" are used to describe a group wherein the alkyl chain can be branched or straight chain forming a linking portion of the heterocyclylalkyl moiety with the terminal heterocyclyl portion, as defined above, for example 3-piperidinylmethyl and the like. The term "heterocycloalkylene" refers to the divalent derivative of heterocycloalkyl.

The term "$C_{1-10}$alkyl-heterocycyl" refers to a group as defined above where the alkyl moiety contains 1 to 10 carbon atoms. Either portion of the moiety is unsubstituted or substituted.

The term "heterocycyl-$C_{1-10}$alkyl" refers to a group containing a terminal heterocyclic group attached to a linking alkyl group which contains 1 to 10 carbons and is branched or straight chain, such as, for example, 4-morpholinyl ethyl, and the like. Either portion of the moiety is unsubstituted or substituted.

The terms "heterocyclylalkenyl", "heterocyclyl-alkenyl", "hetcyclylalkenyl" and "hetcyclyl-alkenyl" are used to describe a group wherein the alkenyl chain can be branched or straight chain forming a linking portion of the heterocyclylalkenyl moiety with the terminal heterocyclyl portion, as defined above, for example 2-morpholinyl-1-propenyl and the like. The term "heterocycloalkenylene" refers to the divalent derivative of heterocyclylalkenyl. Either portion of the moiety is unsubstituted or substituted.

The term "heterocycyl-$C_{2-10}$ alkenyl" refers to a group as defined above where the alkenyl group contains 2 to 10 carbon atoms and is branched or straight chain, such as, for example, 4-(N-piperazinyl)-but-2-en-1-yl, and the like. Either portion of the moiety is unsubstituted or substituted.

The terms "heterocyclylalkynyl", "heterocyclyl-alkynyl", "hetcyclylalkynyl" and "hetcyclyl-alkynyl" are used to describe a group wherein the alkynyl chain can be branched or straight chain forming a linking portion of the heterocyclylalkynyl moiety with the terminal heterocyclyl portion, as defined above, for example 2-pyrrolidinyl-1-butynyl and the like. Either portion of the moiety is unsubstituted or substituted.

The term "heterocycyl-$C_{2-10}$ alkynyl" refers to a group as defined above where the alkynyl group contains 2 to 10 carbon atoms and is branched or straight chain, such as, for example, 4-(N-piperazinyl)-but-2-yn-1-yl, and the like.

The term "aryl-heterocycyl" refers to a group containing a terminal aryl group attached to a linking heterocyclic group, such as for example, N4-(4-phenyl)-piperazinyl, and the like. Either portion of the moiety is unsubstituted or substituted.

The term "heteroaryl-heterocycyl" refers to a group containing a terminal heteroaryl group attached to a linking heterocyclic group, such as for example, N4-(4-pyridyl)-piperazinyl, and the like. Either portion of the moiety is unsubstituted or substituted.

The term "carboxylalkyl" refers to a terminal carboxyl (—COOH) group attached to branched or straight chain alkyl groups as defined above.

The term "carboxylalkenyl" refers to a terminal carboxyl (—COOH) group attached to branched or straight chain alkenyl groups as defined above.

The term "carboxylalkynyl" refers to a terminal carboxyl (—COOH) group attached to branched or straight chain alkynyl groups as defined above.

The term "carboxylcycloalkyl" refers to a terminal carboxyl (—COOH) group attached to a cyclic aliphatic ring structure as defined above.

The term "carboxylcycloalkenyl" refers to a terminal carboxyl (—COOH) group attached to a cyclic aliphatic ring structure having ethylenic bonds as defined above.

The terms "cycloalkylalkyl" and "cycloalkyl-alkyl" refer to a terminal cycloalkyl group as defined above attached to an alkyl group, for example cyclopropylmethyl, cyclohexylethyl, and the like. Either portion of the moiety is unsubstituted or substituted.

The terms "cycloalkylalkenyl" and "cycloalkyl-alkenyl" refer to a terminal cycloalkyl group as defined above attached to an alkenyl group, for example cyclohexylvinyl, cycloheptylallyl, and the like. Either portion of the moiety is unsubstituted or substituted.

The terms "cycloalkylalkynyl" and "cycloalkyl-alkynyl" refer to a terminal cycloalkyl group as defined above attached to an alkynyl group, for example cyclopropylpropargyl, 4-cyclopentyl-2-butynyl, and the like. Either portion of the moiety is unsubstituted or substituted.

The terms "cycloalkenylalkyl" and "cycloalkenyl-alkyl" refer to a terminal cycloalkenyl group as defined above attached to an alkyl group, for example 2-(cyclopenten-1-yl) ethyl and the like. Either portion of the moiety is unsubstituted or substituted.

The terms "cycloalkenylalkenyl" and "cycloalkenyl-alkenyl" refer to terminal a cycloalkenyl group as defined above attached to an alkenyl group, for example 1-(cyclohexen-3-yl)allyl and the like.

The terms "cycloalkenylalkynyl" and "cycloalkenyl-alkynyl" refer to terminal a cycloalkenyl group as defined above attached to an alkynyl group, for example 1-(cyclohexen-3-yl)propargyl and the like. Either portion of the moiety is unsubstituted or substituted.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

The term "haloalkoxy" refers to an alkoxy group substituted with one or more halo groups, for example chloromethoxy, trifluoromethoxy, difluoromethoxy, perfluoroisobutoxy, and the like.

The term "alkoxyalkoxyalkyl" refers to an alkyl group substituted with an alkoxy moiety which is in turn is substituted with a second alkoxy moiety, for example methoxymethoxymethyl, isopropoxymethoxyethyl, and the like. This moiety is substituted with further substituents or not substituted with other substituents.

The term "alkylthio" includes both branched and straight chain alkyl groups attached to a linking sulfur atom, for example methylthio and the like.

The term "alkoxyalkyl" refers to an alkyl group substituted with an alkoxy group, for example isopropoxymethyl and the like. Either portion of the moiety is unsubstituted or substituted.

The term "alkoxyalkenyl" refers to an alkenyl group substituted with an alkoxy group, for example 3-methoxyallyl and the like. Either portion of the moiety is unsubstituted or substituted.

The term "alkoxyalkynyl" refers to an alkynyl group substituted with an alkoxy group, for example 3-methoxypropargyl and the like. Either portion of the moiety is unsubstituted or substituted.

The term "$C_{2-10}$alkenyl$C_{3-8}$cycloalkyl" refers to an alkenyl group as defined above substituted with a three to eight membered cycloalkyl group, for example, 4-(cyclopropyl)-2-butenyl and the like. Either portion of the moiety is unsubstituted or substituted.

The term "$C_{2-10}$alkynyl$C_{3-8}$cycloalkyl" refers to an alkynyl group as defined above substituted with a three to eight membered cycloalkyl group, for example, 4-(cyclopropyl)-2-butynyl and the like. Either portion of the moiety is unsubstituted or substituted.

The term "heterocyclyl-$C_{1-10}$alkyl" refers to a heterocyclic group as defined above substituted with an alkyl group as defined above having 1 to 10 carbons, for example, 4-(N-methyl)-piperazinyl, and the like. Either portion of the moiety is unsubstituted or substituted.

The term "heterocyclyl-$C_{2-10}$alkenyl" refers to a heterocyclic group as defined above, substituted with an alkenyl group as defined above, having 2 to 10 carbons, for example, 4-(N-allyl)piperazinyl, and the like. Moieties wherein the heterocyclic group is substituted on a carbon atom with an alkenyl group are also included. Either portion of the moiety is unsubstituted or substituted.

The term "heterocyclyl-$C_{2-10}$alkynyl" refers to a heterocyclic group as defined above, substituted with an alkynyl group as defined above, having 2 to 10 carbons, for example, 4-(N-propargyl)piperazinyl, and the like. Moieties wherein the heterocyclic group is substituted on a carbon atom with an alkenyl group are also included. Either portion of the moiety is unsubstituted or substituted.

The term "oxo" refers to an oxygen that is double bonded to a carbon atom. One in the art understands that an "oxo" requires a second bond from the atom to which the oxo is attached. Accordingly, it is understood that oxo cannot be substituted onto an aryl or heteroaryl ring, unless it forms part of the aromatic system as a tautomer.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

"Sulfonamidyl" or "sulfonamido" refers to a $S(=O)_2$—NR'R' radical, where each R' is selected independently from the group consisting of hydrogen, alkyl, cycloalkyl, aryl, heteroaryl (bonded through a ring carbon) and heteroalicyclic (bonded through a ring carbon). The R' groups in NR'R' of the $S(=O)_2$—NR'R' radical may be taken together with the nitrogen to which it is attached to form a 4-, 5-, 6-, or 7-membered ring. A sulfonamido group is optionally substituted by one or more of the substituents described for alkyl, cycloalkyl, aryl, heteroaryl respectively.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. Compounds may be shown without a definitive stereochemistry at certain positions. The present invention includes all stereoisomers of the disclosed compounds and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The present invention includes all manner of rotamers and conformationally restricted states of an inhibitor of the invention.

Substituents for alkyl, heteroalkyl, cycloalkyl, heterocloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: alkyl, heteroalkyl, alkenyl, alkynyl, cycloalkyl, heterocycloalkyl, aryl, arylalkyl, heteroaryl, heteroarylalkyl, —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR$^7$—C(O)NR"R''', —NR"C(O)OR', —NR—C(NR'R")=NR''', —S(O)R', —S(O)$_2$R', —S(O)$_2$NR'R", —NRSO$_2$R', —CN and NO$_2$ in a number ranging from zero to (2 m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When an inhibitor of the invention includes more than one R group, for example, each of the R groups is independently selected as are each R', R", R''' and R'''' groups when more than one of these groups is present.

When R' and R" or R" and R''' are attached to the same nitrogen atom, they can be combined with the nitrogen atom to form a 4-, 5-, 6-, or 7-membered ring. For example, —NR'R" is meant to include, but not be limited to, 1-pyrrolidinyl, 4 piperazinyl, and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, alkyl, heteroalkyl, alkenyl, alkynyl, cycloalkyl, heterocycloalkyl, aryl, arylalkyl, heteroaryl, heteroarylalkyl, —OR', —NR'R", —SR', -halogen, —SiR'R"R"', —OC(O)R', —C(O)R', —CO$_2$R', —C(O)NR'R", —OC(O)NR'R", —NR"C(O)R', —NR$^7$—C(O)NR"R"', —NR"C(O)OR', —NR—C(NR'R"R"')=NR"", —NR—C(NR'R")=NR"', —S(O)R', —S(O)$_2$R', —S(O)$_2$NR'R", —NRSO$_2$R', —CN and NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When an inhibitor of the invention includes more than one R group, for example, each of the R groups is independently selected as are each R', R", R"' and R"" groups when more than one of these groups is present.

As used herein, 0-2 in the context of —S(O)$_{(0-2)}$— are integers of 0, 1, and 2.

Two of the substituents on adjacent atoms of aryl or heteroaryl ring may optionally form a ring of the formula -T-C(O)—(CRR')$_q$—U—, wherein T and U are independently NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR$^7$—, —S—, —S(O)—, —S(O)$_2$—, or —S(O)$_2$NR'—. The substituents, R', R" and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

Treatment Regimens

The invention provides an intermittent treatment regimen in which an mTorC1/mTorC2 inhibitor is administered to a subject and where the intermittent regimen is effective to achieve an mTorC1/mTorC2 inhibitor plasma concentration at or above about 100 nM for a duration of time that is longer than that achieved by administering an equivalent dose of the mTorC1/mTorC2 inhibitor once daily. As used herein, the term "equivalent dose" refers to a single or multiple dose administered to a subject over a period of time, including a day, several days, a week, a month or longer. In some embodiments, equivalence is evaluated during the length of a treatment cycle, e.g. a week. The term equivalent dose is not limited to identical amounts of a compound administered of a specified period of time, but also refers to dose amounts which result in a similar level of tolerability. By way of example, when comparing a regimen of the invention in which an mTorC1/mTorC2 inhibitor is administered intermittently at a weekly cumulative dose of 50 mg, with a regimen in which the mTorC1/mTorC2 inhibitor is administered daily, it may only possible to achieve a weekly cumulative dose of less than 50 mg (e.g. about 40-45 mg) using daily administration due to dose-limiting toxicity and/or limited tolerability. In such a case, administration of the weekly cumulative 50 mg dose in the intermittent regimen is "equivalent" to the about 40-45 mg weekly cumulative dose administered daily.

For example, the intermittent regimen is effective to achieve an mTorC1/mTorC2 inhibitor plasma concentration of greater than about 80, 90, 100, 100, 120, 130, 140, 150, or 160 nM for a duration longer than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 hours during a 7-day period of administration. In some instances, the intermittent regimen is effective to achieve an mTorC1/mTorC2 inhibitor plasma concentration of greater than about 100 nM for a duration longer than about 20, 21, 22, 23, 24, 25, 26, 27, 28, 29, 30, 31, 32, 33, 34, or 35 hours during a 7-day period of administration. In other instances, the intermittent regimen is effective to achieve an mTorC1/mTorC2 inhibitor plasma concentration of greater than about 100 nM for a duration longer than about 20 or about 30 hours during a 7-day period of administration.

The invention also provides a treatment regimen which is effective to achieve a Cmax which is greater by about 10%, 15%, 20%, 25%, 30%, 35%, 40%, 45%, 50%, 60%, 70%, 80%, 90%, 100%, 150%, 200%, 250%, or 300% than the Cmax achieved by administering an equivalent dose of the mTorC1/mTorC2 inhibitor once daily. For example, the Cmax achieved is greater than about 100, 200, 250, 300, 350, 400, 450, 500, 550 or 600 nM. In some instances, the Cmax achieved is greater than about 200, 250, 300, 350, 400, 450, 500, 550 or 600 nM. For example, the Cmax is greater than 200 nM. Alternatively, the Cmax is greater than 300 nM. In other instances, the Cmax achieved is between 200 and 600 nM. In yet other instances, the Cmax achieved is between 200 and 500 nM. In yet other instances, the Cmax achieved is between 200 and 500 nM.

In some embodiments, an intermittent treatment regimen of the invention achieves similar or better pathway inhibition than administering an equivalent dose of the mTorC1/mTorC2 inhibitor once daily. Pathway inhibition may be measured, for example, as a percentage decrease in phosphorylation of a protein chosen from p4EBP1, pS6, and pRAS40. In some embodiments, pathway inhibition is measured as a 40%, 45%, 50%, 55%, 60%, 65%, 70%, 75%, 80%, 85%, 90%, 95% or greater decrease in phosphorylation of p4EBP1. For example, phosphorylation of p4EBP1 is reduced by at least 60%. In other embodiments, pathway inhibition is measured as a 40%, 45%, 50%, 55%, 60%, 65%, 70%, 75%, 80%, 85%, 90%, 95% or greater decrease in phosphorylation of pS6. For example, phosphorylation of pS6 is reduced by at least 60%. In yet other embodiments, pathway inhibition is measured as a 40%, 45%, 50%, 55%, 60%, 65%, 70%, 75%, 80%, 85%, 90%, 95% or greater decrease in phosphorylation of pRAS40. For example, phosphorylation of pRAS40 is reduced by at least 60%. In yet other embodiments, pathway inhibition is measured as a 40%, 45%, 50%, 55%, 60%, 65%, 70%, 75%, 80%, 85%, 90%, 95% or greater decrease in phosphorylation of p4EBP1, pS6, and pRAS40. For example, phosphorylation of p4EBP1, pS6, and pRAS40 is reduced by at least 60%. In some embodiments, pathway inhibition is measured in peripheral blood cells. In other embodiments, pathway inhibition is measured in a biopsy, for example a skin biopsy.

In some embodiments, an intermittent treatment regimen of the invention achieves similar or better level of tolerability as compared to administering an equivalent dose of the mTorC1/mTorC2 inhibitor once daily. The level of tolerability may be measured, for example, as the occurrence or lack of occurrence of a grade 3 or higher adverse event. In some embodiments, the adverse event is rash, hyperglycaemia, lymphopenia, diarrhea, gamma-glutamyltransferase increase, hypokalaemia, hyponatraemia, pruritus, thrombocytopenia, upper abdominal pain, anaemia, aspartate aminotransferase increase, asthenia, catheter related infection, cellulitis, disease progression, enterocutaneous fistula, gastroenteritis, acute pancreatitis, pleural effusion, macular rash, somnolence, or urinary tract infection. For example, the adverse event is rash.

In some embodiments, a given dosing schedule comprises one or more administrations of an mTorC1/mTorC2 inhibitor, wherein at least one administration of an mTorC1/mTorC2 inhibitor, such as described herein, may be repeated or cycled on a daily, weekly, biweekly, monthly, bimonthly, annually, semi-annually, or any other period. A repeated dosing schedule or cycle may be repeated for a fixed period of time determined at the start of the schedule; may be terminated, extended, or otherwise adjusted based on a measure of therapeutic effect, such as a level of reduction in the presence of detectable disease tissue (e.g. a reduction of at least 50%, 60%, 70%, 80%, 90%, 95%, 99%, or 100%); or may be terminated, extended, or otherwise adjusted for any other reason as determined by a medical professional.

In some embodiments, the intermittent regimen comprises at least one cycle in which the mTorC1/mTorC2 inhibitor is administered for at least 1 day, followed by an intermission in which the mTorC1/mTorC2 inhibitor is not administered for at least 1 day. For example, the mTorC1/mTorC2 inhibitor is administered for 2, 3, 4, 5, 6 or 7 consecutive days followed by an intermission in which the mTorC1/mTorC2 inhibitor is not administered for at least 1 day, for example not administered for at least 1, 2, 3, 4, 5, 6, or 7 days. In some embodiments, the mTorC1/mTorC2 inhibitor is administered for 7, 8, 9, 10, 11, 12, 13, or 14 consecutive days, followed by an intermission where the mTorC1/mTorC2 inhibitor is not administered for at least 2, 3, 4, 5, 6, or 7 days. In other embodiments, the mTorC1/mTorC2 inhibitor is administered for 2, 3, 4, 5, 6 or 7 consecutive days followed by an intermission in which the mTorC1/mTorC2 inhibitor is not administered for at least 3, 4, or 5 consecutive days. In yet other embodiments, the regimen comprises at least one 7-day cycle in which the mTorC1/mTorC2 inhibitor is administered for 3 consecutive days followed by an intermission of 4 consecutive days. In yet other embodiments, the regimen comprises at least one 7-day cycle in which the mTorC1/mTorC2 inhibitor is administered for 4 consecutive days followed by an intermission of 3 consecutive days. In yet other embodiments, the regimen comprises at least one 7-day cycle in which the mTorC1/mTorC2 inhibitor is administered for 5 consecutive days followed by an intermission of 2 consecutive days. In yet other embodiments, the regimen comprises at least one 7-day cycle in which the mTorC1/mTorC2 inhibitor is administered for 6 consecutive days followed by an intermission of 1 day.

In some embodiments, an mTorC1/mTorC2 inhibitor, and/or any additional therapeutic compound of the invention is administered in multiple doses. Dosing may be about once, twice, three times, four times, five times, six times, or more than six times per day or per week. Dosing may be about once a month, once every two weeks, once a week, or once every other day. In some embodiments, cycles of administering an mTorC1/mTorC2 inhibitor followed by periods of rest (intermission) are repeated for more than about 6, 10, 14, 28 days, two months, six months, or one year. In some cases, repetition of a dosing cycle comprising administration of an mTorC1/mTorC2 inhibitor followed by rest are continued as long as necessary. Administration of the treatment regimens of the invention may continue as long as necessary. In some embodiments, an mTorC1/mTorC2 inhibitor of the invention is administered for more than 1, 2, 3, 4, 5, 6, 7, 14, or 28 days. In some embodiments, an mTorC1/mTorC2 inhibitor of the invention is administered for less than 28, 14, 7, 6, 5, 4, 3, 2, or 1 day. In some embodiments, an mTorC1/mTorC2 inhibitor of the invention is administered chronically on an ongoing basis, e.g., for the treatment of chronic effects.

The amount of the mTorC1/mTorC2 inhibitor administered herein may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

A dosage form of the invention refers to the physical formulation of a drug for administration to the patient. When the dosage form is a solid, the dosage form can be a single capsule, tablet, or pill, or alternatively can be comprised of multiple capsules, tablets or pills. A dosage form may be administered to a subject once or multiple times per day. Methods of determining the most effective means and dosage of administration are well known to those of skill in the art and will vary with the composition used for therapy, the purpose of the therapy, the target cell or tissue being treated, and the subject being treated. Single or multiple administrations (e.g. about or more than about 1, 2, 3, 4, 5, 6, 7, 8, 9, 10, 11, 12, 13, 14, 15, 16, 17, 18, 19, 20, 25, 30, or more doses) can be carried out with the dose level and pattern being selected by the treating physician.

An inhibitor may be administered in any suitable amount. In some embodiments, an inhibitor is administered to a subject within a range of about 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 mg per week. For example, the inhibitor is administered to a subject within a range of about 35, 36, 37, 38, 39, 40, 41, 42, 43, 44, 45, 46, 47, 48, 49, 50, 51, 52, 53, 54, or 55 mg per week. In some embodiments, the inhibitor is administered to a subject within a range of about 40, 41, 42, 43, 44, 45, 46, 47, 48, 49, 50, 51, 52, 53, 54, or 55 mg per week.

In some embodiments, an inhibitor is administered to a subject in an amount greater than 6, 6.5, 7, 7.5, 8, 8.5, 9, 9.5, or 10 mg per day on average over the course of a treatment cycle. For example, the inhibitor is administered to a subject in an amount between about 6 and 10 mg, between about 6.5 and 9.5 mg, between about 6.5 and 8.5 mg, between about 6.5 and 8 mg, or between about 7 and 9 mg on average over the course of a treatment cycle.

In some embodiments, an inhibitor is administered to a subject within a range of about 0.1 mg/kg-50 mg/kg per day, such as about, less than about, or more than about, 0.1 mg/kg, 0.2 mg/kg, 0.3 mg/kg, 0.4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, or 50 mg/kg per day. In some embodiments, an inhibitor is administered to a subject within a range of about 0.1 mg/kg-400 mg/kg per week, such as about, less than about, or more than about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 100 mg/kg, 150 mg/kg, 200 mg/kg, 250 mg/kg, 300 mg/kg, 350 mg/kg, or 400 mg/kg per week. In some embodiments, an inhibitor is administered to a subject within a range of about 0.1 mg/kg-1500 mg/kg per month, such as about, less than about, or more than about 50 mg/kg, 100 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, or 1000 mg/kg per month. In some embodiments, an inhibitor is administered to a subject within a range of about 0.1 mg/m$^2$-200 mg/m$^2$ per week, such as about, less than about, or more than about 5 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, 100 mg/m$^2$, 125 mg/m$^2$, 150 mg/m$^2$, 175 mg/m$^2$, or 200 mg/m$^2$ per week. The target dose may be administered in a single dose. Alternatively, the target dose may be administered in about or more than about 1, 2, 3, 4, 5, 6, 7, 8, 9, 10, 11, 12, 13, 14, 15, 16, 17, 18, 19, 20, 25, 30, or more doses. For example, a dose of about 20 mg/kg per week may be delivered weekly at a dose of about 20 mg/kg, or may be delivered at a dose of about 6.67 mg/kg administered on each of three days over the course of the week, which days may or may not be consecutive. The administration schedule may be repeated according to any regimen according to the invention, including any administration schedule described herein. In some embodiments, an inhibitor is administered to a subject in the range of about 0.1 mg/m$^2$-500 mg/m$^2$, such as about, less than about, or more than about 5 mg/m$^2$, 10 mg/m$^2$, 15 mg/m$^2$, 20 mg/m$^2$, 25 mg/m$^2$, mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, 100 mg/m$^2$, 130 mg/m$^2$, 135 mg/m$^2$, 155 mg/m$^2$, 175 mg/m$^2$, 200 mg/m$^2$, 225 mg/m$^2$, 250 mg/m$^2$, 300 mg/m$^2$, 350 mg/m$^2$, 400 mg/m$^2$, 420 mg/m$^2$, 450 mg/m$^2$, or 500 mg/m$^2$.

A dose of mTorC1/mTorC2 inhibitor may be about, at least about, or at most about 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000 mg or mg/kg, or any range derivable therein. It is contemplated that a dosage of mg/kg refers to the mg amount of inhibitor per kg of total body weight of the subject. It is contemplated that when multiple doses are given to a patient, the doses may vary in amount or they may be the same.

The amount of each inhibitor administered will be dependent on the mammal being treated, the severity of the disorder or condition, the rate of administration, the disposition of the compound and the discretion of the prescribing physician.

mTORC1/mTORC2 Inhibitor Compounds

An mTorC1/mTorC2 inhibitor for use in the present invention can be any mTorC1/mTorC2 inhibitor that is known in the art, and can include any chemical entity that, upon administration to a patient, results in inhibition of mTOR in the patient. An mTorC1/mTorC2 inhibitor can inhibit mTorC1/mTorC2 by any biochemical mechanism, including competition at the ATP binding site, competition elsewhere at the catalytic site of mTOR kinase, non-competitive inhibition, irreversible inhibition (e.g. covalent protein modification), or modulation of the interactions of other protein subunits or binding proteins with mTOR kinase in a way that results in inhibition of mTOR kinase activity (e.g. modulation of the interaction of mTOR with FKBP12, GβL, (mLST8), RAPTOR (mKOG1), or RICTOR (mAVO3)). Such inhibitors useful in the invention described herein include those disclosed and claimed in U.S. Pat. No. 7,700,594 and in U.S. Pat. No. 7,651,687, a series of compounds that inhibit mTOR by binding to and directly inhibiting both mTORC1 and mTORC2 kinases. Similar results can be obtained with any compound that inhibits mTOR by binding to and directly inhibiting both mTORC1 and mTORC2 kinases, such as those whose structures are disclosed herein. Additional such compounds can readily be identified by determining their ability to inhibit both mTORC1 and mTORC2 kinase activities using immunoprecipitation-kinase assays with antibodies specific to either the raptor or rictor proteins of the mTORC1 and mTORC2 complexes (for an example of such assays, see Jacinto, E. et al. (2004) Nature Cell Biol. 6(11): 1122-1128). Also useful in the invention described herein are mTorC1/mTorC2 inhibitors that are dual PI3K/mTOR kinase inhibitors, such as for example the compound PI-103 as described in Fan, Q-W et al (2006) Cancer Cell 9:341-349 and Knight, Z. A. et al. (2006) Cell 125:733-747.

In some embodiments, the capacity of an mTorC1/mTorC2 inhibitor to inhibit mTorC1/mTorC2 is expressed in terms of an IC50 value. As used herein, the term "IC50" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50% of a maximum effect in vivo.

Determination of IC50 can be made by determining and constructing a dose-response curve and examining the effect of different concentrations of an inhibitor on reversing agonist activity. In vitro assays that are useful in making these determinations are referred to as "in vitro kinase assays."

In some embodiments, an in vitro kinase assay includes the use of labeled ATP as phosphodonor, and following the kinase reaction the substrate peptide is captured on an appropriate filter. Unreacted labeled ATP and metabolites are resolved from the radioactive peptide substrate by various techniques, such as involving trichloroacetic acid precipitation and extensive washing. Addition of several positively charged residues allows capture on phosphocellulose paper followed by washing. Radioactivity incorporated into the substrate peptide is detected by scintillation counting. This assay is relatively simple, reasonably sensitive, and the peptide substrate can be adjusted both in terms of sequence and concentration to meet the assay requirements. Other exemplary kinase assays are detailed in U.S. Pat. No. 5,759,787 and U.S. application Ser. No. 12/728,926, both of which are incorporated herein by reference.

The ability of an mTorC1/mTorC2 inhibitor utilized in the subject methods to bind to and directly inhibit both mTORC1 and mTORC2 can be ascertained using any method known in the art or described herein. For example, inhibition of mTorC1 and/or mTorC2 activity can be determined by a reduction in signal transduction of the PI3K/Akt/mTor pathway. A wide variety of readouts can be utilized to establish a reduction of the output of such signaling pathway. Some non-limiting exemplary readouts include (1) a decrease in phosphorylation of Akt at residues, including but not limited to S473 and T308; (2) a decrease in activation of Akt as evidenced by a reduction of phosphorylation of Akt substrates including but not limited to FoxO1/O3a T24/32, GSK3α/β S21/9, and TSC2 T1462; (3) a decrease in phosphorylation of signaling molecules downstream of mTor, including but not limited to ribosomal S6S240/244, 70S6K T389, and 4EBP1T37/46; (4) inhibition of proliferation of cells including but not limited to normal or neoplastic cells, mouse embryonic fibroblasts, leukemic blast cells, cancer stem cells, and cells that mediate autoimmune reactions; (5) induction of apoptosis of cells or cell cycle arrest (e.g. accumulation of cells in G1 phase); (6) reduction of cell chemotaxis; and (7) an increase in binding of 4EBP1 to eIF4E.

mTOR exists in two types of complexes, mTorC1 containing the raptor subunit and mTorC2 containing rictor. As known in the art, "rictor" refers to a cell growth regulatory protein having human gene locus 5p13.1. These complexes are regulated differently and have a different spectrum of substrates. For instance, mTorC1 phosphorylates S6 kinase (S6K) and 4EBP1, promoting increased translation and ribosome biogenesis to facilitate cell growth and cell cycle progression. S6K also acts in a feedback pathway to attenuate PI3K/Akt activation. Thus, inhibition of mTorC1 (e.g. by a biologically active agent as discussed herein) results in activation of 4EBP1, resulting in inhibition of (e.g. a decrease in) RNA translation.

mTorC2 is generally insensitive to rapamycin and selective inhibitors and is thought to modulate growth factor signaling by phosphorylating the C-terminal hydrophobic motif of some AGC kinases such as Akt. In many cellular contexts, mTorC2 is required for phosphorylation of the S473 site of Akt. Thus, mTorC1 activity is partly controlled by Akt whereas Akt itself is partly controlled by mTorC2.

Growth factor stimulation of PI3K causes activation of Akt by phosphorylation at the two key sites, S473 and T308. It has been reported that full activation of Akt requires phosphorylation of both S473 and T308Active. Akt promotes cell survival and proliferation in many ways including suppressing apoptosis, promoting glucose uptake, and modifying cellular metabolism. Of the two phosphorylation sites on Akt, activation loop phosphorylation at T308, mediated by PDK1, is believed to be indispensable for kinase activity, while hydrophobic motif phosphorylation at S473 enhances Akt kinase activity.

Inhibition of Akt phosphorylation can be determined using any methods known in the art or described herein. Representative assays include but are not limited to immunoblotting and immunoprecipitation with antibodies such as anti-phosphotyrosine antibodies that recognize the specific phosphorylated proteins. Cell-based ELISA kit quantifies the amount of activated (phosphorylated at S473) Akt relative to total Akt protein is also available (SuperArray Biosciences).

Selective mTor inhibition may also be determined by expression levels of the mTor genes, its downstream signaling genes (for example by RT-PCR), or expression levels of the proteins (for example by immunocytochemistry, immunohistochemistry, Western blots) as compared to other PI3-kinases or protein kinases.

Cell-based assays for establishing selective inhibition of mTorC1 and/or mTorC2 can take a variety of formats. This generally will depend on the biological activity and/or the signal transduction readout that is under investigation. For example, the ability of the agent to inhibit mTorC1 and/or mTorC2 to phosphorylate downstream substrate(s) can be determined by various types of kinase assays known in the art. Representative assays include but are not limited to immunoblotting and immunoprecipitation with antibodies such as anti-phosphotyrosine, anti-phosphoserine or anti-phosphothreonine antibodies that recognize phosphorylated proteins. Alternatively, antibodies that specifically recognize a particular phosphorylated form of a kinase substrate (e.g. anti-phospho AKT S473 or anti-phospho AKT T308) can be used. In addition, kinase activity can be detected by high throughput chemiluminescent assays such as AlphaScreen™ (available from Perkin Elmer) and eTag™ assay (Chan-Hui, et al. (2003) *Clinical Immunology* 111: 162-174). In another aspect, single cell assays such as flow cytometry as described in the phosflow experiment can be used to measure phosphorylation of multiple downstream mTOR substrates in mixed cell populations.

One advantage of the immunoblotting and phosflow methods is that the phosphorylation of multiple kinase substrates can be measured simultaneously. This provides the advantage that efficacy and selectivity can be measured at the same time. For example, cells may be contacted with an mTorC1/mTorC2 inhibitor at various concentrations and the phosphorylation levels of substrates of both mTOR and other kinases can be measured. In one aspect, a large number of kinase substrates are assayed in what is termed a "comprehensive kinase survey." Selective mTorC1/mTorC2 inhibitors are expected to inhibit phosphorylation of mTOR substrates without inhibiting phosphorylation of the substrates of other kinases. Alternatively, selective mTorC1/mTorC2 inhibitors may inhibit phosphorylation of substrates of other kinases through anticipated or unanticipated mechanisms such as feedback loops or redundancy.

Effect of inhibition of mTorC1 and/or mTorC2 can be established by cell colony formation assay or other forms of cell proliferation assay. A wide range of cell proliferation assays are available in the art, and many of which are available as kits. Non-limiting examples of cell proliferation assays include testing for tritiated thymidine uptake assays, BrdU (5'-bromo-2'-deoxyuridine) uptake (kit marketed by Calibochem), MTS uptake (kit marketed by Promega), MTT uptake (kit marketed by Cayman Chemical), CyQUANT® dye uptake (marketed by Invitrogen).

Apoptosis and cell cycle arrest analysis can be performed with any methods exemplified herein as well other methods known in the art. Many different methods have been devised to detect apoptosis. Exemplary assays include but are not limited to the TUNEL (TdT-mediated dUTP Nick-End Labeling) analysis, ISEL (in situ end labeling), and DNA laddering analysis for the detection of fragmentation of DNA in populations of cells or in individual cells, Annexin-V analysis that measures alterations in plasma membranes, detection of apoptosis related proteins such p53 and Fas.

A cell-based assay typically proceeds with exposing the target cells (e.g., in a culture medium) to a test compound which is a potential mTorC1 and/or mTorC2 selective inhibitor, and then assaying for readout under investigation. Depending on the nature of the candidate mTorC1/mTorC2 inhibitors, they can directly be added to the cells or in conjunction with carriers. For instance, when the agent is nucleic acid, it can be added to the cell culture by methods well known in the art, which include without limitation calcium phosphate precipitation, microinjection or electroporation. Alternatively, the nucleic acid can be incorporated into an expression or insertion vector for incorporation into the cells. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of vectors are viruses, such as baculovirus and retrovirus, bacteriophage, adenovirus, adeno-associated virus, cosmid, plasmid, fungal vectors and other recombination vehicles typically used in the art which have been described for expression in a variety of eukaryotic and prokaryotic hosts, and may be used for gene therapy as well as for simple protein expression. Among these are several nonviral vectors, including DNA/liposome complexes, and targeted viral protein DNA complexes. To enhance delivery to a cell, the nucleic acid or proteins of this invention can be conjugated to antibodies or binding fragments thereof which bind cell surface antigens. Liposomes that also comprise a targeting antibody or fragment thereof can be used in the methods of this invention. Other biologically acceptable carriers can be utilized, including those described in, for example, REMINGTON'S PHARMACEUTICAL SCIENCES, 19th Ed. (2000), in conjunction with the subject compounds. Additional methods for cell-based assays for determining effects of agents on cell-cycle progression are described in U.S. Pat. No. 7,612,189, incorporated herein by reference.

In practicing the subject methods, any cells that express PI3-kinase α, mTorC1, mTorC2 and/or Akt can be target cells. Non-limiting examples of specific cell types whose proliferation can be inhibited include fibroblast, cells of skeletal tissue (bone and cartilage), cells of epithelial tissues (e.g. liver, lung, breast, skin, bladder and kidney), cardiac and smooth muscle cells, neural cells (glia and neurones), endocrine cells (adrenal, pituitary, pancreatic islet cells), melanocytes, and many different types of haemopoietic cells (e.g., cells of B-cell or T-cell lineage, and their corresponding stem cells, lymphoblasts). Also of interest are cells exhibiting a neoplastic propensity or phenotype. Of particular interest is the type of cells that differentially expresses (over-expresses or under-expresses) a disease-causing gene. The types of diseases involving abnormal functioning of genes include but are not limited to autoimmune diseases, cancer, obesity, hypertension, diabetes, neuronal and/or muscular degenerative diseases, cardiac diseases, endocrine disorders, and any combinations thereof.

In some embodiments, the mTorC1/mTorC2 inhibitor utilized in the subject methods inhibits one of mTORC1 and mTORC2 selectively with an IC50 value of about 1000, 500, 100, 75, 50, 25, 10, 5, 1, or 0.5 nM or less as ascertained in an in vitro kinase. For example, an mTorC1/mTorC2 inhibitor utilized in the subject methods inhibits mTORC1 selectively with an IC50 value of about 1000, 500, 100, 75, 50, 25, 10, 5, 1, or 0.5 nM or less as ascertained in an in vitro kinase assay.

In some embodiments, the mTorC1/mTorC2 inhibitor inhibits one of mTORC1 and mTORC2 with an IC50 value of about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM or less as ascertained in an in vitro kinase assay, and said IC50 value is at least 2, 3, 4, 5, 6, 7, 8, 9, 10, 15, 20, 25, 30, 35, 40, 45, 50, 100, or 1000 times less than its IC50 value against all other type I PI3-kinases selected from the group consisting of PI3-kinase α, PI3-kinase β, PI3-kinase γ, and PI3-kinase δ. For example, the mTorC1/mTorC2 inhibitor inhibits one of mTORC1 and mTORC2 with an IC50 value of about 200, 100, 75, 50, 25, 10, 5, 1 or 0.5 nM or less as ascertained in an in vitro kinase assay. In one instance, the mTorC1/mTorC2 inhibitor inhibits one of mTORC1 and mTORC2 with an IC50 value of about 100 nM or less as ascertained in an in vitro kinase assay. As another example, the mTorC1/mTorC2 inhibitor inhibits one of mTORC1 and mTORC2 with an IC50 value of about 10 nM or less as ascertained in an in vitro kinase assay.

In some embodiments, the mTorC1/mTorC2 inhibitor inhibits both mTORC1 and mTORC2 with an IC50 value of about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM or less as ascertained in an in vitro kinase assay, and said IC50 value is at least 2, 3, 4, 5, 6, 7, 8, 9, 10, 15, 20, 25, 30, 35, 40, 45, 50, 100, or 1000 times less than its IC50 value against all other type I PI3-kinases selected from the group consisting of PI3-kinase α, PI3-kinase β, PI3-kinase γ, and PI3-kinase δ. For example, the mTorC1/mTorC2 inhibitor inhibits both mTORC1 and mTORC2 with an IC50 value of about 200, 100, 75, 50, 25, 10, 5, 1 or 0.5 nM or less as ascertained in an in vitro kinase assay. In one instance, the mTorC1/mTorC2 inhibitor inhibits both mTORC1 and mTORC2 with an IC50 value of about 100 nM or less as ascertained in an in vitro kinase assay. As another example, the mTorC1/mTorC2 inhibitor inhibits both mTORC1 and mTORC2 with an IC50 value of about 10 nM or less as ascertained in an in vitro kinase assay.

In some embodiments, the present invention provides the use of an mTorC1/mTorC2 inhibitor, wherein the mTorC1/mTorC2 inhibitor directly binds to and inhibits one of mTORC1 and mTORC2 with an IC50 value of about or less than a predetermined value, as ascertained in an in vitro kinase assay. In some embodiments, the mTorC1/mTorC2 inhibitor inhibits one of mTORC1 and mTORC2 with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30

μM or less, 40 μM or less, 50 μM or less, 60 μM or less, 70 μM or less, 80 μM or less, 90 μM or less, 100 μM or less, 200 μM or less, 300 μM or less, 400 μM or less, or 500 μM or less.

In some embodiments, the present invention provides the use of an mTorC1/mTorC2 inhibitor, wherein the mTorC1/mTorC2 inhibitor directly binds to and inhibits both mTORC1 and mTORC2 with an IC50 value of about or less than a predetermined value, as ascertained in an in vitro kinase assay. In some embodiments, the mTorC1/mTorC2 inhibitor inhibits both mTORC1 and mTORC2 with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 μM or less, 1.2 μM or less, 1.3 μM or less, 1.4 μM or less, 1.5 μM or less, 1.6 μM or less, 1.7 μM or less, 1.8 μM or less, 1.9 μM or less, 2 μM or less, 5 μM or less, 10 μM or less, 15 μM or less, 20 μM or less, 25 μM or less, 30 μM or less, 40 μM or less, 50 μM or less, 60 μM or less, 70 μM or less, 80 μM or less, 90 μM or less, 100 μM or less, 200 μM or less, 300 μM or less, 400 μM or less, or 500 μM or less.

In some embodiments, the mTorC1/mTorC2 inhibitor inhibits one of mTORC1 and mTORC2 with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 μM or less, 1.2 μM or less, 1.3 μM or less, 1.4 μM or less, 1.5 μM or less, 1.6 μM or less, 1.7 μM or less, 1.8 μM or less, 1.9 μM or less, 2 μM or less, 5 μM or less, 10 μM or less, 15 μM or less, 20 μM or less, 25 μM or less, 30 μM or less, 40 μM or less, 50 μM or less, 60 μM or less, 70 μM or less, 80 μM or less, 90 μM or less, 100 μM or less, 200 μM or less, 300 μM or less, 400 μM or less, or 500 μM or less, and the mTorC1/mTorC2 inhibitor is substantially inactive against one or more types I PI3-kinases selected from the group consisting of PI3-kinase α, PI3-kinase β, PI3-kinase γ, and PI3-kinase δ. In some embodiments, the mTorC1/mTorC2 inhibitor inhibits one of mTORC1 and mTORC2 with an IC50 value of about 10 nM or less as ascertained in an in vitro kinase assay, and the mTorC1/mTorC2 inhibitor is substantially inactive against one or more types I PI3-kinases selected from the group consisting of PI3-kinase α, PI3-kinase β, PI3-kinase γ, and PI3-kinase δ.

In some embodiments, the mTorC1/mTorC2 inhibitor inhibits both mTORC1 and mTORC2 with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 μM or less, 1.2 μM or less, 1.3 μM or less, 1.4 μM or less, 1.5 μM or less, 1.6 μM or less, 1.7 μM or less, 1.8 μM or less, 1.9 μM or less, 2 μM or less, 5 μM or less, 10 μM or less, 15 μM or less, 20 μM or less, 25 μM or less, 30 μM or less, 40 μM or less, 50 μM or less, 60 μM or less, 70 μM or less, 80 μM or less, 90 μM or less, 100 μM or less, 200 μM or less, 300 μM or less, 400 μM or less, or 500 μM or less, and the mTorC1/mTorC2 inhibitor is substantially inactive against one or more types I PI3-kinases selected from the group consisting of PI3-kinase α, PI3-kinase β, PI3-kinase γ, and PI3-kinase δ. In some embodiments, the mTorC1/mTorC2 inhibitor inhibits both mTORC1 and mTORC2 with an IC50 value of about 10 nM or less as ascertained in an in vitro kinase assay, and the mTorC1/mTorC2 inhibitor is substantially inactive against one or more types I PI3-kinases selected from the group consisting of PI3-kinase α, PI3-kinase β, PI3-kinase γ, and PI3-kinase δ.

As used herein, the terms "substantially inactive" refers to an inhibitor that inhibits the activity of its target by less than approximately 1%, 5%, 10%, 15% or 20% of its maximal activity in the absence of the inhibitor, as determined by an in vitro enzymatic assay (e.g. in vitro kinase assay).

In some embodiments, the mTorC1/mTorC2 inhibitor inhibits one of mTORC1 and mTORC2 with an IC50 value of about 1000, 500, 100, 75, 50, 25, 10, 5, 1, or 0.5 nM or less as ascertained in an in vitro kinase assay, and said IC50 value is at least 2, 5, 10, 15, 20, 50, 100 or 100 times less than its IC50 value against all other type I PI3-kinases selected from the group consisting of PI3-kinase α, PI3-kinase β, PI3-kinase γ, and PI3-kinase δ. For example, the mTorC1/mTorC2 inhibitor inhibits one of mTORC1 and mTORC2 with an IC50 value of about 100 nM or less as ascertained in an in vitro kinase assay, and said IC50 value is at least 5 times less than its IC50 value against all other type I PI3-kinases selected from the group consisting of PI3-kinase α, PI3-kinase β, PI3-kinase γ, and PI3-kinase δ.

In other embodiments, the mTorC1/mTorC2 inhibitor inhibits both mTORC1 and mTORC2 with an IC50 value of about 1000, 500, 100, 75, 50, 25, 10, 5, 1, or 0.5 nM or less as ascertained in an in vitro kinase assay, and said IC50 value is at least 2, 5, 10, 15, 20, 50, 100 or 100 times less than its IC50 value against all other type I PI3-kinases selected from the group consisting of PI3-kinase α, PI3-kinase β, PI3-kinase γ, and PI3-kinase δ. For example, the mTorC1/mTorC2 inhibitor inhibits both mTORC1 and mTORC2 with an IC50 value of about 100 nM or less as ascertained in an in vitro kinase assay, and said IC50 value is at least 5 times less than its IC50 value against all other type I PI3-kinases selected from the group consisting of PI3-kinase α, PI3-kinase β, PI3-kinase γ, and PI3-kinase δ.

In some embodiments, the mTorC1/mTorC2 inhibitor inhibits one of mTORC1 and mTORC2 with an IC50 value of about 100 nM or less as ascertained in an in vitro kinase assay, and said IC50 value is at least 5 times less than its IC50 value against all other type I PI3-kinases selected from the group consisting of PI3-kinase α, PI3-kinase β, PI3-kinase γ, and PI3-kinase δ. In other embodiments, the mTorC1/mTorC2 inhibitor inhibits one of mTORC1 and mTORC2 with an IC50 value of about 50 nM or less as ascertained in an in vitro kinase assay, and said IC50 value is at least 5 times less than its IC50 value against all other type I PI3-kinases selected from the group consisting of PI3-kinase α, PI3-kinase β, PI3-kinase γ, and PI3-kinase δ.

In other embodiments, the mTorC1/mTorC2 inhibitor inhibits both mTORC1 and mTORC2 with an IC50 value of about 100 nM or less as ascertained in an in vitro kinase assay, and said IC50 value is at least 5 times less than its IC50 value against all other type I PI3-kinases selected from the group consisting of PI3-kinase α, PI3-kinase β, PI3-kinase γ, and PI3-kinase δ. In other embodiments, the mTorC1/mTorC2 inhibitor inhibits both mTORC1 and mTORC2 with an IC50 value of about 50 nM or less as ascertained in an in vitro kinase assay, and said IC50 value is at least 5 times less than its IC50 value against all other type I PI3-kinases selected from the group consisting of PI3-kinase α, PI3-kinase β, PI3-kinase γ, and PI3-kinase δ.

mTorC1/mTorC2 inhibitors suitable for use in the subject methods can be selected from a variety types of molecules. For example, an inhibitor can be biological or chemical compound such as a simple or complex organic or inorganic molecule, peptide, peptide mimetic, protein (e.g. antibody), liposome, or a polynucleotide (e.g. small interfering RNA, microRNA, anti-sense, aptamer, ribozyme, or triple helix). Some exemplary classes of chemical compounds suitable for use in the subject methods are detailed in the sections below.

The advantages of selective inhibition of a cellular target as a way of treating a disease condition mediated by such target are manifold. Because healthy cells depend on the signaling pathways that are activated in cancers for survival, inhibition of these pathways during cancer treatment can cause harmful side effects. In order for a method of treating cancer to be successful without causing excessive damage to healthy cells, a very high degree of specificity in targeting the aberrant signaling component or components is desirable. Moreover, cancer cells may depend on overactive signaling for their survival (known as the oncogene addiction hypothesis). In this way, cancer cells are frequently observed to adapt to drug inhibition of an aberrant signaling component by selecting for mutations in the same pathway that overcome the effect of the drug. Therefore, cancer therapies may be more successful in overcoming the problem of drug resistance if they target a signaling pathway as a whole, or target more than one component within a signaling pathway.

One major downstream effector of mTOR signaling is the Akt serine/threonine kinase. Akt possesses a protein domain known as a PH domain, or Pleckstrin Homology domain, which binds to phosphoinositides with high affinity. In the case of the PH domain of Akt, it binds either PIP3 (phosphatidylinositol (3,4,5)-trisphosphate, PtdIns(3,4,5)P3) or PIP2 (phosphatidylinositol (3,4)-bisphosphate, PtdIns(3,4)P2). PI3K phosphorylates PIP2 in response to signals from chemical messengers, such as ligand binding to G protein-coupled receptors or receptor tyrosine kinases. Phosphorylation by PI3K converts PIP2 to PIP3, recruiting Akt to the cell membrane where it is phosphorylated at serine 473 (S473) by mTORC2. Phosphorylation of Akt at another site, threonine 308 (T308), is not directly dependent on mTORC2, but requires PI3K activity. Therefore, PI3K activity towards Akt can be isolated from mTOR activity by examining Akt threonine 308 phosphorylation status in cells lacking mTORC2 activity.

In one aspect, the invention provides a compound which is an inhibitor of mTorC1/mTorC2 of the Formula I:

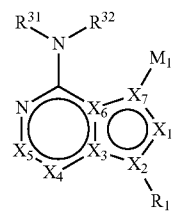

Formula I or a pharmaceutically acceptable salt thereof, wherein:
$X_1$ is N or C-$E^1$, $X_2$ is N or C, $X_3$ is N or C, $X_4$ is C—$R^9$ or N, $X_5$ is N or C-$E^1$, $X_6$ is C or $N_1$ and $X_7$ is C or N; and wherein no more than two nitrogen ring atoms are adjacent;
$R_1$ is H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;
L is absent, —(C═O)—, —C(═O)O—, —C(═O)N($R^{31}$)—, —S—, —S(O)—, —S(O)$_2$—, —S(O)$_2$N($R^{31}$)—, or —N($R^{31}$)—;
$E^1$ and $E^2$ are independently —(W$^1$)$_j$—R$^4$;
$M_1$ is a 5, 6, 7, 8, 9, or -10 membered ring system, wherein the ring system is monocyclic or bicyclic, substituted with $R_5$ and additionally optionally substituted with one or more —(W$^2$)$_k$—R$^2$;
each k is 0 or 1;
j in $E^1$ or j in $E^2$, is independently 0 or 1;
$W^1$ is —O—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2$$R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;
$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2$$R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;
$R^2$ is hydrogen, halogen, —OH, —$R^{31}$, —CF$_3$, —OCF$_3$, —O$R^{31}$, —N$R^{31}$$R^{32}$, —N$R^{34}$$R^{35}$, (O)$R^{31}$, —CO$_2$$R^{31}$, —C(═O)N$R^{31}$$R^{32}$, —C(═O)N$R^{34}$$R^{35}$, —NO$_2$, —CN, —S(O)$_{0-2}$$R^{31}$, —SO$_2$N$R^{31}$$R^{32}$, —SO$_2$N$R^{34}$$R^{35}$, —N$R^{31}$C(═O)$R^{32}$, —N$R^{31}$C(═O)O$R^{32}$, —N$R^{31}$C(═O)N$R^{32}$$R^{33}$, —N$R^{31}$S(O)$_{0-2}$$R^{32}$, —C(═S)O$R^{31}$, —C(═O)S$R^{31}$, —N$R^{31}$C(═N$R^{32}$)N$R^{33}$$R^{32}$, —N$R^{31}$C(═N$R^{32}$)O$R^{33}$, —N$R^{31}$C(═N$R^{32}$)S$R^{33}$, —OC(═O)O$R^{33}$, —OC(═O)N$R^{31}$$R^{32}$, —OC(═O)S$R^{31}$, —SC(═O)O$R^{31}$, —P(O)O$R^{31}$O$R^{32}$, —SC(═O)N$R^{31}$$R^{32}$, aryl (e.g. bicyclic aryl, unsubstituted aryl, or substituted monocyclic aryl), hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocycicyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, (O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —OC(=S)$OR^{31}$, —OC(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(O=O)$OR^{31}$, P(O)$OR^{31}OR^{32}$, —SC(=O)$NR^{31}R^{32}$, aryl, hetaryl, $C_{1-4}$alkyl, $C_{1-10}$alkyl, $C_{3-8}$Cycloalkyl, $C_{1-10}$alkyl-$C_{3-8}$ cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocycicyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, (O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH ($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}$ $C_{1-10}$alkyl, —S(O)$_{0-2}$ $C_{1-10}$alkylaryl, —S(O)$_{0-2}$ aryl, —$SO_2$N(aryl), —$SO_2$ N($C_{1-10}$alkyl)($C_{1-10}$alkyl), —$SO_2$NH($C_{1-10}$alkyl) or —$SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, C(=O)$NR^{34}R^{35}$, —$NO_2$, —CN, —S(O)$_{0-2}$ $C_{1-10}$alkyl, —S(O)$_{0-2}$ aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo $C_{2-10}$alkenyl, halo $C_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$; and R$^9$ is H, halo —OR$^{31}$, —SH, —NH$_2$, —NR$^{34}$, R$^{35}$— NR$^{31}$R$^{32}$, —CO$_2$R$^{31}$, —CO$_2$aryl, —C(=O)NR$^{31}$R$^{32}$, C(=O)NR$^{34}$R$^{35}$, —NO$_2$, —CN, —S(O)$_{0-2}$ C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl; aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, hetaryl-C$_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, halo C$_{2-10}$alkenyl, halo C$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$.

$M_1$ is a 5, 6, 7, 8, 9, or -10 membered ring system, wherein the ring system is monocyclic or bicyclic. The monocyclic $M_1$ ring is unsubstituted or substituted with one or more R$^5$ substituents (including 0, 1, 2, 3, 4, or 5 R$^5$ substituents). In some embodiments, the monocyclic $M_1$ ring is aromatic (including phenyl) or heteroaromatic (including but not limited to pyridinyl, pyrrolyl, imidazolyl, thiazolyl, or pyrimidinyl). The monocyclic $M_1$ ring may be a 5 or 6 membered ring (including but not limited to pyridinyl, pyrrolyl, imidazolyl, thiazolyl, or pyrimidinyl). In some embodiments, $M_2$ is a five membered heteroaromatic group with one heteroatom, wherein the heteroatom is N, S, or O. In another embodiment, $M_2$ is a five membered heteroaromatic group with two heteroatoms, wherein the heteroatoms are nitrogen and oxygen or nitrogen and sulfur.

The bicyclic $M_1$ ring is unsubstituted or substituted with one or more R$^5$ substituents (including 0, 1, 2, 3, 4, 5, 6 or 7 R$^5$ substituents). Bicyclic $M_1$ ring is a 7, 8, 9, or 10 membered aromatic or heteroaromatic. Examples of an aromatic bicyclic $M_1$ ring include naphthyl. In other embodiments the bicyclic $M_1$ ring is heteroaromatic and includes but is not limited to benzothiazolyl, quinolinyl, quinazolinyl, benzoxazolyl, and benzoimidazolyl.

The invention also provides compounds wherein $M_1$ is a moiety having a structure of Formula M1-A or Formula M1-B:

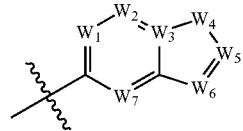

Formula M1-A

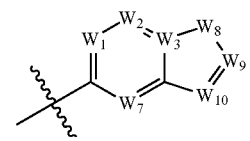

Formula M1-B wherein $W_1$, $W_2$, and $W_7$ are independently N or C—R$^5$; $W_4$ and $W_{10}$ are independently N—R$^5$, O, or S; $W_6$ and $W_8$ are independently N or C—R$^5$; $W_5$ and $W_9$ are independently N or C—R$^2$; and $W_3$ is C or N, provided no more than two N and/or N—R$^5$ are adjacent and no two O or S are adjacent.

In some embodiments of the invention, the $M_1$ moiety of Formula M1-A is a moiety of Formula M1-A1, Formula M1-A2, Formula M1-A3, or Formula M1-A4:

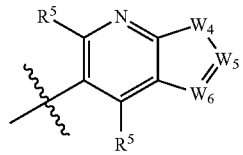

Formula M1-A1

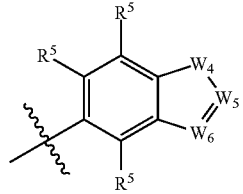

Formula M1-A2

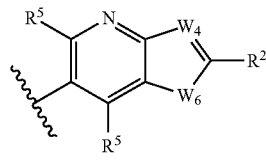

Formula M1-A3

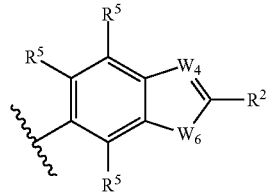

Formula M1-A4 wherein $W_4$ is N—R$^5$, O, or S; $W_6$ is N or C—R$^5$ and $W_5$ is N or C—R$^2$.

Some nonlimiting examples of the $M_1$ moiety of Formula M1-A include:

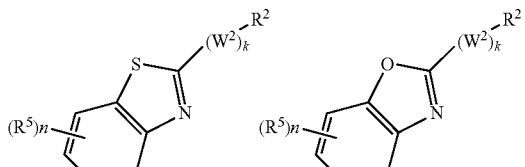

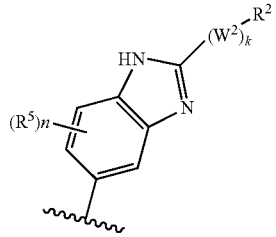

wherein R$^5$ is —(W$^1$)$_k$—R$^{53}$ or R$^{55}$; each k is independently 0 or 1, n is 0, 1, 2, or 3, and (W$^1$)$_k$—R$^{53}$ and R$^{55}$ are as defined above.

In other embodiments of the invention, the $M_1$ moiety of Formula M1-B is a moiety of Formula M1-B1, Formula M1-B2, Formula M1-B3, or Formula M1-B4:

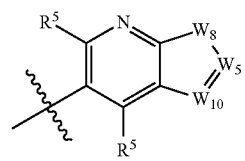
Formula M1-B1

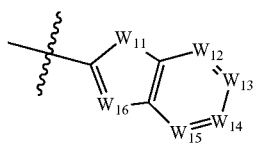
Formula M1-C

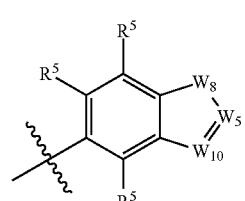
Formula M1-B2

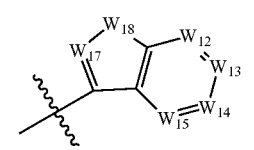
Formula M1-D

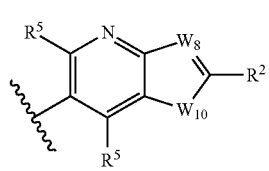
Formula M1-B3 wherein $W_{12}$, $W_{13}$, $W_{14}$, and $W_{15}$ are independently N or C—$R^5$; $W_{11}$ and $W_{18}$ are independently N—$R^5$, O, or S; $W_{16}$ and $W_{17}$ are independently N or C—$R^5$; provided no more than two N are adjacent.

In other embodiments of the invention, the $M_1$ moiety of Formula M1-C or Formula M1-D is a moiety of Formula M1-C1 or Formula M1-D1:

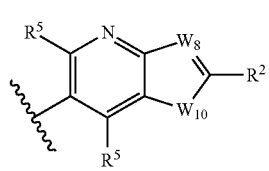
Formula M1-B4

Formula M1-D1

Formula M1-C1

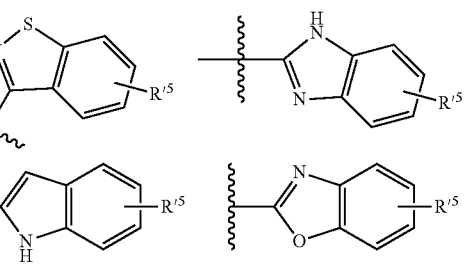

wherein $W_{10}$ is N—$R^5$, O, or S, $W_8$ is N or C—$R^5$, and $W_5$ is N or C—$R^2$.

Some nonlimiting examples of the $M_1$ moiety of Formula M1-B include:

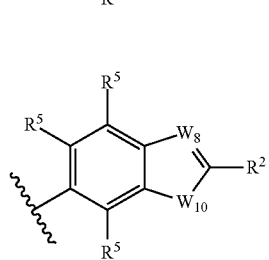

wherein $W_{11}$ and $W_{18}$ are N—$R^5$, O, or S; and $W_{16}$ and $W_{17}$ are N or C—$R^5$.

Some nonlimiting examples of the $M_1$ moiety of Formula M1-C and Formula M1-D include:

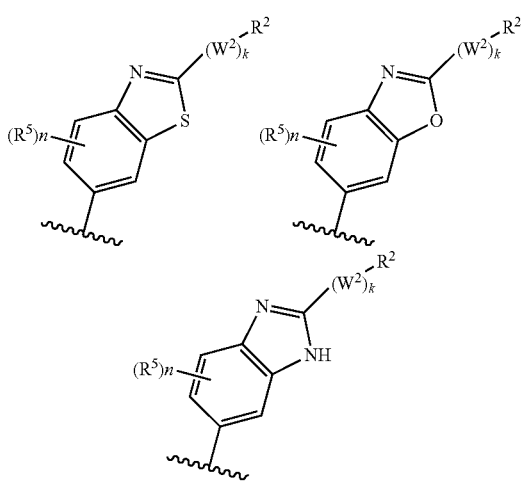

wherein $R'^5$ is $(W^1)_k$—$R^{53}$ or $R^{55}$; k is 0 or 1, n is 0, 1, 2, or 3, and $(W^1)_k$—$R^{53}$ and $R^{55}$ are as defined above.

The invention also provides compounds wherein $M_1$ is a moiety having a structure of Formula M1-C or Formula M1-D:

wherein $R'^5$ is $(W^1)_k$—$R^{53}$ or $R^{55}$; k is 0 or 1, and $(W^1)_k$—$R^{53}$ and $R^{55}$ are as defined above.

The invention also provides compounds wherein $M_1$ is a moiety having a structure of Formula M1-E:

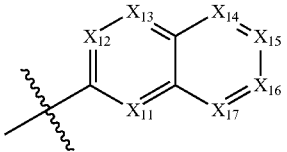

Formula M1-E wherein $X_{11}$, $X_{12}$, $X_{13}$, $X_{14}$, $X_{15}$, $X_{16}$, and $X_{17}$ are independently N, or C—$R^5$; provided that no more than two N are adjacent.

In some embodiments of the invention, the $M_1$ moiety having a structure of Formula M1-E, is a moiety having a structure of Formula M1-E1, M1-E2, M1-E3, M1-E4, M1-E5, M1-E6, M1-E7, or M1-E8:

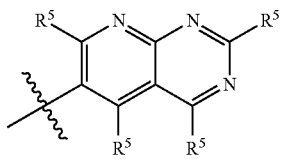

Formula M1-E1

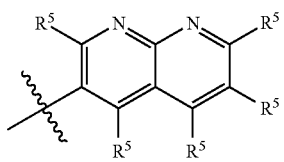

Formula M1-E2

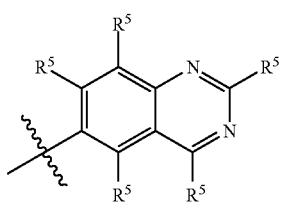

Formula M1-E3

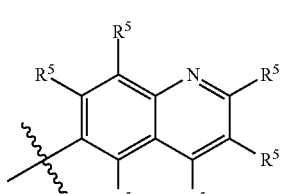

Formula M1-E4

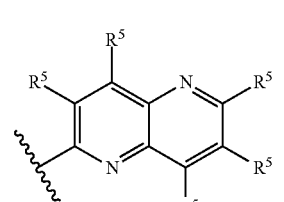

Formula M1-E5

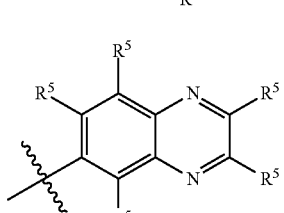

Formula M1-E6

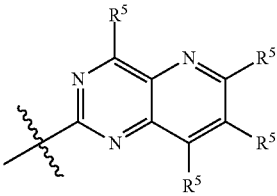

Formula M1-E7

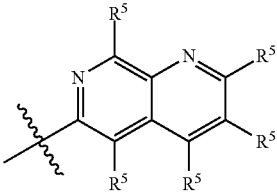

Formula M1-E8

In some embodiments of the invention, the $M_1$ moiety having a structure of Formula M1-E, is a moiety having a structure:

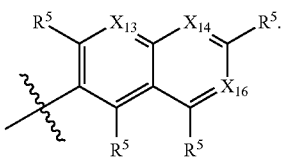

Some nonlimiting examples of the $M_1$ moiety of Formula M1-E include:

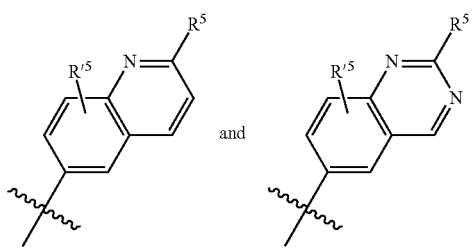

and wherein $R'^5$ is $(W^1)_k$—$R^{53}$ or $R^{55}$; k is 0 or 1, n is 0, 1, 2, or 3, and $(W^1)_k$—$R^{53}$ or $R^{55}$ are as defined above. In some embodiments, k is 0, and $R^5$ is $R^{53}$.

In some embodiments, $R^{53}$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_8$cycloalkyl (which includes but is not limited to cyclopropyl, cyclobutyl, cyclopentyl, and cyclohexyl). In other embodiments, $R^{53}$ is monocyclic or bicyclic aryl, wherein the $R^{53}$ aryl is unsubstituted or substituted. Some examples of aryl include but are not limited to phenyl, naphthyl or fluorenyl. In some other embodiments, $R^{53}$ is unsubstituted or substituted heteroaryl, including but not limited to monocyclic and bicyclic heteroaryl. Monocyclic heteroaryl $R^{53}$ includes but is not limited to pyrrolyl, thienyl, furyl, pyridinyl, pyranyl, imidazolyl, thiazolyl, pyrazolyl, and oxazolyl. Bicyclic heteroaryl $R^{53}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, and purinyl. Additionally, $R^{53}$ may be alkylcycloalkyl (including but not limited to cyclopropylethyl, cyclopentylethyl, and cyclobutylpropyl), -alkylaryl (including but not limited to benzyl, phenylethyl, and phenylnaphthyl), -alkylhetaryl (including but not limited to pyridinylmethyl, pyrrolylethyl, and imidazolylpropyl), or -alkylheterocyclyl (non-limiting examples are morpholinylmethyl, 1-piperazinylmethyl, and azetidinylpropyl). For each of alkylcycloalkyl, alkylaryl, alkylhetaryl, or -alkylheterocyclyl, the moiety is connected to $M_1$ through the alkyl portion of the moiety In other embodiments, $R^{53}$ is unsubstituted or substituted $C_2$-$C_{10}$alkenyl (including but not limited to alkenyl such as, for example, vinyl, allyl, 1-methyl propen-1-yl, butenyl, or pentenyl) or unsubstituted or substituted alkynyl (including but not limited to unsubstituted or substituted $C_2$-$C_{10}$alkynyl such as acetylenyl, propargyl, butynyl, or pentynyl).

Further embodiments provide $R^{53}$ wherein $R^{53}$ is alkenylaryl, alkenylheteroaryl, alkenylheteroalkyl, or alkenylheterocycicyl, wherein each of alkenyl, aryl, heteroaryl, heteroalkyl, and heterocyclyl is as described herein and wherein the alkenylaryl, alkenylhetaryl, alkenylheteroalkyl, or alkenylheterocycicyl moiety is attached to $M_1$ through the alkenyl. Some nonlimiting examples in include styryl, 3-pyridinylallyl, 2-methoxyethoxyvinyl, and 3-morpholinlylallyl In other embodiments, $R^{53}$ is -alkynylaryl, -alkynylhetaryl, -alkynylheteroalkyl, -alkynylheterocylyl, -alkynylcycloalkyl, or -alkynyl$C_{3-8}$cycloalkenyl, wherein each of alkynyl, aryl, heteroaryl, heteroalkyl, and heterocyclyl is as described herein and wherein the alkynylaryl, alkynylhetaryl, alkynylheteroalkyl, or alkynylheterocycicyl moiety is attached to $M_1$ through the alkynyl. Alternatively, $R^{53}$ is -alkoxyalkyl, -alkoxyalkenyl, or -alkoxyalkynyl, wherein each of alkoxy, alkyl, alkenyl, and alkynyl is as described herein and wherein the -alkoxyalkyl, -alkoxyalkenyl, or -alkoxyalkynyl moiety is attached to $M_1$ through the alkoxy. In yet other embodiments, $R^{53}$ is -heterocyclylalkyl, -heterocyclylalkenyl, or -heterocyclylalkynyl, wherein the heterocyclyl, alkyl, alkenyl, or alkynyl is as described herein and wherein the -heterocyclylalkyl, -heterocyclylalkenyl, or -heterocyclylalkynyl is attached to $M_1$ through the heterocyclyl portion of the moiety. Further, $R^{53}$ may be aryl-alkenyl, aryl-alkynyl, or aryl-heterocyclyl, wherein the aryl, alkenyl, alkynyl, or heterocyclyl is as described herein and wherein the aryl-alkenyl, aryl-alkynyl, or aryl-heterocyclyl moiety is attached to $M_1$ through the aryl portion of the moiety. In some other embodiments, $R^{53}$ is heteroaryl-alkyl, heteroaryl-alkenyl, heteroaryl-alkynyl, heteroaryl-cycloalkyl, heteroaryl-heteroalkyl, or heteroaryl-heterocyclyl, wherein each of heteroaryl, alkyl, alkenyl, alkynyl, cycloalkyl, heteroalkyl, and heterocyclyl is as described herein and wherein the heteroaryl-alkyl, heteroaryl-alkenyl, heteroaryl-alkynyl, heteroaryl-cycloalkyl, heteroaryl-heteroalkyl, or heteroaryl-heterocyclyl moiety is attached to $M_1$ through the heteroaryl portion of the moiety.

For each of the aryl or heteroaryl moieties forming part or all of $R^{53}$, the aryl or heteroaryl is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NNR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$ substituents. Additionally, each of the alkyl, cycloalkyl, heterocyclyl, or heteroalkyl moieties forming part of all of $R^{53}$ is unsubstituted or substituted with one or more halo, —OH, —$R^{31}$, —$CF_3$, —$OCF_3$, —$OR^{31}$, —O-aryl, —N=N, —C(O)$R^{31}$, —$CO_2R^{31}$, —C(=O)$NNR^{34}R^{35}$, or —C(=O)$NR^{31}R^{32}$ substituents.

In other embodiments, $R^5$ is —$W^1$—$R^{53}$. In some embodiments, $R^5$ is —$OR^{53}$, including but not limited to Oalkyl (including but not limited to methoxy or ethoxy), —Oaryl (including but not limited to phenoxy), —O-heteroaryl (including but not limited to pyridinoxy) and —O-heterocycloxy(including but not limited to 4-N-piperidinoxy). In some embodiments $R^5$ is —$NR^6R^{53}$ including but not limited to anilinyl, diethylamino, and 4-N-piperidinylamino. In yet other embodiments $R^5$ is —$S(O)_{0-2}R^{53}$, including but not limited to phenylsulfonyl and pyridinylsulfonyl. The invention also provides compounds wherein $R^5$ is —C(O) (including but not limited to acetyl, benzoyl, and pyridinoyl) or —C(O)O $R^{53}$ (including but not limited to carboxyethyl, and carboxybenzyl). In other embodiments, $R^5$ is —C(O)N($R^6$)$R^{53}$ (including but not limited to C(O)NH(cyclopropyl) and C(O)N(Me)(phenyl)) or —CH($R^6$)N($R^7$)$R^{53}$ (including but not limited to —$CH_2$—NH-pyrrolidinyl, $CH_2$—NHcyclopropyl, and $CH_2$-anilinyl). Alternatively, $R^5$ is —N($R^6$)C(O) $R^{53}$ (including but not limited to —NHC(O)phenyl, —NHC(O)cyclopentyl, and to —NHC(O)piperidinyl) or —N($R^6$)S(O)$_2$ $R^{53}$ (including but not limited to —NHS(O)$_2$-phenyl, —NHS(O)$_2$piperazinyl, and —NHS(O)$_2$-methyl. Additionally, $R^5$ is —N($R^6$)S(O)$R^{53}$, —CH($R^6$)N(C(O)$OR^7$)$R^{53}$, —CH($R^7$)N(C(O)$R^7$)$R^{53}$, —CH($R^6$)N($SO_2R^7$)$R^{53}$, —CH($R^6$)N($R^7$)$R^{53}$, —CH($R^6$)C(O)N($R^7$)$R^{53}$, —CH($R^6$)N($R^7$)C(O)$R^{53}$, —CH($R^6$)N($R^7$)S(O)$R^{53}$, or —CH($R^6$)N($R^7$)S(O)$_2$ $R^{53}$.

Alternatively, $R^5$ is $R^{55}$. $R^{55}$ is halo, —OH, —$NO_2$, —$CF_3$, —$OCF_3$, or —CN. In some other embodiments, $R^{55}$ is —$R^{31}$, —$OR^{31}$ (including but not limited to methoxy, ethoxy, and butoxy)-C(O)$R^{31}$ (non-limiting examples include acetyl, propionyl, and pentanoyl), or —$CO_2R^{31}$ (including but not limited to carboxymethyl, carboxyethyl and carboxypropyl). In further embodiments, $R^{55}$ is —$NR^{31}R^{32}$, —C(=O)$NR^{31}R^{32}$, —$SO_2NR^{31}R^{32}$, or —$S(O)_{0-2}R^{31}$. In other embodiments, $R^{55}$ is —$NR^{34}R^{35}$ or —$SO_2$ $NR^{34}R^{35}$, wherein $R^{34}R^{35}$ are taken together with the nitrogen to which $R^{34}R^{35}$ are attached to form a cyclic moiety. The cyclic moiety so formed may be unsubstituted or substituted, wherein the substituents are selected from the group consisting of alkyl, —C(O)alkyl, —S(O)$_2$alkyl, and —S(O)$_2$aryl. Examples include but are not limited to morpholinyl, piperazinyl, or —$SO_2$—(4-N-methyl-piperazin-1-yl. Additionally, $R^{55}$ is —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32}$, —$NR^{31}C(NR^{32})OR^{33}$, —$NR^{31}C(=NR^{32})SR^{33}$, —OC(=O)$OR^{33}$, —OC(=O)$NR^{31}R^{32}$, —C(=O)$NNR^{34}R^{35}$, —OC(=O)$SR^{31}$, —SC(=O)$OR^{31}$, —P(O)$OR^{31}OR^{32}$, or —SC(=O)$NR^{31}R^{32}$. In yet another embodiment, $R^{55}$ is —O-aryl, including but not limited to phenoxy, and naphthyloxy.

The invention further provides a compound which is an mTorC1/mTorC2 inhibitor, wherein the compound has the Formula I-A:

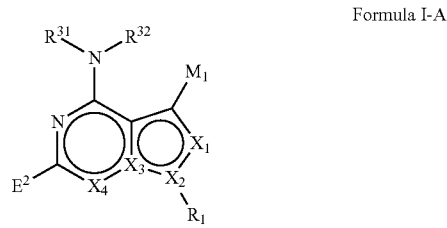

Formula I-A or a pharmaceutically acceptable salt thereof, wherein:
$X_1$ is N or C-$E^1$, $X_2$ is N, $X_3$ is $C_1$ and $X_4$ is C—$R^9$ or N; or
$X_1$ is N or C-$E^1$, $X_2$ is C, $X_3$ is $N_1$ and $X_4$ is C—$R^9$ or N;

R₁ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylheteroaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$M_1$ is a moiety having the structure of Formula M1-F1 or M1-F2:

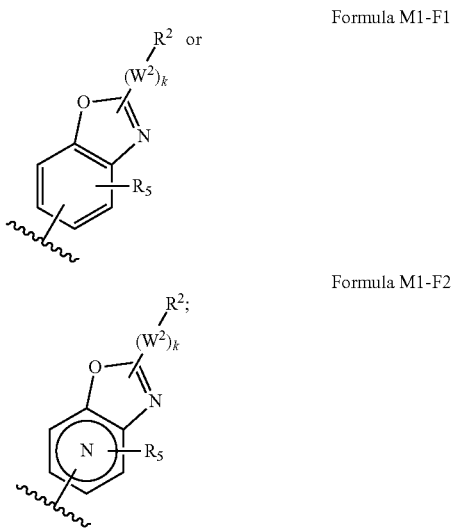

Formula M1-F1

Formula M1-F2 k is 0 or 1;
$E^1$ and $E^2$ are independently —$(W^1)_j$—$R^4$;
j, in each instance (i.e., in $E^1$ or j in $E^2$), is independently 0 or 1
$W^1$ is —O—, —$NR^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —$NR^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^2$ is hydrogen, halogen, —OH, —$R^{31}$, —CF$_3$, —OCF$_3$, —O$R^{31}$, —N$R^{31}R^{32}$, —N$R^{34}R^{35}$, (O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}O^{32}$, —SC(=O)N$R^{31}R^{32}$, aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{1-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenylheteroalkyl, $C_{2-10}$alkenylheterocycicyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —OC(=S)O$R^{31}$, —C(=O)S$R^{31}$, —N$R^{31}$C(=N$R^{32}$)N$R^{33}R^{32}$, —N$R^{31}$C(=N$R^3$)O$R^{33}$, —N$R^{31}$C(=N$R^3$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}O^{32}$, or —SC(=O)N$R^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(=O)N$R^{34}R^{35}$, or —C(=O)N$R^{31}R^{32}$;

$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —OC(=S)O$R^{31}$, —OC(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}O^{32}$, —SC aryl, heteroaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenylheteroalkyl, $C_{2-10}$alkenylheterocycicyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl- $C_{2-10}$alkynyl, aryl-$C_{1-10}$alkyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroalkyl, heteroaryl-heteroalkyl, or heteroaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —N—C(O)$R^{31}$, —$CO_2R^{31}$, —C(=O)$NR^{31}R^{32}$, —C(=O)$NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32}$, —N—$NR^{31}C(=NR^{32})SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, (O)$R^{31}$, —$CO_2R^{31}$, —C(=O)$NR^{31}R^{32}$, —C(=O)$NR^{34}R^{35}$, —$NO_2$, —CN, —$S(O)_{0-2}R^{31}$—$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group, wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl)$(C_{1-10}$alkyl), —NH$(C_{1-10}$alkyl), —NH(aryl), —$NR^{34}R^{35}$, —C(O)$(C_{1-10}$alkyl), —C(O)$(C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)$N(C_{1-10}$alkyl)$(C_{1-10}$alkyl), —C(=O)$NH(C_{1-10}$alkyl), —C(=O)$NR^{34}R^{35}$, —C(=O)$NH_2$, —$OCF_3$, —O($C_{1-10}$alkyl), —O-aryl, —N(aryl)$(C_{1-10}$alkyl), —$NO_2$, —CN, —$S(O)_{0-2}$ $C_{1-10}$alkyl, —$S(O)_{0-2}$ $C_{1-10}$alkylaryl, —$S(O)_{0-2}$ aryl, —$SO_2N(aryl)$, —$SO_2$ $N(C_{1-10}$alkyl)$(C_{1-10}$alkyl), —$SO_2$ $NH(C_{1-10}$alkyl) or —$SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, C(=O)$NR^{34}R^{35}$, —$NO_2$, —CN, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo $C_{2-10}$alkenyl, halo $C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, C(=O)$NR^{34}R^{35}$, —$NO_2$, —CN, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo $C_{2-10}$alkenyl, halo $C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$.

In some embodiments, $X_4$ is C—$R^9$.

The invention also provides an inhibitor as defined above, wherein the compound is of Formula I:

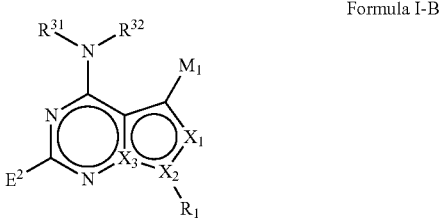

Formula I-B or a pharmaceutically acceptable salt thereof, and wherein the substituents are as defined above.

In various embodiments the compound of Formula I-B or its pharmaceutically acceptable salt thereof, is a compound having the structure of Formula I-B1 or Formula I-B2:

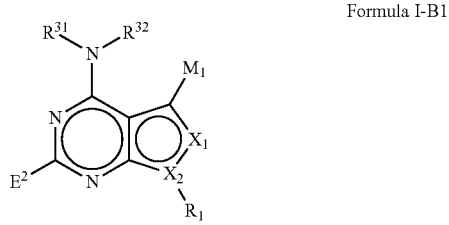

Formula I-B1

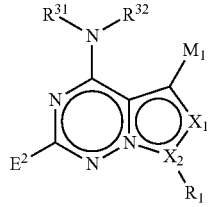

Formula I-B2 or a pharmaceutically acceptable salt thereof.

In various embodiments of Formula I-B1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In various embodiments of Formula I-B2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —$S(O)_{0-2}$—. In various embodiments of $X_1$, j is 1, and $W^1$ is —C(O)—. In various embodiments of $X_1$, j is 1, and $W^1$ is —C(O)N($R^7$)—. In various embodiments of $X_1$, j is 1, and $W^1$ is —N($R^7$)C(O)—. In various embodiments of $X_1$, j is 1, and $W^1$ is —N($R^7$)S(O)—. In various embodiments of $X_1$, j is 1, and $W^1$ is —N($R^7$)S(O)$_2$—. In various embodiments of $X_1$, j is 1, and $W^1$ is —C(O)O—. In various embodiments of $X_1$, j is 1, and $W^1$ is CH($R^7$)N(C(O)O$R^8$)—. In various embodiments of $X_1$, j is 1, and $W^1$ is —CH($R^7$)N(C(O)$R^8$)—. In various embodiments of $X_1$, j is 1, and $W^1$ is —CH($R^7$)N(SO$_2$$R^8$)—. In various embodiments of $X_1$, j is 1, and $W^1$ is —CH($R^7$)N($R^8$)—. In various embodiments of $X_1$, j is 1, and $W^1$ is —CH($R^7$)C(O)N($R^8$)—. In various embodiments of $X_1$, j is 1, and $W^1$ is —CH($R^7$)N($R^8$)C(O)—. In various embodiments of $X_1$, j is 1, and $W^1$ is —CH($R^7$)N($R^8$)S(O)—. In various embodiments of $X_1$, j is 1, and $W^1$ is —CH($R^7$)N($R^8$)S(O)$_2$—.

In another embodiment, $X_1$ is CH$_2$. In yet another embodiment, $X_1$ is CH-halogen, where halogen is Cl, F, Br, or I.

In another embodiment, $X_1$ is N.

In various embodiments, $X_2$ is N. In other embodiments, $X_2$ is C.

In various embodiments, $E^2$ is —$(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is —$(W^1)_j$—$R^4$. In various embodiments of $E^2$, j is 1, and $W^1$ is —O—. In various embodiments of $E^2$, j is 1, and $W^1$ is —$NR^7$—. In various embodiments of $E^2$, j is 1, and $W^1$ is —NH—. In various embodiments of $E^2$, j is 1, and $W^1$ is —$S(O)_{0-2}$—. In various embodiments of $E^2$, j is 1, and $W^1$ is —C(O)—. In various embodiments of $E^2$, j is 1, and $W^1$ is —C(O)N($R^7$)—. In various embodiments of $E^2$, j is 1, and $W^1$ is —N($R^7$)C(O)—. In various embodiments of $E^2$, j is 1, and $W^1$ is —N($R^7$)S(O)—. In various embodiments of $E^2$, j is 1, and $W^1$ is —N($R^7$)S(O)$_2$—. In various embodiments of $E^2$, j is 1, and $W^1$ is —C(O)O—. In various embodiments of $E^2$, j is 1, and $W^1$ is CH($R^7$)N(C(O)O$R^8$)—. In various embodiments of $E^2$, j is 1, and $W^1$ is —CH($R^7$)N(C(O)$R^8$)—. In various embodiments of $E^2$, j is 1, and $W^1$ is —CH($R^7$)N(SO$_2$$R^8$)—. In various embodiments of $E^2$, j is 1, and $W^1$ is —CH($R^7$)N($R^8$)—. In various embodiments of $E^2$, j is 1, and $W^1$ is —CH($R^7$)C(O)N($R^8$)—. In various embodiments of $E^2$, j is 1, and $W^1$ is —CH($R^7$)N($R^8$)C(O)—. In various embodiments of $E^2$, j is 1, and $W^1$ is —CH($R^7$)N($R^8$)S(O)—. In various embodiments of $E^2$, j is 1, and $W^1$ is —CH($R^7$)N($R^8$)S(O)$_2$—.

In various embodiments when $M_1$ is a moiety of Formula M1-F1, $M_1$ is benzoxazolyl substituted with —$(W_2)_k$—$R_2$. In some embodiments, $M_1$ is a benzoxazolyl substituted at the 2-position with —$(W^2)_j$—$R^2$. In some embodiments, $M_1$ is either a 5-benzoxazolyl or a 6-benzoxazolyl moiety, optionally substituted at the 2-position with —$(W^2)_j$—$R^2$. Exemplary Formula M1-F1 $M_1$ moieties include but are not limited to the following:

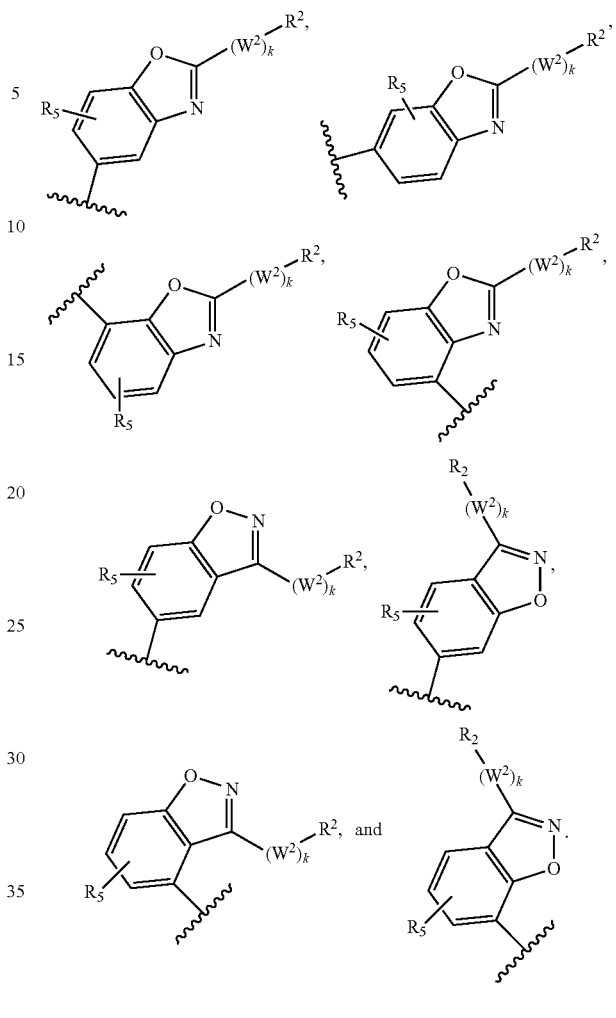

In various embodiments when $M_1$ is a moiety of Formula M1-F2, Formula M1-F2 is an aza-substituted benzoxazolyl moiety having a structure of one of the following formulae:

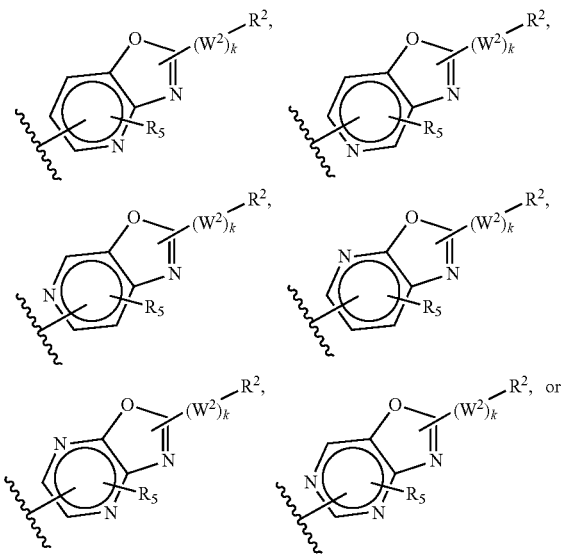

-continued

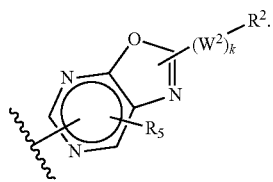

Exemplary Formula M1-F2 $M_1$ moieties include but are not limited to the following:

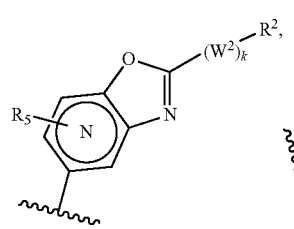

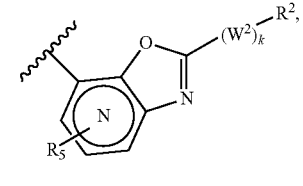 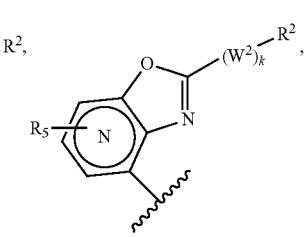

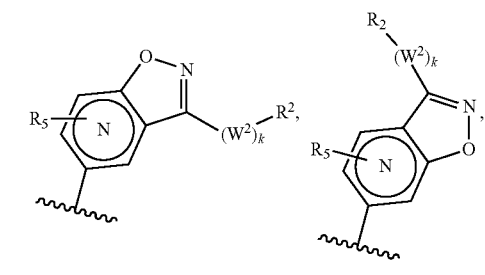

In various embodiments of $M_1$, k is O. In other embodiments of $M_1$, k is 1, and $W^2$ is selected from one of the following: —O—, —$NR^7$—, —$S(O)_{0-2}$—, —C(O)—, —C(O)N($R^7$)—, —N($R^7$)C(O)—, or —N($R^7$)C(O)N($R^8$)—. In yet another embodiment of $M_1$, k is 1, and $W^2$ is —N($R^7$)S(O)—, —N($R^7$)S(O)$_2$—, —C(O)O—, —CH($R^7$)N(C(O)O$R^8$)—, —CH($R^7$)N(C(O)$R^8$)—, or —CH($R^7$)N(SO$_2R^8$)—. In a further embodiment of $M_1$, k is 1, and $W^2$ is —CH($R^7$)N($R^8$)—, —CH($R^7$)C(O)N($R^8$)—, —CH($R^7$)N($R^8$)C(O)—, or —CH($R^7$)N($R^8$)S(O)—. In yet another embodiment of $M_1$, k is 1, and $W^2$ is —CH($R^7$)N($R^8$)S(O)$_2$—.

The invention provides an inhibitor of mTor which is a compound of Formula I-C or Formula I-D:

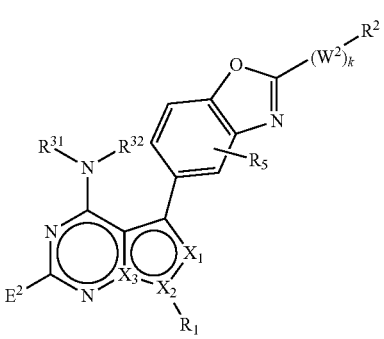

Formula I-C

Formula I-D or a pharmaceutically acceptable salt thereof, wherein $X_1$ is N or C-$E^1$, $X_2$ is $N_1$ and $X_3$ is C; or $X_1$ is N or C-$E^1$, $X_2$ is $C_1$ and $X_3$ is N;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkyl-heteroaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$ alkynyl-$C_{3-8}$cycloalkyl, -L-heteroalkyl, -L-heteroalkylaryl, -L-heteroalkylheteroaryl, -L-heteroalkyl-heterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$E^1$ and $E^2$ are independently —($W^1$)$_j$—$R^4$;
j in $E^1$ or j in $E^2$, is independently 0 or 1;

$W^1$ is —O—, —$NR^7$—, —$S(O)_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —$NR^7$—, —$S(O)_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

k is 0 or 1;

$R^2$ is hydrogen, halogen, —OH, —$R^{31}$, —$CF_3$, —$OCF_3$, —$OR^{31}$, —$NR^{31}R^{32}$, —$NR^{34}R^{35}$, (O)$R^{31}$, —$CO_2R^{31}$, —C(=O)$NR^{31}R^{32}$, —C(=O)$NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, aryl (e.g. bicyclic aryl, unsubstituted aryl, or substituted monocyclic aryl), heteroaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl (e.g. C$_{2-10}$alkyl-monocyclic aryl, C$_{1-10}$alkyl-substituted monocyclic aryl, or C$_{1-10}$alkylbicycloaryl), C$_{1-10}$alkylheteroaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylheteroaryl, C$_{2-10}$alkenylheteroalkyl, C$_{2-10}$alkenylheterocyclyl, C$_{2-10}$alkenyl-C$_{3-8}$cycloalkyl, C$_{2-10}$alkynylaryl, C$_{2-10}$alkynylheteroaryl, C$_{2-10}$alkynylheteroalkyl, C$_{2-10}$alkynylheterocyclyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl-C$_{1-10}$alkyl, heterocyclyl-C$_{2-10}$alkenyl, heterocyclyl-C$_{2-10}$alkynyl, aryl-C$_{1-10}$alkyl (e.g. monocyclic aryl-C$_{2-10}$alkyl, substituted monocyclic aryl-C$_{1-10}$alkyl, or bicycloaryl-C$_{1-10}$alkyl), aryl-C$_{2-10}$alkenyl, aryl-C$_{2-10}$alkynyl, aryl-heterocyclyl, heteroaryl-C$_{1-10}$alkyl, heteroaryl-C$_{2-10}$alkenyl, heteroaryl-C$_{2-10}$alkynyl, heteroaryl-C$_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$ s, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR—NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^3$ and R$^4$ are independently hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —OC(=S)OR$^{31}$, —OC(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC aryl, heteroaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl, C$_{1-10}$alkylheteroaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylheteroaryl, C$_{2-10}$alkenylheteroalkyl, C$_{2-10}$alkenylheterocycicyl, C$_{2-10}$alkenyl-C$_{3-8}$cycloalkyl, C$_{2-10}$alkynylaryl, C$_{2-10}$alkynylheteroaryl, C$_{2-10}$alkynylheteroalkyl, C$_{2-10}$alkynylheterocyclyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl-C$_{1-10}$alkyl, heterocyclyl-C$_{2-10}$alkenyl, heterocyclyl-C$_{2-10}$alkynyl, aryl-C$_{1-10}$alkyl, aryl-C$_{2-10}$alkenyl, aryl-C$_{2-10}$alkynyl, aryl-hetero cyclyl, heteroaryl-C$_{1-10}$alkyl, heteroaryl-C$_{2-10}$alkenyl, heteroaryl-C$_{2-10}$alkynyl, heteroaryl-C$_{3-8}$cycloalkyl, heteroaryl-heteroalkyl, or heteroaryl-heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR—NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^5$ is hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$;

R$^{31}$, R$^{32}$, and R$^{33}$, in each instance, are independently H or C$_{1-10}$alkyl, wherein the C$_{1-10}$alkyl is unsubstituted or is substituted with one or more aryl, heteroalkyl, heterocyclyl, or heteroaryl group, wherein each of said aryl, heteroalkyl, heterocyclyl, or heteroaryl group is unsubstituted or is substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$ alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$ C$_{1-10}$alkyl, —S(O)$_{0-2}$ C$_{1-10}$alkylaryl, —S(O)$_{0-2}$ aryl, —SO$_2$N(aryl), —SO$_2$ N(C$_{1-10}$alkyl)(C$_{1-10}$ alkyl), —SO$_2$ NH(C$_{1-10}$alkyl) or —SO$_2$NR$^{34}$R$^{35}$;

R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, heteroaryl, C$_{1-6}$alkyl, or O-aryl, and wherein said 3-10 membered saturated or unsaturated ring independently contains 0, 1, or 2 more heteroatoms in addition to the nitrogen atom; and R$^7$ and R$^8$ are each independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$; and R$^6$ is halo, —OR$^{31}$, —SH, NH$_2$, —NR$^{34}$R$^{35}$, —NR$^{31}$R$^{32}$, —CO$_2$R$^{31}$, —CO$_2$aryl, —C(=O)NR$^{31}$R$^{32}$, —C(=O)NR$^{34}$R$^{35}$, —NO$_2$, —CN, —S(O)$_{0-2}$ C$_{1-10}$alkyl, —S(O)$_{0-2}$ aryl, —SO$_2$NR$^{34}$R$^{35}$, —SO$_2$NR$^{31}$R$^{32}$, C$_{1-10}$alkyl, C$_{2-10}$alkenyl, or C$_{2-10}$alkynyl; or R$^6$ is aryl-C$_{1-10}$alkyl, aryl-C$_{2-10}$alkenyl, aryl-C$_{2-10}$alkynyl, heteroaryl-C$_{1-10}$alkyl, heteroaryl- $C_{2-10}$alkenyl, heteroaryl-$C_{2-10}$alkynyl, each of which is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)N$R^{31}R^{32}$, —C(=O)N$R^{34}R^{35}$, —SO$_2$N$R^{34}R^{35}$, —SO$_2$ N$R^{31}R^{32}$, —N$R^{31}R^{32}$, or —N$R^{34}R^{35}$.

In various embodiments of the compound of Formula I-C, the compound has a structure of Formula I-C1 or Formula I-C2:

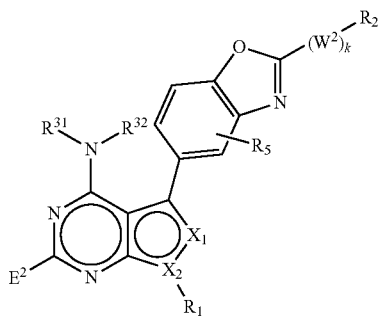

Formula I-C1

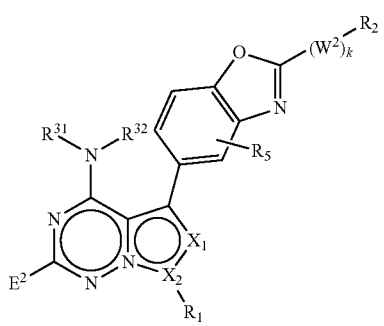

Formula I-C2 or a pharmaceutically acceptable salt thereof.

In some embodiments of Formula I-C1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In several embodiments of Formula I-C2, $X_1$ is N and $X_2$ is C. In yet other embodiments, $X_1$ is NH and $X_2$ is C. In further embodiments, $X_1$ is CH-$E^1$ and $X_2$ is C.

In various embodiments of the compound of Formula I-D, the compound has a structure of Formula I-D1 or Formula I-D2:

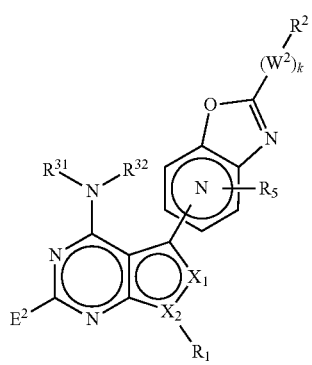

Formula I-D1

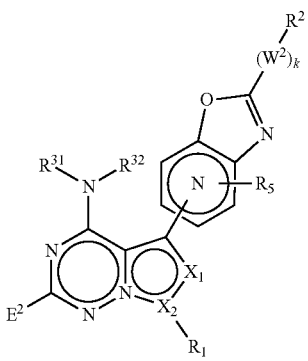

Formula I-D2 or a pharmaceutically acceptable salt thereof.

In some embodiments of Formula I-D1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In several embodiments of Formula I-D2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —N$R^7$—. In various embodiments of $X_1$, j is 1, and $W^1$ is —NH—. In various embodiments of $X_1$, j is 1, and $W^1$ is —S(O)$_{0-2}$—. In various embodiments of $X_1$, j is 1, and $W^1$ is —C(O)—. In various embodiments of $X_1$, j is 1, and $W^1$ is —C(O)N($R^7$)—. In various embodiments of $X_1$, j is 1, and $W^1$ is —N($R^7$)C(O)—. In various embodiments of $X_1$, j is 1, and $W^1$ is —N($R^7$)S(O)—. In various embodiments of $X_1$, j is 1, and $W^1$ is —N($R^7$)S(O)$_2$—. In various embodiments of $X_1$, j is 1, and $W^1$ is —C(O)O—. In various embodiments of $X_1$, j is 1, and $W^1$ is CH($R^7$)N(C(O)O$R^8$)—. In various embodiments of $X_1$, j is 1, and $W^1$ is —CH($R^7$)N(C(O)$R^8$)—. In various embodiments of $X_1$, j is 1, and $W^1$ is —CH($R^7$)N(SO$_2$$R^8$)—. In various embodiments of $X_1$, j is 1, and $W^1$ is —CH($R^7$)N($R^8$)—. In various embodiments of $X_1$, j is 1, and $W^1$ is —CH($R^7$)C(O)N($R^8$)—. In various embodiments of $X_1$, j is 1, and $W^1$ is —CH($R^7$)N($R^8$)C(O)—. In various embodiments of $X_1$, j is 1, and $W^1$ is —CH($R^7$)N($R^8$)S(O)—. In various embodiments of $X_1$, j is 1, and $W^1$ is —CH($R^7$)N($R^8$)S(O)$_2$—.

In various embodiments, $X_1$ is CH—$(W^1)_j$—$R^4$, where j is 0.

In another embodiment, $X_1$ is CH$_2$. In yet another embodiment, $X_1$ is CH-halogen, where halogen is Cl, F, Br, or I.

In various embodiments of $X_1$, it is CH—$(W^1)_j$—$R^4$. In various embodiments of $X_1$, j is 1, and $W^1$ is —O—. In various embodiments of $X_1$, j is 1, and $W^1$ is —N$R^7$—. In various embodiments of $X_1$, j is 1, and $W^1$ is —NH—. In various embodiments of $X_1$, j is 1, and $W^1$ is —S(O)$_{0-2}$—. In various embodiments of $X_1$, j is 1, and $W^1$ is —C(O)—. In various embodiments of $X_1$, j is 1, and $W^1$ is —C(O)N($R^7$)—. In various embodiments of $X_1$, j is 1, and $W^1$ is —N($R^7$)C(O)—. In various embodiments of $X_1$, j is 1, and $W^1$ is —N(R⁷)S(O)—. In various embodiments of X₁, j is 1, and W¹ is —N(R⁷)S(O)₂—. In various embodiments of X₁, j is 1, and W¹ is —C(O)O—. In various embodiments of X₁, j is 1, and W¹ is CH(R⁷)N(C(O)OR⁸)—. In various embodiments of X₁, j is 1, and W¹ is —CH(R⁷)N(C(O)R⁸)—. In various embodiments of X₁, j is 1, and W¹ is —CH(R⁷)N(SO₂R⁸)—. In various embodiments of X₁, j is 1, and W¹ is —CH(R⁷)N(R⁸)—. In various embodiments of X₁, j is 1, and W¹ is —CH(R⁷)C(O)N(R⁸)—. In various embodiments of X₁, j is 1, and W¹ is —CH(R⁷)N(R⁸)C(O)—. In various embodiments of X₁, j is 1, and W¹ is —CH(R⁷)N(R⁸)S(O)—. In various embodiments of X₁, j is 1, and W¹ is —CH(R⁷)N(R⁸)S(O)₂—.

In another embodiment, X₁ is N.

In various embodiments, X₂ is N. In other embodiments, X₂ is C.

In various embodiments, E² is —(W¹)ⱼ—R⁴, where j is 0.

In another embodiment, E² is CH. In yet another embodiment, E² is C-halogen, where halogen is Cl, F, Br, or I.

In various embodiments of E², it is —(W¹)ⱼ—R⁴. In various embodiments of E², j is 1, and W¹ is —O—. In various embodiments of E², j is 1, and W¹ is —NR⁷—. In various embodiments of E², j is 1, and W¹ is —NH—. In various embodiments of E², j is 1, and W¹ is —S(O)₀₋₂—. In various embodiments of E², j is 1, and W¹ is —C(O)—. In various embodiments of E², j is 1, and W¹ is —C(O)N(R⁷)—. In various embodiments of E², j is 1, and W¹ is —N(R⁷)C(O)—. In various embodiments of E², j is 1, and W¹ is —N(R⁷)S(O)—. In various embodiments of E², j is 1, and W¹ is —N(R⁷)S(O)₂—. In various embodiments of E², j is 1, and W¹ is —C(O)O—. In various embodiments of E², j is 1, and W¹ is CH(R⁷)N(C(O)OR⁸)—. In various embodiments of E², j is 1, and W¹ is —CH(R⁷)N(C(O)R⁸)—. In various embodiments of E², j is 1, and W¹ is —CH(R⁷)N(SO₂R⁸)—. In various embodiments of E², j is 1, and W¹ is —CH(R⁷)N(R⁸)—. In various embodiments of E², j is 1, and W¹ is —CH(R⁷)C(O)N(R⁸)—. In various embodiments of E², j is 1, and W¹ is —CH(R⁷)N(R⁸)C(O)—. In various embodiments of E², j is 1, and W¹ is —CH(R⁷)N(R⁸)S(O)—. In various embodiments of E², j is 1, and W¹ is —CH(R⁷)N(R⁸)S(O)₂—.

In various embodiments, k is 0. In other embodiments, k is 1 and W² is —O—. In another embodiment, k is 1 and W² is —NR⁷—. In yet another embodiment of, k is 1, and W² is —S(O)₀₋₂—. In another embodiment of, k is 1 and W² is —C(O)—. In a further embodiment, k is 1 and W² is —C(O)N(R⁷)—. In another embodiment, k is 1, and W² is —N(R⁷)C(O)—. In another embodiment, k is 1 and W² is —N(R⁷)C(O)N(R⁸)—. In yet another embodiment, k is 1 and W² is —N(R⁷)S(O)—. In still yet another embodiment, k is 1 and W² is —N(R⁷)S(O)₂—. In a further embodiment, k is 1 and W² is C(O)O. In another embodiment, k is 1 and W² is —CH(R⁷)N(C(O)OR⁸)—. In another embodiment, k is 1 and W² is —CH(R⁷)N(C(O)R⁸)—. In another embodiment, k is 1 and W² is —CH(R⁷)N(SO₂R⁸)—. In a further embodiment, k is 1 and W² is —CH(R⁷)N(R⁸)—. In another embodiment, k is 1 and W² is —CH(R⁷)C(O)N(R⁸)—. In yet another embodiment, k is 1 and W² is —CH(R⁷)N(R⁸)C(O)—. In another embodiment, k is 1 and W² is —CH(R⁷)N(R⁸)S(O)—. In yet another embodiment, k is 1 and W² is —CH(R⁷)N(R⁸)S(O)₂—.

The invention also provides a compound which is an mTorC1/mTorC2 inhibitor of Formula I-E:

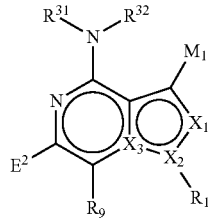

Formula I-E or a pharmaceutically acceptable salt thereof, wherein: $X_1$ is N or C-E¹, $X_2$ is $N_1$ and $X_3$ is C; or $X_1$ is N or C-E¹, $X_2$ is $C_1$ and $X_3$ is N;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylheteroaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkylheterocyclyl, -L-heteroalkyl-$C_{3-8}$cycloalkyl, -L-aralkyl, -L-heteroaralkyl, or -L-heterocyclyl, each of which is unsubstituted or is substituted by one or more independent R³;

L is absent, —(C=O)—, —C(=O)O—, —C(=O)N(R³¹)—, —S—, —S(O)—, —S(O)₂—, —S(O)₂N(R³¹)—, or —N(R³¹)—;

M₁ is a moiety having the structure of Formula M1-F1 or Formula M1-F2:

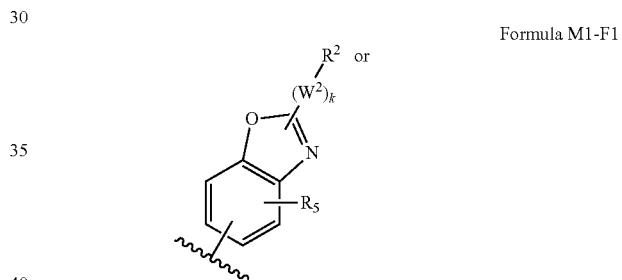

Formula M1-F1

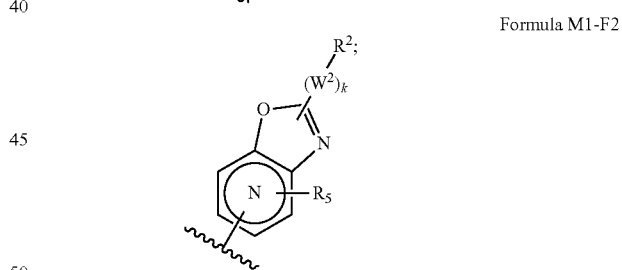

Formula M1-F2 k is 0 or 1;
E¹ and E² are independently —(W¹)ⱼ—R⁴;
j in E¹ or j in E², is independently 0 or 1;
W¹ is —O—, —NR⁷—, —S(O)₀₋₂—, —C(O)—, —C(O)N(R⁷)—, —N(R⁷)C(O)—, —N(R⁷)S(O)—, —N(R⁷)S(O)₂—, —C(O)O—, —CH(R⁷)N(C(O)OR⁸)—, —CH(R⁷)N(C(O)R⁸)—, —CH(R⁷)N(SO₂R⁸)—, —CH(R⁷)N(R⁸)—, —CH(R⁷)C(O)N(R⁸)—, —CH(R⁷)N(R⁸)C(O)—, —CH(R⁷)N(R⁸)S(O)—, or —CH(R⁷)N(R⁸)S(O)₂—;
W² is —O—, —NR⁷—, —S(O)₀₋₂—, —C(O)—, —C(O)N(R⁷)—, —N(R⁷)C(O)—, —N(R⁷)C(O)N(R⁸)—, —N(R⁷)S(O)—, —N(R⁷)S(O)₂—, —C(O)O—, —CH(R⁷)N(C(O)OR⁸)—, —CH(R⁷)N(C(O)R⁸)—, —CH(R⁷)N(SO₂R⁸)—, —CH(R⁷)N(R⁸)—, —CH(R⁷)C(O)N(R⁸)—, —CH(R⁷)N(R⁸)C(O)—, —CH(R⁷)N(R⁸)S(O)—, or —CH(R⁷)N(R⁸)S(O)₂—;

$R^2$ is hydrogen, halogen, —OH, —$R^{31}$, —$CF_3$, —$OCF_3$, —$OR^{31}$, —$NR^{31}R^{32}$, —$NR^{34}R^{35}$, (O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, —SC(=O)$NR^{31}R^{32}$, aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —N—$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —NR—$NR^{34}R^{35}$, —C(O)$R^{31}$, —$CO_2R^{31}$, —C(=O)$NR^{34}R^{35}$, or —C(=O)$NR^{31}R^{32}$;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, —SC(=O)$NR^{31}R^{32}$, aryl, heteroaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$ alkyl, $C_{2-10}$alkenylaryl, $C_{2-10}$alkenylheteroaryl, $C_{2-10}$alkenylheteroalkyl, $C_{2-10}$alkenylheterocyicyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$ alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$ alkenyl, heteroaryl-$C_{2-10}$alkynyl, heteroaryl-$C_{3-8}$cycloalkyl, heteroalkyl, heteroaryl-heteroalkyl, or heteroaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —N—$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, (O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}$ $C_{1-10}$alkyl, —S(O)$_{0-2}$ $C_{1-10}$alkylaryl, —S(O)$_{0-2}$ aryl, —$SO_2$N(aryl), —$SO_2$ N($C_{1-10}$alkyl)($C_{1-10}$alkyl), —$SO_2$ NH($C_{1-10}$alkyl) or —$SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, $-OR^{31}$, $-SH$, $-NH_2$, $-NR^{34}R^{35}$, $-NR^{31}R^{32}$, $-CO_2R^{31}$, $-CO_2aryl$, $-C(=O)NR^{31}R^{32}$, $C(=O)NR^{34}R^{35}$, $-NO_2$, $-CN$, $-S(O)_{0-2}$ $C_{1-10}alkyl$, $-S(O)_{0-2}aryl$, $-SO_2NR^{34}R^{35}$, $-SO_2NR^{31}R^{32}$, $C_{1-10}alkyl$, $C_{2-10}alkenyl$, $C_{2-10}alkynyl$; aryl-$C_{1-10}alkyl$, aryl-$C_{2-10}alkenyl$, aryl-$C_{2-10}alkynyl$, heteroaryl-$C_{1-10}alkyl$, heteroaryl-$C_{2-10}alkenyl$, heteroaryl-$C_{2-10}alkynyl$, wherein each of said alkyl, alkenyl, alkynyl, aryl, heteroalkyl, heterocyclyl, or heteroaryl group is unsubstituted or is substituted with one or more independent halo, cyano, nitro, $-OC_{1-10}alkyl$, $C_{1-10}alkyl$, $C_{2-10}alkenyl$, $C_{2-10}alkynyl$, halo$C_{1-10}alkyl$, halo $C_{2-10}alkenyl$, halo $C_{2-10}alkynyl$, $-COOH$, $-C(=O)NR^{31}R^{32}$, $-C(=O)NR^{34}R^{35}$, $-SO_2NR^{34}R^{35}$, $-SO_2NR^{31}R^{32}$, $-NR^{31}R^{32}$, or $-NR^{34}R^{35}$; and $R^9$ is H, halo, $-OR^{31}$, $-SH$, $-NH_2$, $-NR^{34}R^{35}$, $-NR^{31}R^{32}$, $-CO_2R^{31}$, $-CO_2aryl$, $-C(=O)NR^{31}R^{32}$, $C(=O)NR^{34}R^{35}$, $-NO_2$, $-CN$, $-S(O)_{0-2}$ $C_{1-10}alkyl$, $-S(O)_{0-2}aryl$, $-SO_2NR^{34}R^{35}$, $-SO_2NR^{31}R^{32}$, $C_{1-10}alkyl$, $C_{2-10}alkenyl$, $C_{2-10}alkynyl$; aryl-$C_{1-10}alkyl$, aryl-$C_{2-10}alkenyl$, aryl-$C_{2-10}alkynyl$, heteroaryl-$C_{1-10}alkyl$, heteroaryl-$C_{2-10}alkenyl$, heteroaryl-$C_{2-10}alkynyl$, wherein each of said alkyl, alkenyl, alkynyl, aryl, heteroalkyl, heterocyclyl, or heteroaryl group is unsubstituted or is substituted with one or more independent halo, cyano, nitro, $-OC_{1-10}alkyl$, $C_{1-10}alkyl$, $C_{2-10}alkenyl$, $C_{2-10}alkynyl$, halo$C_{1-10}alkyl$, halo$C_{2-10}alkenyl$, halo$C_{2-10}alkynyl$, $-COOH$, $-C(=O)NR^{31}R^{32}$, $-C(=O)NR^{34}R^{35}$, $-SO_2NR^{34}R^{35}$, $-SO_2NR^{31}R^{32}$, $-NR^{31}R^{32}$, or $-NR^{34}R^{35}$.

In various embodiments of the compound of Formula I-E, the compound has a structure of Formula I-E1 or Formula I-E2:

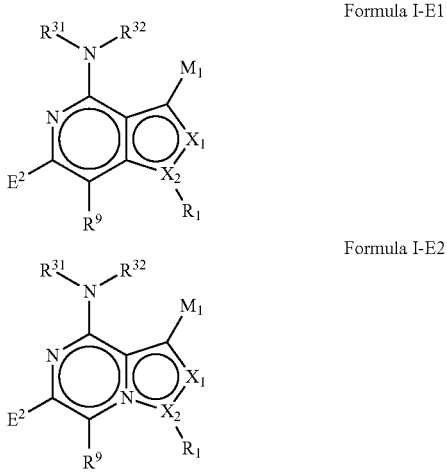

Formula I-E1

Formula I-E2 or a pharmaceutically acceptable salt thereof.

In some embodiments of Formula I-E1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In several embodiments of Formula I-E2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is $-O-$. In various embodiments of $X_1$, j is 1, and $W^1$ is $-NR^7-$. In various embodiments of $X_1$, j is 1, and $W^1$ is $-NH-$. In various embodiments of $X_1$, j is 1, and $W^1$ is $-S(O)_{0-2}-$. In various embodiments of $X_1$, j is 1, and $W^1$ is $-C(O)-$. In various embodiments of $X_1$, j is 1, and $W^1$ is $-C(O)N(R^7)-$. In various embodiments of $X_1$, j is 1, and $W^1$ is $-N(R^7)C(O)-$. In various embodiments of $X_1$, j is 1, and $W^1$ is $-N(R^7)S(O)-$. In various embodiments of $X_1$, j is 1, and $W^1$ is $-N(R^7)S(O)_2-$. In various embodiments of $X_1$, j is 1, and $W^1$ is $-C(O)O-$. In various embodiments of $X_1$, j is 1, and $W^1$ is $CH(R^7)N(C(O)OR^8)-$. In various embodiments of $X_1$, j is 1, and $W^1$ is $-CH(R^7)N(C(O)R^8)-$. In various embodiments of $X_1$, j is 1, and $W^1$ is $-CH(R^7)N(SO_2R^8)-$. In various embodiments of $X_1$, j is 1, and $W^1$ is $-CH(R^7)N(R^8)-$. In various embodiments of $X_1$, j is 1, and $W^1$ is $-CH(R^7)C(O)N(R^8)-$. In various embodiments of $X_1$, j is 1, and $W^1$ is $-CH(R^7)N(R^8)C(O)-$. In various embodiments of $X_1$, j is 1, and $W^1$ is $-CH(R^7)N(R^8)S(O)-$. In various embodiments of $X_1$, j is 1, and $W^1$ is $-CH(R^7)N(R^8)S(O)_2-$.

In another embodiment, $X_1$ is N.

In various embodiments, $X_2$ is N. In other embodiments, $X_2$ is C.

In various embodiments, $E^2$ is $-(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is $-(W^1)_j$—$R^4$. In various embodiments of $E^2$, j is 1, and $W^1$ is $-O-$. In various embodiments of $E^2$, j is 1, and $W^1$ is $-NR^7-$. In various embodiments of $E^2$, j is 1, and $W^1$ is $-NH-$. In various embodiments of $E^2$, j is 1, and $W^1$ is $-S(O)_{0-2}-$. In various embodiments of $E^2$, j is 1, and $W^1$ is $-C(O)-$. In various embodiments of $E^2$, j is 1, and $W^1$ is $-C(O)N(R^7)-$. In various embodiments of $E^2$, j is 1, and $W^1$ is $-N(R^7)C(O)-$. In various embodiments of $E^2$, j is 1, and $W^1$ is $-N(R^7)S(O)-$. In various embodiments of $E^2$, j is 1, and $W^1$ is $-N(R^7)S(O)_2-$. In various embodiments of $E^2$, j is 1, and $W^1$ is $-C(O)O-$. In various embodiments of $E^2$, j is 1, and $W^1$ is $CH(R^7)N(C(O)OR^8)-$. In various embodiments of $E^2$, j is 1, and $W^1$ is $-CH(R^7)N(C(O)R^8)-$. In various embodiments of $E^2$, j is 1, and $W^1$ is $-CH(R^7)N(SO_2R^8)-$. In various embodiments of $E^2$, j is 1, and $W^1$ is $-CH(R^7)N(R^8)-$. In various embodiments of $E^2$, j is 1, and $W^1$ is $-CH(R^7)C(O)N(R^8)-$. In various embodiments of $E^2$, j is 1, and $W^1$ is $-CH(R^7)N(R^8)C(O)-$. In various embodiments of $E^2$, j is 1, and $W^1$ is $-CH(R^7)N(R^8)S(O)-$. In various embodiments of $E^2$, j is 1, and $W^1$ is $-CH(R^7)N(R^8)S(O)_2-$.

In various embodiments when $M_1$ is a moiety of Formula I-E1, $M_1$ is benzoxazolyl substituted with $-(W_2)_k$—$R_2$. In some embodiments, $M_1$ is a benzoxazolyl moiety, substituted at the 2-position with $-(W_2)_k$—$R_2$. In some embodiments, $M_1$ is either a 5-benzoxazolyl or a 6-benzoxazolyl moiety, optionally substituted with $-(W_2)_k$—$R_2$. Exemplary Formula I-E1 $M_1$ moieties include but are not limited to the following:

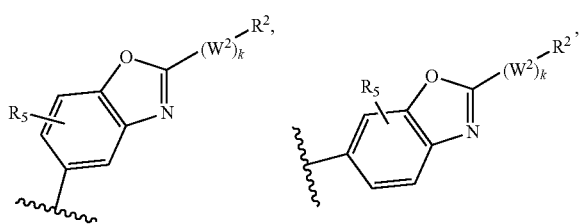

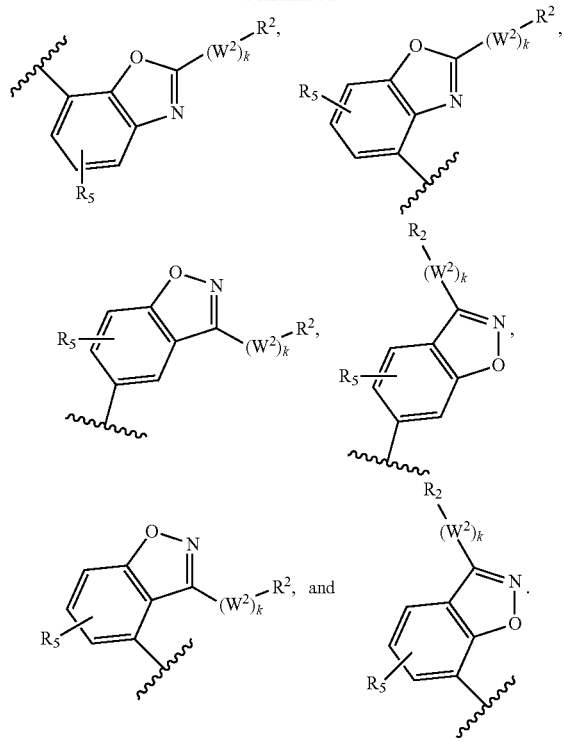

In various embodiments when $M_1$ is a moiety of Formula I-E2, Formula I-E2 is an aza-substituted benzoxazolyl moiety having a structure of one of the following formulae:

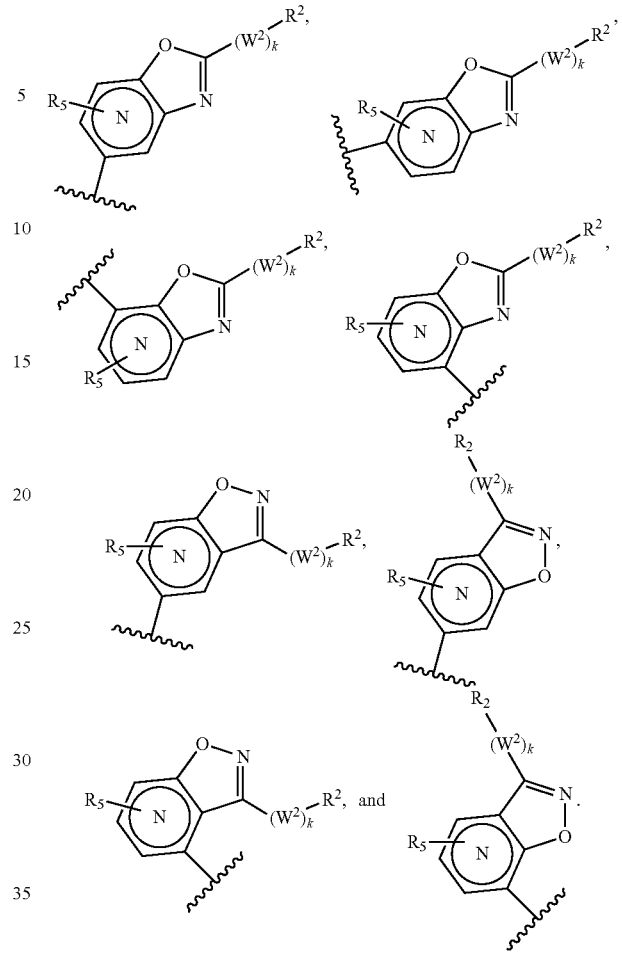

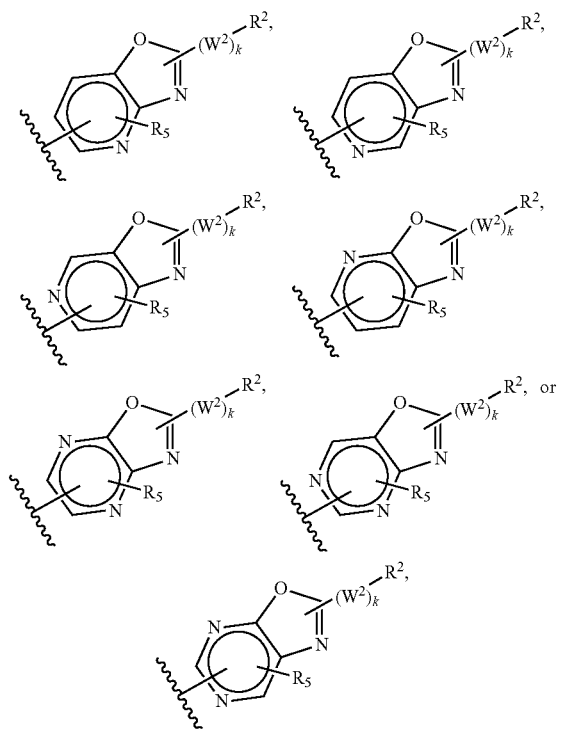

Exemplary Formula I-E2 $M_1$ moieties include but are not limited to the following:

In various embodiments of $M_1$, k is 0. In other embodiments of $M_1$, k is 1 and $W^2$ is —O—. In another embodiment of $M_1$, k is 1 and $W^2$ is —$NR^7$—. In yet another embodiment of $M_1$, k is 1 and $W^2$ is —$S(O)_{0-2}$—. In another embodiment of $M_1$, k is 1 and $W^2$ is —C(O)—. In a further embodiment of $M_1$, k is 1 and $W^2$ is —C(O)N($R^7$)—. In another embodiment of $M_1$, k is 1 and $W^2$ is —N($R^7$)C(O)—. In another embodiment, k is 1 and $W^2$ is —N($R^7$)C(O)N($R^8$)—. In yet another embodiment of $M_1$, k is 1 and $W^2$ is —N($R^7$)S(O)—. In still yet another embodiment of $M_1$, k is 1 and $W^2$ is —N($R^7$)S(O)$_2$—. In a further embodiment of $M_1$, k is 1 and $W^2$ is —C(O)O—. In another embodiment of $M_1$, k is 1 and $W^2$ is —CH($R^7$)N(C(O)O$R^8$)—. In another embodiment of $M_1$, k is 1 and $W^2$ is —CH($R^7$)N(C(O)$R^8$)—. In another embodiment of $M_1$, k is 1 and $W^2$ is —CH($R^7$)N(SO$_2R^8$)—. In a further embodiment of $M_1$, k is 1 and $W^2$ is —CH($R^7$)N($R^8$)—. In another embodiment of $M_1$, k is 1 and $W^2$ is —CH($R^7$)C(O)N($R^8$)—. In yet another embodiment of $M_1$, k is 1 and $W^2$ is —CH($R^7$)N($R^8$)C(O)—. In another embodiment of $M_1$, k is 1 and $W^2$ is —CH($R^7$)N($R^8$)S(O)—. In yet another embodiment of $M_1$, k is 1 and $W^2$ is —CH($R^7$)N($R^8$)S(O)$_2$—.

Additional embodiments of compounds of Formula I, including I-A, I-B, I-C, I-D, I-E and others are described below.

In various embodiments of compounds of Formula I, L is absent. In another embodiment, L is (C=O)—. In another embodiment, L is C(=O)O—. In a further embodiment, L is —C(=O)N$R^{31}$—. In yet another embodiment, L is —S—. In one embodiment, L is —S(O)—. In another embodiment, L is —S(O)$_2$—. In yet another embodiment, L is —S(O)$_2$NR$^{31}$—. In another embodiment, L is —NR$^{31}$—.

In various embodiments of compounds of Formula I, $R_1$ is -L-C$_{1-10}$alkyl, which is unsubstituted. In another embodiment, $R_1$ is -L-C$_{1-10}$alkyl, which is substituted by one or more independent R$^3$. In yet another embodiment, $R_1$ is -L-unsubstituted C$_{1-10}$alkyl, where L is absent. In another embodiment, $R_1$ is -L-C$_{1-10}$alkyl, which is substituted by one or more independent R$^3$, and L is absent.

In various embodiments of compounds of Formula I, $R_1$ is -L-C$_{3-8}$cycloalkyl, which is unsubstituted. In another embodiment, $R_1$ is L-C$_{3-8}$cycloalkyl, which is substituted by one or more independent R$^3$. In yet another embodiment, $R_1$ is -L-C$_{3-8}$cycloalkyl, which is unsubstituted, and L is absent. In a further embodiment, $R_1$ is -L-C$_{3-8}$cycloalkyl which is substituted by one or more independent R$^3$, and L is absent.

In various embodiments of compounds of Formula I, $R_1$ is H.

In various embodiments of compounds of Formula I, $R_1$ is -L-aryl, which is unsubstituted. In another embodiment, $R_1$ is -L-aryl, which is substituted by one or more independent R$^3$. In another embodiment, $R_1$ is -L-aryl which is unsubstituted, and L is absent. In yet another embodiment, $R_1$ is -L-aryl, which is substituted by one or more independent R$^3$, and L is absent.

In various embodiments of compounds of Formula I, $R_1$ is -L-heteroaryl, which is unsubstituted. In another embodiment, $R_1$ is -L-heteroaryl, which is substituted by one or more independent R$^3$. In a further embodiment, $R_1$ is -L-heteroaryl which is unsubstituted and L is absent. In yet another embodiment, $R_1$ is -L-heteroaryl, which is substituted by one or more independent R$^3$, and L is absent.

In various embodiments of compounds of Formula I, $R_1$ is -L-C$_{1-10}$alkyl-C$_{3-8}$cycloalkyl, which is unsubstituted. In another embodiment, $R_1$ is -L-C$_{1-10}$alkyl-C$_{3-8}$cycloalkyl, which is substituted by one or more independent R$^3$. In a further embodiment, $R_1$ is -L-C$_{1-10}$alkyl-C$_{3-8}$ cycloalkyl which is unsubstituted and L is absent. In yet another embodiment, $R_1$ is -L-C$_{1-10}$alkyl —C$_{3-8}$cycloalkyl, which is substituted by one or more independent R$^3$, and L is absent.

In various embodiments of compounds of Formula I, $R_1$ is -L-C$_{1-10}$alkylaryl, which is unsubstituted. In another embodiment, $R_1$ is -L-C$_{1-10}$alkylaryl, which is substituted by one or more independent R$^3$. In a further embodiment, $R_1$ is -L-C$_{1-10}$alkylaryl which is unsubstituted and L is absent. In yet another embodiment, $R_1$ is -L-C$_{1-10}$alkylaryl, which is substituted by one or more independent R$^3$, where L is absent.

In various embodiments of compounds of Formula I, $R_1$ is -L-C$_{1-10}$alkylheteroaryl, which is unsubstituted. In another embodiment, $R_1$ is -L-C$_{1-10}$alkylheteroaryl, which is substituted by one or more independent R$^3$. In a further embodiment, $R_1$ is -L-C$_{1-10}$alkylheteroaryl which is unsubstituted and L is absent. In yet another embodiment, $R_1$ is -L-C$_{1-10}$alkylheteroaryl, which is substituted by one or more independent R$^3$, where L is absent.

In various embodiments of compounds of Formula I, $R_1$ is -L-C$_{1-10}$alkylheterocyclyl, which is unsubstituted. In another embodiment, $R_1$ is -L-C$_{1-10}$alkylheterocyclyl, which is substituted by one or more independent R$^3$. In a further embodiment, $R_1$ is -L-C$_{1-10}$alkylheterocyclyl which is unsubstituted and L is absent. In yet another embodiment, $R_1$ is -L-C$_{1-10}$ alkylheterocyclyl, which is substituted by one or more independent R$^3$, where L is absent.

In various embodiments of compounds of Formula I, $R_1$ is -L-C$_{2-10}$alkenyl, which is unsubstituted. In another embodiment, $R_1$ is -L-C$_{2-10}$alkenyl which is substituted by one or more independent R$^3$. In a further embodiment, $R_1$ is -L-C$_{2-10}$alkenyl which is unsubstituted and L is absent. In yet another embodiment, $R_1$ is -L-C$_{2-10}$alkenyl, which is substituted by one or more independent R$^3$, where L is absent.

In various embodiments of compounds of Formula I, $R_1$ is -L-C$_{2-10}$alkynyl, which is unsubstituted. In another embodiment, $R_1$ is -L-C$_{2-10}$alkynyl which is substituted by one or more independent R$^3$. In a further embodiment, $R_1$ is -L-C$_{2-10}$alkynyl which is unsubstituted and L is absent. In yet another embodiment, $R_1$ is -L-C$_{2-10}$alkynyl, which is substituted by one or more independent R$^3$, where L is absent.

In various embodiments of compounds of Formula I, $R_1$ is -L-C$_{2-10}$alkenyl-C$_{3-8}$cycloalkyl, which is unsubstituted. In another embodiment, $R_1$ is -L-C$_{2-10}$alkenyl-C$_{3-8}$cycloalkyl which is substituted by one or more independent R$^3$. In a further embodiment, $R_1$ is -L-C$_{2-10}$alkenyl-C$_{3-8}$cycloalkyl which is unsubstituted and L is absent. In yet another embodiment, $R_1$ is -L-C$_{2-10}$alkenyl-C$_{3-8}$cycloalkyl, which is substituted by one or more independent R$^3$, where L is absent.

In various embodiments of compounds of Formula I, $R_1$ is -L-C$_{2-10}$alkynyl-C$_{3-8}$cycloalkyl, which is unsubstituted. In another embodiment, $R_1$ is -L-C$_{2-10}$alkynyl-C$_{3-8}$cycloalkyl which is substituted by one or more independent R$^3$. In a further embodiment, $R_1$ is -L-C$_{2-10}$alkynyl-C$_{3-8}$cycloalkyl which is unsubstituted and L is absent. In yet another embodiment, $R_1$ is -L-C$_{2-10}$alkynyl-C$_{3-8}$cycloalkyl, which is substituted by one or more independent R$^3$, where L is absent.

In various embodiments of compounds of Formula I, $R_1$ is -L-C$_{2-10}$alkynyl-C$_{3-8}$cycloalkyl, which is unsubstituted. In another embodiment, $R_1$ is -L-C$_{2-10}$alkynyl-C$_{3-8}$cycloalkyl which is substituted by one or more independent R$^3$. In a further embodiment, $R_1$ is -L-C$_{2-10}$alkynyl-C$_{3-8}$cycloalkyl which is unsubstituted and L is absent. In yet another embodiment, $R_1$ is -L-C$_{2-10}$alkynyl-C$_{3-8}$cycloalkyl, which is substituted by one or more independent R$^3$, where L is absent.

In various embodiments of compounds of Formula I, $R_1$ is -L-heteroalkyl, which is unsubstituted. In another embodiment, $R_1$ is -L-heteroalkyl which is substituted by one or more independent R$^3$. In a further embodiment, $R_1$ is -L-heteroalkyl which is unsubstituted and L is absent. In yet another embodiment, $R_1$ is -L-heteroalkyl, which is substituted by one or more independent R$^3$, where L is absent.

In various embodiments of compounds of Formula I, $R_1$ is -L-heteroalkylaryl, which is unsubstituted. In another embodiment, $R_1$ is -L-heteroalkylaryl which is substituted by one or more independent R$^3$. In a further embodiment, $R_1$ is -L-heteroalkylaryl which is unsubstituted and L is absent. In yet another embodiment, $R_1$ is -L-heteroalkylaryl, which is substituted by one or more independent R$^3$, where L is absent.

In various embodiments of compounds of Formula I, $R_1$ is -L-heteroalkylheteroaryl, which is unsubstituted. In another embodiment, $R_1$ is -L-heteroalkylheteroaryl, which is substituted by one or more independent R$^3$. In a further embodiment, $R_1$ is -L-heteroalkylheteroaryl which is unsubstituted and L is absent. In yet another embodiment, $R_1$ is -L-heteroalkylheteroaryl, which is substituted by one or more independent R$^3$, where L is absent.

In various embodiments of compounds of Formula, $R_1$ is -L-heteroalkyl-heterocyclyl, which is unsubstituted. In another embodiment, $R_1$ is -L-heteroalkyl-heterocyclyl, which is substituted by one or more independent R$^3$. In a further embodiment, $R_1$ is -L-heteroalkyl-heterocyclyl which is unsubstituted, and L is absent. In yet another embodiment, $R_1$ is -L-heteroalkyl-heterocyclyl, which is substituted by one or more independent R$^3$, where L is absent.

In various embodiments of compounds of Formula I, $R_1$ is -L-heteroalkyl-C$_{3-8}$cycloalkyl, which is unsubstituted. In another embodiment, $R_1$ is -L-heteroalkyl-$C_{3-8}$cycloalkyl, which is substituted by one or more independent $R^3$. In a further embodiment, $R_1$ is -L-heteroalkyl-$C_{3-8}$cycloalkyl which is unsubstituted and L is absent. In yet another embodiment, $R_1$ is -L-heteroalkyl-$C_{3-8}$cycloalkyl, which is substituted by one or more independent $R^3$, where L is absent.

In various embodiments of compounds of Formula I, $R_1$ is -L-aralkyl, which is unsubstituted. In another embodiment, $R_1$ is -L-aralkyl, which is substituted by one or more independent $R^3$. In a further embodiment, $R_1$ is -L-aralkyl which is unsubstituted. In yet another embodiment, $R_1$ is -L-aralkyl, which is substituted by one or more independent $R^3$, where L is absent.

In various embodiments of compounds of Formula I, $R_1$ is -L-heteroaralkyl, which is unsubstituted. In another embodiment, $R_1$ is -L-heteroaralkyl, which is substituted by one or more independent $R^3$. In a further embodiment, $R_1$ is -L-heteroaralkyl which is unsubstituted and L is absent. In yet another embodiment, $R_1$ is -L-heteroaralkyl, which is substituted by one or more independent $R^3$, where L is absent.

In various embodiments of compounds of Formula I, $R_1$ is -L-heterocyclyl, which is unsubstituted. In another embodiment, $R_1$ is -L-heterocyclyl, which is substituted by one or more independent $R^3$. In a further embodiment, $R_1$ is -L-heterocyclyl which is unsubstituted and L is absent. In yet another embodiment, $R_1$ is -L-heterocyclyl, which is substituted by one or more independent $R^3$, where L is absent.

In various embodiments of compounds of Formula I, $R_1$ is a substituent as shown below:

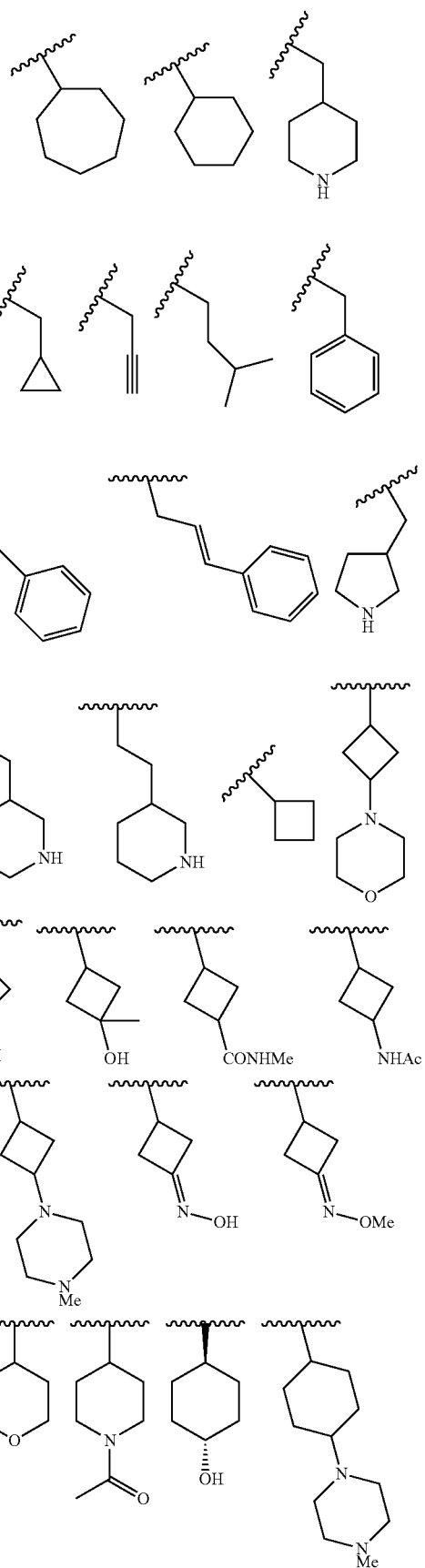

-continued

75
-continued

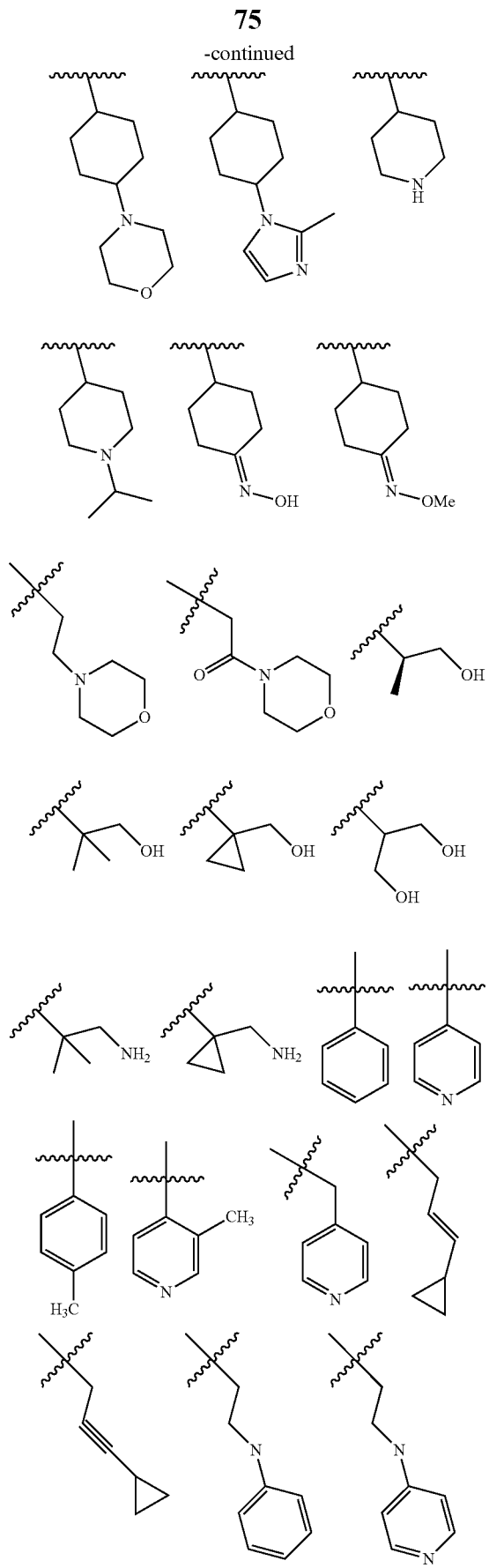

76
-continued

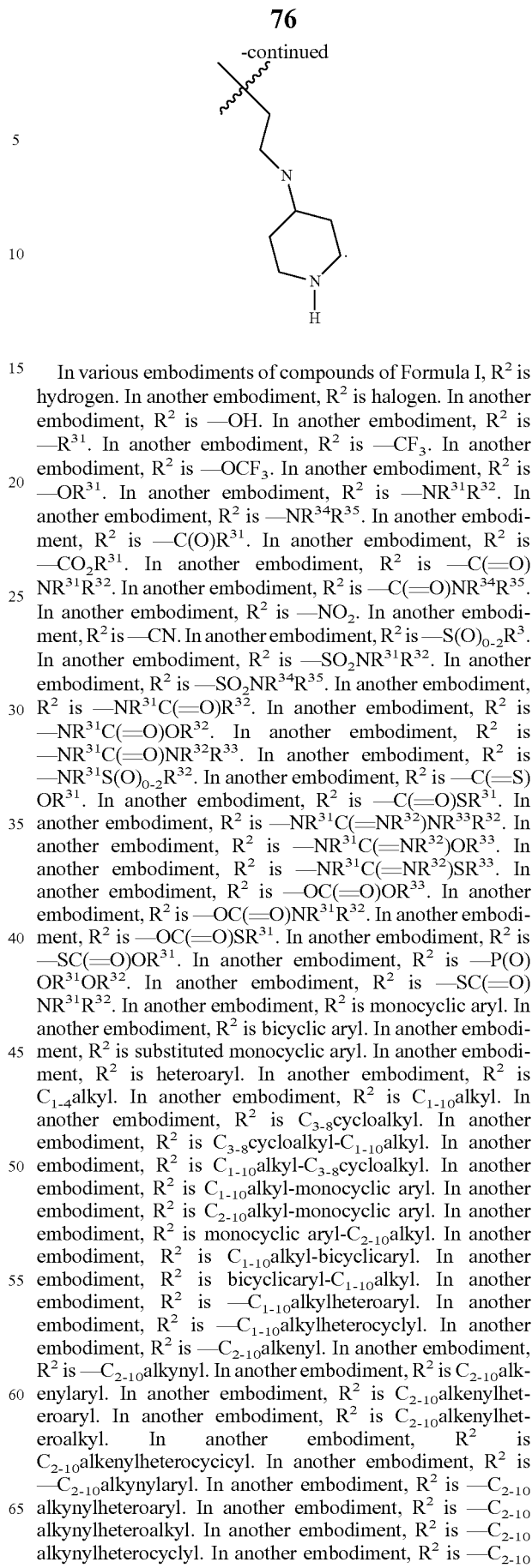

In various embodiments of compounds of Formula I, $R^2$ is hydrogen. In another embodiment, $R^2$ is halogen. In another embodiment, $R^2$ is —OH. In another embodiment, $R^2$ is —$R^{31}$. In another embodiment, $R^2$ is —$CF_3$. In another embodiment, $R^2$ is —$OCF_3$. In another embodiment, $R^2$ is —$OR^{31}$. In another embodiment, $R^2$ is —$NR^{31}R^{32}$. In another embodiment, $R^2$ is —$NR^{34}R^{35}$. In another embodiment, $R^2$ is —$C(O)R^{31}$. In another embodiment, $R^2$ is —$CO_2R^{31}$. In another embodiment, $R^2$ is —$C(=O)NR^{31}R^{32}$. In another embodiment, $R^2$ is —$C(=O)NR^{34}R^{35}$. In another embodiment, $R^2$ is —$NO_2$. In another embodiment, $R^2$ is —CN. In another embodiment, $R^2$ is —$S(O)_{0-2}R^3$. In another embodiment, $R^2$ is —$SO_2NR^{31}R^{32}$. In another embodiment, $R^2$ is —$SO_2NR^{34}R^{35}$. In another embodiment, $R^2$ is —$NR^{31}C(=O)R^{32}$. In another embodiment, $R^2$ is —$NR^{31}C(=O)OR^{32}$. In another embodiment, $R^2$ is —$NR^{31}C(=O)NR^{32}R^{33}$. In another embodiment, $R^2$ is —$NR^{31}S(O)_{0-2}R^{32}$. In another embodiment, $R^2$ is —$C(=S)OR^{31}$. In another embodiment, $R^2$ is —$C(=O)SR^{31}$. In another embodiment, $R^2$ is —$NR^{31}C(=NR^{32})NR^{33}R^{32}$. In another embodiment, $R^2$ is —$NR^{31}C(=NR^{32})OR^{33}$. In another embodiment, $R^2$ is —$NR^{31}C(=NR^{32})SR^{33}$. In another embodiment, $R^2$ is —$OC(=O)OR^{33}$. In another embodiment, $R^2$ is —$OC(=O)NR^{31}R^{32}$. In another embodiment, $R^2$ is —$OC(=O)SR^{31}$. In another embodiment, $R^2$ is —$SC(=O)OR^{31}$. In another embodiment, $R^2$ is —$P(O)OR^{31}OR^{32}$. In another embodiment, $R^2$ is —$SC(=O)NR^{31}R^{32}$. In another embodiment, $R^2$ is monocyclic aryl. In another embodiment, $R^2$ is bicyclic aryl. In another embodiment, $R^2$ is substituted monocyclic aryl. In another embodiment, $R^2$ is heteroaryl. In another embodiment, $R^2$ is $C_{1-4}$alkyl. In another embodiment, $R^2$ is $C_{1-10}$alkyl. In another embodiment, $R^2$ is $C_{3-8}$cycloalkyl. In another embodiment, $R^2$ is $C_{3-8}$cycloalkyl-$C_{1-10}$alkyl. In another embodiment, $R^2$ is $C_{1-10}$alkyl-$C_{3-8}$cycloalkyl. In another embodiment, $R^2$ is $C_{1-10}$alkyl-monocyclic aryl. In another embodiment, $R^2$ is $C_{2-10}$alkyl-monocyclic aryl. In another embodiment, $R^2$ is monocyclic aryl-$C_{2-10}$alkyl. In another embodiment, $R^2$ is $C_{1-10}$alkyl-bicyclicaryl. In another embodiment, $R^2$ is bicyclicaryl-$C_{1-10}$alkyl. In another embodiment, $R^2$ is —$C_{1-10}$alkylheteroaryl. In another embodiment, $R^2$ is —$C_{1-10}$alkylheterocyclyl. In another embodiment, $R^2$ is —$C_{2-10}$alkenyl. In another embodiment, $R^2$ is —$C_{2-10}$alkynyl. In another embodiment, $R^2$ is $C_{2-10}$alkenylaryl. In another embodiment, $R^2$ is $C_{2-10}$alkenylheteroaryl. In another embodiment, $R^2$ is $C_{2-10}$alkenylheteroalkyl. In another embodiment, $R^2$ is $C_{2-10}$alkenylheterocycicyl. In another embodiment, $R^2$ is —$C_{2-10}$alkynylaryl. In another embodiment, $R^2$ is —$C_{2-10}$alkynylheteroaryl. In another embodiment, $R^2$ is —$C_{2-10}$alkynylheteroalkyl. In another embodiment, $R^2$ is —$C_{2-10}$alkynylheterocyclyl. In another embodiment, $R^2$ is —$C_{2-10}$ alkynyl$C_{3-8}$cycloalkyl. In another embodiment, $R^2$ is —$C_{2-10}$alkynyl$C_{3-8}$cycloalkenyl. In another embodiment, $R^2$ is —$C_{1-10}$ alkoxy-$C_{1-10}$alkyl. In another embodiment, $R^2$ is —$C_{1-10}$alkoxy-$C_{2-10}$alkenyl. In another embodiment, $R^2$ is —$C_{1-10}$alkoxy-$C_{2-10}$alkynyl. In another embodiment, $R^2$ is -heterocyclyl $C_{1-10}$alkyl. In another embodiment, $R^2$ is heterocyclyl$C_{2-10}$alkenyl. In another embodiment, $R^2$ is heterocyclyl$C_{2-10}$alkynyl. In another embodiment, $R^2$ is aryl-$C_{2-10}$alkyl. In another embodiment, $R^2$ is aryl-$C_{1-10}$alkyl. In another embodiment, $R^2$ is aryl-$C_{2-10}$alkenyl. In another embodiment, $R^2$ is aryl-$C_{2-10}$alkynyl. In another embodiment, $R^2$ is aryl-heterocyclyl. In another embodiment, $R^2$ is heteroaryl-$C_{1-10}$alkyl. In another embodiment, $R^2$ is heteroaryl-$C_{2-10}$alkenyl. In another embodiment, $R^2$ is heteroaryl-$C_{2-10}$alkynyl. In another embodiment, $R^2$ is heteroaryl-$C_{3-8}$cycloalkyl. In another embodiment, $R^2$ is heteroaryl-heteroalkyl. In another embodiment, $R^2$ is heteroaryl-heterocyclyl.

In various embodiments of compounds of Formula I, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is unsubstituted. In various embodiments, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent halo. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OH. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$R^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$CF_3$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OCF. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$OR^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{34}R^{35}$. In another embodiment, when $R^4$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$C(O)R^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$CO_2R^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$C(=O)NR^{31}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$C(=O)NR^{34}R^{35}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NO_2$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —CN. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$S(O)_{0-2}R^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$SO_2NR^{31}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$SO_2NR^{34}R^{35}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent $NR^{31}C(=O)R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)OR^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)NR^{32}R^{33}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}S(O)_{0-2}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$ alkyl, heterocyclyl $C_{1-10}$alkyl, or $C_{3-8}$cycloalkyl-$C_{1-10}$alkyl, it is substituted with one or more independent —C(=S)OR$^{31}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —C(=O)SR$^{31}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —NR$^{31}$C(=NR$^{32}$)NR$^{33}$R$^{32}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl $C_{2-10}$alkynyl monocyclic aryl-$C_{2-10}$alkyl, heterocyclyl $C_{1-10}$alkyl, or $C_{3-8}$cycloalkyl-$C_{1-10}$alkyl, it is substituted with one or more independent, —NR$^{31}$C(=NR$^{32}$)OR$^{33}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —NR$^{31}$C(=NR$^{32}$)SR$^{33}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OC(=O)OR$^{33}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl $C_{2-10}$alkynyl, monocyclic aryl-$C_{2-10}$alkyl heterocyclyl $C_{1-10}$alkyl, or $C_{3-8}$cycloalkyl-$C_{1-10}$alkyl, it is substituted with one or more independent —OC(=O)NR$^{31}$R$^{32}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OC(=O)SR$^{31}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —SC(=O)OR$^{31}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —P(O)OR$^{31}$OR$^{32}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —SC(=O)NR$^{31}$R$^{32}$. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent alkyl. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent heteroalkyl. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent alkenyl. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent alkynyl. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent cycloalkyl. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent heterocycloalkyl. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent aryl. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent arylalkyl. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent heteroaryl. In another embodiment, when R$^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent heteroarylalkyl.

In various embodiments of compounds of Formula I, R$^3$ is hydrogen. In another embodiment, R$^3$ is halogen. In another embodiment, R$^3$ is —OH. In another embodiment, R$^3$ is —R$^{31}$. In another embodiment, R$^3$ is —CF$_3$. In another embodiment, R$^3$ is —OCF$_3$. In another embodiment, R$^3$ is —OR$^{31}$. In another embodiment, R$^3$ is —NR$^{31}$R$^{32}$. In another embodiment, R$^3$ is —NR$^{34}$R$^{35}$. In another embodiment, R$^3$ is —C(O)R$^{31}$. In another embodiment, R$^3$ is —CO$_2$R$^{31}$. In another embodiment, R$^3$ is —C(=O)NR$^{31}$R$^{32}$. In another embodiment, R$^3$ is —C(=O)NR$^{34}$R$^{35}$. In another embodiment, R$^3$ is —NO$_2$. In another embodiment, R$^3$ is —CN. In another embodiment, R$^3$ is —S(O)$_{0-2}$R$^3$. In another embodiment, R$^3$ is —SO$_2$NR$^{31}$R$^{32}$. In another embodiment, R$^3$ is —SO$_2$NR$^{34}$R$^{35}$. In another embodiment, R$^3$ is —NR$^{31}$C(=O)R$^{32}$. In another embodiment, R$^3$ is —NR$^{31}$C(=O)OR$^{32}$. In another embodiment, R$^3$ is —NR$^{31}$C(=O)NR$^{32}$R$^{33}$. In another embodiment, R$^3$ is —NR$^{31}$S(O)$_{0-2}$R$^{32}$. In another embodiment, R$^3$ is —C(=S)OR$^{31}$. In another embodiment, R$^3$ is —C(=O)SR$^{31}$. In another embodiment, R$^3$ is —NR$^{31}$C(=NR$^{32}$)NR$^{33}$R$^{32}$. In another embodiment, R$^3$ is —NR$^{31}$C(=NR$^{32}$)OR$^{33}$. In another embodiment, R$^3$ is —NR$^{31}$C(=NR$^{32}$)SR$^{33}$. In another embodiment, R$^3$ is —OC(=O)OR$^{33}$. In another embodiment, R$^3$ is —OC(=O)NR$^{31}$R$^{32}$. In another embodiment, R$^3$ is —OC(=O)SR$^{31}$. In another embodiment, R$^3$ is —SC(=O)OR$^{31}$. In another embodiment, R$^3$ is —P(O)

$OR^{31}OR^{32}$. In another embodiment, $R^3$ is —SC(=O)$NR^{31}R^{32}$. In another embodiment, $R^3$ is aryl. In another embodiment, $R^2$ is heteroaryl. In another embodiment, $R^3$ is $C_{1-4}$alkyl. In another embodiment, $R^3$ is $C_{1-10}$alkyl. In another embodiment, $R^3$ is $C_{3-8}$cycloalkyl. In another embodiment, $R^3$ is $C_{3-8}$cycloalkyl-$C_{1-10}$alkyl. In another embodiment, $R^3$ is —$C_{1-10}$alkyl-$C_{3-8}$cycloalkyl. In another embodiment, $R^3$ is $C_{2-10}$alkyl-monocyclic aryl. In another embodiment, $R^3$ is monocyclic aryl-$C_{2-10}$alkyl. In another embodiment, $R^3$ is $C_{1-10}$alkyl-bicyclicaryl. In another embodiment, $R^3$ is bicyclicaryl-$C_{1-10}$alkyl. In another embodiment, $R^3$ is $C_{1-10}$alkylheteroaryl. In another embodiment, $R^3$ is $C_{1-10}$alkylheterocyclyl. In another embodiment, $R^3$ is $C_{2-10}$alkenyl. In another embodiment, $R^3$ is $C_{2-10}$alkynyl. In another embodiment, $R^3$ is $C_{2-10}$alkenylaryl. In another embodiment, $R^3$ is $C_{2-10}$alkenylheteroaryl. In another embodiment, $R^3$ is $C_{2-10}$alkenylheteroalkyl. In another embodiment, $R^3$ is $C_{2-10}$alkenylheterocicyl. In another embodiment, $R^3$ is —$C_{2-10}$alkynylaryl. In another embodiment, $R^3$ is —$C_{2-10}$alkynylheteroaryl. In another embodiment, $R^3$ is —$C_{2-10}$alkynylheteroalkyl. In another embodiment, $R^3$ is $C_{2-10}$alkynylheterocyclyl. In another embodiment, $R^3$ is —$C_{2-10}$alkynyl$C_{3-8}$cycloalkyl. In another embodiment, $R^3$ is $C_{2-10}$alkynyl$C_{3-8}$cycloalkenyl. In another embodiment, $R^3$ is —$C_{1-10}$alkoxy-$C_{1-10}$alkyl. In another embodiment, $R^3$ is $C_{1-10}$alkoxy-$C_{2-10}$alkenyl. In another embodiment, $R^3$ is —$C_{1-10}$alkoxy-$C_{2-10}$alkynyl. In another embodiment, $R^3$ is heterocyclyl-$C_{1-10}$alkyl. In another embodiment, $R^3$ is -heterocyclyl$C_{2-10}$alkenyl. In another embodiment, $R^3$ is heterocyclyl-$C_{2-10}$alkynyl. In another embodiment, $R^3$ is aryl-$C_{1-10}$alkyl. In another embodiment, $R^3$ is aryl-$C_{2-10}$alkenyl. In another embodiment, $R^3$ is aryl-$C_{2-10}$alkynyl. In another embodiment, $R^3$ is aryl-heterocyclyl. In another embodiment, $R^3$ is heteroaryl-$C_{1-10}$alkyl. In another embodiment, $R^3$ is heteroaryl-$C_{2-10}$alkenyl. In another embodiment, $R^3$ is heteroaryl-$C_{2-10}$alkynyl. In another embodiment, $R^3$ is heteroaryl-$C_{3-8}$cycloalkyl. In another embodiment, $R^3$ is heteroaryl-heteroalkyl. In another embodiment, $R^3$ is heteroaryl-heterocyclyl.

In various embodiments of compounds of Formula I, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is unsubstituted. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent halo. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OH. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$R^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$CF_3$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OCF. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$OR^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{31}R^{32}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{34}R^{35}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$C(O)R^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$CO_2R^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —C(=O)$NR^{31}R^{32}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —C(=O)$NR^{34}R^{35}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NO_2$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —CN. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$S(O)_{0-2}R^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{31}R^{32}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{34}R^{35}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent $NR^{31}$C(=O)$R^{32}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}$C(=O)$OR^{32}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}$C(=O)$NR^{32}R^{33}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}S(O)_{0-2}R^{32}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —C(=S)$OR^{31}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —C(=O)$SR^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —NR$^{31}$C(=NR$^{32}$)NR$^{33}$R$^{32}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent, —NR$^{31}$C(=NR$^{32}$)OR$^{33}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —NR$^{31}$C(=NR$^{32}$)SR$^{33}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —OC(=O)OR$^{33}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —OC(=O)NR$^{31}$R$^{32}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —OC(=O)SR$^{31}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —SC(=O)OR$^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —P(O)OR$^{31}$OR$^{32}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —SC(=O)NR$^{31}$R$^{32}$.

In various embodiments of compounds of Formula I, $R^4$ is hydrogen. In another embodiment, $R^4$ is halogen. In another embodiment, $R^4$ is —OH. In another embodiment, $R^4$ is —R$^{31}$. In another embodiment, $R^4$ is —CF$_3$. In another embodiment, $R^4$ is —OCF$_3$. In another embodiment, $R^4$ is —OR$^{31}$. In another embodiment, $R^4$ is —NR$^{31}$R$^{32}$. In another embodiment, $R^4$ is —NR$^{34}$R$^{35}$. In another embodiment, $R^4$ is —C(O)R$^{31}$. In another embodiment, $R^4$ is —CO$_2$R$^{31}$. In another embodiment, $R^4$ is —C(=O)NR$^{31}$R$^{32}$. In another embodiment, $R^4$ is —C(=O)NR$^{34}$R$^{35}$. In another embodiment, $R^4$ is —NO$_2$. In another embodiment, $R^4$ is —CN. In another embodiment, $R^4$ is —S(O)$_{0-2}$R$^3$. In another embodiment, $R^4$ is —SO$_2$NR$^{31}$R$^{32}$. In another embodiment, $R^4$ is —SO$_2$NR$^{34}$R$^{35}$. In another embodiment, $R^4$ is —NR$^{31}$C(=O)R$^{32}$. In another embodiment, $R^4$ is —NR$^{31}$C(=O)OR$^{32}$. In another embodiment, $R^4$ is —NR$^{31}$C(=O)NR$^{32}$R$^{33}$. In another embodiment, $R^4$ is —NR$^{31}$S(O)$_{0-2}$R$^{32}$. In another embodiment, $R^4$ is —C(=S)OR$^{31}$. In another embodiment, $R^4$ is —C(=O)SR$^{31}$. In another embodiment, $R^4$ is —NR$^{31}$C(=NR$^{32}$)NR$^{33}$R$^{32}$. In another embodiment, $R^4$ is —NR$^{31}$C(=NR$^{32}$)OR$^{33}$. In another embodiment, $R^4$ is —NR$^{31}$C(=NR$^{32}$)SR$^{33}$. In another embodiment, $R^4$ is —OC(=O)OR$^{33}$. In another embodiment, $R^4$ is —OC(=O)NR$^{31}$R$^{32}$. In another embodiment, $R^4$ is —OC(=O)SR$^{31}$. In another embodiment, $R^4$ is —SC(=O)OR$^{31}$. In another embodiment, $R^4$ is —P(O)OR$^{31}$OR$^{32}$. In another embodiment, $R^4$ is —SC(=O)NR$^{31}$R$^{32}$. In another embodiment, $R^4$ is aryl. In another embodiment, $R^4$ is heteroaryl. In another embodiment, $R^4$ is $C_{1-4}$alkyl. In another embodiment, $R^4$ is $C_{1-10}$alkyl. In another embodiment, $R^4$ is $C_{3-8}$cycloalkyl. In another embodiment, $R^4$ is $C_{1-10}$alkyl-$C_{3-8}$cycloalkyl. In another embodiment, $R^4$ is $C_{1-10}$alkylaryl. In another embodiment, $R^4$ is $C_{1-10}$alkylheteroaryl. In another embodiment, $R^4$ is $C_{1-10}$alkylheterocyclyl. In another embodiment, $R^4$ is $C_{2-10}$alkenyl. In another embodiment, $R^4$ is $C_{2-10}$alkynyl. In another embodiment, $R^4$ is $C_{2-10}$alkynyl-$C_{3-8}$cycloalkyl. $R^4$ is $C_{2-10}$alkenyl-$C_{3-8}$cycloalkyl. In another embodiment, $R^4$ is $C_{2-10}$alkenylaryl. In another embodiment, $R^4$ is $C_{2-10}$alkenylheteroaryl. In another embodiment, $R^4$ is $C_{2-10}$alkenylheteroalkyl. In another embodiment, $R^4$ is $C_{2-10}$alkenylheterocycicyl. In another embodiment, $R^4$ is —$C_{2-10}$alkynylaryl. In another embodiment, $R^4$ is $C_{2-10}$alkynylheteroaryl. In another embodiment, $R^4$ is $C_{2-10}$alkynylheteroalkyl. In another embodiment, $R^4$ is $C_{2-10}$alkynylheterocyclyl. In another embodiment, $R^4$ is $C_{2-10}$alkynyl$C_{3-8}$cycloalkyl. In another embodiment, $R^4$ is heterocyclyl $C_{1-10}$alkyl. In another embodiment, $R^4$ is heterocyclylC$_{2-10}$alkenyl. In another embodiment, $R^4$ is heterocyclyl-$C_{2-10}$alkynyl.

In another embodiment, $R^4$ is aryl-$C_{1-10}$alkyl. In another embodiment, $R^4$ is aryl-$C_{2-10}$alkenyl. In another embodiment, $R^4$ is aryl-$C_{2-10}$alkynyl. In another embodiment, $R^4$ is aryl-heterocyclyl. In another embodiment, $R^4$ is heteroaryl-$C_{1-10}$alkyl. In another embodiment, $R^4$ is heteroaryl-$C_{2-10}$alkenyl. In another embodiment, $R^4$ is heteroaryl-$C_{2-10}$alkynyl. In another embodiment, $R^4$ is $C_{3-8}$cycloalkyl-$C_{1-10}$alkyl. In another embodiment, $R^4$ is $C_{3-8}$cycloalkyl-$C_{2-10}$alkenyl. In another embodiment, $R^4$ is $C_{3-8}$cycloalkyl-$C_{2-10}$alkynyl.

In various embodiments of compounds of Formula I, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is unsubstituted. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent halo. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OH. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —R$^{31}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —CF$_3$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OCF. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OR$^{31}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —NR$^{31}$R$^{32}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —NR$^{34}$R$^{35}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —C(O)$R^{31}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$CO_2R^{31}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —C(=O)$NR^{31}R^{32}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —C(=O)$NR^{34}R^{35}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NO_2$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —CN. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$S(O)_{0-2}R^{31}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{31}R^{32}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{34}R^{35}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent $NR^{31}C(=O)R^{32}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)OR^{32}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)NR^{32}R^{33}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}S(O)_{0-2}R^{32}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —C(=S)$OR^{31}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —C(=O)$SR^{31}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{31}C(=NR^{32})NR^{33}R^{32}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent, —$NR^{31}C(=NR^{32})OR^{33}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=NR^{32})SR^{33}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —OC(=O)$OR^{33}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —OC(=O)$NR^{31}R^{32}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —OC(=O)$SR^{31}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —SC(=O)$OR^{31}$. In another embodiment, when $R^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —P(O)$OR^{31}OR^{32}$. In another embodiment, when $R^4$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —SC(=O)$NR^{31}R^{32}$.

In various embodiments of compounds of Formula I, $R^5$ is hydrogen. In another embodiment, $R^5$ is halogen. In another embodiment, $R^5$ is —OH. In another embodiment, $R^5$ is —$R^{31}$. In another embodiment, $R^5$ is —$CF_3$. In another embodiment, $R^5$ is —$OCF_3$. In another embodiment, $R^5$ is —$OR^{31}$. In another embodiment, $R^5$ is —$NR^{31}R^{32}$. In another embodiment, $R^5$ is —$NR^{34}R^{35}$. In another embodiment, $R^5$ is —C(O)$R^{31}$. In another embodiment, $R^5$ is —$CO_2R^{31}$. In another embodiment, $R^5$ is —C(=O)$NR^{31}R^{32}$. In another embodiment, $R^5$ is —C(=O)$NR^{34}R^{35}$. In another embodiment, $R^5$ is —$NO_2$. In another embodiment, $R^5$ is —CN. In another embodiment, $R^5$ is —$S(O)_{0-2}R^{31}$. In another embodiment, $R^5$ is —$SO_2NR^{31}R^{32}$. In another embodiment, $R^5$ is —$SO_2NR^{34}R^{35}$. In another embodiment, $R^5$ is —$NR^{31}C(=O)R^{32}$. In another embodiment, $R^5$ is —$NR^{31}C(=O)OR^{32}$. In another embodiment, $R^5$ is —$NR^{31}C(=O)NR^{32}R^{33}$. In another embodiment, $R^5$ is —$NR^{31}S(O)_{0-2}R^{32}$. In another embodiment, $R^5$ is —C(=S)$OR^{31}$. In another embodiment, $R^5$ is —C(=O)$SR^{31}$. In another embodiment, $R^5$ is —$NR^{31}C(=NR^{32})NR^{33}R^{32}$. In another embodiment, $R^5$ is —$NR^{31}C(=NR^{32})OR^{33}$. In another embodiment, $R^5$ is —$NR^{31}C(=NR^{32})SR^{33}$. In another embodiment, $R^5$ is —OC(=O)$OR^{33}$. In another embodiment, $R^5$ is —OC(=O)$NR^{31}R^{32}$. In another embodiment, $R^5$ is —OC(=O)$SR^{31}$. In another embodiment, $R^5$ is —SC(=O)$OR^{31}$. In another embodiment, $R^5$ is —P(O)$OR^{31}OR^{32}$. In another embodiment, $R^5$ is or —SC(=O)$NR^{31}R^{32}$.

In various embodiments of compounds of Formula I, $R^7$ is hydrogen. In another embodiment, $R^7$ is unsubstituted $C_{1-10}$alkyl. In another embodiment, $R^7$ is unsubstituted $C_{2-10}$alkenyl. In another embodiment, $R^7$ is unsubstituted aryl. In another embodiment, $R^7$ is unsubstituted heteroaryl. In another embodiment, $R^7$ is unsubstituted heterocyclyl. In another embodiment, $R^7$ is unsubstituted $C_{3-10}$cycloalkyl. In another embodiment, $R^7$ is $C_{1-10}$alkyl substituted by one or more independent $R^6$. In another embodiment, $R^7$ is $C_{2-10}$alkenyl substituted by one or more independent $R^6$. In another embodiment, $R^7$ is aryl substituted by one or more independent $R^6$. In another embodiment, $R^7$ is heteroaryl substituted by one or more independent $R^6$. In another embodiment, $R^7$ is heterocyclyl substituted by one or more independent $R^6$. In another embodiment, $R^7$ is $C_{3-10}$cycloalkyl substituted by one or more independent $R^6$.

In various embodiments of compounds of Formula I, $R^8$ is hydrogen. In another embodiment, $R^8$ is unsubstituted $C_{1-10}$alkyl. In another embodiment, $R^8$ is unsubstituted $C_{2-10}$alkenyl. In another embodiment, $R^8$ is unsubstituted aryl. In another embodiment, $R^8$ is unsubstituted heteroaryl. In another embodiment, $R^8$ is unsubstituted heterocyclyl. In another embodiment, $R^8$ is unsubstituted $C_{3-10}$cycloalkyl. In another embodiment, $R^8$ is $C_{1-10}$alkyl substituted by one or more independent $R^6$. In another embodiment, $R^8$ is $C_{2-10}$alkenyl substituted by one or more independent $R^6$. In another embodiment, $R^8$ is aryl substituted by one or more independent $R^6$. In another embodiment, $R^8$ is heteroaryl substituted by one or more independent $R^6$. In another embodiment, $R^8$ is heterocyclyl substituted by one or more independent $R^6$. In another embodiment, leis $C_{3-10}$cycloalkyl substituted by one or more independent $R^6$.

In various embodiments of compounds of Formula I, $R^6$ is halo, In another embodiment, $R^6$ is —$OR^{31}$. In another embodiment, $R^6$ is —SH. In another embodiment, $R^6$ is $NH_2$. In another embodiment, $R^6$ is —$NR^{34}R^{35}$. In another embodiment, $R^6$ is —$NR^{31}R^{32}$. In another embodiment, $R^6$ is —$CO_2R^{31}$. In another embodiment, $R^6$ is —$CO_2$aryl. In another embodiment, $R^6$ is $C(=O)NR^{31}R^{32}$. In another embodiment, $R^6$ is $C(=O)NR^{34}R^{35}$. In another embodiment, $R^6$ is —$NO_2$. In another embodiment, $R^6$ is —CN. In another embodiment, $R^6$ is —$S(O)_{0-2}$ $C_{1-10}$alkyl. In another embodiment, $R^6$ is —$S(O)_{0-2}$aryl. In another embodiment, $R^6$ is —$SO_2NR^{34}R^{35}$. In another embodiment, $R^6$ is —$SO_2NR^{31}R^{32}$. In another embodiment, $R^6$ is $C_{1-10}$alkyl. In another embodiment, $R^6$ is $C_{2-10}$alkenyl. In another embodiment, $R^6$ is $C_{2-10}$alkynyl. In another embodiment, $R^6$ is unsubstituted aryl-$C_{1-10}$alkyl. In another embodiment, $R^6$ is unsubstituted aryl-$C_{2-10}$alkenyl. In another embodiment, $R^6$ is unsubstituted aryl-$C_{2-10}$alkynyl. In another embodiment, $R^6$ is unsubstituted heteroaryl-$C_{1-10}$alkyl. In another embodiment, $R^6$ is unsubstituted heteroaryl-$C_{2-10}$alkenyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent halo. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent cyano. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent nitro. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$OC_{1-10}$alkyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{1-10}$alkyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkenyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkynyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{1-10}$alkyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{2-10}$alkenyl. In another embodiment, $R^6$ is aryl-$C_{1-10}$alkyl, aryl-$C_{1-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{2-10}$alkynyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —COOH. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C(=O)NR^{31}R^{32}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C(=O)$ $NR^{34}R^{35}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$SO_2NR^{34}R^{35}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$SO_2$ $NR^{31}R^{32}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$NR^{31}R^{32}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$NR^{34}R^{35}$.

In various embodiments of compounds of Formula I, $R^9$ is H. In another embodiment, $R^9$ is halo. In another embodiment, $R^9$ is —$OR^{31}$. In another embodiment, $R^9$ is —SH. In another embodiment, $R^9$ is $NH_2$. In another embodiment, $R^9$ is —$NR^{34}R^{35}$. In another embodiment, $R^9$ is —$NR^{31}R^{32}$. In another embodiment, $R^9$ is —$CO_2R^{31}$. In another embodiment, $R^9$ is —$CO_2$aryl. In another embodiment, $R^9$ is —$C(=O)NR^{31}R^{32}$. In another embodiment, $R^9$ is $C(=O)$ $NR^{34}R^{35}$. In another embodiment, $R^9$ is —$NO_2$. In another embodiment, $R^9$ is —CN. In another embodiment, $R^9$ is —$S(O)_{0-2}$ $C_{1-10}$alkyl. In another embodiment, $R^9$ is —$S(O)_{0-2}$aryl. In another embodiment, $R^9$ is —$SO_2NR^{34}R^{35}$. In another embodiment, $R^9$ is —$SO_2NR^{31}R^{32}$. In another embodiment, $R^9$ is $C_{1-10}$alkyl. In another embodiment, $R^9$ is $C_{2-10}$alkenyl. In another embodiment, $R^9$ is $C_{2-10}$alkynyl. In another embodiment, $R^9$ is unsubstituted aryl-$C_{1-10}$alkyl. In another embodiment, $R^9$ is unsubstituted aryl-$C_{2-10}$alkenyl. In another embodiment, $R^9$ is unsubstituted aryl-$C_{2-10}$alkynyl. In another embodiment, $R^9$ is unsubstituted heteroaryl-$C_{1-10}$alkyl. In another embodiment, $R^9$ is unsubstituted heteroaryl-$C_{2-10}$alkenyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent halo. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent cyano. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent nitro. In another embodiment, $R^9$ is aryl-$C_{1-10}$alkyl, aryl-$C_{2-10}$alkenyl, aryl-$C_{2-10}$alkynyl, heteroaryl- $C_{1-10}$alkyl, or heteroaryl-$C_{2-10}$alkenyl substituted by one or more independent —$OC_{1-10}$alkyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{1-10}$alkyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkenyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkynyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{1-10}$alkyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{2-10}$alkenyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{2-10}$alkynyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —COOH. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —C(=O)$NR^{31}R^{32}$. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —C(=O)$NR^{34}R^{35}$. In another embodiment, $R^9$ is aryl-$C_{2-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$SO_2NR^{34}R^{35}$. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$SO_2$ $NR^{31}R^{32}$. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$NR^{31}R^{32}$. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$NR^{34}R^{35}$.

In various embodiments of compounds of Formula I, $R^{31}$ is H. In some embodiments, $R^{31}$ is unsubstituted $C_{1-10}$alkyl. In some embodiments, $R^{31}$ is substituted $C_{1-10}$alkyl. In some embodiments, $R^{31}$ is $C_{1-10}$alkyl substituted with one or more aryl. In some embodiments, $R^{31}$ is $C_{1-10}$alkyl substituted with one or more heteroalkyl. In some embodiments, $R^{31}$ is $C_{1-10}$alkyl substituted with one or more heterocyclyl. In some embodiments, $R^{31}$ is $C_{1-10}$alkyl substituted with one or more heteroaryl. In some embodiments, when $R^{31}$ is $C_{1-10}$alkyl substituted with one or more aryl, each of said aryl substituents is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}$ $C_{1-10}$alkyl, —$S(O)_{0-2}$ $C_{1-10}$alkylaryl, —$S(O)_{0-2}$ aryl, —$SO_2N$(aryl), —$SO_2N$($C_{1-10}$alkyl)($C_{1-10}$alkyl), —$SO_2NH$($C_{1-10}$alkyl) or —$SO_2NR^{34}R^{35}$. In some embodiments, when $R^{31}$ is $C_{1-10}$alkyl substituted with one or more heteroalkyl, each of said heteroalkyl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}$ $C_{1-10}$alkyl, —$S(O)_{0-2}$ $C_{1-10}$alkylaryl, —$S(O)_{0-2}$ aryl, —$SO_2N$(aryl), —$SO_2N$($C_{1-10}$alkyl)($C_{1-10}$alkyl), —$SO_2NH$($C_{1-10}$alkyl) or —$SO_2NR^{34}R^{35}$ substituents. In some embodiments, when $R^{31}$ is $C_{1-10}$alkyl substituted with one or more heterocyclyl, each of said heterocyclyl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}$ $C_{1-10}$alkyl, —$S(O)_{0-2}$ $C_{1-10}$alkylaryl, —$S(O)_{0-2}$ aryl, —$SO_2N$(aryl), —$SO_2$ N($C_{1-10}$alkyl)($C_{1-10}$alkyl), —$SO_2$ NH($C_{1-10}$alkyl) or —$SO_2NR^{34}R^{35}$. In some embodiments, when $R^{31}$ is $C_{1-10}$alkyl substituted with one or more heteroaryl, each of said heteroaryl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}$ $C_{1-10}$alkyl, —$S(O)_{0-2}$ $C_{1-10}$alkylaryl, —$S(O)_{0-2}$ aryl, —$SO_2N$(aryl), —$SO_2$ N($C_{1-10}$alkyl)($C_{1-10}$alkyl), —$SO_2$ NH($C_{1-10}$alkyl) or —$SO_2NR^{34}R^{35}$. In some embodiments, when $R^{31}$ is substituted $C_{1-10}$alkyl, it is substituted by a combination of aryl, heteroalkyl, heterocyclyl, or heteroaryl groups.

In various embodiments of compounds of Formula I, $R^{32}$ is H. In some embodiments, $R^{32}$ is unsubstituted $C_{1-10}$alkyl. In some embodiments, $R^{32}$ is substituted $C_{1-10}$alkyl. In some embodiments, $R^{32}$ is $C_{1-10}$alkyl substituted with one or more aryl. In some embodiments, $R^{32}$ is $C_{1-10}$alkyl substituted with one or more heteroalkyl. In some embodiments, $R^{32}$ is $C_{1-10}$alkyl substituted with one or more heterocyclyl. In some embodiments, $R^{32}$ is $C_{1-10}$alkyl substituted with one or more heteroaryl. In some embodiments, when $R^{32}$ is $C_{1-10}$alkyl substituted with one or more aryl, each of said aryl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}$ $C_{1-10}$alkyl, —$S(O)_{0-2}$ $C_{1-10}$alkylaryl, —$S(O)_{0-2}$ aryl, —$SO_2N$(aryl), —$SO_2$ N($C_{1-10}$alkyl)($C_{1-10}$alkyl), —$SO_2$ NH($C_{1-10}$alkyl) or —$SO_2NR^{34}R^{35}$. In some embodiments, when $R^{32}$ is $C_{1-10}$alkyl substituted with one or more heteroalkyl, each of said heteroalkyl group is unsubstituted or substituted with one or more halo, —OH, —$C_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$ C$_{1-10}$alkyl, —S(O)$_{0-2}$ C$_{1-10}$alkylaryl, —S(O)$_{0-2}$ aryl, —SO$_2$N(aryl), —SO$_2$ N(C$_{1-10}$alkyl)(C$_{1-10}$alkyl), —SO$_2$ NH(C$_{1-10}$alkyl) or —SO$_2$NR$^{34}$R$^{35}$. In some embodiments, when R$^{32}$ is C$_{1-10}$alkyl substituted with one or more heterocyclyl, each of said heterocyclyl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$ C$_{1-10}$alkyl, —S(O)$_{0-2}$ C$_{1-10}$alkylaryl, —S(O)$_{0-2}$ aryl, —SO$_2$N(aryl), —SO$_2$ N(C$_{1-10}$alkyl)(C$_{1-10}$alkyl), —SO$_2$ NH(C$_{1-10}$alkyl) or —SO$_2$NR$^{34}$R$^{35}$. In some embodiments, when R$^{32}$ is C$_{1-10}$alkyl substituted with one or more heteroaryl, each of said heteroaryl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$ C$_{1-10}$alkyl, —S(O)$_{0-2}$ C$_{1-10}$alkylaryl, —S(O)$_{0-2}$ aryl, —SO$_2$N(aryl), —SO$_2$ N(C$_{1-10}$ alkyl)(C$_{1-10}$alkyl), —SO$_2$ NH(C$_{1-10}$alkyl) or —SO$_2$NR$^{34}$R$^{35}$. In some embodiments, when R$^{32}$ is substituted C$_{1-10}$alkyl, it is substituted by a combination of aryl, heteroalkyl, heterocyclyl, or heteroaryl groups.

In various embodiments of compounds of Formula I, R$^{33}$ is unsubstituted C$_{1-10}$alkyl. In some embodiments, R$^{33}$ is substituted C$_{1-10}$alkyl. In some embodiments, R$^{33}$ is C$_{1-10}$alkyl substituted with one or more aryl. In some embodiments, R$^{33}$ is C$_{1-10}$alkyl substituted with one or more heteroalkyl. In some embodiments, R$^{33}$ is C$_{1-10}$alkyl substituted with one or more heterocyclyl. In some embodiments, R$^{33}$ is C$_{1-10}$alkyl substituted with one or more heteroaryl. In some embodiments, when R$^{33}$ is C$_{1-10}$alkyl substituted with one or more aryl, each of said aryl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$ C$_{1-10}$alkyl, —S(O)$_{0-2}$ C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$. In some embodiments, when R$^{33}$ is C$_{1-10}$alkyl substituted with one or more heteroalkyl, each of said heteroalkyl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$ C$_{1-10}$alkyl, —S(O)$_{0-2}$ C$_{1-10}$alkylaryl, —S(O)$_{0-2}$ aryl, —SO$_2$N(aryl), —SO$_2$ N(C$_{1-10}$alkyl)(C$_{1-10}$alkyl), —SO$_2$ NH(C$_{1-10}$alkyl) or —SO$_2$NR$^{34}$R$^{35}$. In some embodiments, when R$^{33}$ is C$_{1-10}$alkyl substituted with one or more heterocyclyl, each of said heterocyclyl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$ C$_{1-10}$alkyl, —S(O)$_{0-2}$ C$_{1-10}$alkylaryl, —S(O)$_{0-2}$ aryl, —SO$_2$N(aryl), —SO$_2$ N(C$_{1-10}$alkyl)(C$_{1-10}$alkyl), —SO$_2$ NH(C$_{1-10}$alkyl) or —SO$_2$NR$^{34}$R$^{35}$. In some embodiments, when R$^{33}$ is C$_{1-10}$alkyl substituted with one or more heteroaryl, each of said heteroaryl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$^0$ alkyl), —NO$_2$, —CN, —S(O)$_{0-2}$ C$^0$ alkyl, —S(O)$_{0-2}$ C$_{1-10}$alkylaryl, —S(O)$_{0-2}$ aryl, —SO$_2$N(aryl), —SO$_2$ N(C$_{1-10}$ alkyl)(C$_{1-10}$alkyl), —SO$_2$ NH(C$_{1-10}$alkyl) or —SO$_2$NR$^{34}$R$^{35}$. In some embodiments, when R$^{33}$ is substituted C$_{1-10}$alkyl, it is substituted by a combination of aryl, heteroalkyl, heterocyclyl, or heteroaryl groups.

In various embodiments of compounds of Formula I, R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, heteroaryl, C$_{1-6}$alkyl, or O-aryl, and wherein said 3-10 membered saturated or unsaturated ring independently contains 0, 1, or 2 more heteroatoms in addition to the nitrogen.

In some embodiments, the R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form:

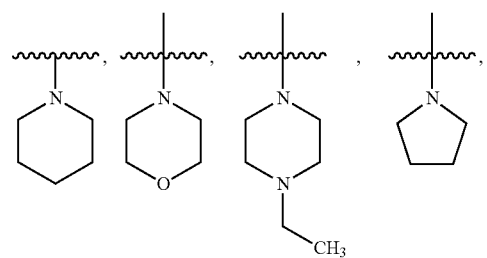

-continued

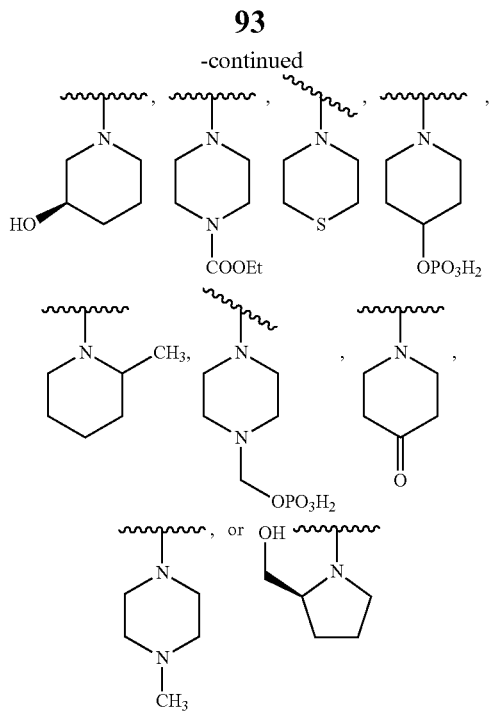

In another embodiment, $X_1$ is C≡NH$_2$.

In various embodiments, $X_1$ is C≡NH—R$^4$, where —NH—R$^4$ is:

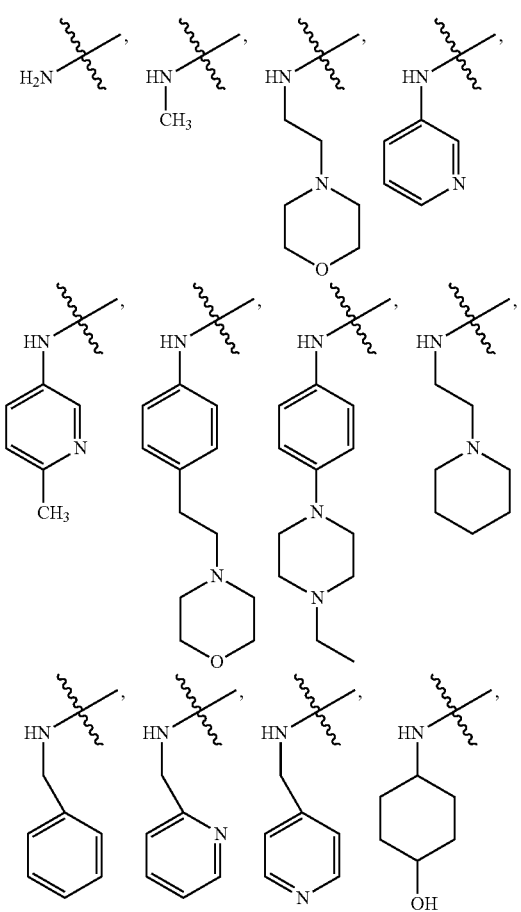

-continued

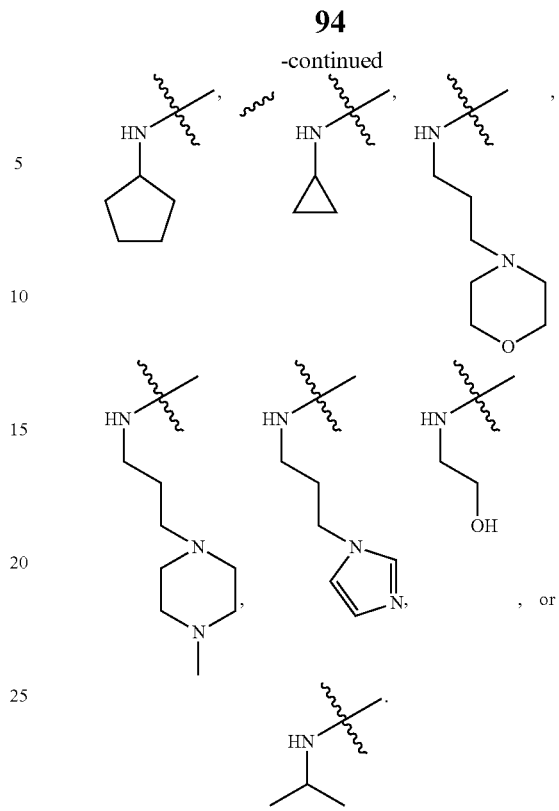

In one embodiment, the invention provides an inhibitor of Formula I-C1 where R$^5$ is H. In another embodiment, the invention provides an inhibitor of Formula I-C2 where R$^5$ is H.

In some embodiments, the invention provides an inhibitor of Formula I-C1a:

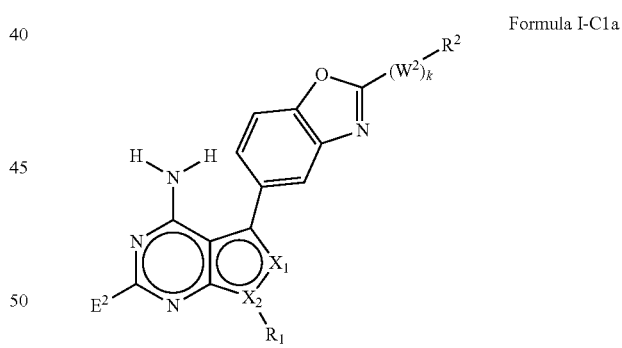

Formula I-C1a or a pharmaceutically acceptable salt thereof wherein:
$E^2$ is —H;
$X_1$ and $X_2$ are N;
$R_1$ is -L-C$_{1-10}$alkyl, -L-C$_{3-8}$cycloalkyl, -L-C$_{1-10}$alkylheterocyclyl, or -L-heterocyclyl, each of which is unsubstituted or is substituted by one or more independent R$^3$;
L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;
R$^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, heteroaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$—CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

—(W$^2$)$_k$— is —NH—, —N(H)C(O)— or —N(H)S(O)$_2$—;

R$^2$ is hydrogen, halogen, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —S(O)$_{0-2}$R$^{31}$, —SO$_2$NR$^{31}$R$^{32}$, —SO$_2$NR$^{34}$R$^{35}$, bicyclic aryl, substituted monocyclic aryl, heteroaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl C$_{3-8}$cycloalkyl-C$_{2-10}$alkynyl, C$_{2-10}$alkyl-monocyclic aryl, monocyclic aryl-C$_{2-10}$alkyl, C$_{1-10}$alkylbicycloaryl, bicycloaryl-C$_{1-10}$alkyl, substituted C$_{1-10}$alkylaryl, substituted aryl-C$_{1-10}$alkyl, C$_{1-10}$alkylheteroaryl, C$_{1-10}$alkylheterocyclyl, C$_{2-10}$alkenyl, C$_{2-10}$alkynyl, C$_{2-10}$alkenylaryl, C$_{2-10}$alkenylheteroaryl, C$_{2-10}$alkenylheteroalkyl, C$_{2-10}$alkenylheterocycicyl, C$_{2-10}$alkynylaryl, C$_{2-10}$alkynylheteroaryl, C$_{2-10}$alkynylheteroalkyl, C$_{2-10}$alkynylheterocyclyl, C$_{2-10}$alkenyl-C$_{3-8}$cycloalkyl, C$_{2-10}$alkynyl-C$_{3-8}$cycloalkenyl, C$_{1-10}$alkoxy C$_{1-10}$alkyl, C$_{1-10}$alkoxyC$_{2-10}$alkenyl, C$_{1-10}$alkoxyC$_{2-10}$alkynyl, heterocyclyl, heterocyclyl C$_{1-10}$alkyl, heterocyclylC$_{2-10}$alkenyl, heterocyclyl-C$_{2-10}$alkynyl, aryl-C$_{2-10}$alkenyl, aryl-C$_{2-10}$alkynyl, aryl-heterocyclyl, heteroaryl-C$_{1-10}$alkyl, heteroaryl-C$_{2-10}$alkenyl, heteroaryl-C$_{2-10}$alkynyl, heteroaryl-C$_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^{31}$, R$^{32}$, and R$^{33}$, in each instance, are independently H or C$_{1-10}$alkyl, wherein the C$_{1-10}$alkyl is unsubstituted; and R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, heteroaryl, C$_{1-6}$alkyl, or O-aryl, and wherein said 3-10 membered saturated or unsaturated ring independently contains 0, 1, or 2 more heteroatoms in addition to the nitrogen.

In another aspect, an inhibitor of Formula I-C1 is a compound of Formula I-C1a:

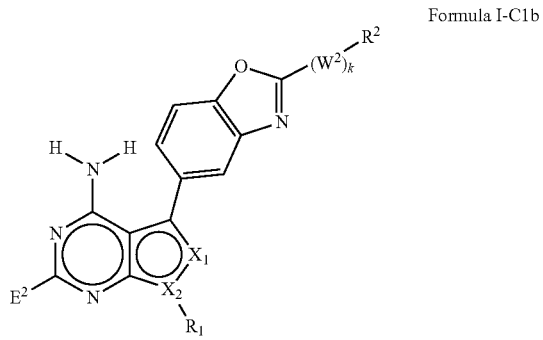

Formula I-C1b or a pharmaceutically acceptable salt thereof, wherein: E$^2$ is —H; X$_1$ is CH and X$_2$ is N;

R$_1$ is -L-C$_{1-10}$alkyl, -L-C$_{3-8}$cycloalkyl, -L-C$_{1-10}$alkylheterocyclyl, or -L-heterocyclyl, each of which is unsubstituted or is substituted by one or more independent R$^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

R$^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, heteroaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

—(W$^2$)$_k$— is —NH—, —N(H)C(O)— or —N(H)S(O)$_2$—;

R$^2$ is hydrogen, halogen, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —S(O)$_{0-2}$R$^{31}$, —SO$_2$NR$^{31}$R$^{32}$, —SO$_2$NR$^{34}$R$^{35}$, bicyclic aryl, substituted monocyclic aryl, heteroaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{2-10}$alkyl-monocyclic aryl, monocyclic aryl-C$_{2-10}$alkyl, C$_{1-10}$alkylbicycloaryl, bicycloaryl-C$_{1-10}$alkyl, substituted C$_{1-10}$alkylaryl, substituted aryl-C$_{1-10}$alkyl, C$_{1-10}$alkylheteroaryl, C$_{1-10}$alkylheterocyclyl, C$_{2-10}$alkenyl, C$_{2-10}$alkynyl, heterocyclyl, heterocyclyl C$_{1-10}$alkyl, heterocyclyl-C$_{2-10}$alkenyl, heterocyclyl-C$_{2-10}$ alkynyl, aryl-heterocyclyl, heteroaryl-$C_{1-10}$alkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^3$)$NR^{33}R^{32}$, —$NR^{31}$C(=$NR^3$)$OR^{33}$, —$NR^{31}$C(=$NR^3$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^{31}$, $R^{32}$, and $R^{33}$, in each instance, are independently H or $C_{1-10}$alkyl, wherein the $C_{1-10}$alkyl is unsubstituted; and $R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen.

The invention further provides a compound which is an mTorC1/mTorC2 inhibitor, wherein the compound has the Formula I-A:

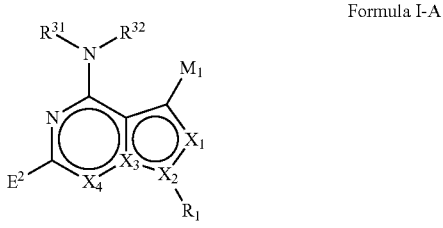

Formula I-A or a pharmaceutically acceptable salt thereof, wherein:

$X_1$ is N or C-$E^1$, $X_2$ is N, $X_3$ is $C_1$ and $X_4$ is C—$R^9$ or N; or $X_1$ is N or C-$E^1$, $X_2$ is C, $X_3$ is $N_1$ and $X_4$ is C—$R^9$ or N;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylheteroaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkylheterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$M_1$ is benzothiazolyl substituted with —(W$^2$)$_k$—$R^2$;

k is 0 or 1;

$E^1$ and $E^2$ are independently —(W$^1$)$_j$—$R^4$;

j, in each instance (i.e., in $E^1$ or j in $E^2$), is independently 0 or 1

$W^1$ is —O—, —$NR^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)$OR^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —$NR^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)$OR^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^2$ is hydrogen, halogen, —OH, —$R^{31}$, —$CF_3$, —$OCF_3$, —$OR^{31}$, —$NR^{31}R^{32}$, —$NR^{34}R^{35}$, (O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$—$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, —SC(=O)$NR^{31}R^{32}$, aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenylheteroalkyl, $C_{2-10}$alkenylheterocycicyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —OC(=S)$OR^{31}$, —OC(=O)$SR^{31}$, —$NR^{31}$C(=$NR^{32}$)$NR^{33}R^{32}$, —$NR^{31}$C(=$NR^3$)$OR^{33}$, —$NR^{31}$C(=$NR^3$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$OC(=S)OR^{31}$, —$OC(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, —SC aryl, heteroaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenylheteroalkyl, $C_{2-10}$alkenylheterocycicyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroalkyl, heteroaryl-heteroalkyl, or heteroaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$—$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —N—$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, $(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group, wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl)$(C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —$C(=O)N(C_{1-10}$alkyl)$(C_{1-10}$alkyl), —$C(=O)NH(C_{1-10}$alkyl), —$C(=O)NR^{34}R^{35}$, —$C(=O)NH_2$, —$OCF_3$, —$O(C_{1-10}$alkyl), —O-aryl, —N(aryl)$(C_{1-10}$alkyl), —$NO_2$, —CN, —$S(O)_{0-2}$ $C_{1-10}$alkyl, —$S(O)_{0-2}$ $C_{1-10}$alkylaryl, —$S(O)_{0-2}$ aryl, —$SO_2N$(aryl), —$SO_2N(C_{1-10}$alkyl)$(C_{1-10}$alkyl), —$SO_2NH(C_{1-10}$alkyl) or —$SO_2NR^{34}R^{35}$;

$R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$.

In some embodiments, $X_4$ is C—$R^9$.

The invention also provides an inhibitor as defined above, wherein the compound is of Formula I-B:

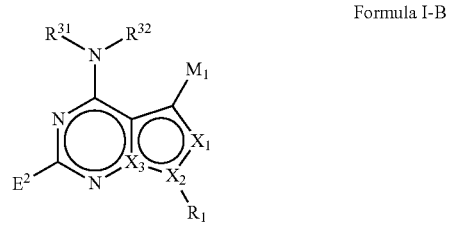

Formula I-B or a pharmaceutically acceptable salt thereof, and wherein the substituents are as defined above.

In various embodiments the compound of Formula I-B or its pharmaceutically acceptable salt thereof, is an inhibitor having the structure of Formula I-B1 or Formula I-B2:

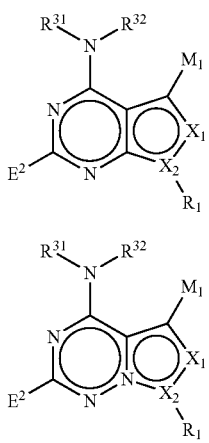

Formula I-B1

Formula I-B2 or a pharmaceutically acceptable salt thereof.

In various embodiments of Formula I-B1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In various embodiments of Formula I-B2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —$S(O)_{0-2}$—. In various embodiments of $X_1$, j is 1, and $W^1$ is —C(O)—. In various embodiments of $X_1$, j is 1, and $W^1$ is —$C(O)N(R^7)$—. In various embodiments of $X_1$, j is 1, and $W^1$ is —$N(R^7)C(O)$—. In various embodiments of $X_1$, j is 1, and $W^1$ is —$N(R^7)S(O)$—. In various embodiments of $X_1$, j is 1, and $W^1$ is —$N(R^7)S(O)_2$—. In various embodiments of $X_1$, j is 1, and $W^1$ is —C(O)O—. In various embodiments of $X_1$, j is 1, and $W^1$ is $CH(R^7)N(C(O)OR^8)$—. In various embodiments of $X_1$, j is 1, and $W^1$ is —$CH(R^7)N(C(O)R^8)$—. In various embodiments of $X_1$, j is 1, and $W^1$ is —$CH(R^7)N(SO_2R^8)$—. In various embodiments of $X_1$, j is 1, and $W^1$ is —$CH(R^7)N(R^8)$—. In various embodiments of $X_1$, j is 1, and $W^1$ is —$CH(R^7)C(O)N(R^8)$—. In various embodiments of $X_1$, j is 1, and $W^1$ is —$CH(R^7)N(R^8)C(O)$—. In various embodiments of $X_1$, j is 1, and $W^1$ is —$CH(R^7)N(R^8)S(O)$—. In various embodiments of $X_1$, j is 1, and $W^1$ is —$CH(R^7)N(R^8)S(O)_2$—.

In another embodiment, $X_1$ is $CH_2$. In yet another embodiment, $X_1$ is CH-halogen, where halogen is Cl, F, Br, or I.

In another embodiment, $X_1$ is N.

In various embodiments, $X_2$ is N. In other embodiments, $X_2$ is C.

In various embodiments, $E^2$ is —$(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is —$(W^1)_j$—$R^4$. In various embodiments of $E^2$, j is 1, and $W^1$ is —O—. In various embodiments of $E^2$, j is 1, and $W^1$ is —$NR^7$—. In various embodiments of $E^2$, j is 1, and $W^1$ is —NH—. In various embodiments of $E^2$, j is 1, and $W^1$ is —$S(O)_{0-2}$—. In various embodiments of $E^2$, j is 1, and $W^1$ is —C(O)—. In various embodiments of $E^2$, j is 1, and $W^1$ is —$C(O)N(R^7)$—. In various embodiments of $E^2$, j is 1, and $W^1$ is —$N(R^7)C(O)$—. In various embodiments of $E^2$, j is 1, and $W^1$ is —$N(R^7)S(O)$—. In various embodiments of $E^2$, j is 1, and $W^1$ is —$N(R^7)S(O)_2$—. In various embodiments of $E^2$, j is 1, and $W^1$ is —C(O)O—. In various embodiments of $E^2$, j is 1, and $W^1$ is $CH(R^7)N(C(O)OR^8)$—. In various embodiments of $E^2$, j is 1, and $W^1$ is —$CH(R^7)N(C(O)R^8)$—. In various embodiments of $E^2$, j is 1, and $W^1$ is —$CH(R^7)N(SO_2R^8)$—. In various embodiments of $E^2$, j is 1, and $W^1$ is —$CH(R^7)N(R^8)$—. In various embodiments of $E^2$, j is 1, and $W^1$ is —$CH(R^7)C(O)N(R^8)$—. In various embodiments of $E^2$, j is 1, and $W^1$ is —$CH(R^7)N(R^8)C(O)$—. In various embodiments of $E^2$, j is 1, and $W^1$ is —$CH(R^7)N(R^8)S(O)$—. In various embodiments of $E^2$, j is 1, and $W^1$ is —$CH(R^7)N(R^8)S(O)_2$—.

In various embodiments of Formula I-A, I-B, I-B1 and I-B2, $M_1$ is:

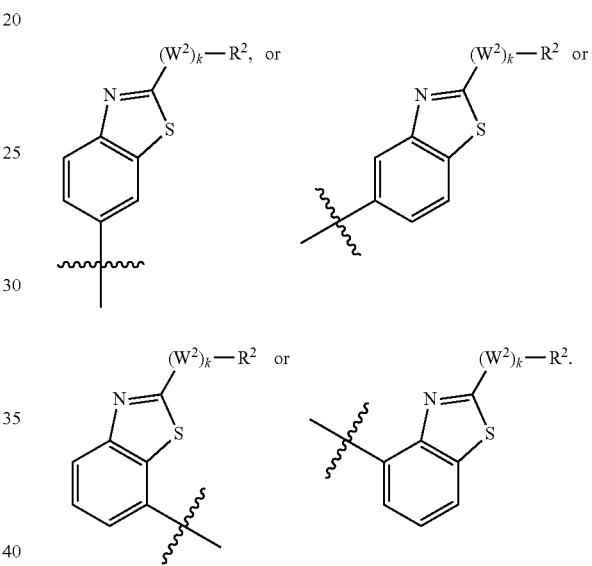

In some embodiments of the invention, $M_1$ is benzothiazolyl substituted with —$(W^2)_k$—$R^2$. $W^2$ can be —O—, —$S(O)_{0-2}$-(including but not limited to —S—, —S(O)—, and —$S(O)_2$—), —C(O)—, or —C(O)O—. In other embodiments, $W^1$ is —$NR^6$— or —$CH(R^6)N(R^7)$—, wherein $R^6$ and $R^7$ are each independently hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), unsubstituted or substituted $C_2$-$C_{10}$alkenyl (including but not limited to alkenyl such as, for example, vinyl, allyl, 1-methyl propen-1-yl, butenyl, or pentenyl). Additionally when $W^2$ is —$NR^6$— or —$CH(R^6)N(R^7)$—, $R^6$ and $R^7$ are each independently unsubstituted or substituted aryl (including phenyl and naphthtyl). In yet other embodiments, when $W^2$ is —$NR^6$— or —$CH(R^6)N(R^7)$—, $R^6$ and $R^7$ are each independently heteroaryl, wherein the heteroaryl is unsubstituted or substituted. $R^6$ and $R^7$ heteroaryl is monocyclic heteroaryl, and includes but is not limited to imidazolyl, pyrrolyl, oxazolyl, thiazolyl, and pyridinyl. In some other embodiments, when $W^2$ is —$NR^6$— or —$CH(R^6)N(R^7)$—, $R^6$ and $R^7$ are each independently unsubstituted or substituted heterocyclyl (which includes but is not limited to pyrrolidinyl, tetrahydrofuranyl, piperidinyl, tetrahydropyranyl, thiazolidinyl, imidazolidinyl, morpholinyl, and piperazinyl) or unsubstituted or substituted $C_{3-8}$cycloalkyl (including but not limited to cyclopropyl, cyclobutyl, and cyclopentyl). Non limiting exemplary $W^2$ include NH—, —N(cyclopropyl), and N(4-N-piperidinyl).

For example, exemplary mTorC1/mTorC2 inhibitors of the invention have the Formulas:

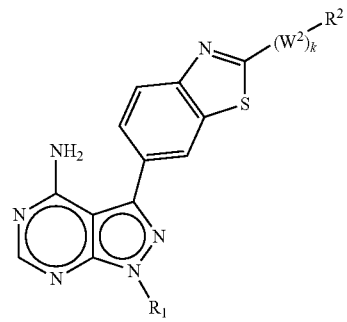

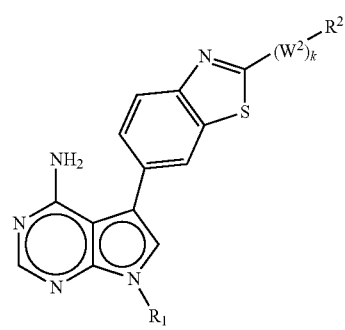

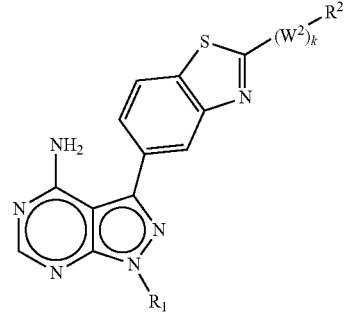

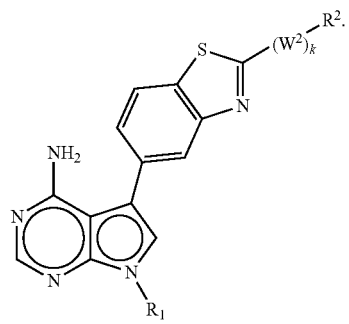

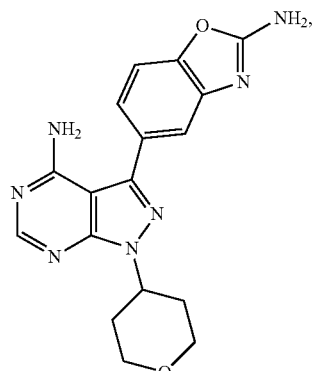

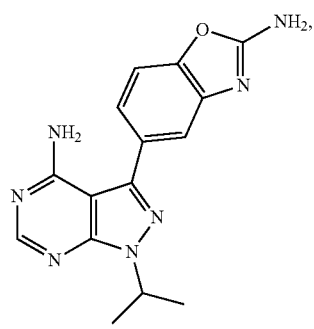

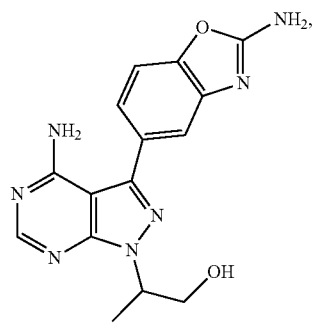

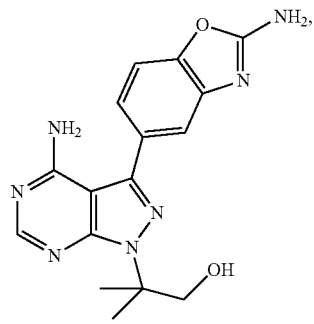

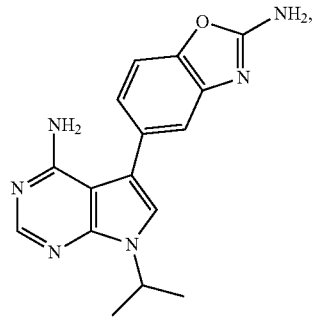

In specific embodiments, the compounds for use in the invention are chosen from the group consisting of:

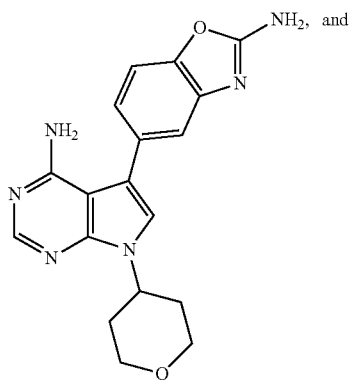

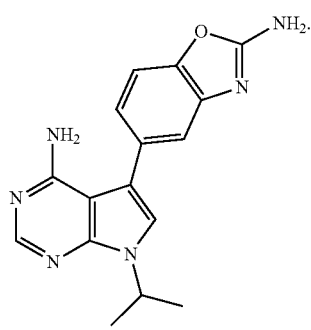

Reaction Schemes—mTorC1/mTorC2 Inhibitor Compounds

The mTorC1/mTorC2 inhibitor compounds disclosed herein may be prepared by the routes described below. Materials used herein are either commercially available or prepared by synthetic methods generally known in the art. These schemes are not limited to the compounds listed or by any particular substituents employed for illustrative purposes. Numbering does not necessarily correspond to that of claims or other tables.

Scheme A

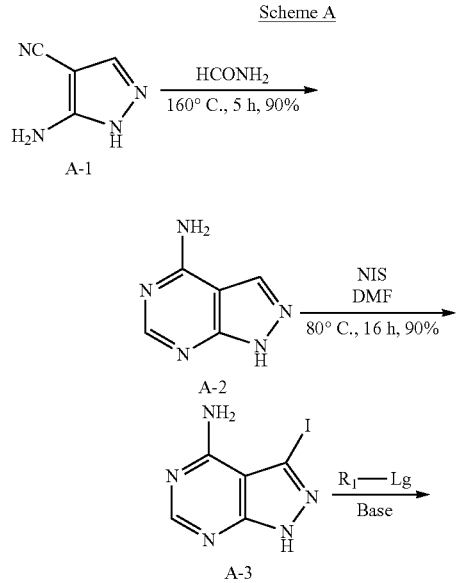

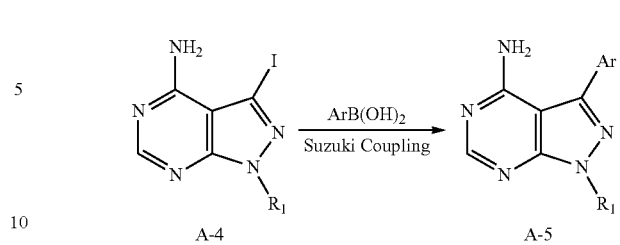

In one embodiment, compounds are synthesized by condensing a functionalized heterocycle A-1 with formamide, to provide a pyrazolopyrimidine A-2. The pyrazolopyrimidine is treated with N-iodosuccinimide, which introduces an iodo substituent in the pyrazole ring as in A-3. The $R_1$ substituent is introduced by reacting the pyrazolopyrimidine A3 with a compound of Formula $R_1$-Lg in the presence of a base such as potassium carbonate to produce a compound of Formula A-4. Other bases that are suitable for use in this step include but are not limited to sodium hydride and potassium t-butoxide. The compound of Formula $R_1$-Lg has a moiety $R_1$ as defined for $R_1$ of a compound of Formula I-A, and wherein Lg is an appropriate leaving group such as halide (including bromo, iodo, and chloro), tosylate, or other suitable leaving group, The substituents corresponding to $M_1$ are thereafter introduced by reacting aryl or heteroaryl boronic acids with the compound of Formula A-4 to obtain compound A-5.

Scheme A-1

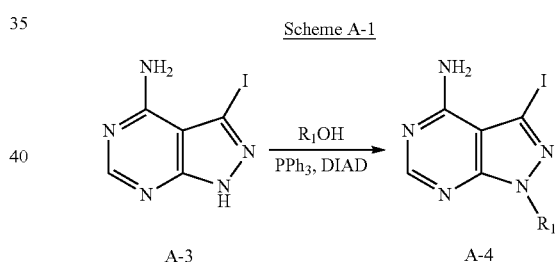

Alternatively, Mitsunobu chemistry can be used to obtain alkylated pyrazolopyrimidine A-4, as shown in Scheme A-1. Iodopyrazolopyrimidine A-3 is reacted with a suitable alcohol, in the presence of triphenylphosphine and diisopropylazodicarboxylate (DIAD) to produce pyrazolopyrimidine A-4.

Scheme B

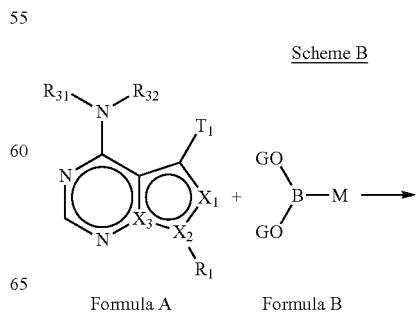

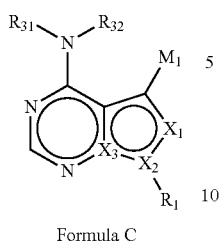

Formula C

The compounds of the invention may be synthesized via a reaction scheme represented generally in Scheme B. The synthesis proceeds via coupling a compound of Formula A with a compound of Formula B to yield a compound of Formula C. The coupling step is typically catalyzed by using, e.g., a palladium catalyst, including but not limited to palladium tetrakis (triphenylphosphine). The coupling is generally performed in the presence of a suitable base, a nonlimiting example being sodium carbonate. One example of a suitable solvent for the reaction is aqueous dioxane.

A compound of Formula A for use in Scheme B has a structure of Formula A, wherein $T_1$ is triflate or halo (including bromo, chloro, and iodo), and wherein $R_1, X_1, X_2, X_3, R_{31}$ and $R_{32}$ are defined as for a compound of Formula I-A. For boronic acids and acid derivatives as depicted in Formula B, M is either $M_1$ or $M_2$. $M_1$ is defined as for a compound of Formula I-A. For example, $M_1$ can be a 5-benzoxazolyl or a 6-benzoxazolyl moiety, including but not limited to those $M_1$ moieties disclosed herein. $M_2$ is a moiety which is synthetically transformed to form $M_1$, after the $M_2$ moiety has been coupled to the bicyclic core of the compound of Formula A.

For a compound of Formula B, G is hydrogen or $R_{G1}$, wherein $R_{G1}$ is alkyl, alkenyl, or aryl. Alternatively, $B(OG)_2$ is taken together to form a 5- or 6-membered cyclic moiety. In some embodiments, the compound of Formula B is a compound having a structure of Formula E:

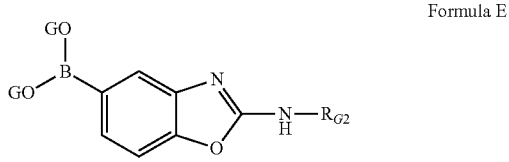

Formula E wherein G is H or $R_{G1}$; $R_{G1}$ is alkyl, alkenyl, or aryl. Alternatively,

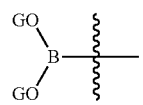

forms a 5- or 6-membered cyclic moiety; and $R_2$ is a $R_{G2}$ moiety, wherein the $R_{G2}$ moiety is H, acyl, or an amino protecting group including but not limited to tert-butyl carbamate (Boc), carbobenzyloxy (Cbz), benzyl (Bz), fluorenylmethyloxycarbonyl (FMOC), p-methoxybenzyl (PMB), and the like.

Scheme C $$T_2-M \longrightarrow \underset{R_{G1}O}{\overset{R_{G1}O}{B}}-M \longrightarrow \underset{HO}{\overset{HO}{B}}-M$$

Formula D    Formula B'    Formula B"

In some embodiments, a compound of Formula B is a compound of Formula B', wherein G is $R_{G1}$, or a compound of Formula B", wherein G is hydrogen. Scheme C depicts an exemplary scheme for synthesizing a compound of Formula B' or, optionally, Formula B" for use in Reaction Scheme C. This reaction proceeds via reacting a compound of Formula D with a trialkyl borate or a boronic acid derivative to produce a compound of Formula B'. The reaction is typically run a solvent such as dioxane or tetrahydrofuran. The trialkyl borate includes but is not limited to triisopropyl borate and the boronic acid derivative includes but is not limited to bis(pinacolato)diboron.

When the reaction is performed with trialkyl borate, a base such as n-butyllithium is first added to the compound of Formula D to generate an anion, prior to the addition of the borate. When the reaction is performed with a boronic acid derivative such as bis(pinacolato)diboron, a palladium catalyst and a base is used. Typical palladium catalysts include but is not limited to palladium chloride (diphenylphosphino)ferrocene). A suitable base includes but is not limited to potassium acetate.

A compound of Formula D for use in Scheme C is a compound wherein $T_2$ is halo or another leaving group, and M is as defined above in Scheme B. The compound of Formula B' may further be converted to a compound of Formula B" by treatment with an acid such as hydrochloric acid.

In one embodiment of a compound of Formula B, B', B", or E, the G groups are hydrogen. In another of a compound of Formula B, B', B", or E, the G groups are $R_{G1}$.

In some embodiments, no further synthetic transformation of $M_1$ moiety is performed after the coupling reaction when, e.g. $M_1$ is 2-N-acetyl-benzoxazol-5-yl.

Some exemplary compounds of Formula B that can be synthesized via Scheme C include but are not limited to compounds of the following formulae:

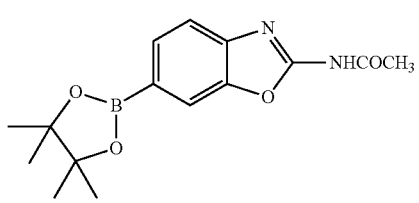

H-7

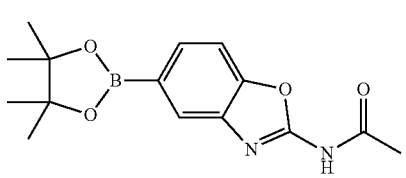

F-7

G-6 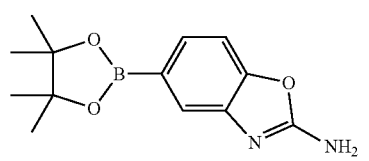
I-4 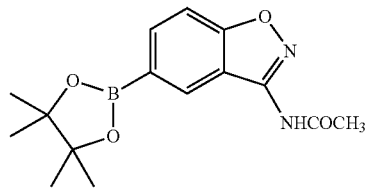
G-7 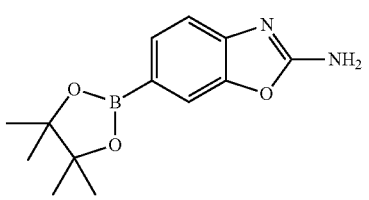
G-8 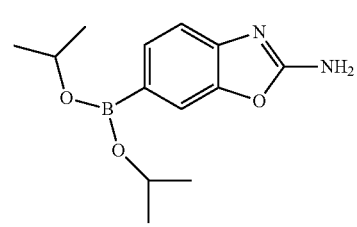
G-9 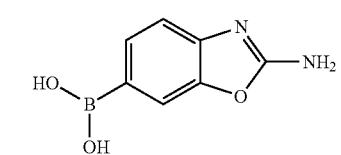
J-4 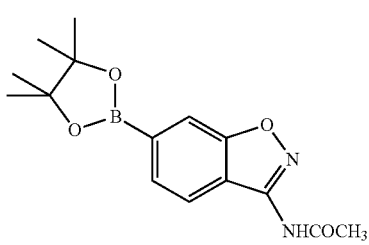
K-6 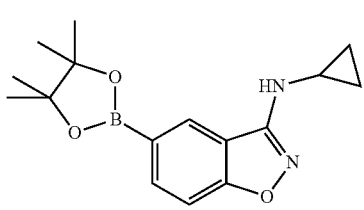
L-6 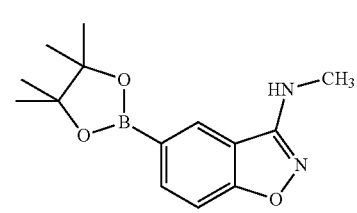
H-7-B 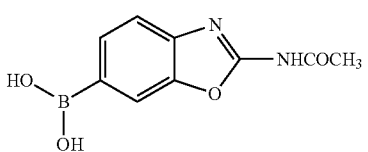
F-7-B 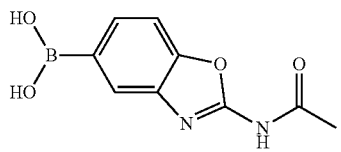
G-6-B 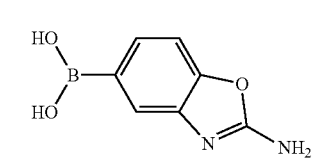
I-4-B 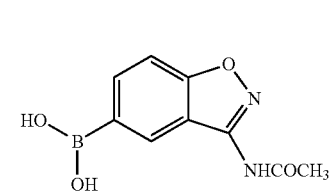
J-4-B 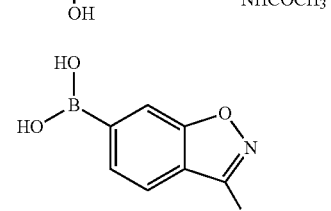
K-6-B 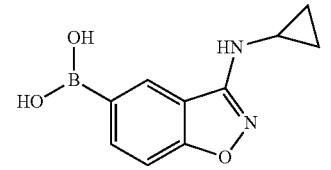
L-6-B 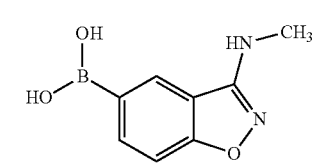
In other embodiments of the invention, a compound of Formula E is synthesized from a compound of Formula F, as shown in Scheme C-1:
Scheme C-1
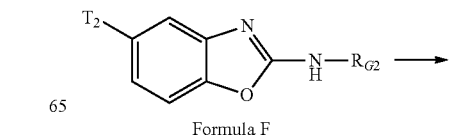
Formula F

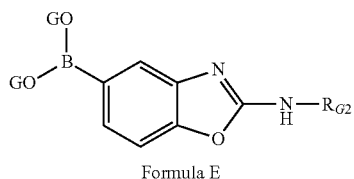

Formula E

Scheme C-1 depicts an exemplary scheme for synthesizing a compound of Formula E. This reaction proceeds via reacting a compound of Formula F with a trialkyl borate or a boronic acid derivative to produce a compound of Formula E. The conditions of the reaction are as described above in Scheme C.

A compound of Formula F for use in Scheme C-1 is a compound wherein $T_2$ is halo (including Br, Cl, and I) or another leaving group (including but not limited to triflate, tosylate, and mesylate), and the $G_p$ moiety is H, acyl, or an amino protecting group including but not limited to tert-butyl carbamate (Boc), carbobenzyloxy (Cbz), benzyl (Bz), fluorenylmethyloxycarbonyl (FMOC), p-methoxybenzyl (PMB), and the like.

The compound of Formula E, wherein G is alkyl, may further be converted to a compound of Formula E, wherein G is hydrogen, by treatment with an acid such as hydrochloric acid Where desired, deprotection of a substituent (e.g., removal of Boc protection from an amino substituent) on the benzoxazolyl moiety (i.e. $M_1$ of Formula C) is performed after coupling the compound of Formula B to the compound of Formula A.

Some exemplary compounds with such protecting groups, include but are not limited to compounds of the following formulae:

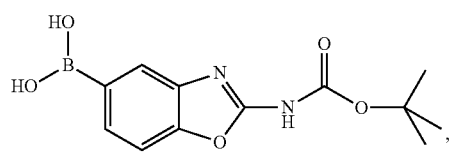

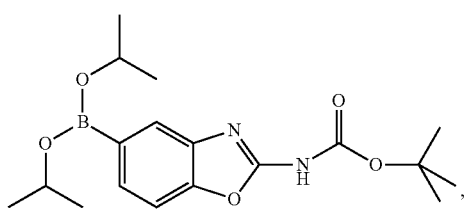

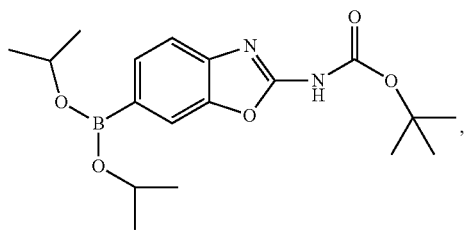

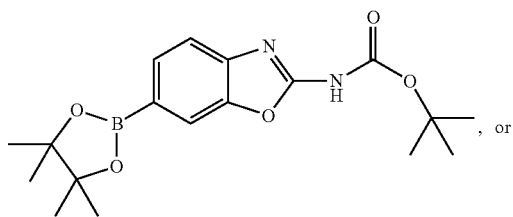

, or

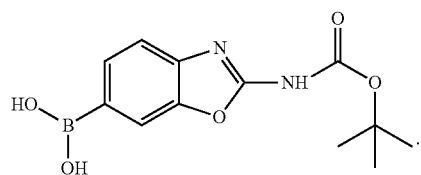

.

An exemplary transformation of $M_2$ to $M_1$ can be carried out via Scheme D as shown below.

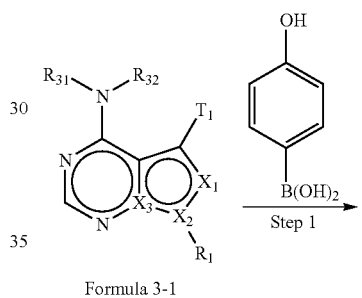

Formula 3-1

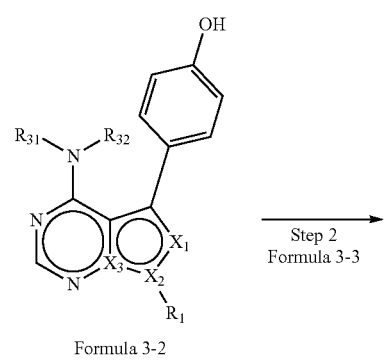

Formula 3-2

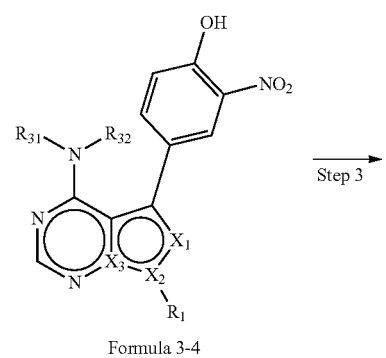

Formula 3-4

113

-continued

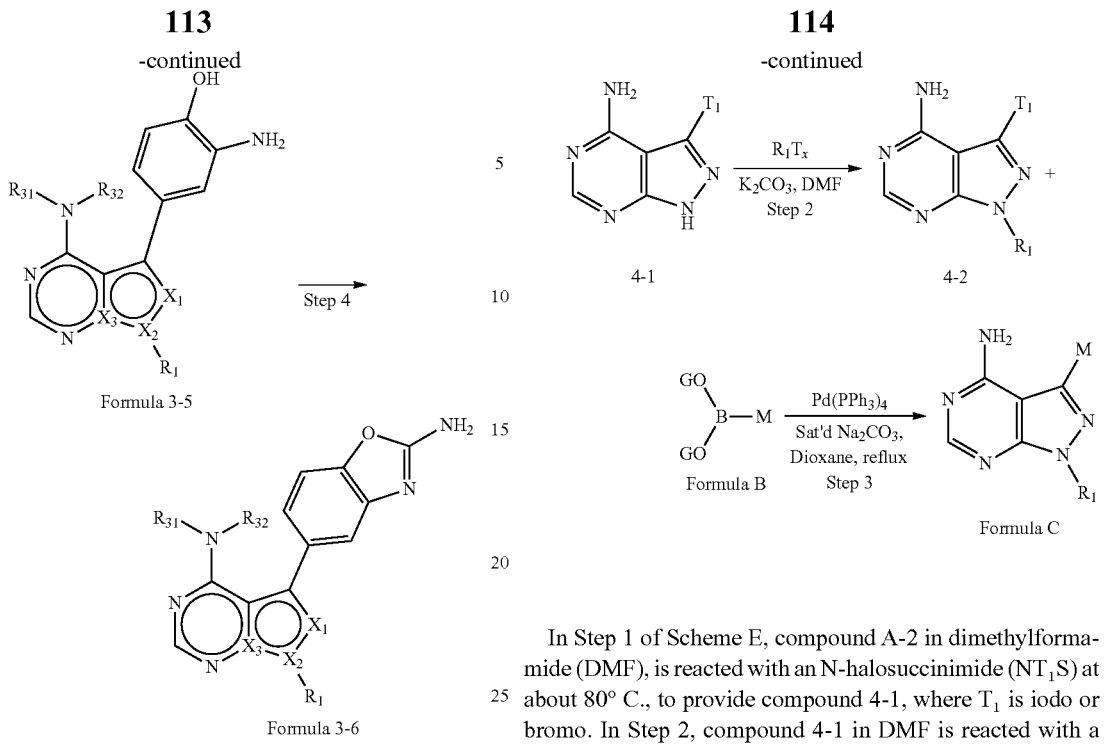

Formula 3-5

Formula 3-6

In Step 1, a compound of Formula 3-1 is reacted with boronic acid 3-2, in the presence of palladium tetrakis (triphenylphosphine) and a suitable base, such as sodium carbonate in an aqueous/organic solvent mixture to produce a compound of Formula 3-3. In Step 2, the compound of Formula 3-3 is reacted with about 2 equivalents of nitric acid in acetic acid as solvent to produce a compound of Formula 3-4. Two alternative transformations may be used to effect the next transformation of Step 3. In the first method, the compound of Formula 3-4 is treated with sodium dithionite and sodium hydroxide in water to produce a compound of Formula 3-5. Alternatively, the compound of Formula 3-4 is reduced using palladium on carbon in a suitable solvent under a hydrogen atmosphere to yield a compound of Formula 3-5.

In Step 4, compound 3-5 is reacted with about 1.2 equivalents of cyanogen bromide in a solvent such as methanol/ tetrahydrofuran mixture to produce a compound of Formula 3-6. The compound of Formula 3-6 may be further transformed by other substitution or derivatization.

A compound of Formula 3-1 useful in the method of Scheme D is a compound having a structure of Formula 3-1, wherein $T_1$ is triflate or halo (including bromo, chloro, and iodo), and wherein $R_1, X_1, X_2, X_3, R_{31}$ and $R_{32}$ are defined as for a compound of Formula I-A.

Exemplary compounds having a pyrazolopyrimidine core can be synthesized via Scheme E.

Scheme E

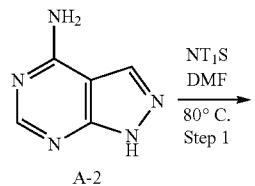

114

-continued 4-1

4-2

Formula B    Step 3

Formula C

In Step 1 of Scheme E, compound A-2 in dimethylformamide (DMF), is reacted with an N-halosuccinimide ($NT_1S$) at about 80° C., to provide compound 4-1, where $T_1$ is iodo or bromo. In Step 2, compound 4-1 in DMF is reacted with a compound $R_1T_x$, in the presence of potassium carbonate, to provide compound 4-2. In Step 4, compound 4-2 is coupled with a compound of Formula B using palladium catalysis such as palladium tetrakis (triphenylphosphine), and in the presence of sodium carbonate, to yield a pyrazolopyrimidine compound as shown.

A compound of Formula $R_1T_x$ suitable for use in Reaction Scheme E is the compound wherein $R_1$ is cycloalkyl or alkyl and $T_x$ is halo (including bromo, iodo, or chloro) or a leaving group, including but not limited to mesylate or tosylate.

Reaction Schemes F-M illustrate methods of synthesis of borane reagents useful in preparing intermediates of use in synthesis of the compounds of the invention as described in Reaction Schemes A, B, and E above, to introduce $M_1$ substituents.

Reaction Scheme F

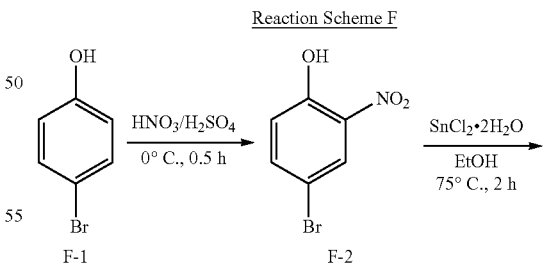

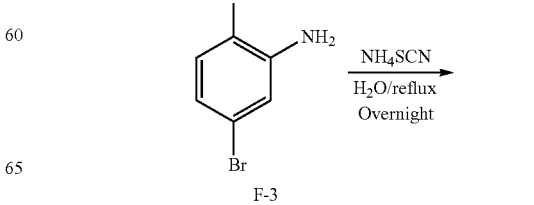

F-3

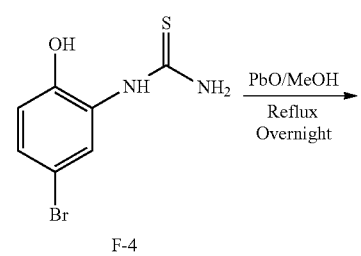
F-4
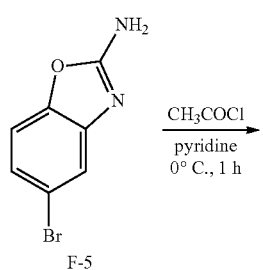
F-5
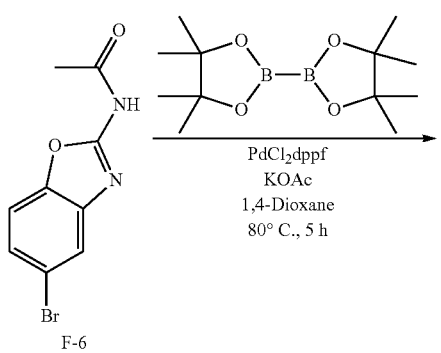
F-6
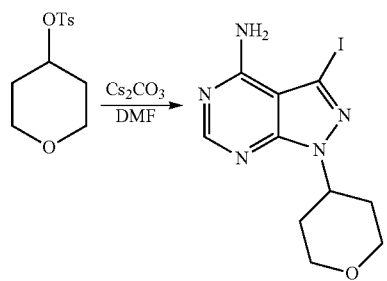
G-3    G-4
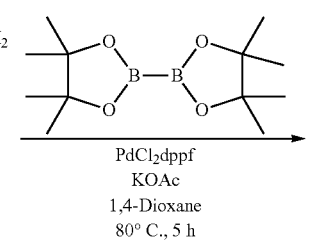
G-5
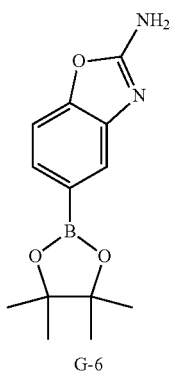
G-6
F-7
Reaction Scheme G
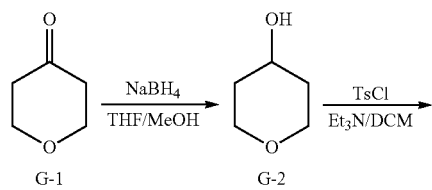
G-1    G-2
Reaction Scheme H
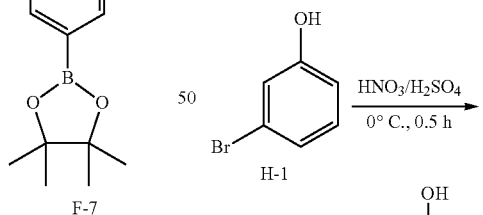
H-1
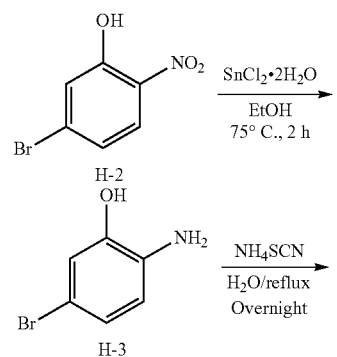
H-2
H-3

117
-continued
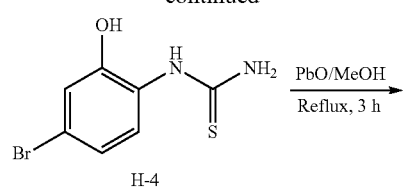
H-4
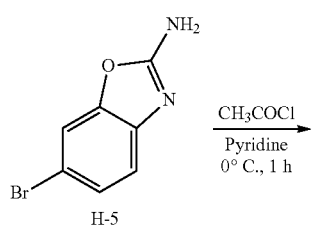
H-5
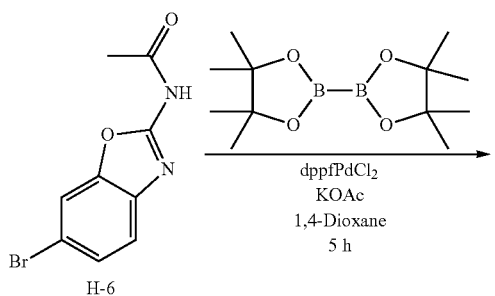
H-6
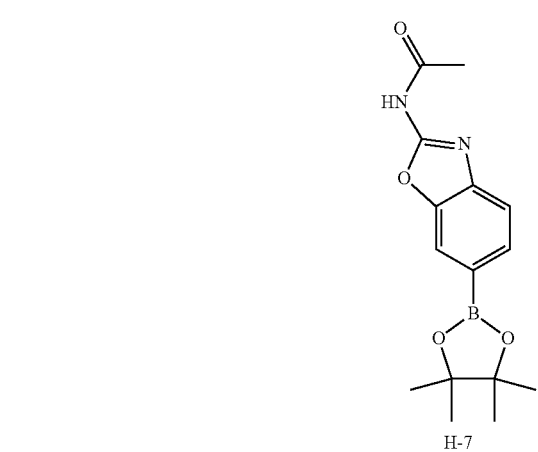
H-7
Reaction Scheme I
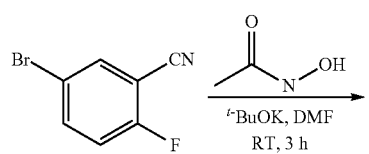
I-1
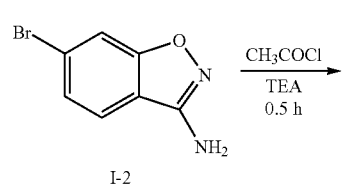
I-2
118
-continued
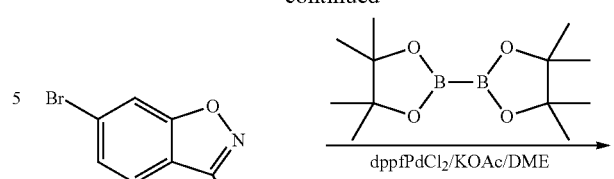
I-3
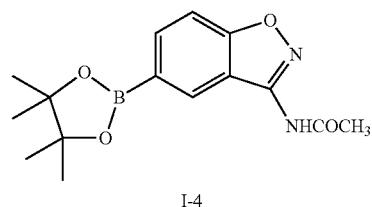
I-4
Reaction Scheme J
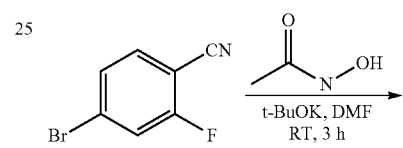
J-1
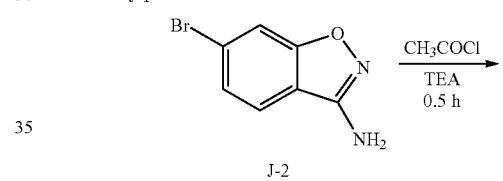
J-2
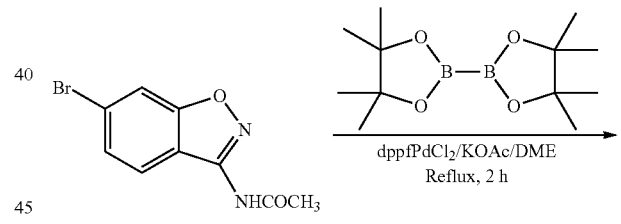
J-3
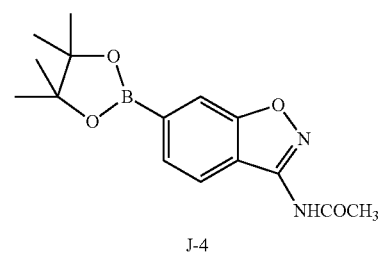
J-4
Reaction Scheme K
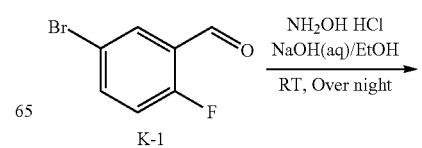
K-1

119
-continued
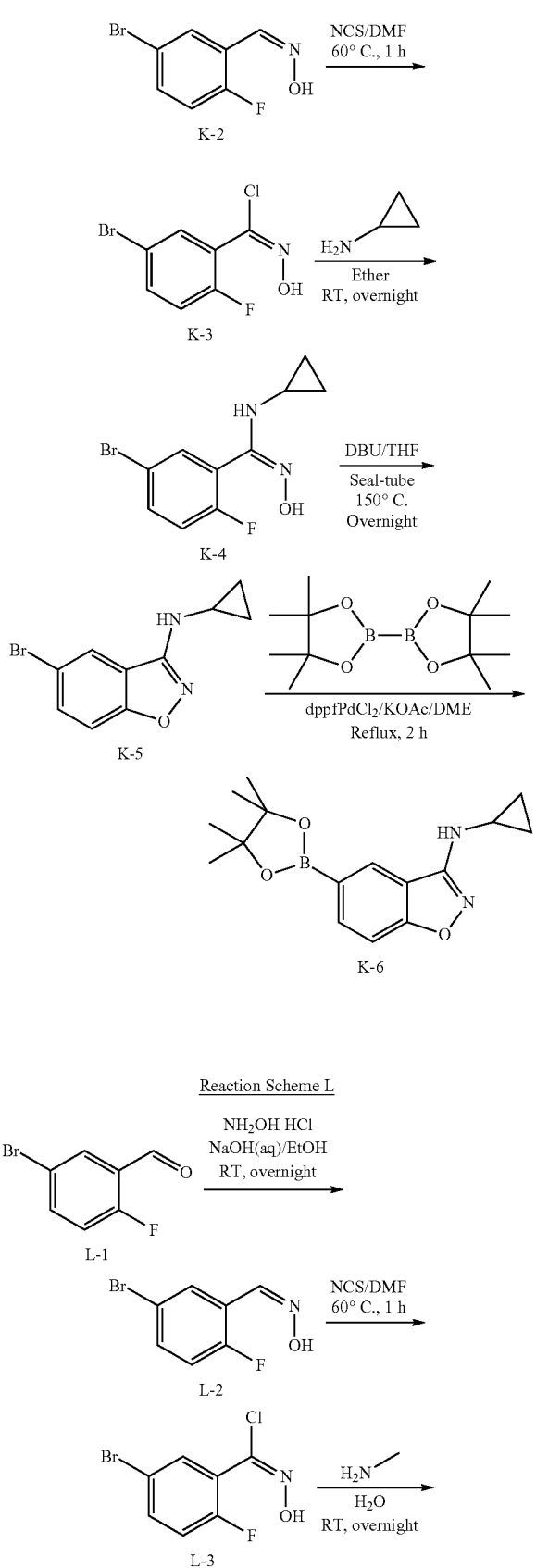
Reaction Scheme L
120
-continued
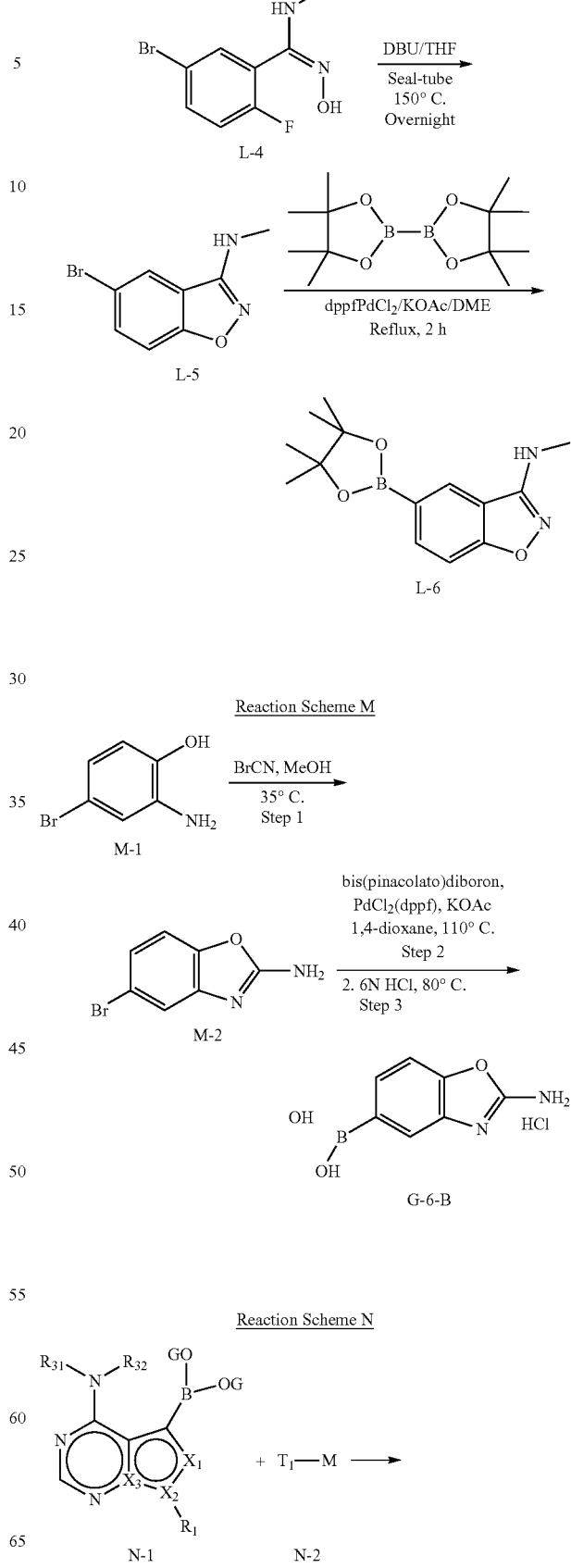
Reaction Scheme M
Reaction Scheme N

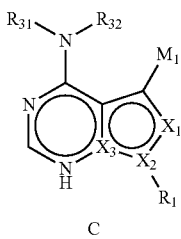

C

In an alternative method of synthesis, a compound of Formula N-1 and a compound of N-2 are coupled to produce a compound of Formula C. The coupling step is typically catalyzed by using, e.g., a palladium catalyst, including but not limited to palladium tetrakis (triphenylphosphine). The coupling is generally performed in the presence of a suitable base, a nonlimiting example being sodium carbonate. One example of a suitable solvent for the reaction is aqueous dioxane.

A compound of Formula N-1 for use in Scheme N has a structure of Formula N-1, wherein G is hydrogen or $R_{G1}$, wherein $R_{G1}$ is alkyl, alkenyl, or aryl. Alternatively, $B(OG)_2$ of the compound of Formula N-1 is taken together to form a 5- or 6-membered cyclic moiety. $R_1$, $X_1$, $X_2$, $X_3$, $R_{31}$ and $R_{32}$ of the compound of Formula N-1 are defined as for a compound of Formula I-A.

A compound of Formula N-2 for use in Scheme N has a structure of Formula N-2 wherein $T_1$ is triflate or halo (including bromo, chloro, and iodo). M of the compound of Formula N-2 is either $M_1$ or $M_2$. $M_1$ is defined as for a compound of Formula I. For example, $M_1$ can be a 5-benzoxazolyl or a 6-benzoxazolyl moiety, including but not limited to those $M_1$ moieties disclosed herein. $M_2$ is a moiety which is synthetically transformed to form $M_1$, after the $M_2$ moiety has been coupled to the bicyclic core of the compound of Formula N-1.

Scheme N-1

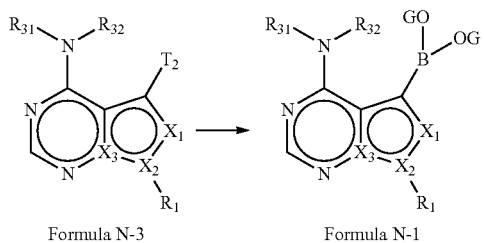

Formula N-3        Formula N-1

A compound of Formula N-1 may be synthesized as shown in Scheme N-1. A compound of Formula N-1 is reacted with a trialkyl borate or a boronic acid derivative to produce a compound of Formula N-1. The reaction is typically run a solvent such as dioxane or tetrahydrofuran. The trialkyl borate includes but is not limited to triisopropyl borate and the boronic acid derivative includes but is not limited to bis(pinacolato)diboron.

When the reaction is performed with trialkyl borate, a base such as n-butyllithium is first added to the compound of Formula N-3 to generate an anion, prior to the addition of the borate. When the reaction is performed with a boronic acid derivative such as bis(pinacolato)diboron, a palladium catalyst and a base is used. Typical palladium catalysts include but is not limited to palladium chloride (diphenylphosphino)ferrocene). A suitable base includes but is not limited to potassium acetate.

A compound of Formula N-3 suitable for use in Scheme N-1 is a compound wherein $T_2$ is halo or another leaving group such as mesylate, tosylate, or triflate. $X_1$, $X_2$, $X_3$, $R_1$, $R_{31}$, and $R_{32}$ of the compound of Formula N-3 is as defined for a compound of Formula I-A.

In some embodiments of the invention, a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3" is provided as its salt, including but not limited to hydrochloride, acetate, formate, nitrate, sulfate, and boronate.

In some embodiments of the invention, a palladium compound, including but not limited to palladium chloride (diphenylphosphino)ferrocene) and palladium tetrakis (triphenylphosphine), is used in the synthesis of a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3". When a palladium compound is present in the synthesis of a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3", it is present in an amount ranging from about 0.005 molar equivalents to about 0.5 molar equivalents, from about 0.05 molar equivalents to about 0.20 molar equivalents, from about 0.05 molar equivalents to about 0.25 molar equivalents, from about 0.07 molar equivalents to about 0.15 molar equivalents, or about 0.8 molar equivalents to about 0.1 molar equivalents of the compound of Formula A, B, B', B", C, D, E, 3-1, 3-2, 3-3, 3-4, 3-5, 3-6, N-1, or N-3. In some embodiments, a a palladium compound, including but not limited to palladium chloride (diphenylphosphino)ferrocene) and palladium tetrakis (triphenylphosphine) is present in the synthesis of a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3" in about 0.07, about 0.08, about 0.09, about 0.10, about 0.11, about 0.12, about 0.13, about 0.14, or about 0.15 molar equivalents of a starting material of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3" that is used to synthesize a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3".

In some embodiments of the above reaction schemes B, D, E, N or N-1, another embodiment of the compounds of Formula A, C, 3-1, 3-3, 3-4, 3-5, 3-6, A-2,4-1, 4-2, N-1 and N-3 is as shown in Schemes B'. D'. E', N' or N-1' below. In these alternative syntheses, producing a compound of Formula C, 3-1, 3-3, 3-4, 3-5, 3-6, A-2,4-1, 4-2, N-1 or N-3, use compounds that comprise an amino moiety having a $R_{G2}$ moiety present during one or more of the synthetic steps, wherein $R_{G2}$ is an amino protecting group including but not limited to tert-butyl carbamate (Boc), carbobenzyloxy (Cbz), benzyl (Bz), fluorenylmethyloxycarbonyl (FMOC), p-methoxybenzyl (PMB), and the like. These compounds include a compound of Formula A", C", 3-1", 3-3", 3-4", 3-5", 3-6", A-2", 4-1", 4-2", N-1" or N-3".

The $R_{G2}$ moiety is removed, using suitable methods, at any point desired, whereupon the compound of Formula C, 3-1, 3-3, 3-4, 3-5, 3-6, A-2,4-1, 4-2, N-1 or N-3 has a $R_{31}$ hydrogen replacing the $R_{G2}$ moiety on the amino moiety. This transformation is specifically illustrated for the conversion of a compound of Formula C" to a compound of C (i.e., as in Step 4 of Scheme E') and for the conversion of a compound of Formula 3-6" to a compound of Formula 3-6 (i.e., as in Step 5 of Scheme D'). This illustration is in no way limiting as to the choice of steps wherein a compound comprising a $NR_{31}R_{G2}$ moiety may be converted to a compound comprising a $NR_{31}R_{32}$ moiety wherein the $R_{32}$ moiety is hydrogen.

Scheme B'
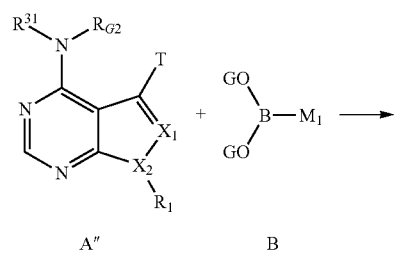
A''  B
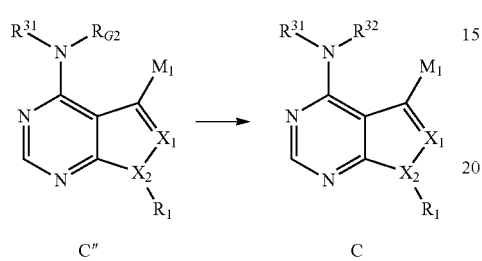
C''  C
Scheme D'
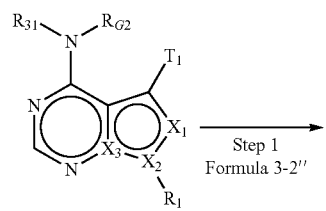
Formula 3-1'
Step 1
Formula 3-2''
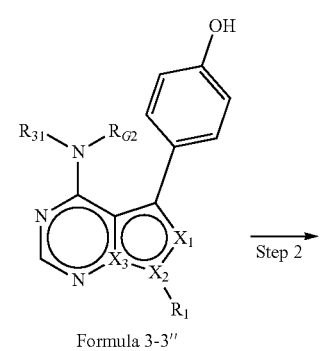
Formula 3-3''
Step 2
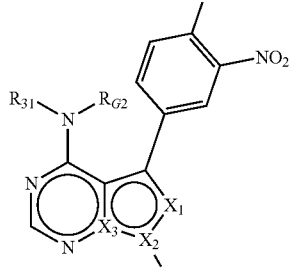
Formula 3-4''
Step 3
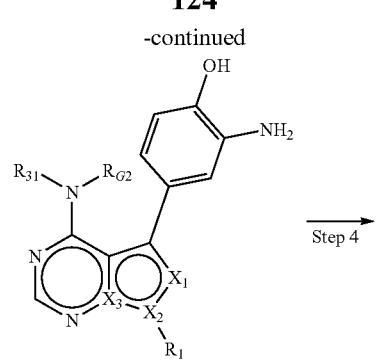
Formula 3-5''
Step 4
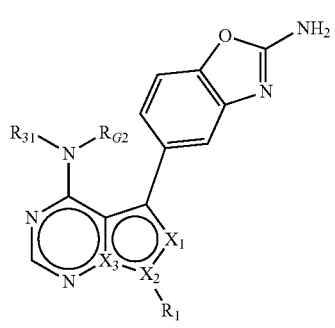
Formula 3-6''
Step 5
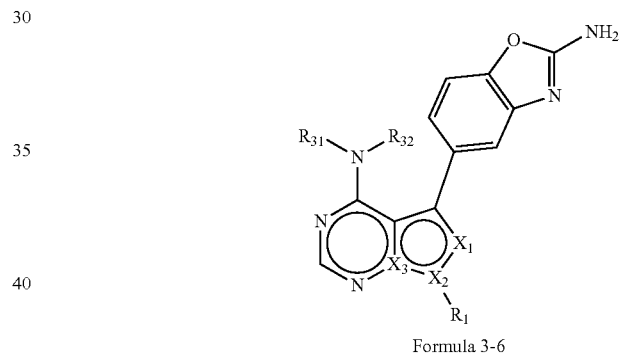
Formula 3-6
Scheme E'
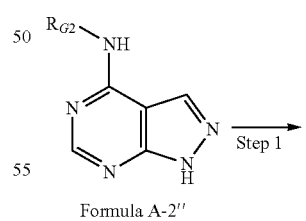
Formula A-2''
Step 1
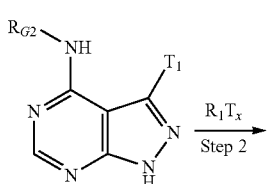
Formula 4-1''
$R_1 T_x$
Step 2

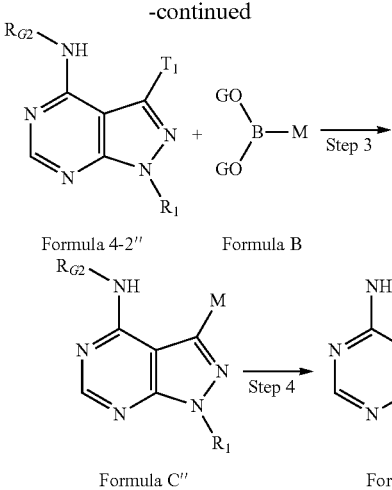

Formula 4-2″   Formula B

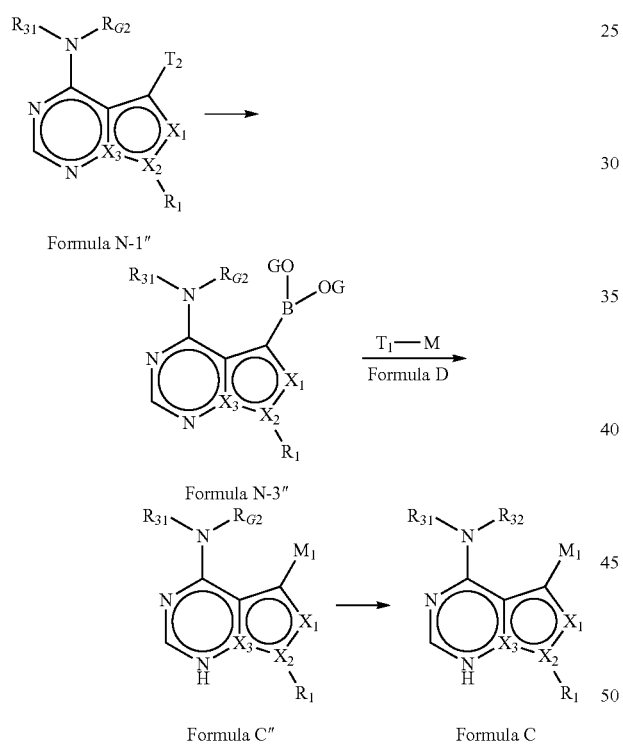

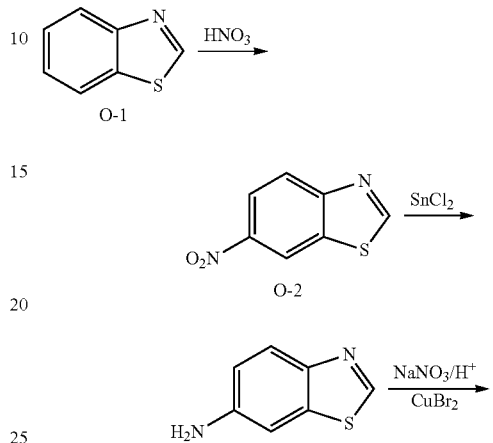

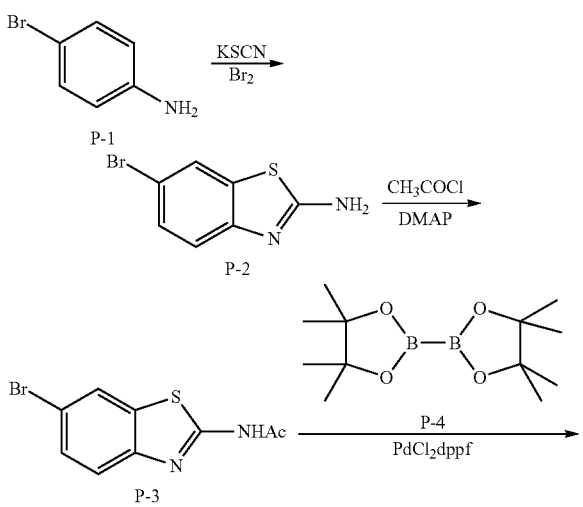

synthesis of the compounds of the invention as described in Reaction Schemes 1 and 2 above, to introduce benzothiazolyl substituents.

A compound of Formula O-1 is treated with, for example, nitric acid to produce a compound of Formula O-2. The compound of Formula O-2 is treated with a reducing agent such as stannous chloride to produce a compound of Formula O-3. The compound of O-3 is treated with sodium nitrate in acid and cupric bromide to produce a compound of Formula O-4. The compound of O-4 is treated a base such as butyl lithium and boron tris-isopropoxide to produce a compound of Formula O-5.

Additionally, the invention encompasses methods of synthesis of the compounds of A, B, B', B″, C, E, 3-1, 3-2, 3-3, 3-4, 3-5, 3-6, N-1 or N-3, wherein one or more of M, $M_1$, or $R_1$ has a protecting group present during one or more steps of the synthesis. Protecting groups suitable for use for a M, $M_1$, or $R_1$ moiety are well known in the art, as well as the methods of incorporation and removal, and the reagents suitable for such transformations.

Compounds of the invention where $X_4$ is C—$R^9$ may be prepared by methods analogous to the ones described in the Schemes illustrated above.

Reaction Schemes O, P and Q illustrate methods of synthesis of borane reagents useful in preparing intermediates of use in

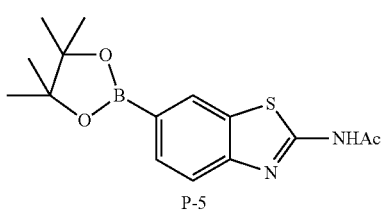

P-5

A compound of Formula P-1 is treated with, for example, potassium thiocyanate and bromine in acetic acid to produce a compound of Formula P-2. The compound of Formula P-2 is treated with an acetylating reagent such as acetyl chloride to produce a compound of Formula P-3. The compound of P-3 is reacted with, for example, bis(pinacolato)diboron (compound P-4) in the presence of a catalyst such as palladium chloride to produce a compound of Formula P-5.

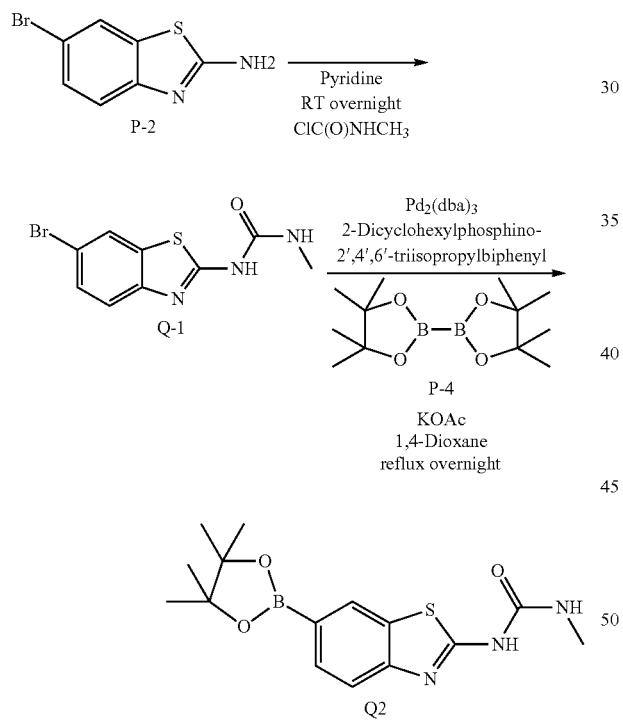

Scheme Q

The compound of Formula P-2 is reacted with, for example, methyl carbamic acid chloride to produce a compound of Formula Q-1. The compound of Formula Q-1 is reacted with bis(pinacolato)diboron (compound P-4) in the presence of a catalyst such as $Pd_2(dba)_3$, 2-chlorohexylphosphino-2,4,6-triisopropylbiphenyl, a base such as potassium acetate, to produce the compound of Formula Q-2.

Some illustrative compounds of the invention which are mTorC1/mTorC2 inhibitors are described below. The compounds of the invention are not limited in any way to the compounds illustrated herein.

Subclass 1a

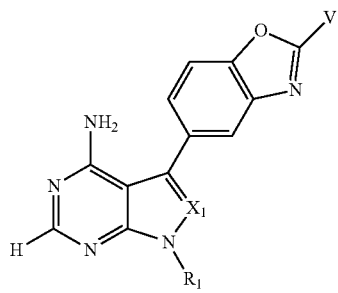

Subclass 1b

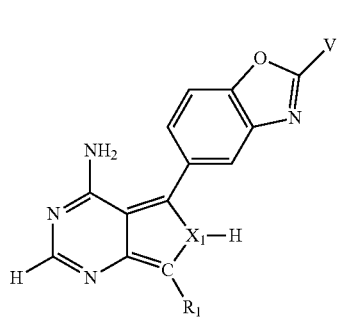

Subclass 2a

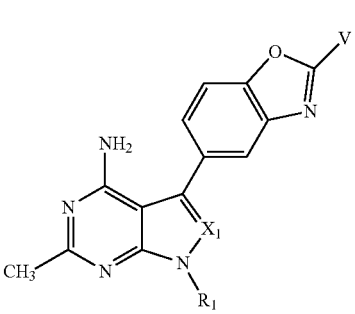

Subclass 2b

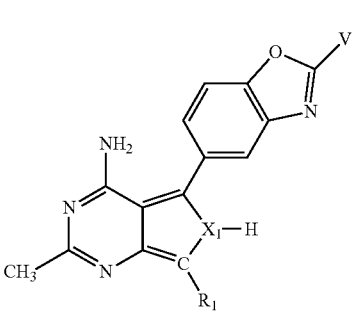

Subclass 3a

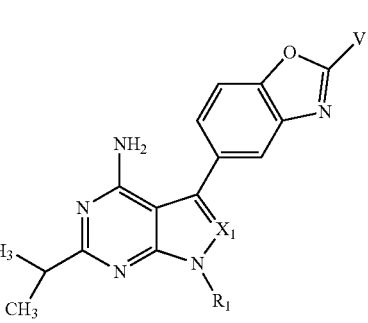

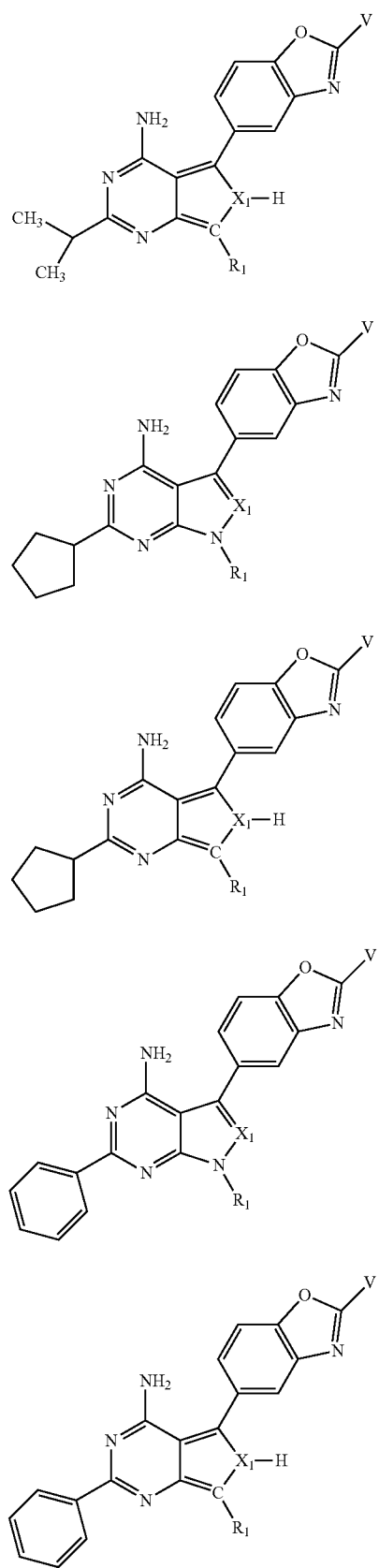
Subclass 3b
Subclass 4a
Subclass 4b
Subclass 5a
Subclass 5b
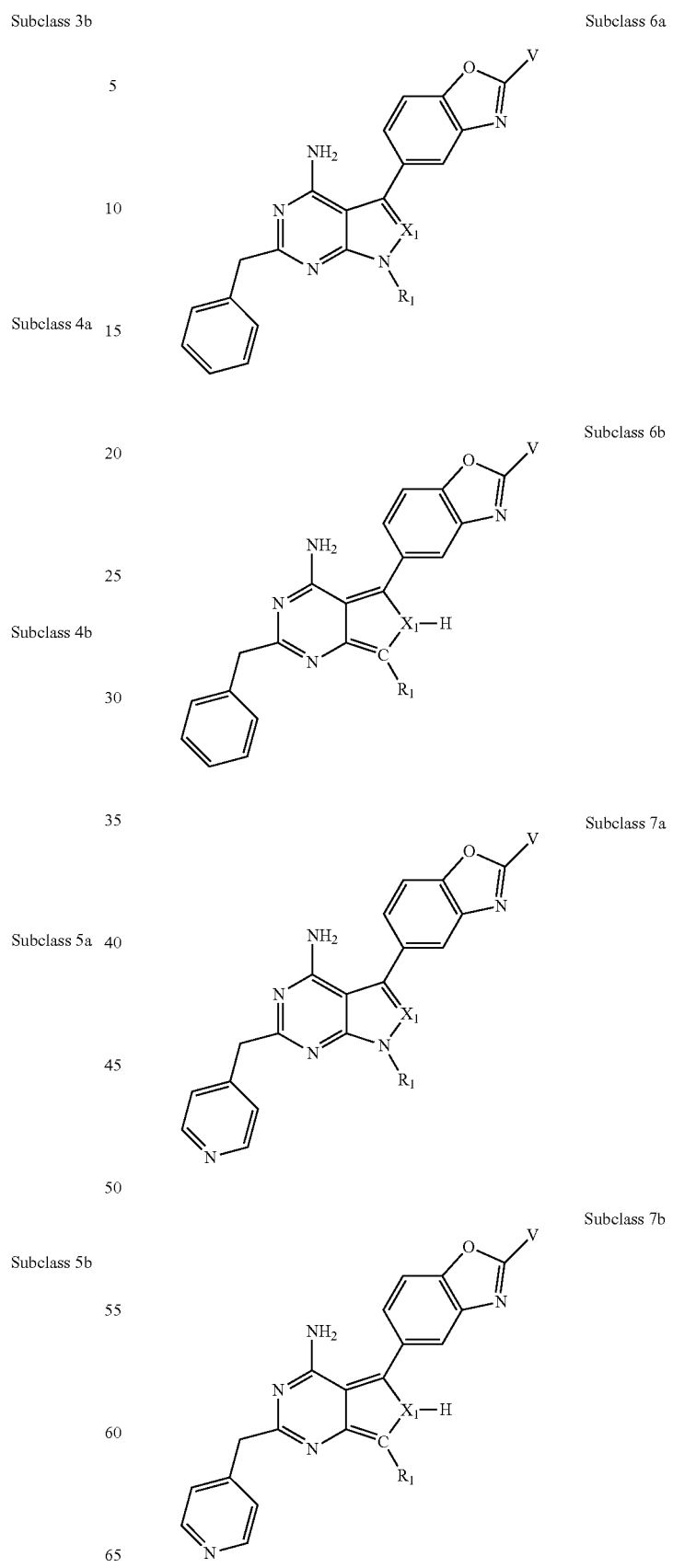
Subclass 6a
Subclass 6b
Subclass 7a
Subclass 7b Subclass 8a
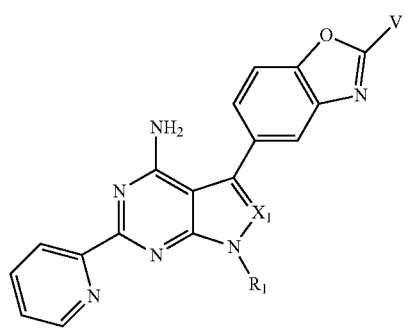
Subclass 8b
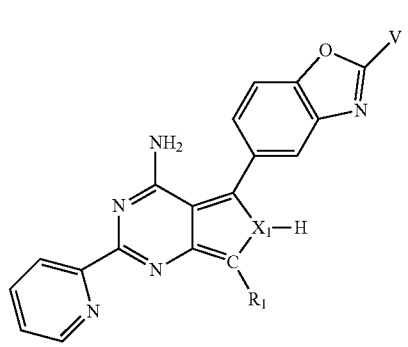
Subclass 9a
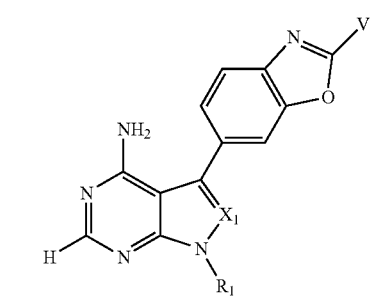
Subclass 9b
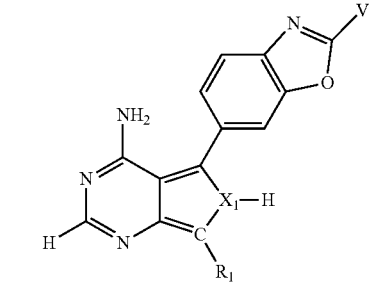
Subclass 10a
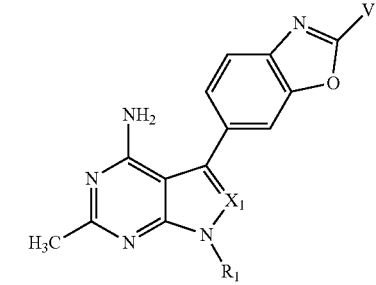
Subclass 10b
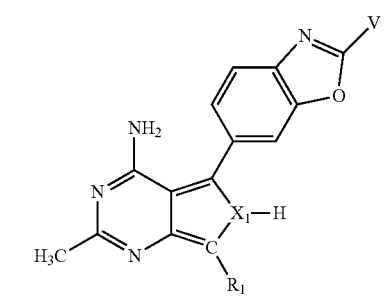
Subclass 11a
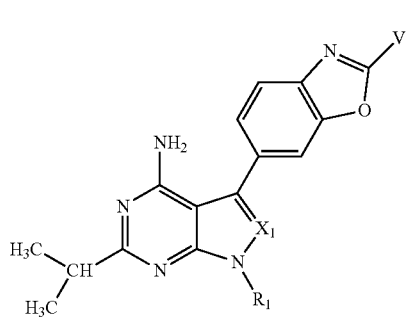
Subclass 11b
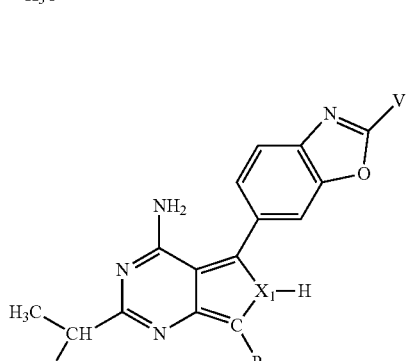
Subclass 12a
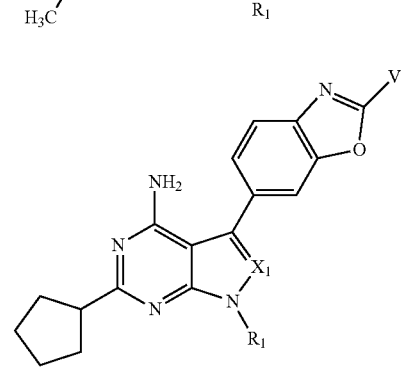
Subclass 12b
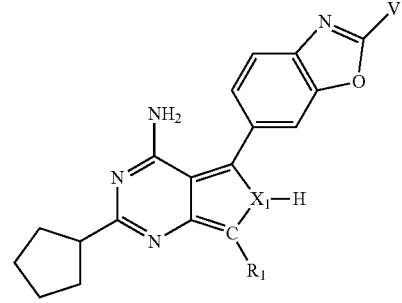

Subclass 13a
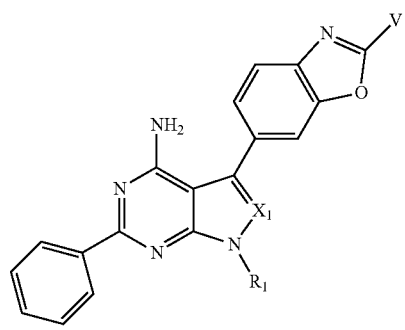
Subclass 13b
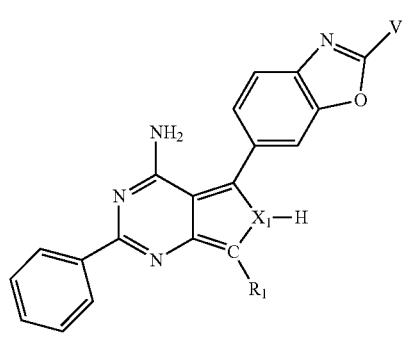
Subclass 14a
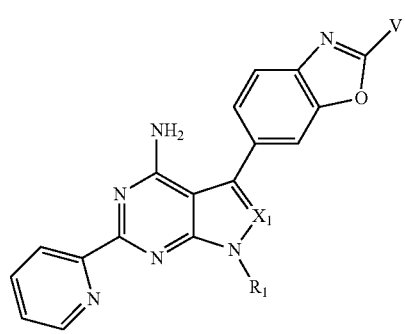
Subclass 14b
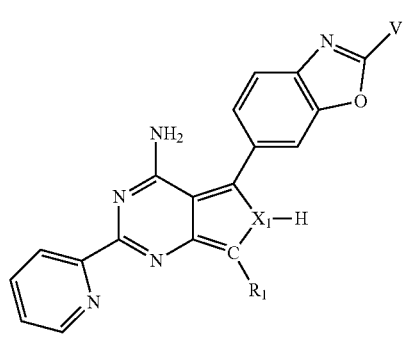
Subclass 15a
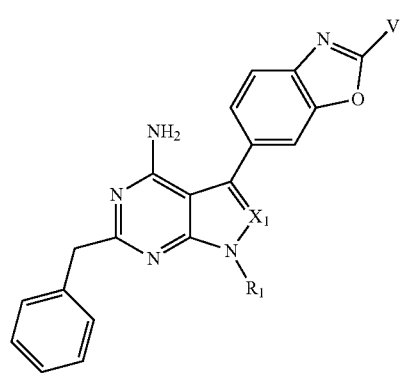
Subclass 15b
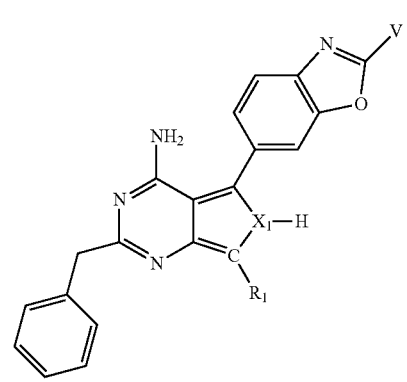
Subclass 16a
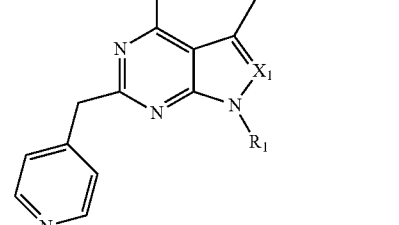
Subclass 16b
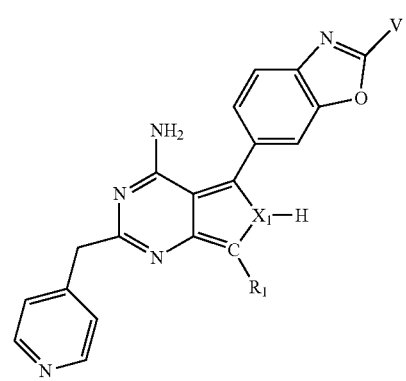
Illustrative compounds of the invention include those of subclass 1a, 1b, 2a, 2b, 3a, 3b, 4a, 4b, 5a, 5b, 6a, 6b, 7a, 7b, 8a, 8b, 9a, 9b, 10a, 10b, 11a, 11b, 12a, 12b, 13a, 13b, 14a, 14b, 15a, 15b, 16a, or 16b, where the substituents $R_1$, $X_1$, and V are as described below.
In some embodiments, when $R_1$ is H and $X_1$ is CH, V is phenylamino, benzyl, phenyl, NHMe, $NH_2$, NHEt, NHCOH, NHCOMe, NHCOEt, NHCOiPr, NHCOOMe, CONHMe, or NHSO$_2$Me. In other embodiments, when R$_1$ is H and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is CH$_3$ and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is CH$_3$ and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is Et and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is Et and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is iPr and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is iPr and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In one embodiment, R$_1$ is iPr, X$_1$ is N, and V is NH$_2$. In another embodiment, R$_1$ is iPr, X$_1$ is N, and V is NHCOMe. In other embodiments, when R$_1$ is cyclobutyl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is cyclobutyl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is cyclopentyl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is cyclopentyl and X$_1$ is N V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is phenyl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is phenyl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is pyridin-2-yl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is pyridin-2-yl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is N-methylaminocyclohex-4-yl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is N-methylaminocyclohex-4-yl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is N-methylpiperidin-4-yl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is N-methylpiperidin-4-yl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is N-methylaminocyclobut-3-yl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is N-methylaminocyclobut-3-yl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is tert-butyl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is tert-butyl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is 1-cyano-but-4-yl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is 1-cyano-but-4-yl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is 1-cyano-prop-3-yl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is 1-cyano-prop-3-yl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is 3-azetidinyl and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is 3-azetidinyl and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me.

In other embodiments, when R$_1$ is

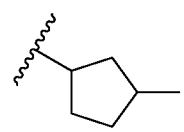

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

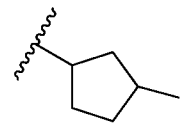 [SMILES: *C1CCC(C)C1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

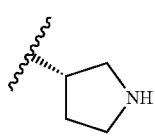 [SMILES: *[C@H]1CCNC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

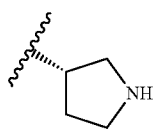

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

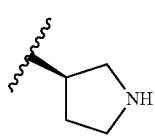 [SMILES: *[C@@H]1CCNC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

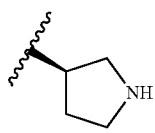 [SMILES: *[C@@H]1CCNC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

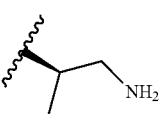 [SMILES: *[C@H](C)CN]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

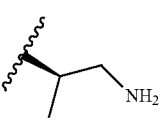 [SMILES: *[C@H](C)CN]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

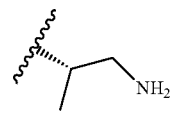

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

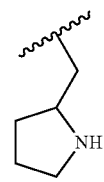 [SMILES: *CC1CCCN1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

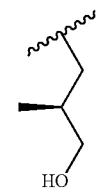 [SMILES: *C[C@H](C)CO]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

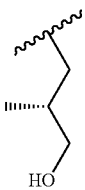

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

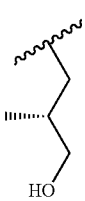 [SMILES: *C[C@@H](C)CO]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

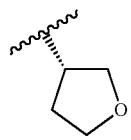 [SMILES: *[C@H]1CCOC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

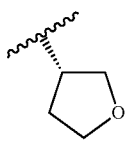 [SMILES: *[C@H]1CCOC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

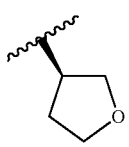 [SMILES: *[C@@H]1CCOC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

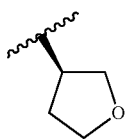 [SMILES: *[C@@H]1CCOC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

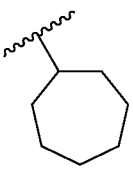 [SMILES: *C1CCCCCC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

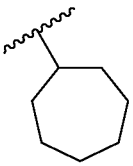 [SMILES: *C1CCCCCC1]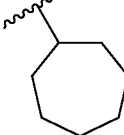

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

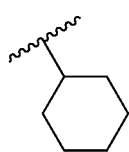 [SMILES: *C1CCCCC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

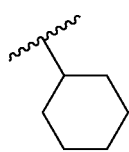 [SMILES: *C1CCCCC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

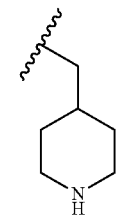 [SMILES: *CC1CCNCC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

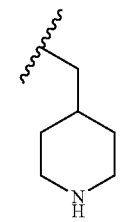 [SMILES: *CC1CCNCC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

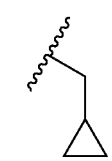

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

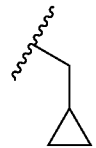

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

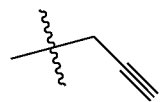

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

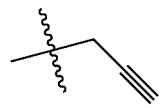 [SMILES: *CC#C]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

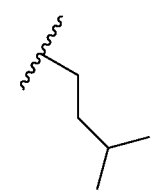 [SMILES: *CCC(C)C]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

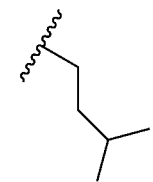 [SMILES: *CCC(C)C]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

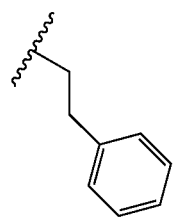 [SMILES: *CCc1ccccc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

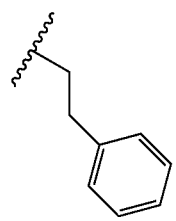 [SMILES: *CCc1ccccc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

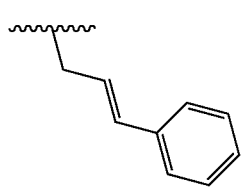 [SMILES: *C/C=C/c1ccccc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

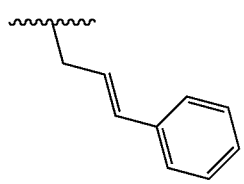 [SMILES: *C/C=C/c1ccccc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

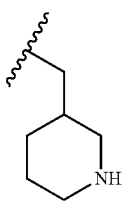 [SMILES: *CC1CCCNC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

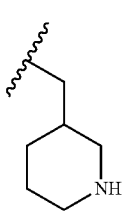 [SMILES: *CC1CCCNC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

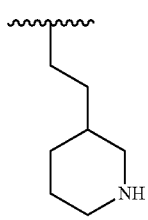 [SMILES: *CCC1CCCNC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_{11}$ and $X_1$ is

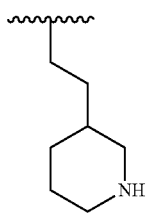 [SMILES: *CCC1CCCNC1]

N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

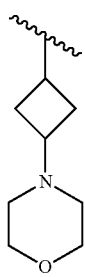 [SMILES: *C1CC(N2CCOCC2)C1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

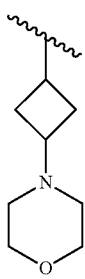

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

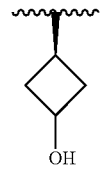

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

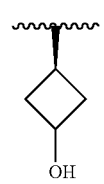

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

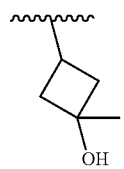

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

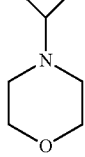

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

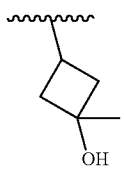

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

147

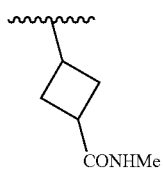

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

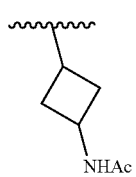 [SMILES: *C1CC(NC(C)=O)C1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

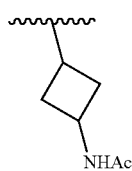 [SMILES: *C1CC(NC(C)=O)C1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

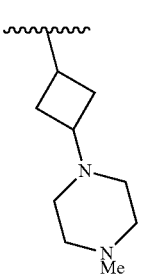 [SMILES: *C1CC(N2CCN(C)CC2)C1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

148

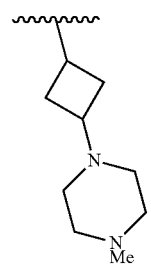 [SMILES: *C1CC(N2CCN(C)CC2)C1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

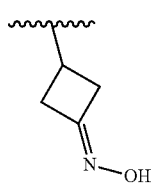 [SMILES: *C1CC(=NO)C1]

and X$_1$ is CH, V is phenylamino, benzyl, phenyl, NHMe, NH$_2$, NHEt, NHCOH, NHCOMe. NHCOEt. NHCOiPr. NHCOOMe, CONHMe, or NHSO$_2$Me. In other embodiments, when R$_1$ is

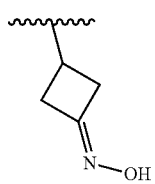 [SMILES: *C1CC(=NO)C1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

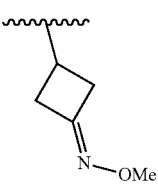

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

149

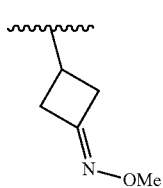 [SMILES: *C1CC(=NOC)C1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

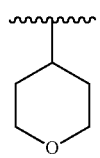

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

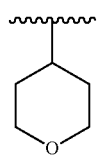 [SMILES: *C1CCOCC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

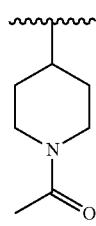

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

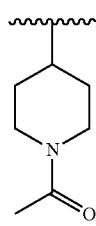

150 and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

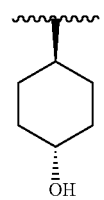 [SMILES: *[C@H]1CC[C@H](O)CC1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

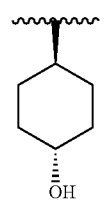 [SMILES: *[C@H]1CC[C@H](O)CC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

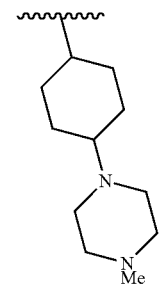 [SMILES: *C1CCC(N2CCN(C)CC2)CC1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

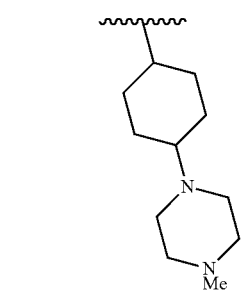 [SMILES: *C1CCC(N2CCN(C)CC2)CC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

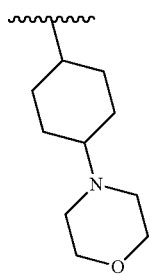 [SMILES: *C1CCC(N2CCOCC2)CC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

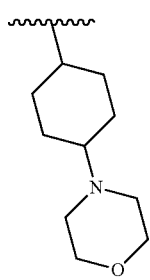 [SMILES: *C1CCC(N2CCOCC2)CC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

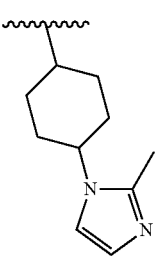 [SMILES: *C1CCC(n2ccnc2C)CC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

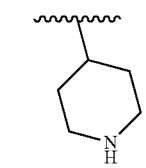

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

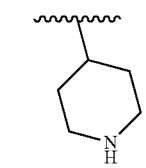

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

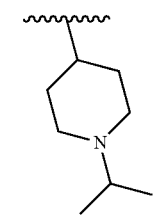

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

153

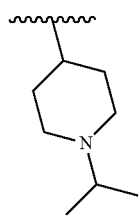 [SMILES: *C1CCN(C(C)C)CC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

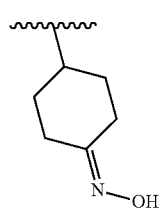 [SMILES: *C1CCC(=NO)CC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

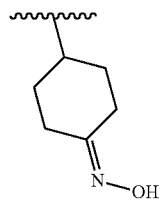 [SMILES: *C1CCC(=NO)CC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

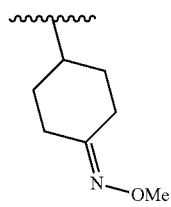 [SMILES: *C1CCC(=NOC)CC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

154

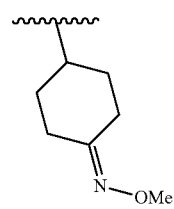 [SMILES: *C1CCC(=NOC)CC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

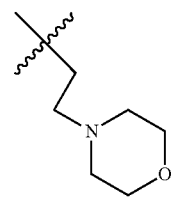 [SMILES: *CCN1CCOCC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

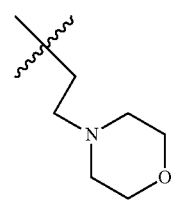 [SMILES: *CCN1CCOCC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

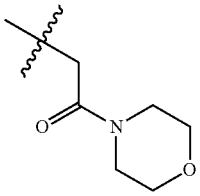 [SMILES: *CC(=O)N1CCOCC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

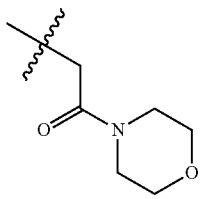 [SMILES: *CC(=O)N1CCOCC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me.

In other embodiments, when $R_1$ is

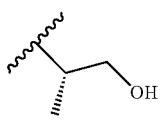

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

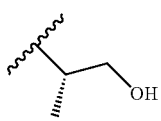 [SMILES: *[C@@H](C)CO]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

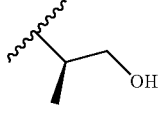 [SMILES: *[C@H](C)CO]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

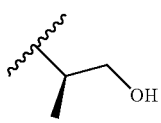 [SMILES: *[C@H](C)CO]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

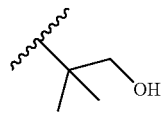 [SMILES: *C(C)(C)CO]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

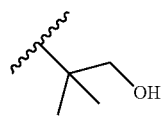

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

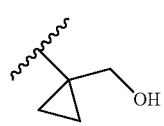 [SMILES: *C1(CO)CC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

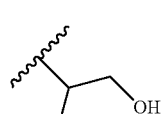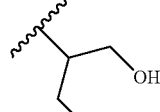

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

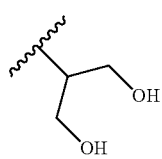 [SMILES: *C(CO)CO]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

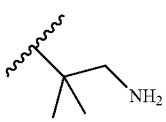

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

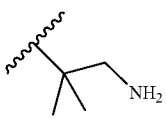

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

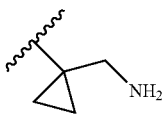 [SMILES: *C1(CN)CC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

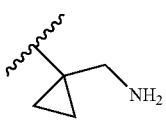 [SMILES: *C1(CN)CC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$.

In other embodiments, when $R_1$ is

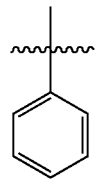 [SMILES: *c1ccccc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

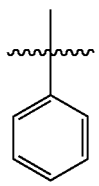 [SMILES: *c1ccccc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

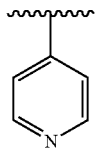 [SMILES: *c1ccncc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

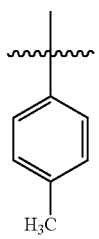 [SMILES: *c1ccc(C)cc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

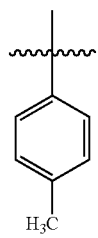

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

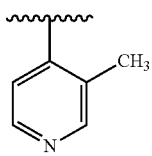

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

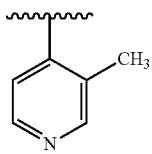 [SMILES: *c1ccncc1C]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

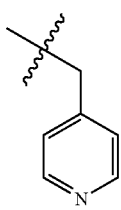 [SMILES: *Cc1ccncc1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

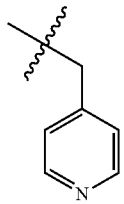

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

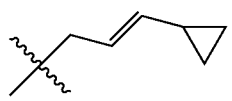

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

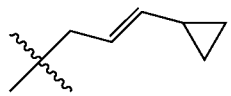 [SMILES: *C/C=C/C1CC1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

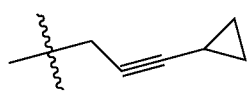 [SMILES: *CC#CC1CC1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

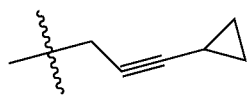 [SMILES: *CC#CC1CC1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

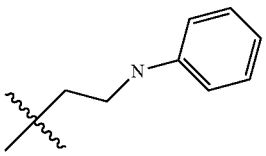 [SMILES: *CCNc1ccccc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

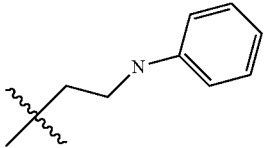 [SMILES: *CCNc1ccccc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

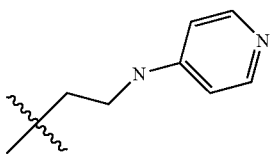 [SMILES: *CCNc1ccncc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

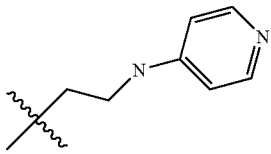 [SMILES: *CCNc1ccncc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

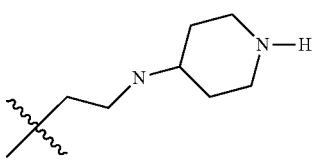 [SMILES: *CCNC1CCNCC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

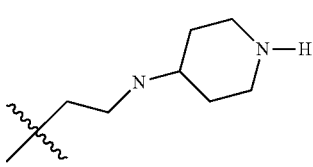 [SMILES: *CCNC1CCNCC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$.

In the noted embodiments, pyridin-2-yl is

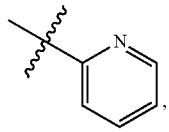 [SMILES: *c1ccccn1]

N-methylaminocyclohex-4-yl is

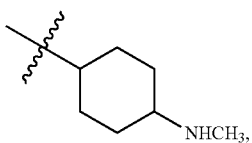 [SMILES: *C1CCC(NC)CC1]

N-methylpiperidin-4-yl is

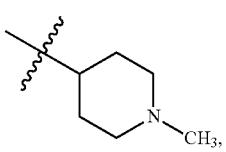

and N-methylaminocyclobut-3-yl is

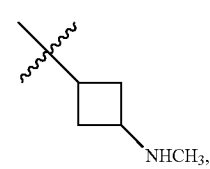 [SMILES: *C1CC(NC)C1]

Illustrative compounds of the invention include those of subclass 1a, 1b, 2a, 2b, 3a, 3b, 4a, 4b, 5a, 5b, 6a, 6b, 7a, 7b, 8a, 8b, 9a, 9b, 10a, 10b, 11a, 11b, 12a, 12b, 13a, 13b, 14a, 14b, 15a, 15b, 16a, or 16b, where the substituents $R_1$, $X_1$, and V are as described below. In some embodiments, when $R_1$ is H and $X_1$ is CH, V is cyclopropanecarboxamido, cyclopropylamino, morpholinoethylamino, hydroxyethylamino, or N-morpholino. In other embodiments, when $R_1$ is H and $X_1$ is N, V is cyclopropanecarboxamido, cyclopropylamino, morpholinoethylamino, hydroxyethylamino, or N-morpholino. In some embodiments, when $R_1$ is $CH_3$ and $X_1$ is CH, V is cyclopropanecarboxamido, cyclopropylamino, morpholinoethylamino, hydroxyethylamino, or N-morpholino. In other embodiments, when $R_1$ is $CH_3$ and $X_1$ is N, V is cyclopropanecarboxamido, cyclopropylamino, morpholinoethylamino, hydroxyethylamino, or N-morpholino. In some embodiments, when $R_1$ is Et and $X_1$ is CH, V is cyclopropanecarboxamido, cyclopropylamino, morpholinoethylamino, hydroxyethylamino, or N-morpholino. In other embodiments, when $R_1$ is Et and $X_1$ is N, V is cyclopropanecarboxamido, cyclopropylamino, morpholinoethylamino, hydroxyethylamino, or N-morpholino. In some embodiments, when $R_1$ is iPr and $X_1$ is CH, V is cyclopropanecarboxamido, cyclopropylamino, morpholinoethylamino, hydroxyethylamino, or N-morpholino. In other embodiments, when $R_1$ is iPr and $X_1$ is N, V is cyclopropanecarboxamido, cyclopropylamino, morpholinoethylamino, hydroxyethylamino, or N-morpholino. In some embodiments, when $R_1$ is cyclobutyl and $X_1$ is CH, V is cyclopropanecarboxamido, cyclopropylamino, morpholinoethylamino, hydroxyethylamino, or N-morpholino. In other embodiments, when $R_1$ is cyclobutyl and $X_1$ is N, V is cyclopropanecarboxamido, cyclopropylamino, morpholinoethylamino, hydroxyethylamino, or N-morpholino. In some embodiments, when $R_1$ is cyclopentyl and $X_1$ is CH, V is cyclopropanecarboxamido, cyclopropylamino, morpholinoethylamino, hydroxyethylamino, or N-morpholino. In other embodiments, when $R_1$ is cyclopentyl and $X_1$ is N, V is cyclopropanecarboxamido, cyclopropylamino, morpholinoethylamino, hydroxyethylamino, or N-morpholino. In some embodiments, when $R_1$ is phenyl and $X_1$ is CH, V is cyclopropanecarboxamido, cyclopropylamino, morpholinoethylamino, hydroxyethylamino, or N-morpholino. In other embodiments, when $R_1$ is phenyl and $X_1$ is N, V is cyclopropanecarboxamido, cyclopropylamino, morpholinoethylamino, hydroxyethylamino, or N-morpholino. In some embodiments, when $R_1$ is pyridin-2-yl and $X_1$ is CH, V is cyclopropanecarboxamido, cyclopropylamino, morpholinoethylamino, hydroxyethylamino, or N-morpholino. In other embodiments, when $R_1$ is pyridin-2-yl and $X_1$ is N, V is cyclopropanecarboxamido, cyclopropylamino, morpholinoethylamino, hydroxyethylamino, or N-morpholino. In some embodiments, when $R_1$ is N-methylaminocyclohex-4-yl and $X_1$ is CH, V is cyclopropanecarboxamido, cyclopropylamino, morpholinoethylamino, hydroxyethylamino, or N-morpholino. In other embodiments, when $R_1$ is N-methylaminocyclohex-4-yl and $X_1$ is N, V is cyclopropanecarboxamido, cyclopropylamino, morpholinoethylamino, hydroxyethylamino, or N-morpholino. In some embodiments, when $R_1$ is N-methylpiperidin-4-yl and $X_1$ is CH, V is cyclopropanecarboxamido, cyclopropylamino, morpholinoethylamino, hydroxyethylamino, or N-morpholino. In other embodiments, when $R_1$ is N-methylpiperidin-4-yl and $X_1$ is N, V is cyclopropanecarboxamido, cyclopropylamino, morpholinoethylamino, hydroxyethylamino, or N-morpholino. In some embodiments, when $R_1$ is N-methylaminocyclobut-3-yl and $X_1$ is CH, V is cyclopropanecarboxamido, cyclopropylamino, morpholinoethylamino, hydroxyethylamino, or N-morpholino. In other embodiments, when $R_1$ is N-methylaminocyclobut-3-yl and $X_1$ is N, V is cyclopropanecarboxamido, cyclopropylamino, morpholinoethylamino, hydroxyethylamino, or N-morpholino. In other embodiments, when $R_1$ is tert-butyl and $X_1$ is CH, V is cyclopropanecarboxamido, cyclopropylamino, morpholinoethylamino, hydroxyethylamino, or N-morpholino. In other embodiments, when $R_1$ is tert-butyl and $X_1$ is N, V is cyclopropanecarboxamido, cyclopropylamino, morpholinoethylamino, hydroxyethylamino, or N-morpholino. In other embodiments, when $R_1$ is 1-cyano-but-4-yl and $X_1$ is CH, V is cyclopropanecarboxamido, cyclopropylamino, morpholinoethylamino, hydroxyethylamino, or N-morpholino. In other embodiments, when $R_1$ is 1-cyano-but-4-yl and $X_1$ is N, V is cyclopropanecarboxamido, cyclopropylamino, morpholinoethylamino, hydroxyethylamino, or N-morpholino. In other embodiments, when $R_1$ is 1-cyano-prop-3-yl and $X_1$ is CH, V is cyclopropanecarboxamido, cyclopropylamino, morpholinoethylamino, hydroxyethylamino, or N-morpholino. In other embodiments, when $R_1$ is 1-cyano-prop-3-yl and $X_1$ is N, V is cyclopropanecarboxamido, cyclopropylamino, morpholinoethylamino, hydroxyethylamino, or N-morpholino. In other embodiments, when $R_1$ is 3-azetidinyl and $X_1$ is CH, V is cyclopropanecarboxamido, cyclopropylamino, morpholinoethylamino, hydroxyethylamino, or N-morpholino. In other embodiments, when $R_1$ is 3-azetidinyl and $X_1$ is N, V is cyclopropanecarboxamido, cyclopropylamino, morpholinoethylamino, hydroxyethylamino, or N-morpholino. In other embodiments, when $R_1$ is

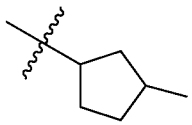 [SMILES: *C1CCC(C)C1]

and $X_1$ is CH, V is cyclopropanecarboxamido, cyclopropylamino, morpholinoethylamino, hydroxyethylamino, or N-morpholino. In other embodiments, when $R_1$ is

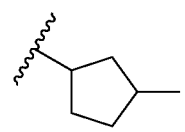

and $X_1$ is N, V is cyclopropanecarboxamido, cyclopropylamino, morpholinoethylamino, hydroxyethylamino, or N-morpholino. In other embodiments, when $R_1$ is

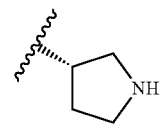 [SMILES: *[C@H]1CCNC1]

and $X_1$ is CH, V is cyclopropanecarboxamido, cyclopropylamino, morpholinoethylamino, hydroxyethylamino, or N-morpholino. In other embodiments, when $R_1$ is

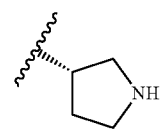 [SMILES: *[C@H]1CCNC1]

and $X_1$ is N, V is cyclopropanecarboxamido, cyclopropylamino, morpholinoethylamino, hydroxyethylamino, or N-morpholino. In other embodiments, when $R_1$ is

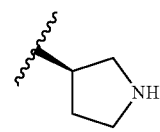 [SMILES: *[C@@H]1CCNC1]

and $X_1$ is CH, V is cyclopropanecarboxamido, cyclopropylamino, morpholinoethylamino, hydroxyethylamino, or N-morpholino. In other embodiments, when $R_1$ is

165

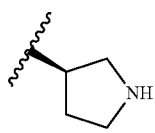 [SMILES: *[C@@H]1CCNC1]

and X$_1$ is N, V is cyclopropanecarboxamido, cyclopropylamino, morpholinoethylamino, hydroxyethylamino, or N-morpholino. In other embodiments, when R$_1$ is

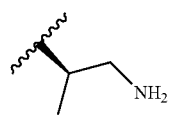 [SMILES: *[C@H](C)CN]

and X$_1$ is CH, V is cyclopropanecarboxamido, cyclopropylamino, morpholinoethylamino, hydroxyethylamino, or N-morpholino. In other embodiments, when R$_1$ is

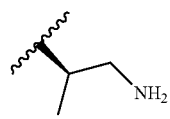 [SMILES: *[C@H](C)CN]

and X$_1$ is N, V is cyclopropanecarboxamido, cyclopropylamino, morpholinoethylamino, hydroxyethylamino, or N-morpholino. In other embodiments, when R$_1$ is

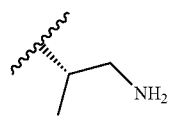

and X$_1$ is CH, V is cyclopropanecarboxamido, cyclopropylamino, morpholinoethylamino, hydroxyethylamino, or N-morpholino. In other embodiments, when R$_1$ is

and X$_1$ is N, V is cyclopropanecarboxamido, cyclopropylamino, morpholinoethylamino, hydroxyethylamino, or N-morpholino. In other embodiments, when R$_1$ is

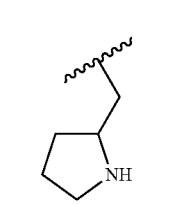 [SMILES: *CC1CCCN1]

and X$_1$ is CH, V is cyclopropanecarboxamido, cyclopropylamino, morpholinoethylamino, hydroxyethylamino, or N-morpholino. In other embodiments, when R$_1$ is

166

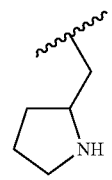 [SMILES: *CC1CCCN1]

and X$_1$ is N, V is cyclopropanecarboxamido, cyclopropylamino, morpholinoethylamino, hydroxyethylamino, or N-morpholino. In other embodiments, when R$_1$ is

and X$_1$ is CH, V is cyclopropanecarboxamido, cyclopropylamino, morpholinoethylamino, hydroxyethylamino, or N-morpholino. In other embodiments, when R$_1$ is

and X$_1$ is N, V is cyclopropanecarboxamido, cyclopropylamino, morpholinoethylamino, hydroxyethylamino, or N-morpholino. In other embodiments, when R$_1$ is

and X$_1$ is CH, V is cyclopropanecarboxamido, cyclopropylamino, morpholinoethylamino, hydroxyethylamino, or N-morpholino. In other embodiments, when R$_1$ is

and X$_1$ is N, V is cyclopropanecarboxamido, cyclopropylamino, morpholinoethylamino, hydroxyethylamino, or N-morpholino. In other embodiments, when R$_1$ is

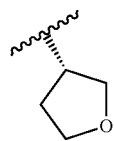

and X$_1$ is CH, V is cyclopropanecarboxamido, cyclopropylamino, morpholinoethylamino, hydroxyethylamino, or N-morpholino. In other embodiments, when R$_1$ is

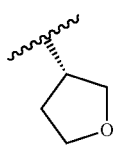

and X$_1$ is N, V is cyclopropanecarboxamido, cyclopropylamino, morpholinoethylamino, hydroxyethylamino, or N-morpholino. In other embodiments, when R$_1$ is

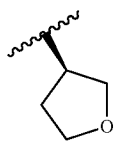

and X$_1$ is CH, V is cyclopropanecarboxamido, cyclopropylamino, morpholinoethylamino, hydroxyethylamino, or N-morpholino. In other embodiments, when R$_1$ is

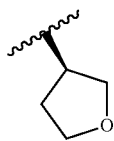 [SMILES: *[C@@H]1CCOC1]

and X$_1$ is N, V is cyclopropanecarboxamido, cyclopropylamino, morpholinoethylamino, hydroxyethylamino, or N-morpholino. In other embodiments, when R$_1$ is

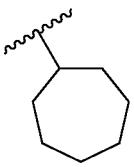 [SMILES: *C1CCCCCC1]

and X$_1$ is CH, V is cyclopropanecarboxamido, cyclopropylamino, morpholinoethylamino, hydroxyethylamino, or N-morpholino. In other embodiments, when R$_1$ is

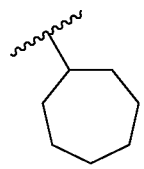 [SMILES: *C1CCCCCC1]

and X$_1$ is N, V is cyclopropanecarboxamido, cyclopropylamino, morpholinoethylamino, hydroxyethylamino, or N-morpholino. In other embodiments, when R$_1$ is

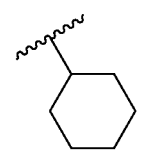 [SMILES: *C1CCCCC1]

and X$_1$ is CH, V is cyclopropanecarboxamido, cyclopropylamino, morpholinoethylamino, hydroxyethylamino, or N-morpholino. In other embodiments, when R$_1$ is

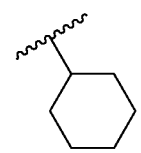

and X$_1$ is N, V is cyclopropanecarboxamido, cyclopropylamino, morpholinoethylamino, hydroxyethylamino, or N-morpholino. In other embodiments, when R$_1$ is

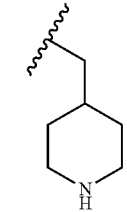 [SMILES: *CC1CCNCC1]

and X$_1$ is CH, V is cyclopropanecarboxamido, cyclopropylamino, morpholinoethylamino, hydroxyethylamino, or N-morpholino. In other embodiments, when R$_1$ is

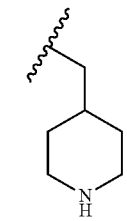 [SMILES: *CC1CCNCC1]

and X$_1$ is N, V is cyclopropanecarboxamido, cyclopropylamino, morpholinoethylamino, hydroxyethylamino, or N-morpholino. In other embodiments, when R$_1$ is

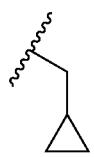

and X₁ is CH, V is cyclopropanecarboxamido, cyclopropylamino, morpholinoethylamino, hydroxyethylamino, or N-morpholino. In other embodiments, when R₁ is

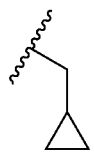

and X₁ is N, V is cyclopropanecarboxamido, cyclopropylamino, morpholinoethylamino, hydroxyethylamino, or N-morpholino. In other embodiments, when R₁ is

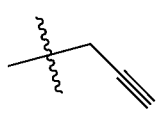 [SMILES: *CC#C]

and X₁ is CH, V is cyclopropanecarboxamido, cyclopropylamino, morpholinoethylamino, hydroxyethylamino, or N-morpholino. In other embodiments, when R₁ is

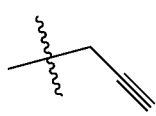 [SMILES: *CC#C]

and X₁ is N, V is cyclopropanecarboxamido, cyclopropylamino, morpholinoethylamino, hydroxyethylamino, or N-morpholino. In other embodiments, when R₁ is

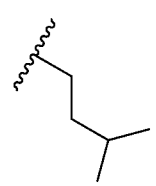 [SMILES: *CCC(C)C]

and X₁ is CH, V is cyclopropanecarboxamido, cyclopropylamino, morpholinoethylamino, hydroxyethylamino, or N-morpholino. In other embodiments, when R₁ is

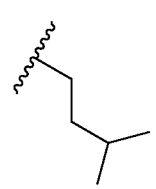 [SMILES: *CCC(C)C]

and X₁ is N, V is cyclopropanecarboxamido, cyclopropylamino, morpholinoethylamino, hydroxyethylamino, or N-morpholino. In other embodiments, when R₁ is

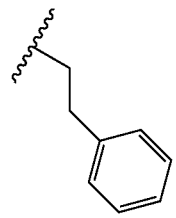 [SMILES: *CCc1ccccc1]

and X₁ is CH, V is cyclopropanecarboxamido, cyclopropylamino, morpholinoethylamino, hydroxyethylamino, or N-morpholino. In other embodiments, when R₁ is

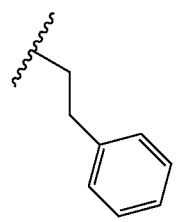

and X₁ is N, V is cyclopropanecarboxamido, cyclopropylamino, morpholinoethylamino, hydroxyethylamino, or N-morpholino. In other embodiments, when R₁ is

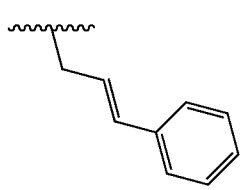 [SMILES: *C/C=C/c1ccccc1]

and X₁ is CH, V is cyclopropanecarboxamido, cyclopropylamino, morpholinoethylamino, hydroxyethylamino, or N-morpholino. In other embodiments, when R₁ is

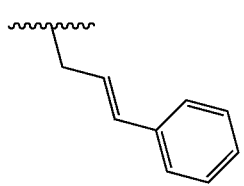 [SMILES: *C/C=C/c1ccccc1]

and X₁ is N, V is cyclopropanecarboxamido, cyclopropylamino, morpholinoethylamino, hydroxyethylamino, or N-morpholino. In other embodiments, when R₁ is

and X₁ is CH, V is cyclopropanecarboxamido, cyclopropylamino, morpholinoethylamino, hydroxyethylamino, or N-morpholino. In other embodiments, when R₁ is

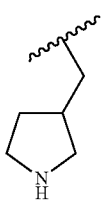

and X₁ is N, V is cyclopropanecarboxamido, cyclopropylamino, morpholinoethylamino, hydroxyethylamino, or N-morpholino. In other embodiments, when R₁ is

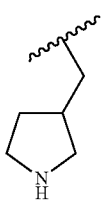

and X₁ is CH, V is cyclopropanecarboxamido, cyclopropylamino, morpholinoethylamino, hydroxyethylamino, or N-morpholino. In other embodiments, when R₁ is

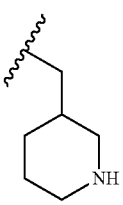 [SMILES: *CC1CCCNC1]

and X₁ is N, V is cyclopropanecarboxamido, cyclopropylamino, morpholinoethylamino, hydroxyethylamino, or N-morpholino. In other embodiments, when R₁ is

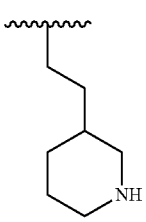 [SMILES: *CCC1CCCNC1]

and X₁ is CH, V is cyclopropanecarboxamido, cyclopropylamino, morpholinoethylamino, hydroxyethylamino, or N-morpholino. In other embodiments, when R₁ is

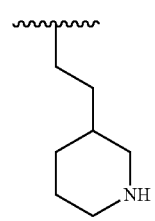

and X₁ is N, V is cyclopropanecarboxamido, cyclopropylamino, morpholinoethylamino, hydroxyethylamino, or N-morpholino. In other embodiments, when R₁ is

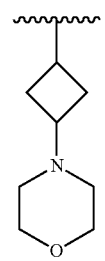 [SMILES: *C1CC(N2CCOCC2)C1]

and X₁ is CH, V is cyclopropanecarboxamido, cyclopropylamino, morpholinoethylamino, hydroxyethylamino, or N-morpholino. In other embodiments, when R₁ is

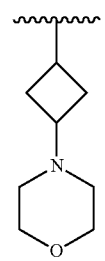 [SMILES: *C1CC(N2CCOCC2)C1]

and X₁ is N, V is cyclopropanecarboxamido, cyclopropylamino, morpholinoethylamino, hydroxyethylamino, or N-morpholino. In other embodiments, when R₁ is

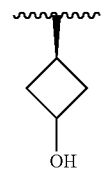

and X₁ is CH, V is cyclopropanecarboxamido, cyclopropylamino, morpholinoethylamino, hydroxyethylamino, or N-morpholino. In other embodiments, when R₁ is

173

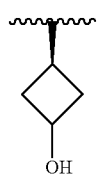

and $X_1$ is N, V is cyclopropanecarboxamido, cyclopropylamino, morpholinoethylamino, hydroxyethylamino, or N-morpholino. In other embodiments, when $R_1$ is

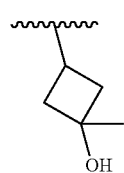 [SMILES: *C1CC(C)(O)C1]

and $X_1$ is CH, V is cyclopropanecarboxamido, cyclopropylamino, morpholinoethylamino, hydroxyethylamino, or N-morpholino. In other embodiments, when $R_1$ is

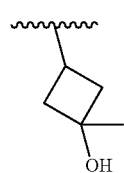 [SMILES: *C1CC(C)(O)C1]

and $X_1$ is N, V is cyclopropanecarboxamido, cyclopropylamino, morpholinoethylamino, hydroxyethylamino, or N-morpholino. In other embodiments, when $R_1$ is

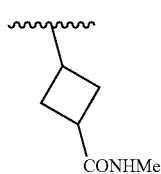

and $X_1$ is CH, V is cyclopropanecarboxamido, cyclopropylamino, morpholinoethylamino, hydroxyethylamino, or N-morpholino. In other embodiments, when $R_1$ is

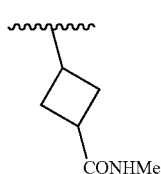

and $X_1$ is N, V is cyclopropanecarboxamido, cyclopropylamino, morpholinoethylamino, hydroxyethylamino, or N-morpholino. In other embodiments, when $R_1$ is

174

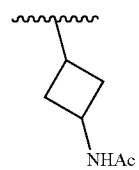

and $X_1$ is CH, V is cyclopropanecarboxamido, cyclopropylamino, morpholinoethylamino, hydroxyethylamino, or N-morpholino. In other embodiments, when $R_1$ is

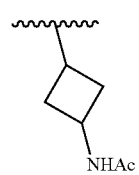 [SMILES: *C1CC(NC(C)=O)C1]

and $X_1$ is N, V is cyclopropanecarboxamido, cyclopropylamino, morpholinoethylamino, hydroxyethylamino, or N-morpholino. In other embodiments, when $R_1$ is

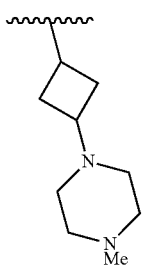 [SMILES: *C1CC(N2CCN(C)CC2)C1]

and $X_1$ is CH, V is cyclopropanecarboxamido, cyclopropylamino, morpholinoethylamino, hydroxyethylamino, or N-morpholino. In other embodiments, when $R_1$ is

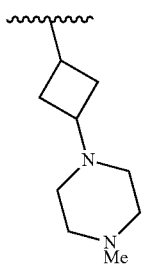 [SMILES: *C1CC(N2CCN(C)CC2)C1]

and $X_1$ is N, V is cyclopropanecarboxamido, cyclopropylamino, morpholinoethylamino, hydroxyethylamino, or N-morpholino. In other embodiments, when $R_1$ is

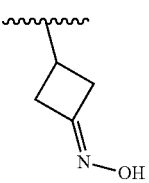 [SMILES: *C1CC(=NO)C1]

and X₁ is CH, V is cyclopropanecarboxamido, cyclopropylamino, morpholinoethylamino, hydroxyethylamino, or N-morpholino. In other embodiments, when R₁ is

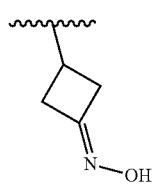 [SMILES: *C1CC(=NO)C1]

and X₁ is N, V is cyclopropanecarboxamido, cyclopropylamino, morpholinoethylamino, hydroxyethylamino, or N-morpholino. In other embodiments, when R₁ is

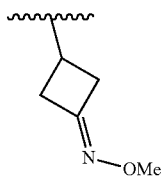 [SMILES: *C1CC(=NOC)C1]

and X₁ is CH, V is cyclopropanecarboxamido, cyclopropylamino, morpholinoethylamino, hydroxyethylamino, or N-morpholino. In other embodiments, when R₁ is

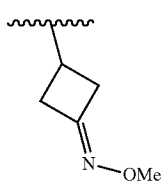 [SMILES: *C1CC(=NOC)C1]

and X₁ is N, V is cyclopropanecarboxamido, cyclopropylamino, morpholinoethylamino, hydroxyethylamino, or N-morpholino. In other embodiments, when R₁ is

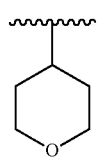

and X₁ is CH, V is cyclopropanecarboxamido, cyclopropylamino, morpholinoethylamino, hydroxyethylamino, or N-morpholino. In other embodiments, when R₁ is

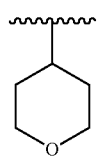

and X₁ is N, V is cyclopropanecarboxamido, cyclopropylamino, morpholinoethylamino, hydroxyethylamino, or N-morpholino. In other embodiments, when R₁ is

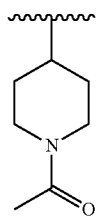

and X₁ is CH, V is cyclopropanecarboxamido, cyclopropylamino, morpholinoethylamino, hydroxyethylamino, or N-morpholino. In other embodiments, when R₁ is

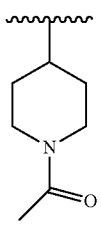

and X₁ is N, V is cyclopropanecarboxamido, cyclopropylamino, morpholinoethylamino, hydroxyethylamino, or N-morpholino. In other embodiments, when R₁ is

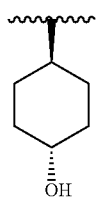 [SMILES: *[C@H]1CC[C@H](O)CC1]

and X₁ is CH, V is cyclopropanecarboxamido, cyclopropylamino, morpholinoethylamino, hydroxyethylamino, or N-morpholino. In other embodiments, when R₁ is

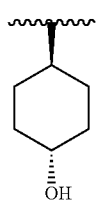 [SMILES: *[C@H]1CC[C@H](O)CC1]

and X₁ is N, V is cyclopropanecarboxamido, cyclopropylamino, morpholinoethylamino, hydroxyethylamino, or N-morpholino. In other embodiments, when R₁ is

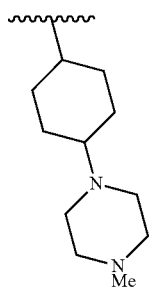 [SMILES: *C1CCC(N2CCN(C)CC2)CC1]

and $X_1$ is CH, V is cyclopropanecarboxamido, cyclopropylamino, morpholinoethylamino, hydroxyethylamino, or N-morpholino. In other embodiments, when $R_1$ is

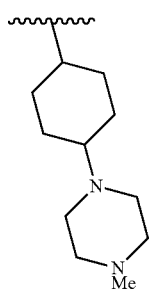 [SMILES: *C1CCC(N2CCN(C)CC2)CC1]

and $X_1$ is N, V is cyclopropanecarboxamido, cyclopropylamino, morpholinoethylamino, hydroxyethylamino, or N-morpholino. In other embodiments, when $R_1$ is

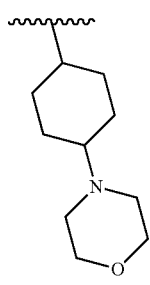 [SMILES: *C1CCC(N2CCOCC2)CC1]

and $X_1$ is CH, V is cyclopropanecarboxamido, cyclopropylamino, morpholinoethylamino, hydroxyethylamino, or N-morpholino. In other embodiments, when $R_1$ is

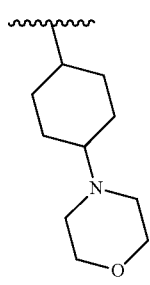 [SMILES: *C1CCC(N2CCOCC2)CC1]

and $X_1$ is N, V is cyclopropanecarboxamido, cyclopropylamino, morpholinoethylamino, hydroxyethylamino, or N-morpholino. In other embodiments, when $R_1$ is

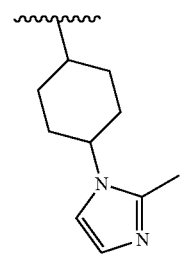 [SMILES: *C1CCC(n2ccnc2C)CC1]

and $X_1$ is CH, V is cyclopropanecarboxamido, cyclopropylamino, morpholinoethylamino, hydroxyethylamino, or N-morpholino. In other embodiments, when $R_1$ is

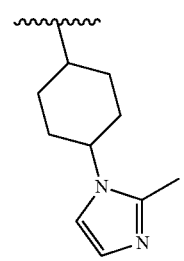 [SMILES: *C1CCC(n2ccnc2C)CC1]

and $X_1$ is N, V is cyclopropanecarboxamido, cyclopropylamino, morpholinoethylamino, hydroxyethylamino, or N-morpholino. In other embodiments, when $R_1$ is

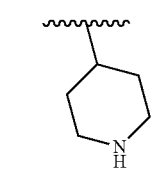

and $X_1$ is CH, V is cyclopropanecarboxamido, cyclopropylamino, morpholinoethylamino, hydroxyethylamino, or N-morpholino. In other embodiments, when $R_1$ is

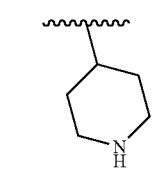

and $X_1$ is N, V is cyclopropanecarboxamido, cyclopropylamino, morpholinoethylamino, hydroxyethylamino, or N-morpholino. In other embodiments, when $R_1$ is

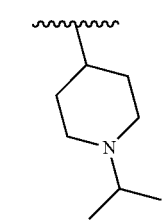

and $X_1$ is CH, V is cyclopropanecarboxamido, cyclopropylamino, morpholinoethylamino, hydroxyethylamino, or N-morpholino. In other embodiments, when $R_1$ is

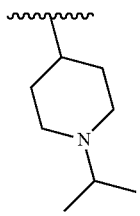 [SMILES: *C1CCN(C(C)C)CC1]

and $X_1$ is N, V is cyclopropanecarboxamido, cyclopropylamino, morpholinoethylamino, hydroxyethylamino, or N-morpholino. In other embodiments, when $R_1$ is

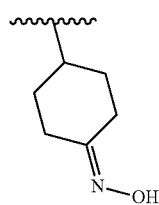

and $X_1$ is CH, V is cyclopropanecarboxamido, cyclopropylamino, morpholinoethylamino, hydroxyethylamino, or N-morpholino. In other embodiments, when $R_1$ is

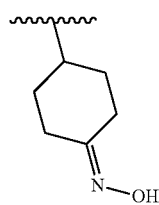 [SMILES: *C1CCC(=NO)CC1]

and $X_1$ is N, V is cyclopropanecarboxamido, cyclopropylamino, morpholinoethylamino, hydroxyethylamino, or N-morpholino. In other embodiments, when $R_1$ is

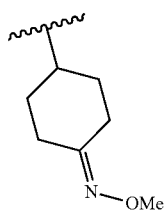 [SMILES: *C1CCC(=NOC)CC1]

and $X_1$ is CH, V is cyclopropanecarboxamido, cyclopropylamino, morpholinoethylamino, hydroxyethylamino, or N-morpholino. In other embodiments, when $R_1$ is

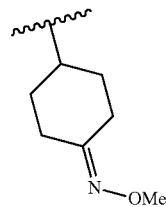 [SMILES: *C1CCC(=NOC)CC1]

and $X_1$ is N, V is cyclopropanecarboxamido, cyclopropylamino, morpholinoethylamino, hydroxyethylamino, or N-morpholino. In other embodiments, when $R_1$ is

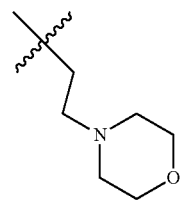 [SMILES: *CCN1CCOCC1]

and $X_1$ is CH, V is cyclopropanecarboxamido, cyclopropylamino, morpholinoethylamino, hydroxyethylamino, or N-morpholino. In other embodiments, when $R_1$ is

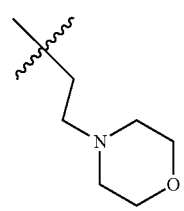 [SMILES: *CCN1CCOCC1]

and $X_1$ is N, V is cyclopropanecarboxamido, cyclopropylamino, morpholinoethylamino, hydroxyethylamino, or N-morpholino. In other embodiments, when $R_1$ is

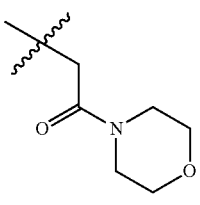 [SMILES: *CC(=O)N1CCOCC1]

and $X_1$ is CH, V is cyclopropanecarboxamido, cyclopropylamino, morpholinoethylamino, hydroxyethylamino, or N-morpholino. In other embodiments, when $R_1$ is and $X_1$ is N, V is cyclopropanecarboxamido, cyclopropylamino, morpholinoethylamino, hydroxyethylamino, or N-morpholino.

In other embodiments, when $R_1$ is

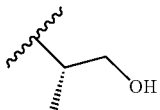

and $X_1$ is CH, V is cyclopropanecarboxamido, cyclopropylamino, morpholinoethylamino, hydroxyethylamino, or N-morpholino. In other embodiments, when $R_1$ is

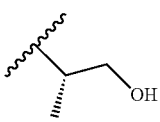 [SMILES: *[C@@H](C)CO]

and $X_1$ is N, V is cyclopropanecarboxamido, cyclopropylamino, morpholinoethylamino, hydroxyethylamino, or N-morpholino. In other embodiments, when $R_1$ is

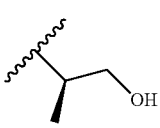

and $X_1$ is CH, V is cyclopropanecarboxamido, cyclopropylamino, morpholinoethylamino, hydroxyethylamino, or N-morpholino. In other embodiments, when $R_1$ is

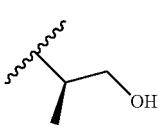 [SMILES: *[C@H](C)CO]

and $X_1$ is N, V is cyclopropanecarboxamido, cyclopropylamino, morpholinoethylamino, hydroxyethylamino, or N-morpholino. In other embodiments, when $R_1$ is

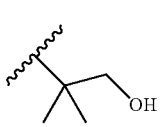

and $X_1$ is CH, V is cyclopropanecarboxamido, cyclopropylamino, morpholinoethylamino, hydroxyethylamino, or N-morpholino. In other embodiments, when $R_1$ is

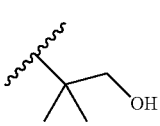 [SMILES: *C(C)(C)CO]

and $X_1$ is N, V is cyclopropanecarboxamido, cyclopropylamino, morpholinoethylamino, hydroxyethylamino, or N-morpholino. In other embodiments, when $R_1$ is

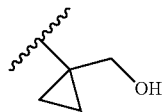 [SMILES: *C1(CO)CC1]

and $X_1$ is CH, V is cyclopropanecarboxamido, cyclopropylamino, morpholinoethylamino, hydroxyethylamino, or N-morpholino. In other embodiments, when $R_1$ is

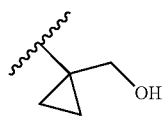 [SMILES: *C1(CO)CC1]

and $X_1$ is N, V is cyclopropanecarboxamido, cyclopropylamino, morpholinoethylamino, hydroxyethylamino, or N-morpholino. In other embodiments, when $R_1$ is

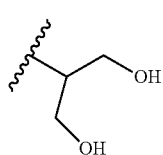 [SMILES: *C(CO)CO]

and $X_1$ is CH, V is cyclopropanecarboxamido, cyclopropylamino, morpholinoethylamino, hydroxyethylamino, or N-morpholino. In other embodiments, when $R_1$ is

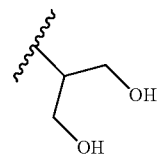

and $X_1$ is N, V is cyclopropanecarboxamido, cyclopropylamino, morpholinoethylamino, hydroxyethylamino, or N-morpholino. In other embodiments, when $R_1$ is

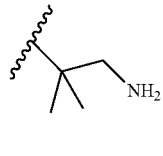 [SMILES: *C(C)(C)CN]

and $X_1$ is CH, V is cyclopropanecarboxamido, cyclopropylamino, morpholinoethylamino, hydroxyethylamino, or N-morpholino. In other embodiments, when $R_1$ is

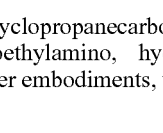

and $X_1$ is N, V is cyclopropanecarboxamido, cyclopropylamino, morpholinoethylamino, hydroxyethylamino, or N-morpholino In other embodiments, when $R_1$ is

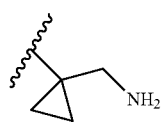 [SMILES: *C1(CN)CC1]

and X₁ is CH, V is cyclopropanecarboxamido, cyclopropylamino, morpholinoethylamino, hydroxyethylamino, or N-morpholino. In other embodiments, when R₁ is

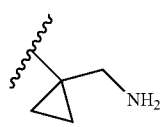 [SMILES: *C1(CN)CC1]

and X₁ is N, V is cyclopropanecarboxamido, cyclopropylamino, morpholinoethylamino, hydroxyethylamino, or N-morpholino. and X₁ is CH, V is cyclopropanecarboxamido, cyclopropylamino, morpholinoethylamino, hydroxyethylamino, or N-morpholino.

In other embodiments, when R₁ is

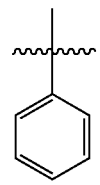

and X₁ is CH, V is cyclopropanecarboxamido, cyclopropylamino, morpholinoethylamino, hydroxyethylamino, or N-morpholino. In other embodiments, when R₁ is

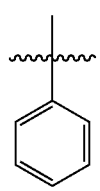 [SMILES: *c1ccccc1]

and X₁ is N, V is cyclopropanecarboxamido, cyclopropylamino, morpholinoethylamino, hydroxyethylamino, or N-morpholino. In other embodiments, when R₁ is

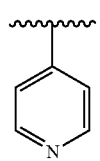

and X₁ is CH, V is cyclopropanecarboxamido, cyclopropylamino, morpholinoethylamino, hydroxyethylamino, or N-morpholino. In other embodiments, when R₁ is

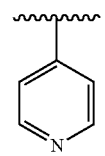 [SMILES: *c1ccncc1]

and X₁ is N, V is cyclopropanecarboxamido, cyclopropylamino, morpholinoethylamino, hydroxyethylamino, or N-morpholino. In other embodiments, when R₁ is

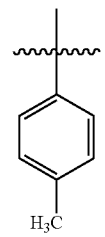 [SMILES: *c1ccc(C)cc1]

and X₁ is CH, V is cyclopropanecarboxamido, cyclopropylamino, morpholinoethylamino, hydroxyethylamino, or N-morpholino. In other embodiments, when R₁ is

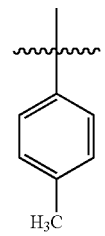

and X₁ is N, V is cyclopropanecarboxamido, cyclopropylamino, morpholinoethylamino, hydroxyethylamino, or N-morpholino. In other embodiments, when R₁ is

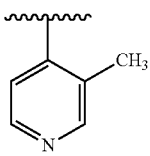 [SMILES: *c1ccncc1C]

and X₁ is CH, V is cyclopropanecarboxamido, cyclopropylamino, morpholinoethylamino, hydroxyethylamino, or N-morpholino. In other embodiments, when R₁ is

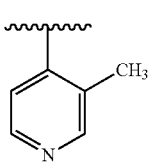 [SMILES: *c1ccncc1C]

and X₁ is N, V is cyclopropanecarboxamido, cyclopropylamino, morpholinoethylamino, hydroxyethylamino, or N-morpholino. In other embodiments, when R₁ is

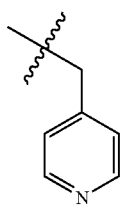 [SMILES: *Cc1ccncc1]

and $X_1$ is CH, V is cyclopropanecarboxamido, cyclopropylamino, morpholinoethylamino, hydroxyethylamino, or N-morpholino. In other embodiments, when $R_1$ is

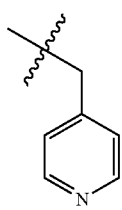 [SMILES: *Cc1ccncc1]

and $X_1$ is N, V is cyclopropanecarboxamido, cyclopropylamino, morpholinoethylamino, hydroxyethylamino, or N-morpholino. In other embodiments, when $R_1$ is

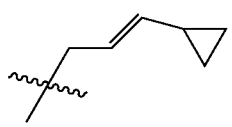 [SMILES: *C/C=C/C1CC1]

and $X_1$ is CH, V is cyclopropanecarboxamido, cyclopropylamino, morpholinoethylamino, hydroxyethylamino, or N-morpholino. In other embodiments, when $R_1$ is

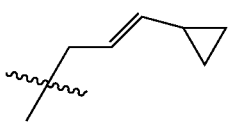 [SMILES: *C/C=C/C1CC1]

and $X_1$ is N, V is cyclopropanecarboxamido, cyclopropylamino, morpholinoethylamino, hydroxyethylamino, or N-morpholino. In other embodiments, when $R_1$ is

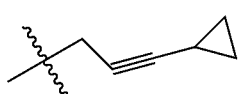 [SMILES: *CC#CC1CC1]

and $X_1$ is CH, V is cyclopropanecarboxamido, cyclopropylamino, morpholinoethylamino, hydroxyethylamino, or N-morpholino. In other embodiments, when $R_1$ is

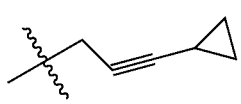 [SMILES: *CC#CC1CC1]

and $X_1$ is N, V is cyclopropanecarboxamido, cyclopropylamino, morpholinoethylamino, hydroxyethylamino, or N-morpholino. In other embodiments, when $R_1$ is

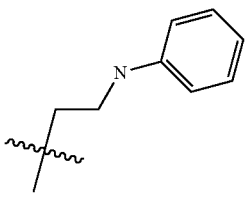 [SMILES: *CCNc1ccccc1]

and $X_1$ is CH, V is cyclopropanecarboxamido, cyclopropylamino, morpholinoethylamino, hydroxyethylamino, or N-morpholino. In other embodiments, when $R_1$ is

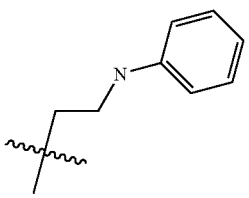 [SMILES: *CCNc1ccccc1]

and $X_1$ is N, V is cyclopropanecarboxamido, cyclopropylamino, morpholinoethylamino, hydroxyethylamino, or N-morpholino. In other embodiments, when $R_1$ is

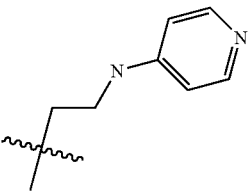 [SMILES: *CCNc1ccncc1]

and $X_1$ is CH, V is cyclopropanecarboxamido, cyclopropylamino, morpholinoethylamino, hydroxyethylamino, or N-morpholino. In other embodiments, when $R_1$ is

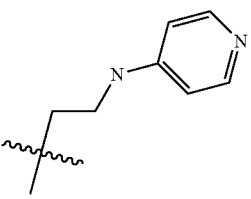 [SMILES: *CCNc1ccncc1]

and $X_1$ is N, V is cyclopropanecarboxamido, cyclopropylamino, morpholinoethylamino, hydroxyethylamino, or N-morpholino. In other embodiments, when $R_1$ is

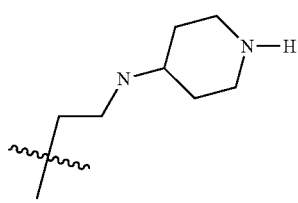 [SMILES: *CCNC1CCNCC1]

and X₁ is CH, V is cyclopropanecarboxamido, cyclopropylamino, morpholinoethylamino, hydroxyethylamino, or N-morpholino. In other embodiments, when R₁ is

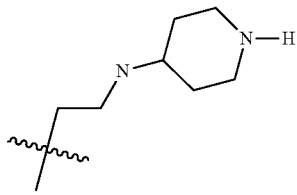 [SMILES: *CCNC1CCNCC1]

and X₁ is N, V is cyclopropanecarboxamido, cyclopropylamino, morpholinoethylamino, hydroxyethylamino, or N-morpholino.

In the noted embodiments, cyclopropanecarboxamido is

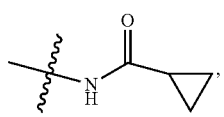 [SMILES: *NC(=O)C1CC1]

cyclopropylamino is

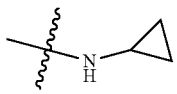 [SMILES: *NC1CC1]

2-morpholinoethylamino is

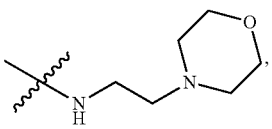 [SMILES: *NCCN1CCOCC1]

hydroxyethylamino is

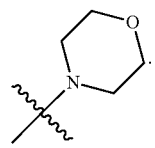

and N-morpholino is

TABLE 1

Biological activity of several illustrative mTorC1/mTorC2 inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 1 | (Compound A) | ++++ | +++ | ++ | ++++ | +++ | ++++ |

TABLE 1-continued

Biological activity of several illustrative mTorC1/mTorC2 inhibitor compounds of the invention.

| Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|
| 2 | ++++ | ++ | + | +++ | +++ | +++ |
| 3 | ++ | + | ++ | ++ | ++ | |
| 4 | +++ | ++ | ++ | +++ | +++ | ++ |
| 5 | ++++ | +++ | ++ | ++++ | +++ | ++++ |

TABLE 1-continued

Biological activity of several illustrative mTorC1/mTorC2 inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 6 | 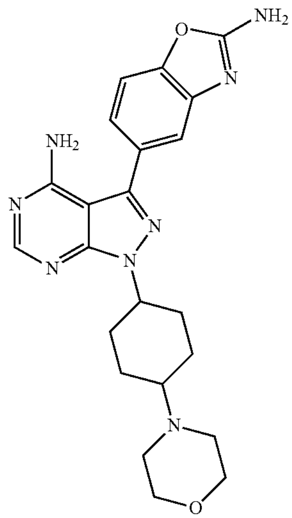 [SMILES: Nc1nc2cc(-c3nn(C4CCC(N5CCOCC5)CC4)c4ncnc(N)c34)ccc2o1] | ++++ | ++ | + | ++ | +++ | +++ |
| 7 | 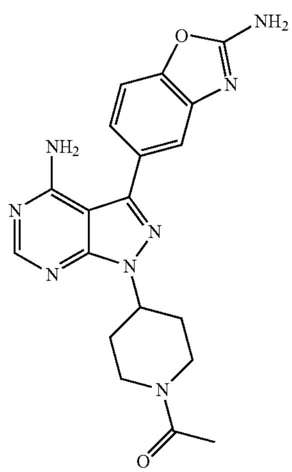 [SMILES: CC(=O)N1CCC(n2nc(-c3ccc4oc(N)nc4c3)c3c(N)ncnc32)CC1] | ++++ | +++ | ++ | ++ | +++ | ++ |
| 8 | 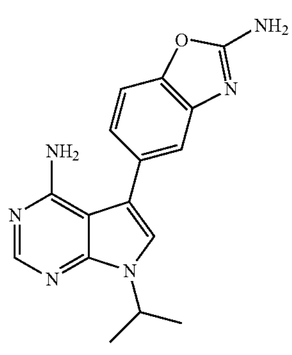 [SMILES: CC(C)n1cc(-c2ccc3oc(N)nc3c2)c2c(N)ncnc21] | ++++ | +++ | + | +++ | +++ | ++++ |

TABLE 1-continued

Biological activity of several illustrative mTorC1/mTorC2 inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 9 | *structure* | ++++ | ++ | + | +++ | +++ | ++++ |
| 10 | *structure* | ++ | | | | | + |
| 11 | *structure* | +++ | | | | | + |
| 12 | *structure* | +++ | | | | | + |

TABLE 1-continued

Biological activity of several illustrative mTorC1/mTorC2 inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 13 | 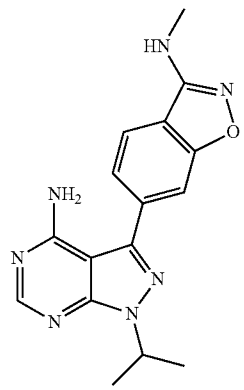 [SMILES: CNc1noc2cc(-c3nn(C(C)C)c4ncnc(N)c34)ccc12] | ++ | ++ | | +++ | +++ | |
| 14 | 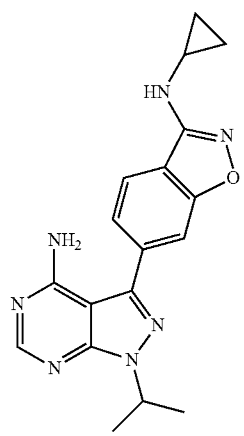 [SMILES: CC(C)n1nc(-c2ccc3c(NC4CC4)noc3c2)c2c(N)ncnc21] | ++ | ++ | | +++ | ++ | |
| 15 | 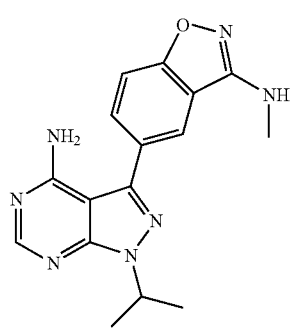 [SMILES: CNc1noc2ccc(-c3nn(C(C)C)c4ncnc(N)c34)cc12] | + | + | | + | + | |
| 16 | 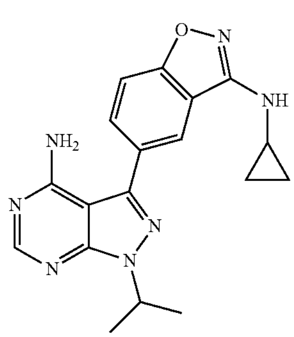 [SMILES: CC(C)n1nc(-c2ccc3onc(NC4CC4)c3c2)c2c(N)ncnc21] | + | + | | ++ | + | |

TABLE 1-continued

Biological activity of several illustrative mTorC1/mTorC2 inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 17 | 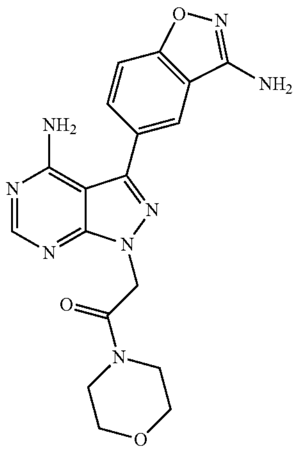 [SMILES: Nc1noc2ccc(-c3nn(CC(=O)N4CCOCC4)c4ncnc(N)c34)cc12] | + | + | | + | + | |
| 18 | 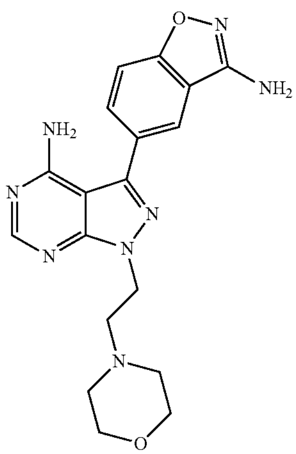 [SMILES: Nc1noc2ccc(-c3nn(CCN4CCOCC4)c4ncnc(N)c34)cc12] | + | + | | + | + | |
| 19 | 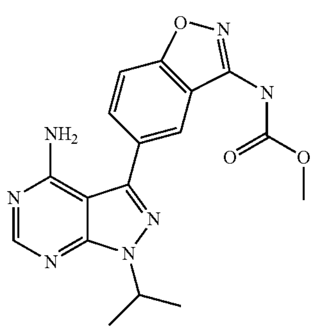 [SMILES: COC(=O)Nc1noc2ccc(-c3nn(C(C)C)c4ncnc(N)c34)cc12] | ++ | + | + | | + | |
| 20 | 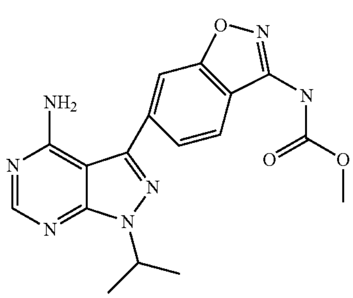 [SMILES: COC(=O)Nc1noc2cc(-c3nn(C(C)C)c4ncnc(N)c34)ccc12] | ++ | ++ | + | | ++ | |

TABLE 1-continued

Biological activity of several illustrative mTorC1/mTorC2 inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 21 | 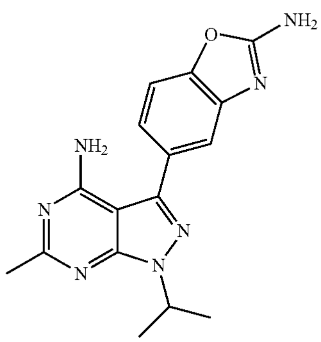 [SMILES: Cc1nc(N)c2c(-c3ccc4oc(N)nc4c3)nn(C(C)C)c2n1] | +++ | + | + | + | + | |
| 22 | 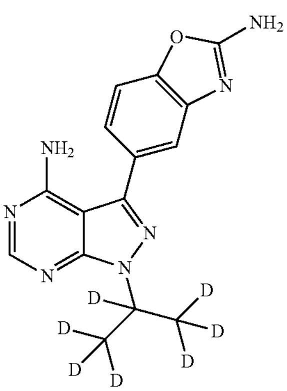 [SMILES: [2H]C([2H])([2H])C([2H])(n1nc(-c2ccc3oc(N)nc3c2)c2c(N)ncnc21)C([2H])([2H])[2H]] | ++++ | ++++ | ++ | +++ | +++ | ++ |
| 23 | 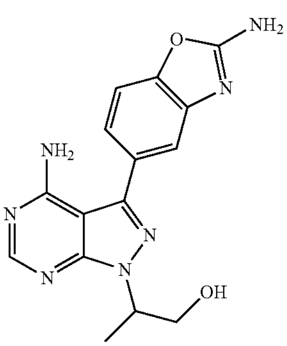 [SMILES: CC(CO)n1nc(-c2ccc3oc(N)nc3c2)c2c(N)ncnc21] | ++++ | ++ | + | ++ | ++ | |
| 24 | 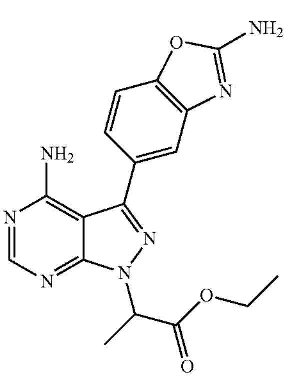 [SMILES: CCOC(=O)C(C)n1nc(-c2ccc3oc(N)nc3c2)c2c(N)ncnc21] | | + | + | + | + | |

TABLE 1-continued

Biological activity of several illustrative mTorC1/mTorC2 inhibitor compounds of the invention.

| Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|
| 25 | | +++ | ++ | ++++ | +++ | |
| 26 | | ++++ | +++ | ++++ | +++ | |
| 27 | | ++ | + | + | +++ | |

Table 1 shows the biological activity in mTOR and PI3K kinase assays of several compounds of the invention. The scale utilized in Table 1 is as follows: ++++less than 100 nM; +++less than 1.0 µM; ++less than 10 µM; and +greater than 10 µM.
In other embodiments, the present invention provides the following compounds:
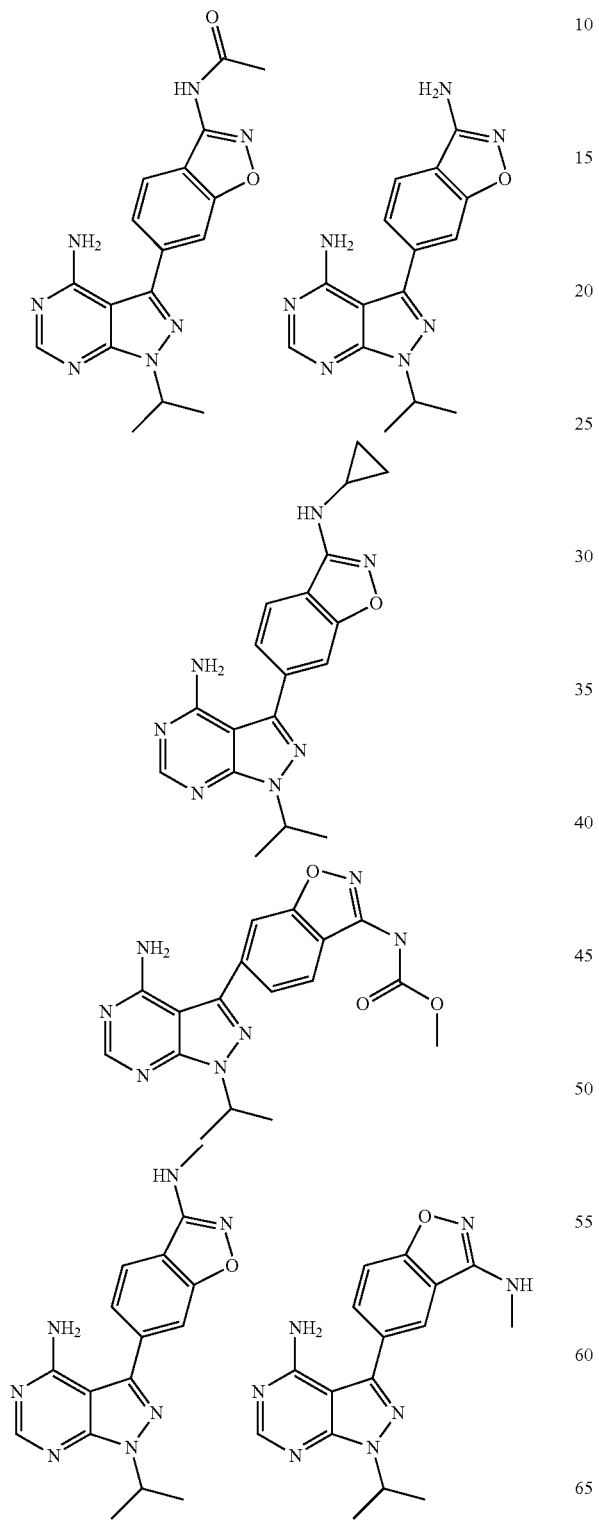
-continued
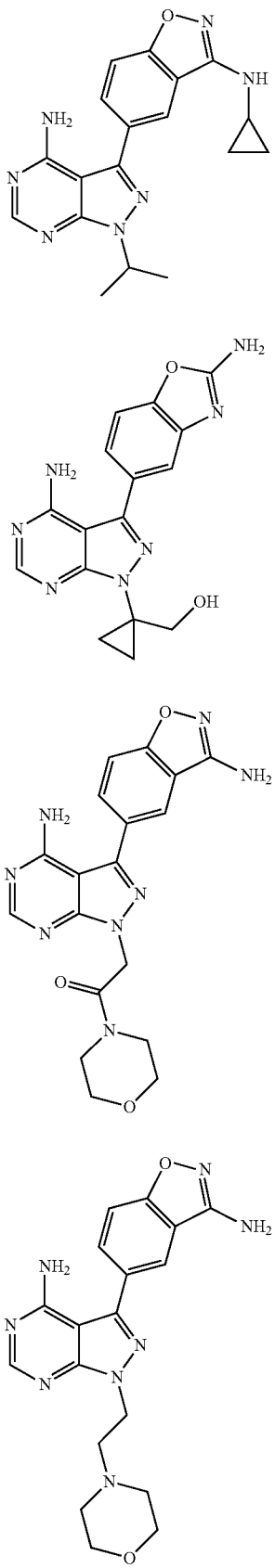

205
-continued

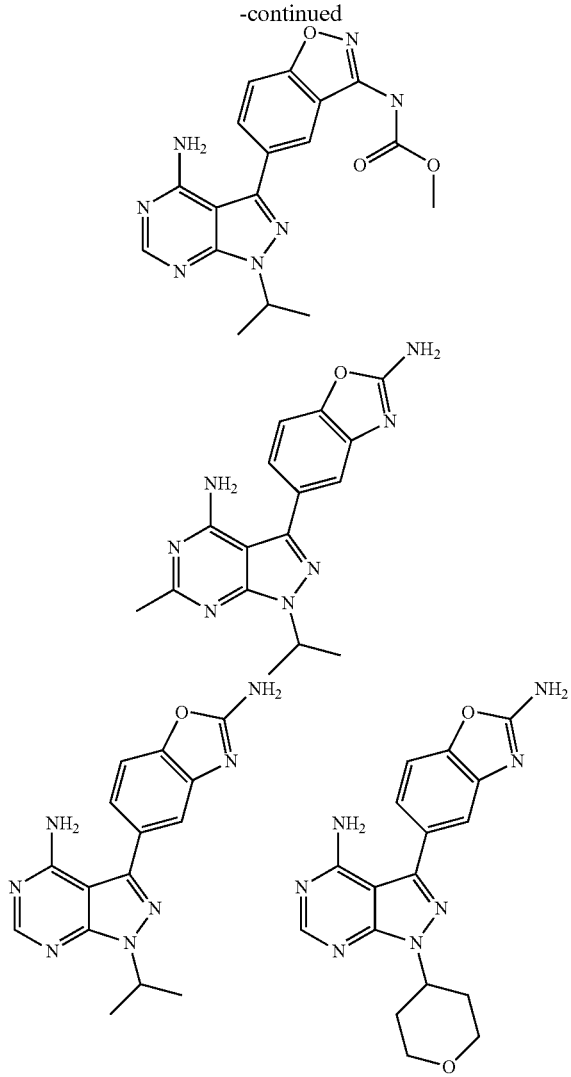

206
-continued

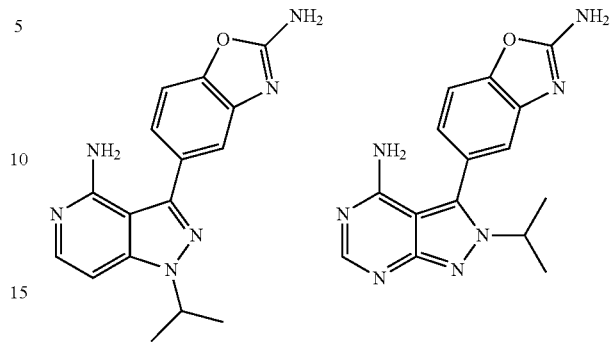

Any of the compounds shown above may show a biological activity in an mTOR or PI3K inhibition assay of between about 0.5 nM and 25 μM (IC50).

Additional compounds which are mTorC1/mTorC2 inhibitors of the invention are shown in Table 2.

TABLE 2

In vitro $IC_{50}$ values for Illustrative mTor Inhibitor Compounds of the Invention.

| # | Structure | mTOR $IC_{50}$ (nM) | PI3K α $IC_{50}$ (nM) | PI3K β $IC_{50}$ (nM) | PI3K γ $IC_{50}$ (nM) | PI3K δ $IC_{50}$ (nM) | PC3 proliferation (nM) |
|---|-----------|---------------------|-----------------------|-----------------------|-----------------------|-----------------------|------------------------|
| 1 | 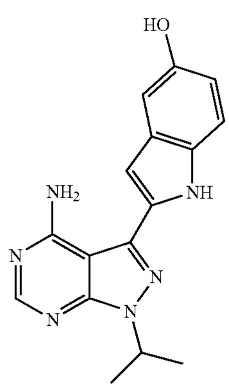 | ++++ | + | + | ++ | ++ | +++ |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 2 | 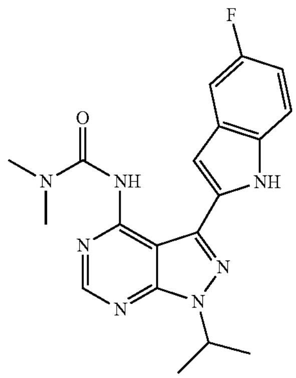 [SMILES: CC(C)n1nc(-c2cc3cc(F)ccc3[nH]2)c2c(NC(=O)N(C)C)ncnc21] | + | − | − | − | − | − |
| 3 | 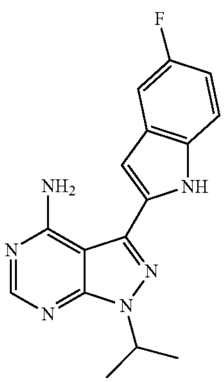 [SMILES: CC(C)n1nc(-c2cc3cc(F)ccc3[nH]2)c2c(N)ncnc21] | ++ | + | − | − | − | − |
| 4 | 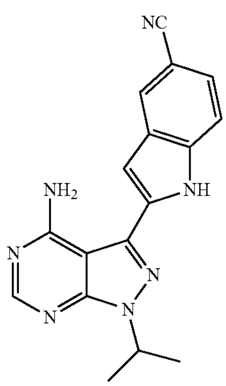 [SMILES: CC(C)n1nc(-c2cc3cc(C#N)ccc3[nH]2)c2c(N)ncnc21] | + | + | | | | − |
| 5 | 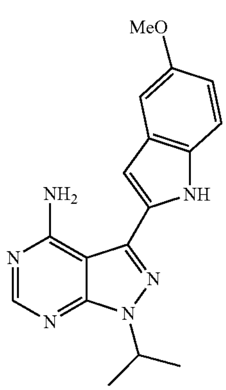 [SMILES: COc1ccc2[nH]c(-c3nn(C(C)C)c4ncnc(N)c34)cc2c1] | + | + | | | | + |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 6 | (structure: 4-amino-3-(1-methylindol-2-yl)-1-isopropyl-pyrazolo[3,4-d]pyrimidine) | + | + | | | | + |
| 7 | (structure: 4-amino-3-(1H-indol-2-yl)-1-isopropyl-pyrazolo[3,4-d]pyrimidine) | +++ | + | | | | + |
| 8 | (structure: 4-amino-3-(6-methoxy-1H-indol-2-yl)-1-isopropyl-pyrazolo[3,4-d]pyrimidine) | + | + | | | | + |
| 9 | (structure: 4-amino-3-(4-chloro-1H-indol-2-yl)-1-isopropyl-pyrazolo[3,4-d]pyrimidine) | ++++ | + | | | | + |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 10 | (7-OMe-indol-2-yl pyrazolopyrimidine, N-isopropyl) | +++++ | + | + | + | + | + |
| 11 | (7-OH-indol-2-yl pyrazolopyrimidine, N-isopropyl) | +++++++ | + | + | ++ | ++ | ++++ |
| 12 | (5-OH-indol-2-yl pyrazolopyrimidine, N-cyclopentyl) | ++++++ | + | + | ++ | + | ++++ |
| 13 | (5-OMe-7-Cl-indol-2-yl pyrazolopyrimidine, N-isopropyl) | + | + | | | | + |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 14 | (structure: MeO-, F-indole, NH$_2$-pyrazolopyrimidine, isopropyl) | + | + | | | | − |
| 15 | (structure: HO-, Cl-indole, NH$_2$-pyrazolopyrimidine, isopropyl) | +++++++ | + | + | ++++ | ++++ | ++++ |
| 16 | (structure: HO-, F-indole, NH$_2$-pyrazolopyrimidine, isopropyl) | +++++++ | + | + | ++ | +++ | ++ |
| 17 | (structure: Cl-indole, NH$_2$-pyrazolopyrimidine, isopropyl) | + | + | | | | + |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 18 | 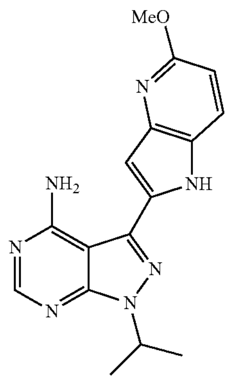 [SMILES: COc1ccc2[nH]c(-c3nn(C(C)C)c4ncnc(N)c34)cc2n1] | + | * | | | | * |
| 19 | 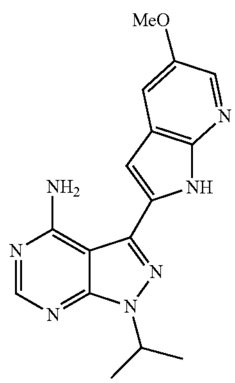 [SMILES: COc1cnc2[nH]c(-c3nn(C(C)C)c4ncnc(N)c34)cc2c1] | + | + | | | | − |
| 20 | 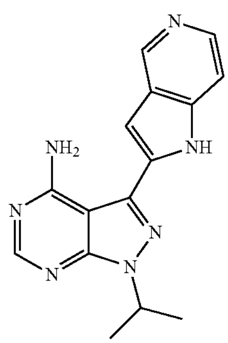 [SMILES: CC(C)n1nc(-c2cc3cnccc3[nH]2)c2c(N)ncnc21] | + | + | | | | − |
| 21 | 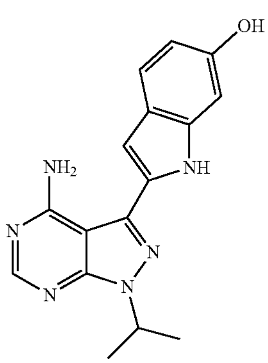 | ++++ | ++ | + | ++ | ++ | + |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 22 | 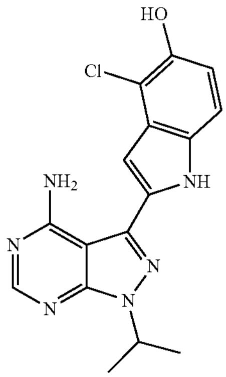 [SMILES: CC(C)n1nc(-c2cc3c(Cl)c(O)ccc3[nH]2)c2c(N)ncnc21] | +++++++ | + | + | − | + | ++ |
| 23 | 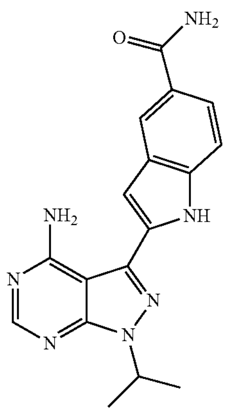 [SMILES: CC(C)n1nc(-c2cc3cc(C(N)=O)ccc3[nH]2)c2c(N)ncnc21] | | + | + | | | − |
| 24 | 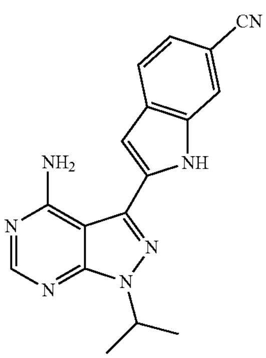 [SMILES: CC(C)n1nc(-c2cc3ccc(C#N)cc3[nH]2)c2c(N)ncnc21] | | + | + | | | + |
| 25 | 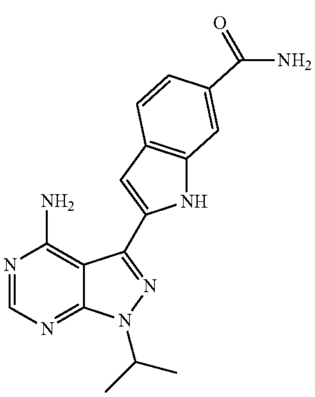 [SMILES: CC(C)n1nc(-c2cc3ccc(C(N)=O)cc3[nH]2)c2c(N)ncnc21] | ++ | + | | | | + |

TABLE 2-continued
In vitro IC$_{50}$ values for Illustrative mTor Inhibitor Compounds of the Invention.
| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|-----------|---------------------|-----------------------|-----------------------|-----------------------|-----------------------|------------------------|
| 26 | 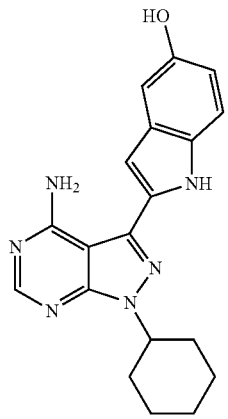 [SMILES: Nc1ncnc2c1c(-c1cc3cc(O)ccc3[nH]1)nn2C1CCCCC1] | ++++++ | + | + | ++ | +++ | ++ |
| 27 | 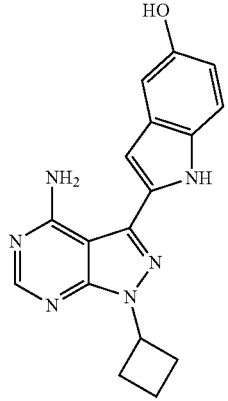 [SMILES: Nc1ncnc2c1c(-c1cc3cc(O)ccc3[nH]1)nn2C1CCC1] | +++++ | | | | | ++ |
| 28 | 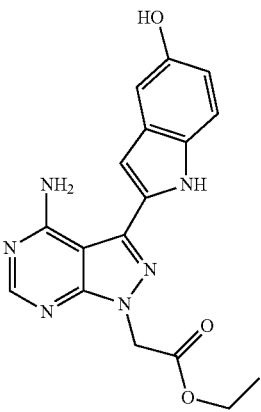 [SMILES: CCOC(=O)Cn1nc(-c2cc3cc(O)ccc3[nH]2)c2c(N)ncnc21] | ++ | + | + | − | + | + |

TABLE 2-continued
In vitro IC$_{50}$ values for Illustrative mTor Inhibitor Compounds of the Invention.
| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 29 | 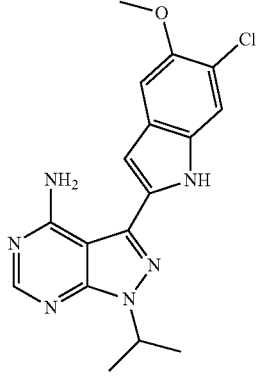 [SMILES: COc1cc2cc(-c3nn(C(C)C)c4ncnc(N)c34)[nH]c2cc1Cl] | + | | | | | − |
| 30 | 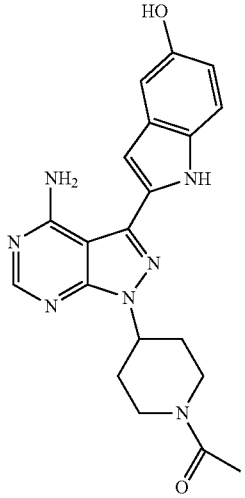 [SMILES: CC(=O)N1CCC(n2nc(-c3cc4cc(O)ccc4[nH]3)c3c(N)ncnc32)CC1] | +++++ | + | + | − | + | + |
| 31 | 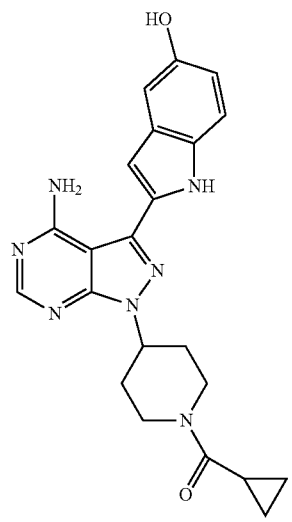 [SMILES: Nc1ncnc2c1c(-c1cc3cc(O)ccc3[nH]1)nn2C1CCN(C(=O)C2CC2)CC1] | +++++ | + | + | − | ++ | + |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 32 | 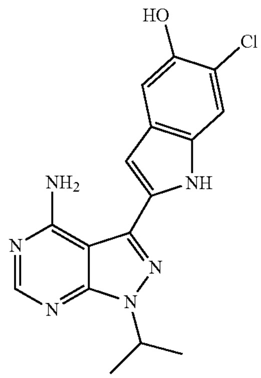 [SMILES: CC(C)n1nc(-c2cc3cc(O)c(Cl)cc3[nH]2)c2c(N)ncnc21] | ++ | + | − | + | + | + |
| 33 | 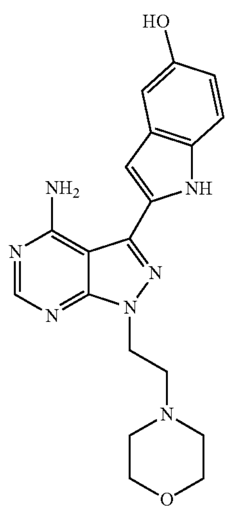 [SMILES: Nc1ncnc2c1c(-c1cc3cc(O)ccc3[nH]1)nn2CCN1CCOCC1] | ++ | + | − | + | + | + |
| 34 | 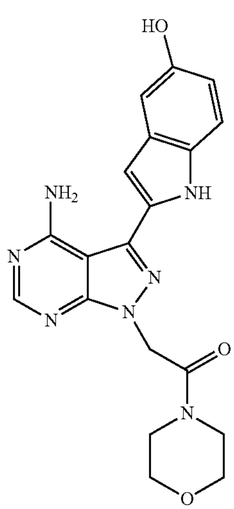 [SMILES: Nc1ncnc2c1c(-c1cc3cc(O)ccc3[nH]1)nn2CC(=O)N1CCOCC1] | + | + | − | + | + | − |

TABLE 2-continued
In vitro IC$_{50}$ values for Illustrative mTor Inhibitor Compounds of the Invention.
| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 35 | 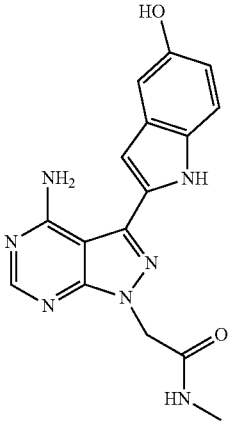 [SMILES: CNC(=O)Cn1nc(-c2cc3cc(O)ccc3[nH]2)c2c(N)ncnc21] | + | + | − | + | + | − |
| 36 | 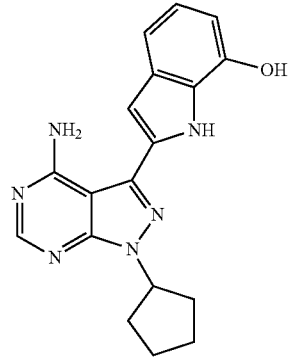 [SMILES: Nc1ncnc2c1c(-c1cc3cccc(O)c3[nH]1)nn2C1CCCC1] | +++++ | + | − | +++ | ++ | +++ |
| 37 | 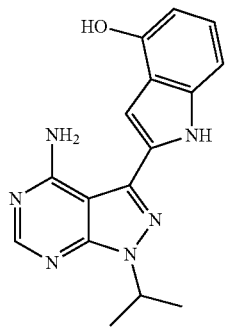 [SMILES: CC(C)n1nc(-c2cc3c(O)cccc3[nH]2)c2c(N)ncnc21] | + | ++ | − | ++ | ++ | − |
| 38 | 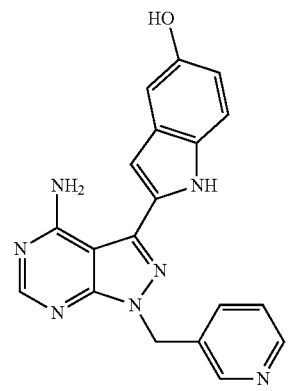 [SMILES: Nc1ncnc2c1c(-c1cc3cc(O)ccc3[nH]1)nn2Cc1cccnc1] | ++ | + | − | + | + | + |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 39 | 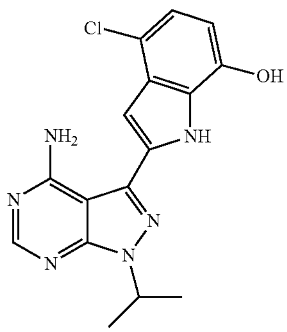 [SMILES: CC(C)n1nc(-c2cc3c(Cl)ccc(O)c3[nH]2)c2c(N)ncnc21] | ++++++ | + | − | + | + | + |
| 40 | 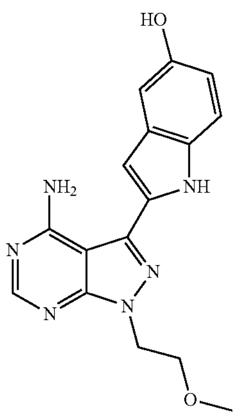 [SMILES: COCCn1nc(-c2cc3cc(O)ccc3[nH]2)c2c(N)ncnc21] | +++ | + | − | + | + | + |
| 41 | 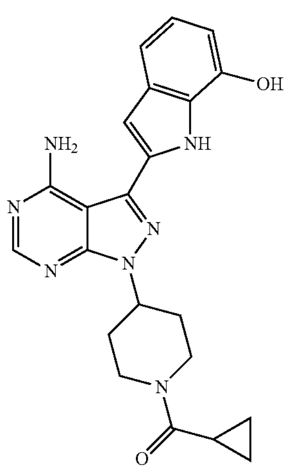 [SMILES: Nc1ncnc2c1c(-c1cc3cccc(O)c3[nH]1)nn2C1CCN(C(=O)C2CC2)CC1] | ++++++ | + | + | ++++ | + | + |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 42 | 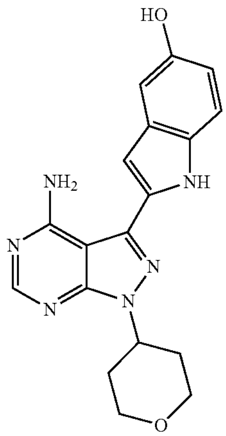 [SMILES: Nc1ncnc2c1c(-c1cc3cc(O)ccc3[nH]1)nn2C1CCOCC1] | +++++++ | + | + | − | +++ | + |
| 43 | 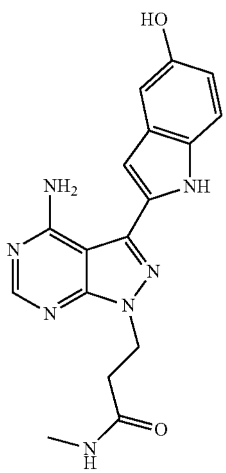 [SMILES: CNC(=O)CCn1nc(-c2cc3cc(O)ccc3[nH]2)c2c(N)ncnc21] | + | + | + | − | + | − |
| 44 | 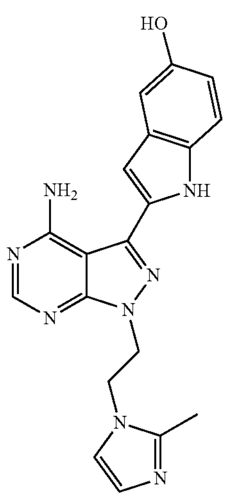 [SMILES: Cc1nccn1CCn1nc(-c2cc3cc(O)ccc3[nH]2)c2c(N)ncnc21] | +++ | + | + | − | + | − |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 45 | 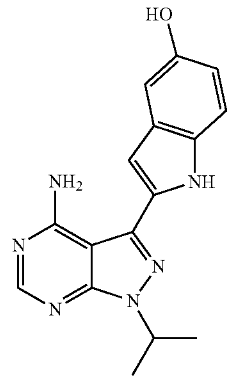 [SMILES: CC(C)n1nc(-c2cc3cc(O)ccc3[nH]2)c2c(N)ncnc21] | + | | | | | |
| 46 | 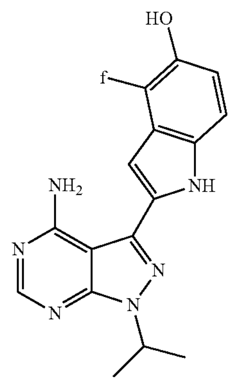 | – | | | | | |
| 47 | 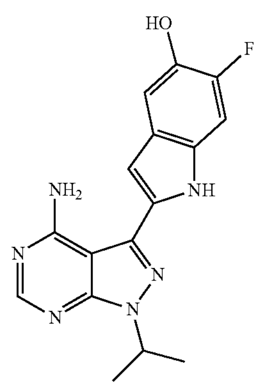 [SMILES: CC(C)n1nc(-c2cc3cc(O)c(F)cc3[nH]2)c2c(N)ncnc21] | – | | | | | |
| 48 | 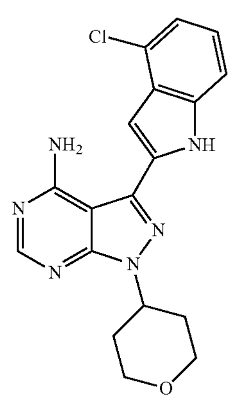 [SMILES: Nc1ncnc2c1c(-c1cc3c(Cl)cccc3[nH]1)nn2C1CCOCC1] | ++++ | + | + | + | + | |

TABLE 2-continued
In vitro IC$_{50}$ values for Illustrative mTor Inhibitor Compounds of the Invention.
| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 49 | 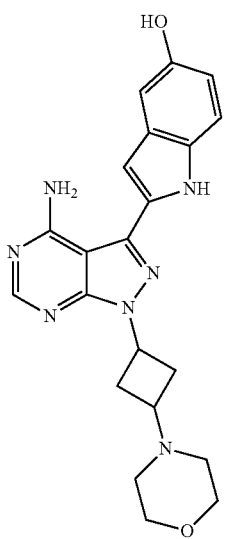 [SMILES: Nc1ncnc2c1c(-c1cc3cc(O)ccc3[nH]1)nn2C1CC(N2CCOCC2)C1] | ++++++ | + | + | ++ | ++ | |
| 50 | 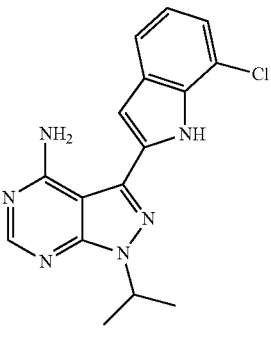 [SMILES: CC(C)n1nc(-c2cc3cccc(Cl)c3[nH]2)c2c(N)ncnc21] | ++++ | + | + | ++ | ++ | |
| 51 | 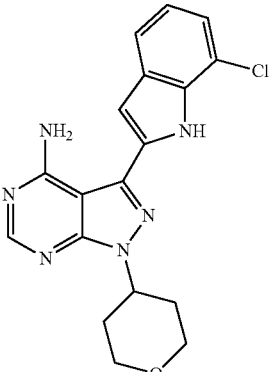 | ++++ | + | + | ++ | ++ | |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 52 | 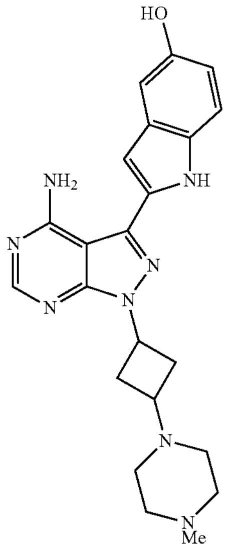 [SMILES: CN1CCN(C2CC(n3nc(-c4cc5cc(O)ccc5[nH]4)c4c(N)ncnc43)C2)CC1] | ++ | + | + | + | ++ | |
| 53 | 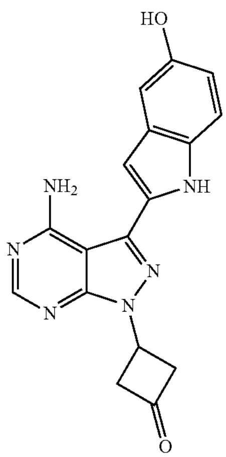 [SMILES: Nc1ncnc2c1c(-c1cc3cc(O)ccc3[nH]1)nn2C1CC(=O)C1] | +++ | + | + | + | − | |
| 54 | 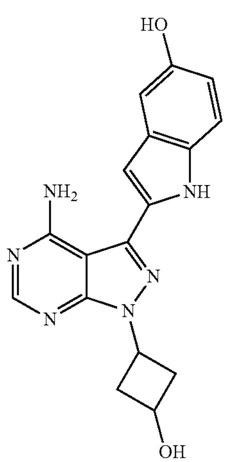 [SMILES: Nc1ncnc2c1c(-c1cc3cc(O)ccc3[nH]1)nn2C1CC(O)C1] | +++++ | + | + | + | − | |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 55 | 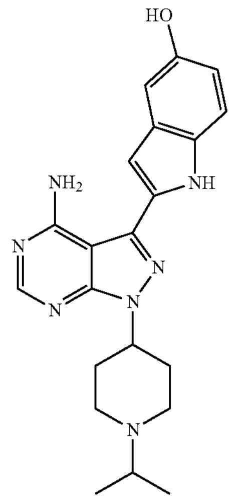 [SMILES: CC(C)N1CCC(n2nc(-c3cc4cc(O)ccc4[nH]3)c3c(N)ncnc32)CC1] | ++ | + | + | + | − | |
| 56 | 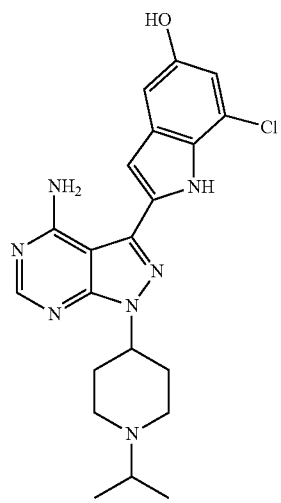 [SMILES: CC(C)N1CCC(n2nc(-c3cc4cc(O)cc(Cl)c4[nH]3)c3c(N)ncnc32)CC1] | + | + | + | + | − | |
| 57 | 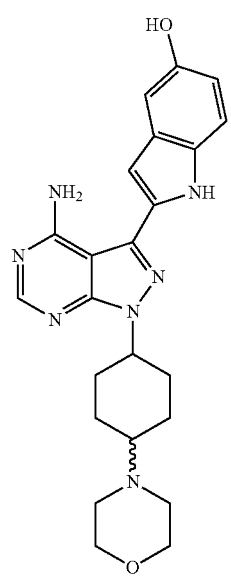 [SMILES: Nc1ncnc2c1c(-c1cc3cc(O)ccc3[nH]1)nn2C1CCC(N2CCOCC2)CC1] | +++++ | + | + | + | − | |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 58 | 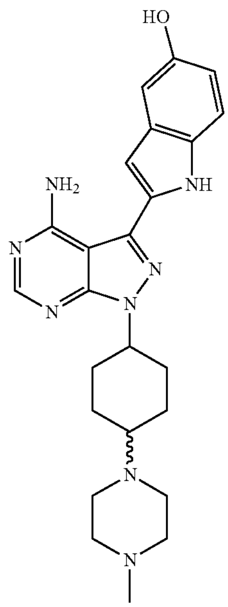 [SMILES: CN1CCN(C2CCC(n3nc(-c4cc5cc(O)ccc5[nH]4)c4c(N)ncnc43)CC2)CC1] | + | + | + | + | − | |
| 59 | 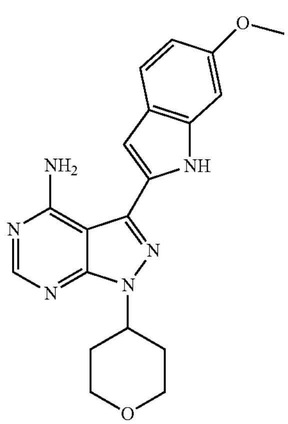 [SMILES: COc1ccc2cc(-c3nn(C4CCOCC4)c4ncnc(N)c34)[nH]c2c1] | + | + | + | + | − | |
| 60 | 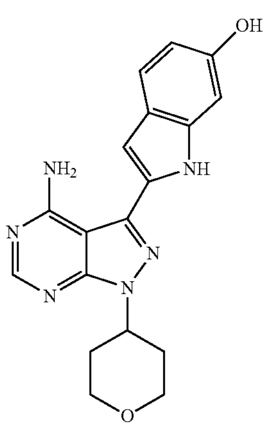 [SMILES: Nc1ncnc2c1c(-c1cc3ccc(O)cc3[nH]1)nn2C1CCOCC1] | +++ | + | + | +++ | − | |

TABLE 2-continued
In vitro IC$_{50}$ values for Illustrative mTor Inhibitor Compounds of the Invention.
| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 61 | 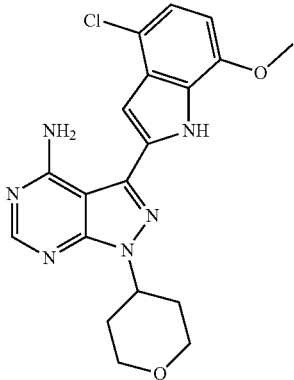 [SMILES: COc1ccc(Cl)c2cc(-c3nn(C4CCOCC4)c4ncnc(N)c34)[nH]c12] | +++++ | + | + | + | + | |
| 62 | 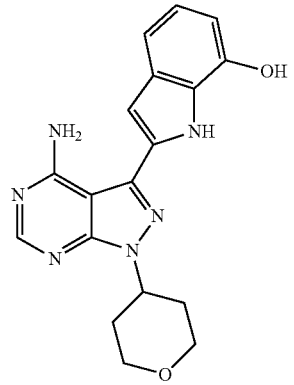 [SMILES: Nc1ncnc2c1c(-c1cc3cccc(O)c3[nH]1)nn2C1CCOCC1] | +++++++ | + | + | + | +++ | |
| 63 | 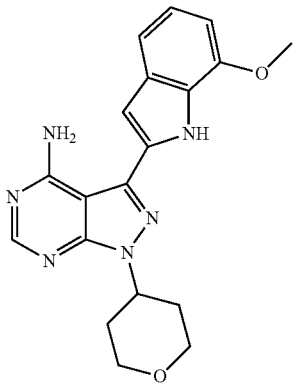 [SMILES: COc1cccc2cc(-c3nn(C4CCOCC4)c4ncnc(N)c34)[nH]c12] | +++++++ | ++ | + | +++++ | +++++ | |

TABLE 2-continued

In vitro IC₅₀ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 64 | 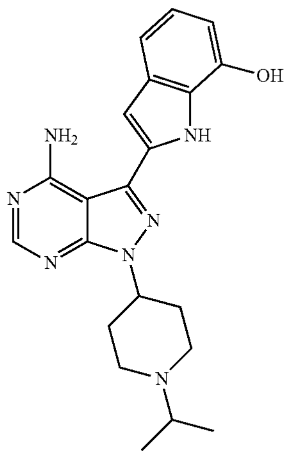 [SMILES: CC(C)N1CCC(n2nc(-c3cc4cccc(O)c4[nH]3)c3c(N)ncnc32)CC1] | +++++ | + | + | ++ | ++ | |
| 65 | 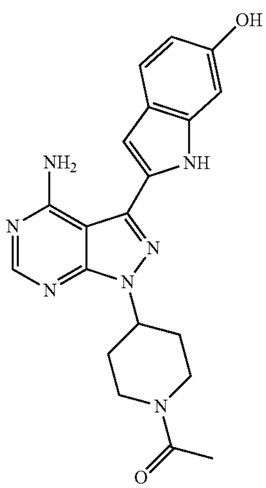 [SMILES: CC(=O)N1CCC(n2nc(-c3cc4ccc(O)cc4[nH]3)c3c(N)ncnc32)CC1] | ++++++ | ++++ | + | +++++ | +++++ | |
| 66 | 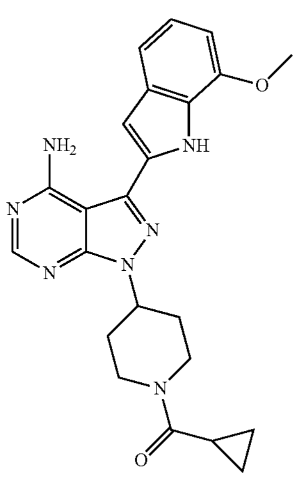 [SMILES: COc1cccc2cc(-c3nn(C4CCN(C(=O)C5CC5)CC4)c4ncnc(N)c34)[nH]c12] | + | + | + | + | + | |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 67 | 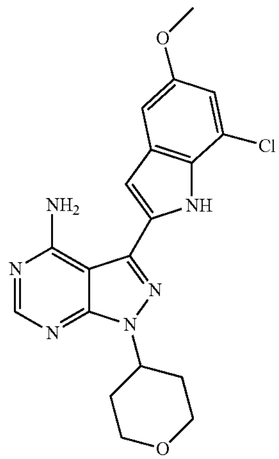 [SMILES: COc1cc(Cl)c2[nH]c(-c3nn(C4CCOCC4)c4ncnc(N)c34)cc2c1] | + | + | + | + | + | |
| 68 | 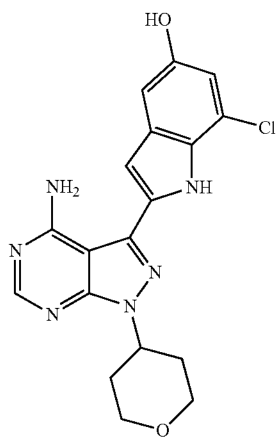 [SMILES: Nc1ncnc2c1c(-c1cc3cc(O)cc(Cl)c3[nH]1)nn2C1CCOCC1] | +++++++ | ++ | + | ++++ | +++++ | |
| 69 | 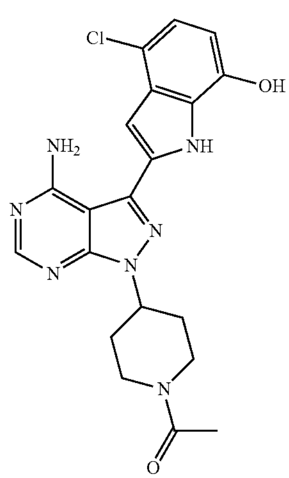 [SMILES: CC(=O)N1CCC(n2nc(-c3cc4c(Cl)ccc(O)c4[nH]3)c3c(N)ncnc32)CC1] | +++++++ | + | + | + | ++ | |

TABLE 2-continued

In vitro IC$_{50}$ values for Illustrative mTor Inhibitor Compounds of the Invention.

| # | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 70 | 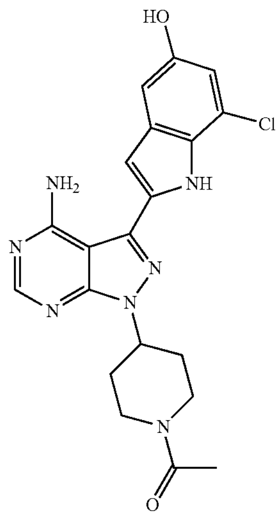 [SMILES: CC(=O)N1CCC(n2nc(-c3cc4cc(O)cc(Cl)c4[nH]3)c3c(N)ncnc32)CC1] | +++++++ | ++ | + | +++ | +++++ | |
| 71 | 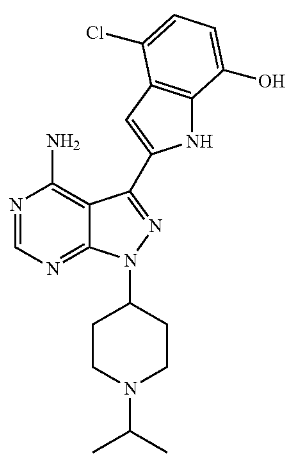 [SMILES: CC(C)N1CCC(n2nc(-c3cc4c(Cl)ccc(O)c4[nH]3)c3c(N)ncnc32)CC1] | +++ | + | + | + | + | |

In Table 2 above, a +++++++ indicates an IC50 of 5 nM or less; a ++++++ indicates an IC50 of 10 nM or less; a +++++ indicates an IC50 of 25 nM or less; an ++++ indicates an IC50 of 50 nm or less, a +++ indicates an IC50 of 100 nM or less, a ++ indicates an IC50 of 500 nM or less, and a + indicates an IC50 of more than 500 nM.

In some embodiments, the mTorC1/mTorC2 inhibitor is a compound of Formula I, Formula I-A, Formula I-B1, Formula I-C, Formula I-C1a, or a compound of Table 1 or Table 2. For example, the mTorC1/mTorC2 inhibitor is a compound of Formula I where M1 is a bicyclic heteroaryl system, including, for instance, benzothiazolyl, quinolinyl, quinazolinyl, benzoxazolyl, and benzoimidazolyl. In other embodiments, the mTorC1/mTorC2 inhibitor is a compound of Formula I where M1 is of formula M1-A, M1-B, M1-C or M1-D. In yet other embodiments, the mTorC1/mTorC2 inhibitor is of Formula I-B1 and M1 is of formula M1-F1. In still other embodiments, the mTorC1/mTorC2 inhibitor is of Formula I-C. In still other embodiments, the mTorC1/mTorC2 inhibitor is of Formula I-C1a.

Disease Targets

The subject methods are useful for treating any disease conditions, for example diseases for which current treatment regimens result in adverse events, limited tolerability, or patient non-compliance. In some embodiments, the disease condition is a proliferative disorder, such as described herein, including but not limited to cancer. In other embodiments, the disorder is diabetes. In still other embodiments, the disorder is an autoimmune disorder.

In some embodiments, the disease condition is associated with mTor and/or PI3-kinase. A vast diversity of disease conditions associated with mTOR and/or PI3-kinase have been reported. PI3-kinase α, one of the four isoforms of type I PI3-kinases has been implicated, for example, in a variety of human proliferative disorders, such as cancers. Angiogenesis has been shown to selectively require the α isoform of PI3K in the control of endothelial cell migration. (Graupera et al, Nature 2008; 453; 662-6). Mutations in the gene coding for PI3K α or mutations which lead to upregulation of PI3K α are believed to occur in many human cancers such as lung, stomach, endometrial, ovarian, bladder, breast, colon, brain and skin cancers. Often, mutations in the gene coding for PI3K α are point mutations clustered within several hotspots in helical and kinase domains, such as E542, E545, and H1047. Many of these mutations have been shown to be oncogenic gain-of-function mutations. Because of the high rate of PI3K α mutations, targeting of this pathway provides valuable therapeutic opportunities. While other PI3K isoforms such as PI3K δ or PI3K γ are expressed primarily in hematopoietic cells, PI3K α, along with PI3K β, is expressed constitutively.

Disease conditions associated with PI3-kinase and/or mTOR can also be characterized by abnormally high level of activity and/or expression of downstream messengers of mTOR and PI3-kinase. For example, proteins or messengers such as PIP2, PIP3, PDK, Akt, PTEN, PRAS40, GSK-3β, p21, p27 may be present in abnormal amounts which can be identified by any assays known in the art.

Deregulation of the mTOR pathway is emerging as a common theme in diverse human diseases and as a consequence drugs that target mTOR have therapeutic value. The diseases associated with deregulation of mTORC1 include, but are not limited to, tuberous sclerosis complex (TSC) and lymphangioleiomyomatosis (LAM), both of which are caused by mutations in TSC1 or TSC2 tumor suppressors. Patients with TSC develop benign tumors that when present in brain, however, can cause seizures, mental retardation and death. LAM is a serious lung disease. Inhibition of mTORC1 may help patients with Peutz-Jeghers cancer-prone syndrome caused by the LKB 1 mutation. mTORC1 may also have role in the genesis of sporadic cancers. Inactivation of several tumor suppressors, in particular PTEN, p53, VHL and NF1, has been linked to mTORC1 activation. Rapamycin and its analogues (eg CCl-779, RAD001 and AP23573) inhibit TORC1 and have shown moderate anti-cancer activity in phase II clinical trials. However, due to the negative signal from S6K1 to the insulin/PI3K/Akt pathway, it is important to note that inhibitors of mTORC1, like rapalogs, can activate PKB/Akt. If this effect persists with chronic rapamycin treatment, it may provide cancer cells with an increased survival signal that may be clinically undesirable. The PI3K/Akt pathway is activated in many cancers. Activated Akt regulates cell survival, cell proliferation and metabolism by phosphorylating proteins such as BAD, FOXO, NF-KB, p21Cip1, p27Kipl, GSK3β and others. Akt might also promote cell growth by phosphorylating TSC2. Akt activation may promote cellular transformation and resistance to apoptosis by collectively promoting growth, proliferation and survival, while inhibiting apoptotic pathways.

Where desired, the subject to be treated is tested prior to treatment using a diagnostic assay to determine the sensitivity of tumor cells to an mTorC1/mTorC2 inhibitor. Any method known in the art that can determine the sensitivity of the tumor cells of a subject to an mTorC1/mTorC2 inhibitor can be employed. In these methods one or more additional anti-cancer agents or treatments can be co-administered according to a treatment regimen of the invention using the mTorC1/mTorC2 inhibitor, as judged to be appropriate by the administering physician given the prediction of the likely responsiveness of the subject to the combination of mTorC1/mTorC2 inhibitor, in combination with any additional circumstances pertaining to the individual subject.

The data presented in the Examples herein below demonstrate that the anti-tumor effects of an intermittent regimen of the invention involving an agent which is an mTorC1/mTorC2 inhibitor (where the mTorC1/mTorC2 inhibitor is administered according to a treatment regimen) are superior to the anti-tumor effects of the agent administered daily. As such, the subject methods are particularly useful for treating a proliferative disorder, such as a neoplastic condition. Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, a treatment regimen involves administering an mTorC1/mTorC2 inhibitor for the treatment of a cancer which is lung cancer, breast cancer, endometrial cancer, ovarian cancer, bladder cancer, prostate cancer, neuroendocrine cancer, renal cancer, lyphoma, myeloma or leukemia.

In some embodiments, a treatment regimen involves administering an mTorC1/mTorC2 inhibitor for the treatment of solid tumors. Solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. Additional exemplary solid tumors include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In some embodiments, a treatment regimen of the invention involves administering an mTorC1/mTorC2 inhibitor for the treatment of multiple myeloma and/or Waldenstrom's macroglobulinemia.

In some embodiments, a treatment regimen involves administering an mTorC1/mTorC2 inhibitor for the treatment of renal cell carcinoma (also known as RCC or hypernephroma). Renal cell carcinoma is a kidney cancer that originates in the lining of the proximal convoluted tubule. Any known type of renal cell carcinoma may be treated using the treatment regimens of the invention, including clear renal cell carcinoma, papillary renal cell carcinoma, chromophobe renal cell carcinoma and collecting duct carcinoma. Any stage of the disease may be treated using the methods of the invention, including early stage as well as later stages (e.g. metastatic renal cell carcinoma).

In other embodiments, the treatment regimen involves administering an mTorC1/mTorC2 inhibitor for treatment of heart conditions including atherosclerosis, heart hypertrophy, cardiac myocyte dysfunction, elevated blood pressure and vasoconstriction. The invention also relates to a method of treating diseases related to vasculogenesis or angiogenesis in a mammal that comprises subjecting said mammal to a therapeutically effective regimen using an mTorC1/mTorC2 inhibitor of the present invention, or any pharmaceutically acceptable salt, ester, prodrug, solvate, hydrate or derivative thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, sarcoma and ovarian, breast, lung, pancreatic, prostate, colon and epidermoid cancer.

In some embodiments, the invention provides a treatment regimen involving administering an mTorC1/mTorC2 inhibitor for treating a disease condition associated with PI3-kinase α and/or mTOR, including, but not limited to, conditions related to an undesirable, over-active, harmful or deleterious immune response in a mammal, collectively termed "autoimmune disease." Autoimmune disorders include, but are not limited to, Crohn's disease, ulcerative colitis, psoriasis, psoriatic arthritis, juvenile arthritis and ankylosing spondilitis, Other non-limiting examples of autoimmune disorders include autoimmune diabetes, multiple sclerosis, systemic lupus erythematosus (SLE), rheumatoid spondylitis, gouty arthritis, allergy, autoimmune uveitis, nephrotic syndrome, multisystem autoimmune diseases, autoimmune hearing loss, adult respiratory distress syndrome, shock lung, chronic pulmonary inflammatory disease, pulmonary sarcoidosis, pulmonary fibrosis, silicosis, idiopathic interstitial lung disease, chronic obstructive pulmonary disease, asthma, restenosis, spondyloarthropathies, Reiter's syndrome, autoimmune hepatitis, inflammatory skin disorders, vasculitis of large vessels, medium vessels or small vessels, endometriosis, prostatitis and Sjogren's syndrome. Undesirable immune response can also be associated with or result in, e.g., asthma, emphysema, bronchitis, psoriasis, allergy, anaphylaxsis, auto-immune diseases, rhuematoid arthritis, graft versus host disease, transplantation rejection, lung injuries, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing. The methods of the invention can be further used to treat multiorgan failure.

The invention also provides a treatment regimen involving administering an mTorC1/mTorC2 inhibitor for treating liver diseases (including diabetes), pancreatitis or kidney disease (including proliferative glomerulonephritis and diabetes-induced renal disease) or pain in a mammal The invention further provides a treatment regimen involving administering an mTorC1/mTorC2 inhibitor for treating sperm motility. The invention also provides a treatment regimen involving administering a an mTorC1/mTorC2 inhibitor for treating neurological or neurodegenerative diseases including, but not limited to, Alzheimer's disease, Huntington's disease, CNS trauma, and stroke.

The invention further provides a treatment regimen involving administering an mTorC1/mTorC2 inhibitor for the prevention of blastocyte implantation in a mammal.

The invention also relates to a treatment regimen involving administering an mTorC1/mTorC2 inhibitor for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, sarcoma and ovarian, breast, lung, pancreatic, prostate, colon and epidermoid cancer.

The invention further provides a treatment regimen involving administering an mTorC1/mTorC2 inhibitor for the treatment of disorders involving platelet aggregation or platelet adhesion, including but not limited to Bernard-Soulier syndrome, Glanzmann's thrombasthenia, Scott's syndrome, von Willebrand disease, Hermansky-Pudlak Syndrome, and Gray platelet syndrome.

In some embodiments, a treatment regimen is provided involving administering an mTorC1/mTorC2 inhibitor to treat disease which is skeletal muscle atrophy, skeletal muscle hypertrophy, leukocyte recruitment in cancer tissue, invasion metastasis, melanoma, sarcoma, acute and chronic bacterial and viral infections, sepsis, glomerulo sclerosis, glomerulo, nephritis, or progressive renal fibrosis.

Certain embodiments contemplate a human subject such as a subject that has been diagnosed as having or being at risk for developing or acquiring a proliferative disorder condition. Certain other embodiments contemplate a non-human subject, for example a non-human primate such as a macaque, chimpanzee, gorilla, vervet, orangutan, baboon or other non-human primate, including such non-human subjects that can be known to the art as preclinical models, including preclinical models for inflammatory disorders. Certain other embodiments contemplate a non-human subject that is a mammal, for example, a mouse, rat, rabbit, pig, sheep, horse, bovine, goat, gerbil, hamster, guinea pig or other mammal There are also contemplated other embodiments in which the subject or biological source can be a non-mammalian vertebrate, for example, another higher vertebrate, or an avian, amphibian or reptilian species, or another subject or biological source. In certain embodiments of the present invention, a transgenic animal is utilized. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells).

Therapeutic Efficacy

In some embodiments, therapeutic efficacy is measured based on an effect of treating a proliferative disorder, such as cancer. In general, therapeutic efficacy of the methods and compositions of the invention, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, and/or a reduction in the size of at least one tumor such that a human is treated for the proliferative disorder. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. The primary efficacy parameter used to evaluate the treatment of cancer by the inventive method and compositions preferably is a reduction in the size of a tumor. Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

In some embodiments, tumor size is reduced as a result of the inventive method preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. The NCI toxicity scale (published April 1999) and Common Toxicity Criteria Manual (updated August 1999) is available through the NCI, e.g., through the NCI internet website at www.ctep.info.nih.gov or in the Investigator's Handbook for participants in clinical trials of investigational agents sponsored by the Division of Cancer Treatment and Diagnosis, NCI. Desirably, the inventive method is associated with minimal adverse events, e.g. Grade 0, Grade 1, or Grade 2 adverse events, as graded by the CTEP/NCI.

As discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Desirably, the growth of a tumor is stabilized (i.e., one or more tumors do not increase more than 1%, 5%, 10%, 15%, or 20% in size, and/or do not metastasize) as a result of the inventive method and compositions. Such stabilization may be evidenced by a longer period of stable disease as chracterized by the RECIST guidelines. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the inventive method reduces the size of a tumor at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

When a tumor is subject to surgical resection following completion of the therapeutic period, the efficacy of the inventive method in reducing tumor size can be determined by measuring the percentage of resected tissue that is necrotic (i.e., dead). In some embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is 100%, that is, no tumor tissue is present or detectable.

A number of secondary parameters can be employed to determine the efficacy of the inventive method. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA) prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also efficiently distinguishes small tumors from surrounding tissue (see, for example, U.S. Pat. No. 4,932,412).

Desirably, in accordance with the inventive method, the treatment of cancer in a human patient is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period or (e) a longer period of stable disease, for example longer by 1, 2, 3, 4, or 5 months. While at least a 2% decrease in a tumor-associated antigen level is preferred, any decrease in the tumor-associated antigen level is evidence of treatment of a cancer in a patient by the inventive method. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the invention can be evidenced in terms of pain intensity, analgesic consumption, and/or the Karnofsky Performance Scale score. The Karnofsky Performance Scale allows patients to be classified according to their functional impairment. The Karnofsky Performance Scale is scored from 0-100. In general, a lower Karnofsky score is predictive of a poor prognosis for survival. Thus, the treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

Detection, monitoring, and rating of various cancers in a human are further described in Cancer Facts and Figures 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also may consider quality of life and survival of the subject in evaluating efficacy of treatment.

In some embodiments, administration of an mTorC1/mTorC2 inhibitor according to an intermittent regiment of the invention provides improved therapeutic efficacy over a treatment where the inhibitor is administered daily. Improved efficacy may be measured using any method known in the art, including but not limited to those described herein. In some embodiments, the improved therapeutic efficacy is an improvement of at least about 10%, 20%, 30%, 40%, 50%, 60%, 70%, 75%, 80%, 90%, 95%, 100%, 110%, 120%, 150%, 200%, 300%, 400%, 500%, 600%, 700%, 1000%, 10000% or more, using an appropriate measure (e.g. tumor size reduction, duration of tumor size stability, duration of time free from metastatic events, duration of disease-free survival). Improved efficacy may also be expressed as fold improvement, such as at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or more, using an appropriate measure (e.g. tumor size reduction, duration of tumor size stability, duration of time free from metastatic events, duration of disease-free survival).

Pharmaceutical Compositions and Administration

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g 0.15 g, 0.2 g 0.25 g, 0.3 g 0.35 g, 0.4 g 0.45 g, 0.5 g, 0.55 g, 0.6 g 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (e.g., a compound) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pregelatinized starch, other starches, clays, other aligns, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences,* 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. No. 5,451,233; U.S. Pat. No. 5,040,548; U.S. Pat. No. 5,061,273; U.S. Pat. No. 5,496,346; U.S. Pat. No. 5,292,331; U.S. Pat. No. 5,674,278; U.S. Pat. No. 3,657,744; U.S. Pat. No. 4,739,762; U.S. Pat. No. 5,195,984; U.S. Pat. No. 5,292,331; U.S. Pat. No. 5,674,278; U.S. Pat. No. 5,879,382; U.S. Pat. No. 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Combination Therapies

The present invention also provides methods for further combination therapies in which, in addition to an mTorC1/mTorC2 inhibitor, one or more agents known to modulate other pathways, or other components of the same pathway, or even overlapping sets of target enzymes is used or a pharmaceutically acceptable salt, ester, prodrug, solvate, hydrate or derivative thereof. In one aspect, such therapy includes but is not limited to the combination of the composition comprising an mTorC1/mTorC2 inhibitor, as described herein, with chemotherapeutic agents, therapeutic antibodies, and radiation treatment, to provide, where desired, a synergistic or additive therapeutic effect. Pathways that my be targeted by administering another agent include, but are not limited to, MAP kinase, Akt, NFkB, WNT, RAS/RAF/MEK/ERK, JNK/SAPK, p38 MAPK, Src Family Kinases, JAK/STAT and/or PKC signaling pathways. Other agents may target one or more members of one or more signaling pathways. Representative members of the nuclear factor-kappaB (NFkB) pathway include but are not limited to RelA (p65), RelB, c-Rel, p50/p105 (NF-κB1), p52/p 100 (NF-κB2), IkB, and IkB kinase. Non-limiting examples of receptor tyrosine kinases that are members of the phosphatidylinositol 3-kinase (PI3K)/AKT pathway that may be targeted by one or more agents include FLT3 LIGAND, EGFR, IGF-1, HER2/neu, VEGFR, and PDGFR. Downstream members of the PI3K/AKT pathway that may be targeted by agents according to the methods of the invention include, but are not limited to, forkhead box 0 transcription factors, Bad, GSK-3β, I-κB, mTOR, MDM-2, and S6 ribosomal subunit.

Other agents useful in the methods of the invention include any capable of modulating a target molecule, either directly or indirectly. Non-limiting examples of target molecules modulated by other agents include enzymes, enzyme substrates, products of transitions, antibodies, antigens, membrane proteins, nuclear proteins, cytosolic proteins, mitochondrial proteins, lysosomal proteins, scaffold proteins, lipid rafts, phosphoproteins, glycoproteins, membrane receptors, G-protein-coupled receptors, nuclear receptors, protein tyrosine kinases, protein serine/threonine kinases, phosphatases, proteases, hydrolases, lipases, phospholipases, ligases, reductases, oxidases, synthases, transcription factors, ion channels, RNA, DNA, RNAse, DNAse, phospholipids, sphingolipids, nuclear receptors, ion channel proteins, nucleotide-binding proteins, calcium-binding proteins, chaperones, DNA binding proteins, RNA binding proteins, scaffold proteins, tumor suppressors, cell cycle proteins, and histones.

Other agents may target one or more signaling molecules including but not limited to the following: HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6 Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PK, PI3-Kinase class 1, class 2, class 3, mTor, SAPK/JNK1,2,3, p38s, PK, DNA-PK, ATM, AT, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PPS, inositol phosphatases, PTEN, SHIPs, myotubularins, phosphoinositide kinases, phopsholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon β, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, Bc1-2, Mc1-1, Bcl-XL, Bcl-w, Bcl-B, A1, Bax, Bak, Bok, Bik, Bad, Bid, Bim, Bmf, Hrk, Noxa, Puma, IAPs, XIAP, Smac, Cdk4, Cdk 6, Cdk 2, alkl, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pinl prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Glycoprotein, nucleoside transporters, Ets, Elk, SMADs, Rel-A (p65-NFκB), CREB, NFAT, ATF-2, AFT, Myc, Fos, Spl, Egr-1, T-bet, β-catenin, HIFs, FOXOs, E2 Fs, SRFs, TCFs, Egr-1, {tilde over (β)}-catenin, FOX(O)STAT1, STAT 3, STAT 4, STAT 5, STAT 6, p53, WT-1, HMGA, pS6, 4EPB-1, eIF4E-binding protein, RNA polymerase, initiation factors, and elongation factors.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned herein, for example as potentiators of therapeutic activity of such drugs or as a means of reducing required dosaging or potential side effects of such drugs. An inhibitor of the invention may be mixed with the other drug substance in a fixed pharmaceutical composition or it may be administered separately, before, simultaneously with or after the other drug substance. Accordingly the invention includes a combination of an inhibitor of the invention as described with an anti-inflammatory, bronchodilatory, antihistamine or anti-tussive drug substance, said compound of the invention and said drug substance being in the same or different pharmaceutical composition. Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY29311 1, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-1 1294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, as well as compounds (in free or salt or solvate form) of formula I of WO 04/16601, and also compounds of WO 04/033412. Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/041 18, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Other useful combinations of compounds of the invention with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351 125, SCH-55700 and SCH-D, Takeda antagonists such as TAK-770, and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g., methotrexate and cyclosporin are used to control the symptoms of lupus. Anticoagulants are employed to prevent blood from clotting rapidly. They range from aspirin at very low dose which prevents platelets from sticking, to heparin/coumadin.

In one aspect, this invention also relates to methods and pharmaceutical compositions for inhibiting abnormal cell growth in a mammal which comprises an amount of an mTorC1/mTorC2 inhibitor of the present invention, or a pharmaceutically acceptable salt, ester, prodrug, solvate, hydrate or derivative thereof, in combination with an amount of an anti-cancer agent (e.g., a chemotherapeutic agent). Many chemotherapeutics are presently known in the art and can be used in combination with the compounds of the invention.

This invention further relates to a method for using the compounds or pharmaceutical composition in combination with other tumor treatment approaches, including surgery, ionizing radiation, photodynamic therapy, or implants, e.g., with corticosteroids, hormones, or used as radiosensitizers.

One such approach may be, for example, radiation therapy in inhibiting abnormal cell growth or treating the proliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, $R^2$-186, $R^2$-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of an mTorC1/mTorC2 inhibitor of the present invention, or a pharmaceutically acceptable salt, ester, prodrug, solvate, hydrate or derivative thereof, which combined amounts are effective in sensitizing abnormal cells to treatment with radiation. The amount of the compound, salt, or solvate in this method can be determined according to the means for ascertaining effective amounts of such compounds described herein.

Photodynamic therapy includes therapy which uses certain chemicals known as photosensitizing compounds to treat or prevent cancers. Examples of photodynamic therapy include treatment with compounds, such as e.g., VISUDYNE and porfimer sodium. Angiostatic steroids include compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids include compounds, such as e.g., fluocinolone and dexamethasone. Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The invention also relates to a method of and to a pharmaceutical composition of treating a cardiovascular disease in a mammal which comprises administering an amount of an mTorC1/mTorC2 inhibitor of the present invention, or a pharmaceutically acceptable salt, ester, prodrug, solvate, hydrate or derivative thereof, or an isotopically-labeled derivative thereof, and, separately or in combination with the mTorC1/mTorC2 inhibitor, administering an amount of one or more therapeutic agents useful for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

Medicaments which may be administered in conjunction with the methods described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino] methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments may be used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Expression and Inhibition Assays of mTOR

Inhibition of mTor can be measured according to any procedures known in the art or methods disclosed below. The compounds described herein and any other mTorC1/mTorC2 inhibitors known in the art can be tested against recombinant mTOR (Invitrogen) in an assay containing 50 mM HEPES, pH 7.5, 1 mM EGTA, 10 mM $MgCl_2$, 2.5 mM, 0.01% Tween, 10 μM ATP (2.5 μCi of μ-32P-ATP), and 3 μg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially available. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH7.5, 0.01% Polysorbate 20, 1 mM EGTA, 10 mM $MnCl_2$, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 μM ATP and 0.5 μM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 2

Kinase Signaling Assays

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent dinstinction of signaling states in different populations defined by other markers. Phosflow is also highly quantitative. Unfractionated splenocytes, or peripheral blood mononuclear cells are stimulated with anti-CD3 to initiate T-cell receptor signaling. The cells are then fixed and stained for surface markers and intracellular phosphoproteins.

Human Peripheral Blood Mono-Nucleocyte Biomarker Assay.

Figure 5:
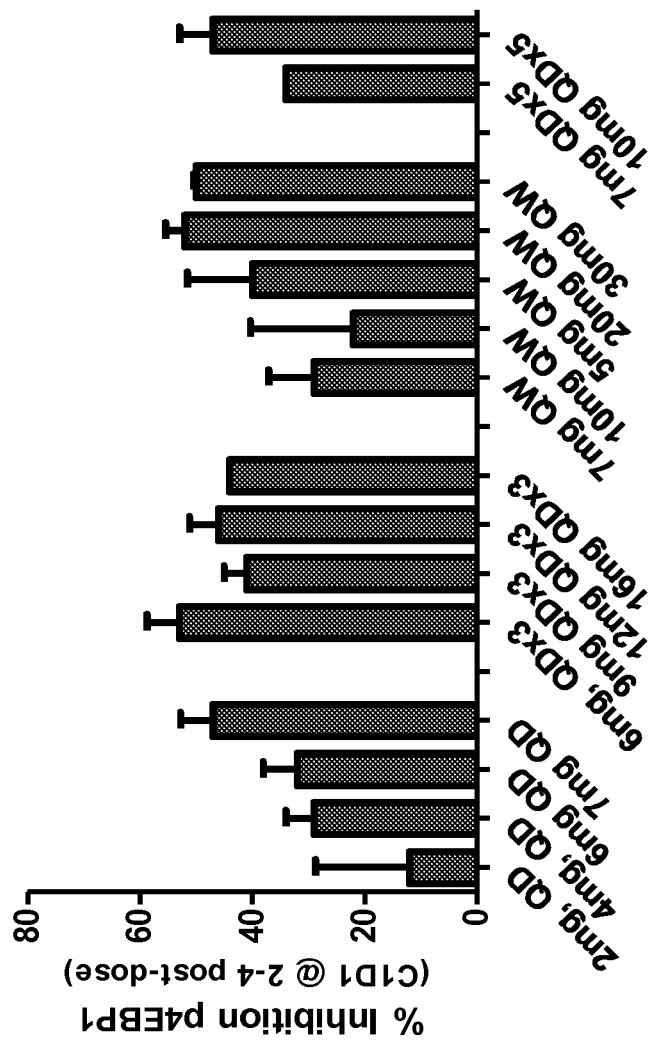
FIG. 5 shows mTor C pathway inhibition in peripheral blood mono-nucleocytes by an intermittent dosing regimen using compound A.
Figure 6:
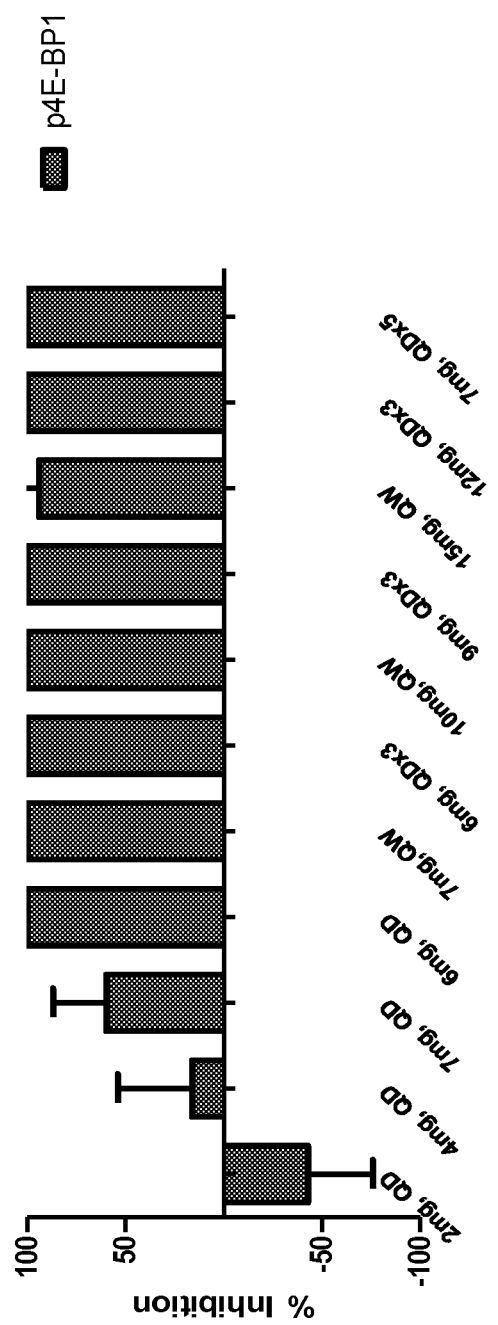
FIG. 6 shows mTor C pathway inhibition (p4EBP1) in skin biopsies by an intermittent dosing regimen using compound A.
Figure 7:
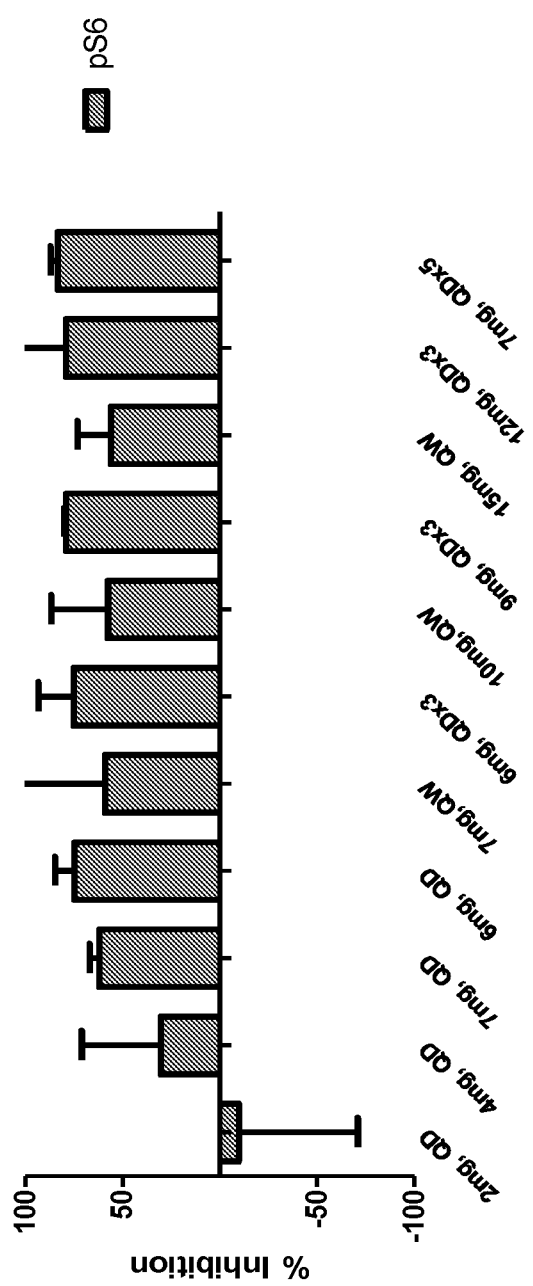
FIG. 7 shows mTor C pathway inhibition (pS6) in skin biopsies by an intermittent dosing regimen using compound A.

A BD Biosciences Phosflow assay was conducted using human peripheral blood cells. Whole blood was lysed and fixed using the provided BD Lyse/Fix buffer and permeabilized with BD Perm III buffer. Peripheral blood cells were isolated and stained using CD33 and CD20 as extracellular markers and p4E-BP1 (T37/46) as the intracellular biomarker. Cell type populations were identified as monocytes (CD33+), granulocytes (CD33 dim), lymphocytes (CD33−), B-cells (CD33−, CD20+) and T &NK cells (CD33−, CD20−) by FACS analysis. The median fluorescense intensity (MFI) of each cell type was analyzed along with the percentage of p4E-BP1 positive cells. Results are shown in FIG. 5.

Human Skin Immunohistochemistry Assay.

Skin tissue was fixed in 10% neutral-buffered formalin solution for 24 hours and then processed and embedded in paraffin block. Sections (4 µm) were cut and mounted onto microscopic slides. Sections were incubated with primary antibodies (p4EBP1, pS6, or pRAS40) overnight and developed using a chromogenic substrate.

Example 3

Phase I Clinical Trial

Adult patients with histologically confirmed advanced solid tumors were enrolled in a 3+3 dose escalation Phase I study evaluating 3 intermittent schedules of administration for compound A: QW (once weekly), QDx3d QW (3 days on 4 days off), and QDx5d QW (5 days on 2 days off), in comparison with daily dosing (QD). Safety, maximum tolerated dose (MTD), pharmacokinetics (PK) and preliminary antitumor activity were evaluated.

Figure 2:
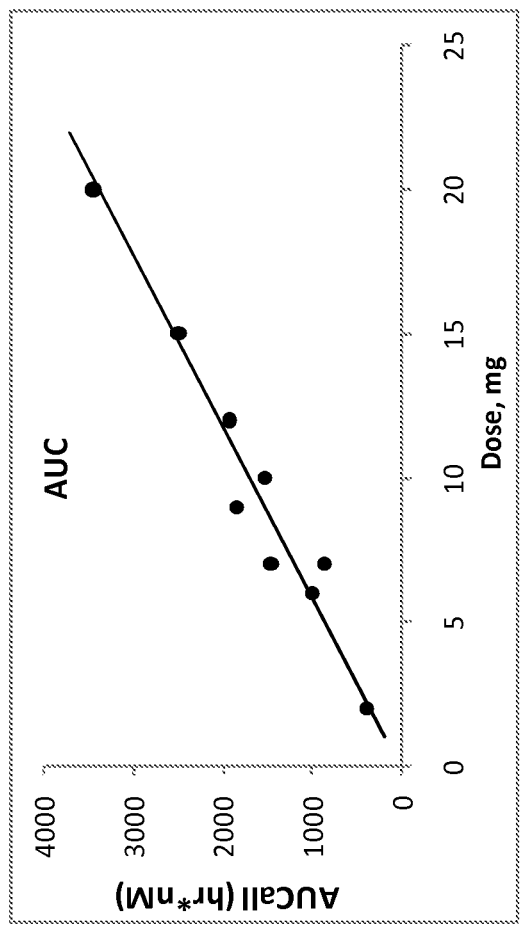
FIG. 2 shows the area under the curve (AUC) upon administration of compound A at various dose levels.
Figure 3:
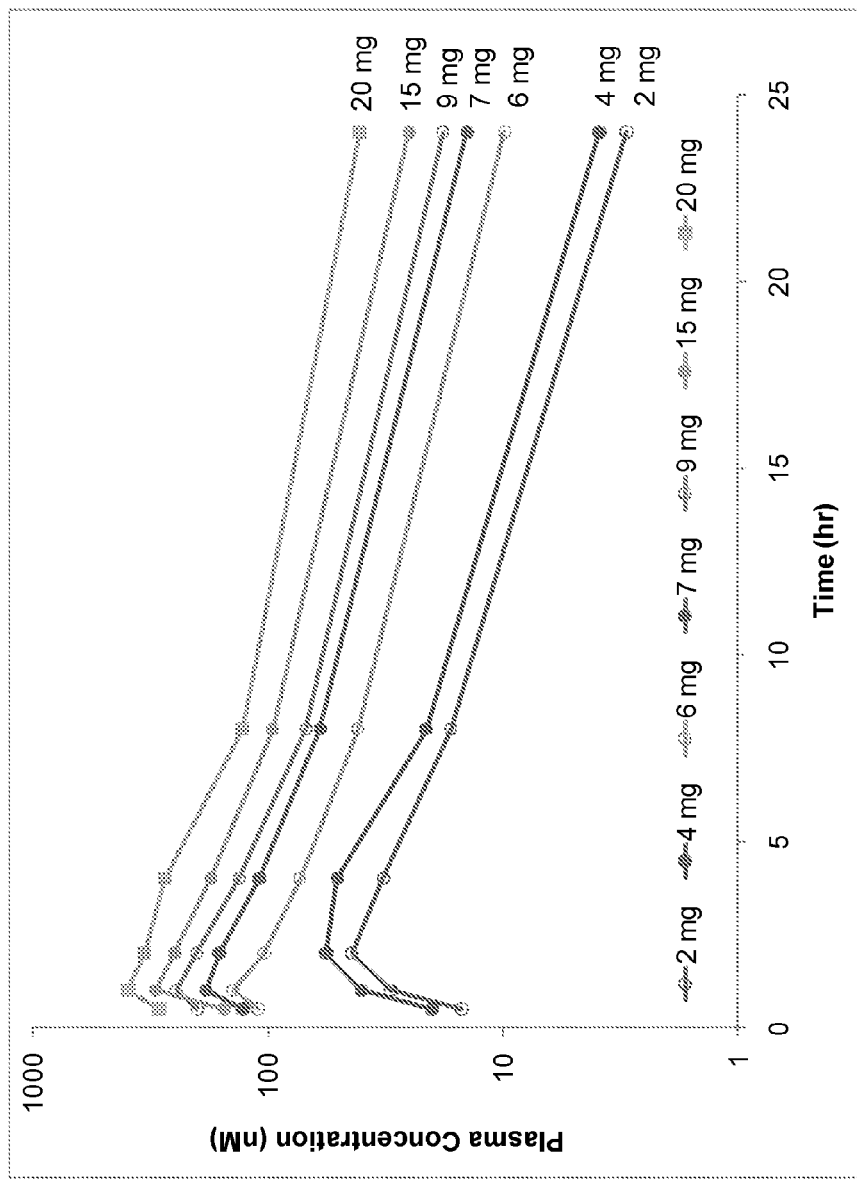
FIG. 3 shows plasma concentration-time profiles for compound A administered at various dose levels.
Figure 4:
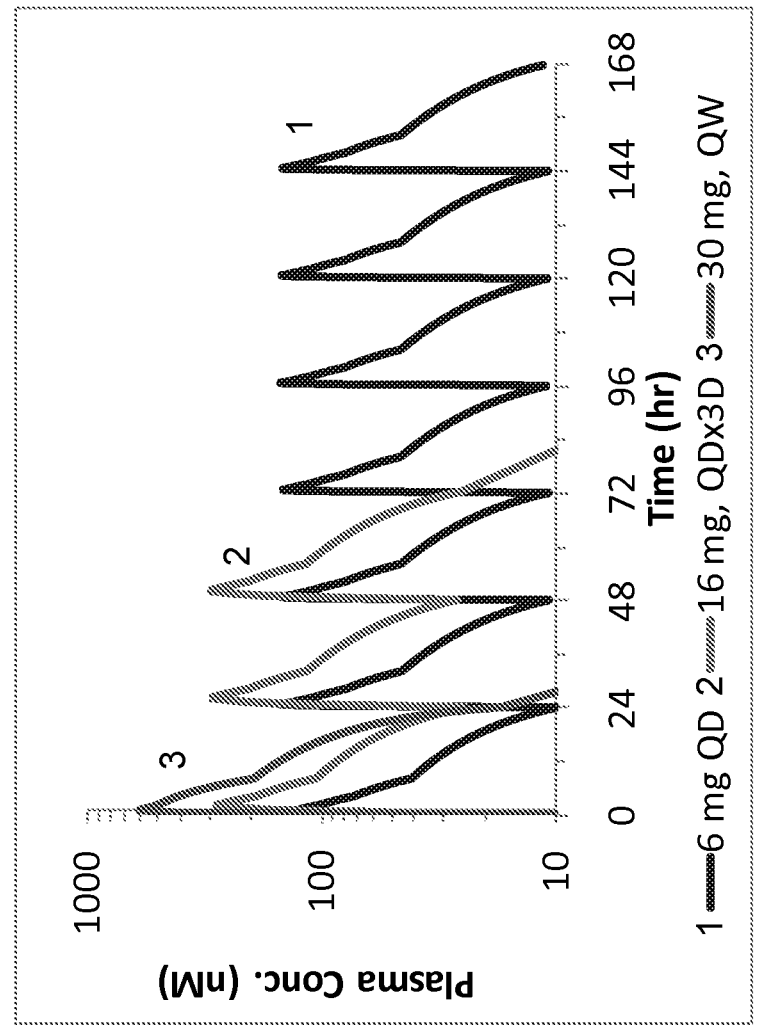
FIG. 4 shows modeled pharmacokinetic properties of compound A.

Comparison of the treatment regimens of the invention showed consistent and dose-dependent PK as described in FIGS. 1-3. Compound A was absorbed with a $T_{max}$ ranging from 0.5 to 4 h and a mean elimination plasma $t_{1/2}$ of 8 h. Plasma exposures ($C_{max}$ and $AUC_{0-24}$) following oral doses suggest dose-linear plasma PK. Decreases in p4EBP1 levels were seen in PBC in all dosing regimens. Skin biopsies showed 60-100% pathway inhibition of TORC1 (p4EBP1 and pS6) and TORC2 (pPRAS40). Preliminary anti-tumor activity was seen in patients with lung and renal cancer.

Pharmacodynamic (PD) endpoints were evaluated in surrogate (peripheral blood cells [PBCs], skin) and tumor tissues for the phosphorylation of TORC1-dependent markers (4EBP1/S6), and TORC2-dependent markers (AKT/PRAS40). 50 patients were treated in 3 intermittent dosing regimens; 21 in 6 cohorts ranging 7-40 mg QW, 20 in 5 cohorts ranging 6-20 mg QDx3d QW, and 9 in 3 cohorts ranging 7-13 mg QDxSd QW. Dose limiting toxicities of Grade (G) 3 asthenia and G3 mucositis were reported in the 40 mg QW, 20 mg QDx3d QW; and 13 mg QDxSd QW cohorts. The MTD for intermittent dosing was not reached. All adverse events (AEs) reported were reversible. The most common (≥20%, n=35) AEs considered possibly related to compound A reported in all 3 dosing regimens included nausea (51%), hyperglycemia (37%), mucosal inflammation (29%), rash (23%), asthenia (23%), vomiting (26%), and diarrhea (20%). The majority of AEs considered possibly related to compound A in any regimen were Grade 1 or 2. The only reported Grade ≥3 AE (≥5%) possibly related to compound A in 3 regimens was lymphopenia (6%). Tables 4-9 show summaries of observed adverse events for various treatment regimens of the invention.

TABLE 3

Observed pharmacokinetic and pharmacodynamic parameters for various treatment regimens using compound A.

| Dose/Schedule | 6 mg QD | 16 mg Q3D | 20 mg Q3D | 10 mg Q5D | 13 mg Q5D | 30 mg QW | 40 mg QW |
|---|---|---|---|---|---|---|---|
| Total dose (weekly) | 42 | 48 | 60 | 50 | 65 | 30 | 40 |
| $C_{max}$ (nM) | 150 | 350 | 400 | 250 | 300 | 600 | 700 |
| $AUC_{wk}$ (h · nM) | 8000 | 8000 | 10000 | 10000 | 13000 | 5000 | 6500 |
| Time per week (hrs) above 100 nM plasma conc. | 20 | 30 | 35 | 25 | 30 | 15 | 20 |
| PD (% inhibition, H score) Skin: 4EBP1/PRAS40 | 60% | 80% | 80% | 80% | 80% | 80% | 80% |
| Dose limiting toxicity | Rash | NA | Mucositis | NA | NA | NA | Asthenia |

TABLE 4

Observed treatment-emergent adverse events in decreasing order of frequency (daily dosing).

| Preferred Term | Cpd A 2 mg/day (N = 3) | Cpd A 4 mg/day (N = 7) | Cpd A 7 mg/day (N = 8) | Cpd A 6 mg/day (N = 7) | Total QD Dosing (N = 25) |
|---|---|---|---|---|---|
| Patients Reporting at Least One Related TEAE | 3 (100%) | 7 (100%) | 8 (100%) | 7 (100%) | 25 (100%) |
| Hyperglycaemia | 2 (67%) | 5 (71%) | 8 (100%) | 7 (100%) | 22 (88%) |
| Rash | 1 (33%) | 3 (43%) | 4 (50%) | 5 (71%) | 13 (52%) |
| Nausea | 1 (33%) | 2 (29%) | 3 (38%) | 3 (43%) | 9 (36%) |
| Pruritus | 0 (0%) | 2 (29%) | 2 (25%) | 5 (71%) | 9 (36%) |
| Diarrhoea | 0 (0%) | 0 (0%) | 3 (38%) | 5 (71%) | 8 (32%) |

TABLE 4-continued

Observed treatment-emergent adverse events in decreasing order of frequency (daily dosing).

| Preferred Term | Cpd A 2 mg/day (N = 3) | Cpd A 4 mg/day (N = 7) | Cpd A 7 mg/day (N = 8) | Cpd A 6 mg/day (N = 7) | Total QD Dosing (N = 25) |
|---|---|---|---|---|---|
| Dysgeusia | 2 (67%) | 3 (43%) | 2 (25%) | 1 (14%) | 8 (32%) |
| Mucosal inflammation | 0 (0%) | 2 (29%) | 4 (50%) | 2 (29%) | 8 (32%) |
| Asthenia | 0 (0%) | 0 (0%) | 4 (50%) | 2 (29%) | 6 (24%) |
| Blood creatinine increased | 0 (0%) | 1 (14%) | 4 (50%) | 1 (14%) | 6 (24%) |
| Decreased appetite | 1 (33%) | 1 (14%) | 3 (38%) | 1 (14%) | 6 (24%) |
| Fatigue | 1 (33%) | 2 (29%) | 2 (25%) | 1 (14%) | 6 (24%) |
| Vomiting | 0 (0%) | 0 (0%) | 3 (38%) | 3 (43%) | 6 (24%) |
| Dry mouth | 1 (33%) | 1 (14%) | 3 (38%) | 0 (0%) | 5 (20%) |
| Hypercholesterolaemia | 0 (0%) | 1 (14%) | 1 (13%) | 3 (43%) | 5 (20%) |
| Thrombocytopenia | 0 (0%) | 1 (14%) | 3 (38%) | 0 (0%) | 4 (16%) |
| Lymphopenia | 0 (0%) | 1 (14%) | 2 (25%) | 0 (0%) | 3 (12%) |
| Anaemia | 0 (0%) | 0 (0%) | 2 (25%) | 0 (0%) | 2 (8%) |
| Dehydration | 0 (0%) | 0 (0%) | 2 (25%) | 0 (0%) | 2 (8%) |
| Coagulopathy | 0 (0%) | 0 (0%) | 1 (13%) | 0 (0%) | 1 (4%) |
| Confusional state | 0 (0%) | 0 (0%) | 1 (13%) | 0 (0%) | 1 (4%) |
| Cough | 0 (0%) | 0 (0%) | 1 (13%) | 0 (0%) | 1 (4%) |
| Dizziness | 0 (0%) | 0 (0%) | 1 (13%) | 0 (0%) | 1 (4%) |
| Dry skin | 0 (0%) | 0 (0%) | 1 (13%) | 0 (0%) | 1 (4%) |
| Dyspepsia | 1 (33%) | 0 (0%) | 0 (0%) | 0 (0%) | 1 (4%) |
| Dyspnoea | 0 (0%) | 0 (0%) | 1 (13%) | 0 (0%) | 1 (4%) |
| Dyspnoea exertional | 0 (0%) | 1 (14%) | 0 (0%) | 0 (0%) | 1 (4%) |
| Eye infection | 0 (0%) | 0 (0%) | 0 (0%) | 1 (14%) | 1 (4%) |
| Gastritis | 0 (0%) | 0 (0%) | 1 (13%) | 0 (0%) | 1 (4%) |
| Gravitational oedema | 0 (0%) | 0 (0%) | 1 (13%) | 0 (0%) | 1 (4%) |
| Hypocalcaemia | 0 (0%) | 0 (0%) | 1 (13%) | 0 (0%) | 1 (4%) |
| Insomnia | 0 (0%) | 0 (0%) | 0 (0%) | 1 (14%) | 1 (4%) |
| Muscle spasms | 0 (0%) | 0 (0%) | 0 (0%) | 1 (14%) | 1 (4%) |
| Orthostatic hypotension | 0 (0%) | 0 (0%) | 1 (13%) | 0 (0%) | 1 (4%) |
| Panniculitis | 0 (0%) | 0 (0%) | 1 (13%) | 0 (0%) | 1 (4%) |
| Polyuria | 0 (0%) | 1 (14%) | 0 (0%) | 0 (0%) | 1 (4%) |
| Skin discolouration | 0 (0%) | 0 (0%) | 1 (13%) | 0 (0%) | 1 (4%) |
| Skin exfoliation | 0 (0%) | 0 (0%) | 1 (13%) | 0 (0%) | 1 (4%) |
| Weight decreased | 0 (0%) | 0 (0%) | 1 (13%) | 0 (0%) | 1 (4%) |

TABLE 5

Observed treatment-emergent adverse events in decreasing order of frequency (weekly dosing).

| Preferred Term | Cpd A 7 mg/week (N = 3) | Cpd A 10 mg/week (N = 3) | Cpd A 15 mg/week (N = 3) | Cpd A 20 mg/week (N = 3) | Cpd A 30 mg/week (N = 3) | Total QW Dosing (N = 15) |
|---|---|---|---|---|---|---|
| Patients Reporting at Least One Related TEAE | 3 (100%) | 2 (67%) | 3 (100%) | 2 (67%) | 3 (100%) | 13 (87%) |
| Nausea | 1 (33%) | 2 (67%) | 2 (67%) | 2 (67%) | 3 (100%) | 10 (67%) |
| Hyperglycaemia | 1 (33%) | 1 (33%) | 2 (67%) | 1 (33%) | 0 (0%) | 5 (33%) |
| Vomiting | 2 (67%) | 1 (33%) | 0 (0%) | 1 (33%) | 1 (33%) | 5 (33%) |
| Diarrhoea | 1 (33%) | 0 (0%) | 0 (0%) | 2 (67%) | 0 (0%) | 3 (20%) |
| Mucosal inflammation | 0 (0%) | 0 (0%) | 0 (0%) | 2 (67%) | 1 (33%) | 3 (20%) |
| Aspartate aminotransferase increased | 1 (33%) | 1 (33%) | 0 (0%) | 0 (0%) | 0 (0%) | 2 (13%) |
| Asthenia | 0 (0%) | 0 (0%) | 0 (0%) | 2 (67%) | 0 (0%) | 2 (13%) |
| HYPERGLYCEMIA | 0 (0%) | 0 (0%) | 0 (0%) | 0 (0%) | 2 (67%) | 2 (13%) |
| ASTHENIA | 0 (0%) | 0 (0%) | 0 (0%) | 0 (0%) | 1 (33%) | 1 (7%) |
| ATHENIA | 0 (0%) | 0 (0%) | 0 (0%) | 0 (0%) | 1 (33%) | 1 (7%) |
| Alanine aminotransferase increased | 1 (33%) | 0 (0%) | 0 (0%) | 0 (0%) | 0 (0%) | 1 (7%) |

TABLE 5-continued

Observed treatment-emergent adverse events in decreasing order of frequency (weekly dosing).

| Preferred Term | Cpd A 7 mg/week (N = 3) | Cpd A 10 mg/week (N = 3) | Cpd A 15 mg/week (N = 3) | Cpd A 20 mg/week (N = 3) | Cpd A 30 mg/week (N = 3) | Total QW Dosing (N = 15) |
|---|---|---|---|---|---|---|
| Blood creatinine increased | 0 (0%) | 0 (0%) | 1 (33%) | 0 (0%) | 0 (0%) | 1 (7%) |
| Blood triglycerides increased | 0 (0%) | 0 (0%) | 1 (33%) | 0 (0%) | 0 (0%) | 1 (7%) |
| DIARRHEA | 0 (0%) | 0 (0%) | 0 (0%) | 0 (0%) | 1 (33%) | 1 (7%) |
| Decreased appetite | 0 (0%) | 0 (0%) | 0 (0%) | 1 (33%) | 0 (0%) | 1 (7%) |
| Dysgeusia | 1 (33%) | 0 (0%) | 0 (0%) | 0 (0%) | 0 (0%) | 1 (7%) |
| Dyspepsia | 0 (0%) | 0 (0%) | 0 (0%) | 1 (33%) | 0 (0%) | 1 (7%) |
| Lymphopenia | 1 (33%) | 0 (0%) | 0 (0%) | 0 (0%) | 0 (0%) | 1 (7%) |
| Malaise | 0 (0%) | 0 (0%) | 0 (0%) | 0 (0%) | 1 (33%) | 1 (7%) |
| Muscle spasms | 0 (0%) | 0 (0%) | 0 (0%) | 1 (33%) | 0 (0%) | 1 (7%) |
| Oral discomfort | 0 (0%) | 1 (33%) | 0 (0%) | 0 (0%) | 0 (0%) | 1 (7%) |
| Pruritus | 0 (0%) | 0 (0%) | 0 (0%) | 1 (33%) | 0 (0%) | 1 (7%) |
| RASH | 0 (0%) | 0 (0%) | 0 (0%) | 0 (0%) | 1 (33%) | 1 (7%) |
| Rash | 0 (0%) | 0 (0%) | 0 (0%) | 1 (33%) | 0 (0%) | 1 (7%) |
| WEAKNESS | 0 (0%) | 0 (0%) | 0 (0%) | 0 (0%) | 1 (33%) | 1 (7%) |

TABLE 6

Observed treatment-emergent adverse events in decreasing order of frequency (3 days on/4 days off dosing).

| Preferred Term | Cpd A 6 mg/ 3 W (N = 3) | Cpd A 9 mg/ 3 W (N = 5) | Cpd A 12 mg/ 3 W (N = 3) | Cpd A 16 mg/ 3 W (N = 3) | Total QDx3d QW (N = 14) |
|---|---|---|---|---|---|
| Patients Reporting at Least One Related TEAE | 3 (100%) | 4 (80%) | 2 (67%) | 2 (67%) | 11 (79%) |
| Mucosal inflammation | 2 (67%) | 2 (40%) | 1 (33%) | 2 (67%) | 7 (50%) |
| Hyperglycaemia | 1 (33%) | 1 (20%) | 2 (67%) | 2 (67%) | 6 (43%) |
| Nausea | 2 (67%) | 2 (40%) | 2 (67%) | 0 (0%) | 6 (43%) |
| Pruritus | 1 (33%) | 2 (40%) | 1 (33%) | 0 (0%) | 4 (29%) |
| Rash | 1 (33%) | 3 (60%) | 0 (0%) | 0 (0%) | 4 (29%) |
| Asthenia | 0 (0%) | 1 (20%) | 1 (33%) | 1 (33%) | 3 (21%) |
| Vomiting | 1 (33%) | 2 (40%) | 0 (0%) | 0 (0%) | 3 (21%) |
| Diarrhoea | 0 (0%) | 1 (20%) | 0 (0%) | 1 (33%) | 2 (14%) |
| Asthenia | 0 (0%) | 0 (0%) | 0 (0%) | 1 (33%) | 1 (7%) |
| Alanine aminotransferase increased | 1 (33%) | 0 (0%) | 0 (0%) | 0 (0%) | 1 (7%) |
| Catheter site inflammation | 0 (0%) | 0 (0%) | 1 (33%) | 0 (0%) | 1 (7%) |
| Catheter site pain | 0 (0%) | 0 (0%) | 1 (33%) | 0 (0%) | 1 (7%) |
| Decreased appetite | 0 (0%) | 0 (0%) | 1 (33%) | 0 (0%) | 1 (7%) |
| Dry skin | 0 (0%) | 1 (20%) | 0 (0%) | 0 (0%) | 1 (7%) |
| Dysgeusia | 0 (0%) | 0 (0%) | 1 (33%) | 0 (0%) | 1 (7%) |
| Dyspnoea | 0 (0%) | 1 (20%) | 0 (0%) | 0 (0%) | 1 (7%) |
| Fatigue | 0 (0%) | 0 (0%) | 0 (0%) | 1 (33%) | 1 (7%) |
| Headache | 0 (0%) | 0 (0%) | 0 (0%) | 1 (33%) | 1 (7%) |
| Hyperbilirubinaemia | 1 (33%) | 0 (0%) | 0 (0%) | 0 (0%) | 1 (7%) |
| Hypercholesterolaemia | 0 (0%) | 1 (20%) | 0 (0%) | 0 (0%) | 1 (7%) |
| Hypertransaminasaemia | 0 (0%) | 1 (20%) | 0 (0%) | 0 (0%) | 1 (7%) |
| Hypertriglyceridaemia | 0 (0%) | 1 (20%) | 0 (0%) | 0 (0%) | 1 (7%) |
| Hypomagnesaemia | 0 (0%) | 1 (20%) | 0 (0%) | 0 (0%) | 1 (7%) |
| Hypotension | 0 (0%) | 1 (20%) | 0 (0%) | 0 (0%) | 1 (7%) |
| Low fever | 0 (0%) | 0 (0%) | 0 (0%) | 1 (33%) | 1 (7%) |
| Lymphopenia | 0 (0%) | 1 (20%) | 0 (0%) | 0 (0%) | 1 (7%) |
| Palmar-plantar erythrodysaesthesia syndrome | 0 (0%) | 1 (20%) | 0 (0%) | 0 (0%) | 1 (7%) |
| Platelet count decreased | 1 (33%) | 0 (0%) | 0 (0%) | 0 (0%) | 1 (7%) |
| Pyrexia | 0 (0%) | 0 (0%) | 0 (0%) | 1 (33%) | 1 (7%) |
| Rash macular | 0 (0%) | 0 (0%) | 1 (33%) | 0 (0%) | 1 (7%) |
| Urinary tract infection | 0 (0%) | 1 (20%) | 0 (0%) | 0 (0%) | 1 (7%) |

TABLE 7

Observed treatment-emergent adverse events in decreasing order of frequency (5 days on/2 days off dosing).

| Preferred Term | Cpd A 7 mg/5 W (N = 3) | Cpd A 10 mg/5 W (N = 3) | Total QDx5d QW (N = 6) |
|---|---|---|---|
| Patients Reporting at Least One Related TEAE | 1 (33%) | 1 (33%) | 2 (33%) |
| Diarrhoea | 1 (33%) | 0 (0%) | 1 (17%) |
| Nausea | 0 (0%) | 1 (33%) | 1 (17%) |
| Nausea | 1 (33%) | 0 (0%) | 1 (17%) |
| Rash | 1 (33%) | 0 (0%) | 1 (17%) |
| Urine tract infection | 0 (0%) | 1 (33%) | 1 (17%) |
| Vomiting | 0 (0%) | 1 (33%) | 1 (17%) |

TABLE 8

Observed treatment-emergent adverse events in various treatment regimens.

| Preferred Term | Total QD Dosing (N = 25) | Total QW Dosing (N = 15) | Total QDx3d QW (N = 14) | Total QDx5d QW (N = 6) | Total (N = 60) |
|---|---|---|---|---|---|
| Catheter site inflammation | 0 (0%) | 0 (0%) | 1 (7%) | 0 (0%) | 1 (2%) |
| Catheter site pain | 0 (0%) | 0 (0%) | 1 (7%) | 0 (0%) | 1 (2%) |
| Coagulopathy | 1 (4%) | 0 (0%) | 0 (0%) | 0 (0%) | 1 (2%) |
| Confusional state | 1 (4%) | 0 (0%) | 0 (0%) | 0 (0%) | 1 (2%) |
| Cough | 1 (4%) | 0 (0%) | 0 (0%) | 0 (0%) | 1 (2%) |
| Diarrhea | 0 (0%) | 1 (7%) | 0 (0%) | 0 (0%) | 1 (2%) |
| Dizziness | 1 (4%) | 0 (0%) | 0 (0%) | 0 (0%) | 1 (2%) |
| Dyspnoea exertional | 1 (4%) | 0 (0%) | 0 (0%) | 0 (0%) | 1 (2%) |
| Eye infection | 1 (4%) | 0 (0%) | 0 (0%) | 0 (0%) | 1 (2%) |
| Fatigue | 0 (0%) | 0 (0%) | 1 (7%) | 0 (0%) | 1 (2%) |
| Gastritis | 1 (4%) | 0 (0%) | 0 (0%) | 0 (0%) | 1 (2%) |
| Gravitational oedema | 1 (4%) | 0 (0%) | 0 (0%) | 0 (0%) | 1 (2%) |
| Headache | 0 (0%) | 0 (0%) | 1 (7%) | 0 (0%) | 1 (2%) |
| Hyperbilirubinaemia | 0 (0%) | 0 (0%) | 1 (7%) | 0 (0%) | 1 (2%) |
| Hypertransaminasaemia | 0 (0%) | 0 (0%) | 1 (7%) | 0 (0%) | 1 (2%) |
| Hypertriglyceridaemia | 0 (0%) | 0 (0%) | 1 (7%) | 0 (0%) | 1 (2%) |
| Hypocalcaemia | 1 (4%) | 0 (0%) | 0 (0%) | 0 (0%) | 1 (2%) |
| Hypomagnesaemia | 0 (0%) | 0 (0%) | 1 (7%) | 0 (0%) | 1 (2%) |
| Hypotension | 0 (0%) | 0 (0%) | 1 (7%) | 0 (0%) | 1 (2%) |
| Insomnia | 1 (4%) | 0 (0%) | 0 (0%) | 0 (0%) | 1 (2%) |
| Low fever | 0 (0%) | 0 (0%) | 1 (7%) | 0 (0%) | 1 (2%) |
| Malaise | 0 (0%) | 1 (7%) | 0 (0%) | 0 (0%) | 1 (2%) |
| Nausea | 0 (0%) | 0 (0%) | 0 (0%) | 1 (17%) | 1 (2%) |
| Oral discomfort | 0 (0%) | 1 (7%) | 0 (0%) | 0 (0%) | 1 (2%) |
| Orthostatic hypotension | 1 (4%) | 0 (0%) | 0 (0%) | 0 (0%) | 1 (2%) |
| Palmar-plantar erythrodysaesthesia syndrome | 0 (0%) | 0 (0%) | 1 (7%) | 0 (0%) | 1 (2%) |
| Panniculitis | 1 (4%) | 0 (0%) | 0 (0%) | 0 (0%) | 1 (2%) |
| Platelet count decreased | 0 (0%) | 0 (0%) | 1 (7%) | 0 (0%) | 1 (2%) |
| Polyuria | 1 (4%) | 0 (0%) | 0 (0%) | 0 (0%) | 1 (2%) |
| Pyrexia | 0 (0%) | 0 (0%) | 1 (7%) | 0 (0%) | 1 (2%) |
| Rash | 0 (0%) | 1 (7%) | 0 (0%) | 0 (0%) | 1 (2%) |
| Rash macular | 0 (0%) | 0 (0%) | 1 (7%) | 0 (0%) | 1 (2%) |
| Skin discolouration | 1 (4%) | 0 (0%) | 0 (0%) | 0 (0%) | 1 (2%) |
| Skin exfoliation | 1 (4%) | 0 (0%) | 0 (0%) | 0 (0%) | 1 (2%) |
| Urine tract infection | 0 (0%) | 0 (0%) | 0 (0%) | 1 (17%) | 1 (2%) |
| Urinary tract infection | 0 (0%) | 0 (0%) | 1 (7%) | 0 (0%) | 1 (2%) |
| Vomiting | 0 (0%) | 0 (0%) | 0 (0%) | 1 (17%) | 1 (2%) |
| Weakness | 0 (0%) | 1 (7%) | 0 (0%) | 0 (0%) | 1 (2%) |
| Weight decreased | 1 (4%) | 0 (0%) | 0 (0%) | 0 (0%) | 1 (2%) |

TABLE 9

Grade 3 or greater treatment-emergent adverse events for various treatment regimens.

| Preferred Term | Total QD Dosing (N = 25) | Total QW Dosing (N = 15) | Total QDx3d QW (N = 14) | Total QDx5d QW (N = 6) | Total (N = 60) |
|---|---|---|---|---|---|
| Patients Reporting at Least One Grade 3 or Greater TEAE | 15 (60%) | 3 (20%) | 7 (50%) | 0 (0%) | 25 (42%) |
| Rash | 7 (28%) | 0 (0%) | 0 (0%) | 0 (0%) | 7 (12%) |
| Hyperglycaemia | 4 (16%) | 0 (0%) | 1 (7%) | 0 (0%) | 5 (8%) |

TABLE 9-continued

Grade 3 or greater treatment-emergent adverse events for various treatment regimens.

| Preferred Term | Total QD Dosing (N = 25) | Total QW Dosing (N = 15) | Total QDx3d QW (N = 14) | Total QDx5d QW (N = 6) | Total (N = 60) |
|---|---|---|---|---|---|
| Lymphopenia | 2 (8%) | 1 (7%) | 1 (7%) | 0 (0%) | 4 (7%) |
| Diarrhoea | 1 (4%) | 1 (7%) | 1 (7%) | 0 (0%) | 3 (5%) |
| Gamma-glutamyltransferase increased | 0 (0%) | 1 (7%) | 1 (7%) | 0 (0%) | 2 (3%) |
| Hypokalaemia | 2 (8%) | 0 (0%) | 0 (0%) | 0 (0%) | 2 (3%) |
| Hyponatraemia | 2 (8%) | 0 (0%) | 0 (0%) | 0 (0%) | 2 (3%) |
| Pruritus | 2 (8%) | 0 (0%) | 0 (0%) | 0 (0%) | 2 (3%) |
| Thrombocytopenia | 2 (8%) | 0 (0%) | 0 (0%) | 0 (0%) | 2 (3%) |
| Abdominal pain upper | 1 (4%) | 0 (0%) | 0 (0%) | 0 (0%) | 1 (2%) |
| Anaemia | 1 (4%) | 0 (0%) | 0 (0%) | 0 (0%) | 1 (2%) |
| Aspartate aminotransferase increased | 0 (0%) | 1 (7%) | 0 (0%) | 0 (0%) | 1 (2%) |
| Asthenia | 0 (0%) | 0 (0%) | 1 (7%) | 0 (0%) | 1 (2%) |
| Catheter related infection | 1 (4%) | 0 (0%) | 0 (0%) | 0 (0%) | 1 (2%) |
| Cellulitis | 1 (4%) | 0 (0%) | 0 (0%) | 0 (0%) | 1 (2%) |
| Disease progression | 0 (0%) | 0 (0%) | 1 (7%) | 0 (0%) | 1 (2%) |
| Enterocutaneous fistula | 1 (4%) | 0 (0%) | 0 (0%) | 0 (0%) | 1 (2%) |
| Gastroenteritis | 0 (0%) | 0 (0%) | 1 (7%) | 0 (0%) | 1 (2%) |
| Pancreatitis acute | 1 (4%) | 0 (0%) | 0 (0%) | 0 (0%) | 1 (2%) |
| Pleural effusion | 1 (4%) | 0 (0%) | 0 (0%) | 0 (0%) | 1 (2%) |
| Rash macular | 0 (0%) | 0 (0%) | 1 (7%) | 0 (0%) | 1 (2%) |
| Somnolence | 1 (4%) | 0 (0%) | 0 (0%) | 0 (0%) | 1 (2%) |
| Urinary tract infection | 0 (0%) | 0 (0%) | 1 (7%) | 0 (0%) | 1 (2%) |

TABLE 10

Results of an additional study showing grade 3 or greater treatment-emergent adverse events for various treatment regimens.

| Preferred Term | Total QD Dosing (N = 29) | Total QW Dosing (N = 22) | Total QDx3d QW (N = 25) | Total QDx5d QW (N = 15) | Total (N = 91) |
|---|---|---|---|---|---|
| Patients Reporting at least one Grade 3 or greater TEAE | 17 (59%) | 10 (45%) | 18 (72%) | 8 (53%) | 53 (58%) |
| Hyperglycaemia | 4 (14%) | 0 (0%) | 4 (16%) | 1 (7%) | 9 (10%) |
| Rash | 7 (24%) | 0 (0%) | 1 (4%) | 1 (7%) | 9 (10%) |
| Mucosal Inflammation | 0 (0%) | 0 (0%) | 4 (16%) | 3 (20%) | 7 (8%) |
| Anaemia | 1 (3%) | 2 (9%) | 2 (8%) | 1 (7%) | 6 (7%) |
| Lymphopenia | 2 (7%) | 1 (5%) | 2 (8%) | 1 (7%) | 6 (7%) |
| Hypophsphataemia | 0 (0%) | 0 (0%) | 3 (12%) | 2 (13%) | 5 (5%) |
| Asthenia | 1 (3%) | 1 (5%) | 1 (4%) | 1 (7%) | 4 (4%) |
| Diarrhoea | 1 (3%) | 1 (5%) | 1 (4%) | 0 (0%) | 3 (3%) |
| Fatigue | 0 (0%) | 1 (5%) | 0 (0%) | 2 (13%) | 3 (3%) |
| Gamma-glutamyltransferase increase | 0 (0%) | 1 (5%) | 1 (4%) | 1 (7%) | 3 (3%) |
| Hypokalaemia | 2 (7%) | 1 (5%) | 0 (0%) | 0 (0%) | 3 (3%) |
| Pruritus | 2 (7%) | 0 (0%) | 1 (4%) | 0 (0%) | 3 (3%) |
| Vomiting | 0 (0%) | 1 (5%) | 1 (4%) | 1 (7%) | 3 (3%) |
| Aspartate aminotransferase increase | 0 (0%) | 1 (5%) | 0 (0%) | 1 (7%) | 2 (2%) |
| Blood creatinine increase | 0 (0%) | 0 (0%) | 2 (8%) | 0 (0%) | 2 (2%) |
| Deep vein thrombosis | 0 (0%) | 1 (5%) | 1 (4%) | 0 (0%) | 2 (2%) |
| Disease progression | 0 (0%) | 2 (9%) | 0 (0%) | 0 (0%) | 2 (2%) |
| Hyponatraemia | 2 (7%) | 0 (0%) | 0 (0%) | 0 (0%) | 2 (2%) |
| Muscular weakness | 0 (0%) | 1 (5%) | 1 (4%) | 0 (0%) | 2 (2%) |
| Nausea | 0 (0%) | 0 (0%) | 1 (4%) | 1 (7%) | 2 (2%) |
| Neutropenia | 0 (0%) | 1 (5%) | 0 (0%) | 1 (7%) | 2 (2%) |
| Thrombocytopenia | 2 (7%) | 0 (0%) | 0 (0%) | 0 (0%) | 2 (2%) |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating cancer in a subject in need thereof, comprising administering an mTorC1/mTorC2 inhibitor to said subject according to an intermittent regimen which comprises at least one cycle in which the mTorC1/mTorC2 inhibitor is administered for at least 1 day, followed by an intermission in which the mTorC1/mTorC2 inhibitor is not administered for at least 1 day; wherein the cancer is renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, myeloma, nasopharyngeal cancer, prostate cancer, lung cancer, glioblastoma, bladder cancer, mesothelioma, head cancer, or neck cancer;

wherein the mTorC1/mTorC2 inhibitor has the Formula:

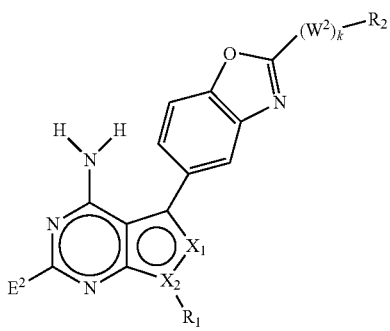

or a pharmaceutically acceptable salt thereof, wherein:
$E^2$ is H; $X_1$ is N; $X_2$ is N; $W^2$ is NH; k is 1; $R_2$ is H; and $R_1$ is isopropyl.

2. The method of claim 1, wherein the intermittent regimen is effective to achieve an mTorC1/mTorC2 inhibitor plasma concentration of greater than about 100 nM for a duration longer than about 20 hours during a 7-day period of administration.

3. The method of claim 1, wherein the intermittent regimen is effective to achieve an mTorC1/mTorC2 inhibitor plasma concentration of greater than about 100 nM for a duration of at least about 30 hours during a 7-day period of administration.

4. The method of claim 1, wherein the intermittent regimen is effective to achieve a Cmax of greater than about 200, 250, 300, 350, 400, 450, 500, 550 or 600 nM.

5. The method of claim 1, wherein the intermittent regimen is effective to achieve a Cmax of greater than about 300 nM.

6. The method of claim 1, wherein the mTorC1/mTorC2 inhibitor is administered for 2, 3, 4, 5, 6 or 7 consecutive days followed by an intermission in which the mTorC1/mTorC2 inhibitor is not administered for at least 1 day.

7. The method of claim 1, wherein the regimen comprises at least one cycle in which the mTorC1/mTorC2 inhibitor is administered for 2, 3, 4, 5, 6 or 7 consecutive days followed by an intermission in which the mTorC1/mTorC2 inhibitor is not administered for at least 3, 4, or 5 consecutive days.

8. The method of claim 1, wherein the regimen comprises at least one cycle in which the mTorC1/mTorC2 inhibitor is administered for 1 day followed by an intermission in which the mTorC1/mTorC2 inhibitor is not administered for 6 consecutive days.

9. The method of claim 1, wherein the regimen comprises at least one 7-day cycle in which the mTorC1/mTorC2 inhibitor is administered for 3 consecutive days followed by an intermission of 4 consecutive days.

10. The method of claim 1, wherein the regimen comprises at least one 7-day cycle in which the mTorC1/mTorC2 inhibitor is administered for 5 consecutive days followed by an intermission of 2 consecutive days.

11. The method of claim 1, wherein the wherein the regimen comprises at least one 7-day cycle in which the mTorC1/mTorC2 inhibitor is administered at least 3 times on alternate days within the 7 days.

12. The method of claim 1, wherein the mTorC1/mTorC2 inhibitor is administered parenterally, orally, intraperitoneally, intravenously, intraarterially, transdermally, intramuscularly, liposomally, via local delivery by catheter or stent, subcutaneously, intraadiposally, or intrathecally.

13. The method of claim 1, wherein the mTorC1/mTorC2 inhibitor is administered orally.

14. The method of claim 1, wherein the cancer is renal cancer.

15. The method of claim 1, wherein cancer is renal cell carcinoma.

16. The method of claim 1, wherein the cancer is ovarian cancer.

17. The method of claim 1, wherein the cancer is breast cancer.

18. The method of claim 1, wherein the cancer is uterine sarcoma.

19. The method of claim 1, wherein the cancer is endometrial uterine cancer.

20. The method of claim 1, wherein the cancer is cervical cancer.

21. The method of claim 1, wherein the cancer is gastric cancer.

* * * * *